US007875431B2

(12) United States Patent
Diehl et al.

(10) Patent No.: US 7,875,431 B2
(45) Date of Patent: Jan. 25, 2011

(54) METHODS FOR DETECTING INFLAMMATORY BOWEL DISEASE

(75) Inventors: Lauri Diehl, Los Altos, CA (US); Kenneth Flanagan, San Francisco, CA (US); Lian Mo, Palo Alto, CA (US)

(73) Assignee: Genentech, Inc., South San Francisco, CA (US)

( * ) Notice: Subject to any disclaimer, the term of this patent is extended or adjusted under 35 U.S.C. 154(b) by 350 days.

(21) Appl. No.: 12/036,183

(22) Filed: Feb. 22, 2008

(65) Prior Publication Data

US 2009/0111102 A1 Apr. 30, 2009

Related U.S. Application Data

(60) Provisional application No. 60/891,196, filed on Feb. 22, 2007, provisional application No. 60/987,752, filed on Nov. 13, 2007, provisional application No. 61/024,170, filed on Jan. 28, 2008.

(51) Int. Cl.
C12Q 1/68 (2006.01)
G01N 33/53 (2006.01)

(52) U.S. Cl. ........................................... 435/6; 435/7.1

(58) Field of Classification Search ........................ None
See application file for complete search history.

(56) References Cited

U.S. PATENT DOCUMENTS 7,144,990 B2 12/2006 Goddard et al.
7,157,558 B2 1/2007 Goddard et al.

FOREIGN PATENT DOCUMENTS

WO WO 00/61629 10/2000
WO WO 00/77026 12/2000

OTHER PUBLICATIONS

Database Gene Sequence Online, *Human Secreted Protein Gene 13 SEQ ID No. 23*, XP002489471, Apr. 6, 2001.
Database Gene Sequence Online, *Human Secreted Protein Gene 28 SEQ ID No. 38*, XP002489472, Mar. 26, 2001.
Apostolopoulos, et al., "Ly6d-L, a cell surface ligand for mouse Ly6d", Immunity, vol. 12, pp. 223-232, (2000).
Baksheev, et al., Gene expression in the adapting small bowel after massive small bowel resection, J. Gastroenterol, 41: 1041-1052, (2006).
Bamezai, "Mouse Ly-6 proteins and their extended family: markers of cell differentiation and regulators of cell signaling", Arch. Immunol. Ther. Exp., 52: 255-266, (2004).
Banks, et al., "Chemokine expression in IBD. Mucosal chemokine expression is unselectively increased in both ulcerative colitis and crohn's disease", J. Pathol., 199: 28-35, (2003).
Bohuslav, et al., "Large, detergent-resistant complexes containing murine antigens Thy-1 and Ly-6 and protein tyrosine kinase p56$^{lck*}$", Eur. J. Immunol., 23: 825-831, (1993).
Bouma, et al., "The immunological and genetic basis of inflammatory bowel disease", Nature Reviews, vol. 3, pp. 521-533, (2003).
Brand, et al., "IL-22 is increased in active Crohn's disease and promotes proinflammatory gene expression and intestinal epithelial cell migration", Am. J. Physiol. Gastrointest. Liver Physiol., 290: G827-G838, (2006).
Breider, et al., "Intercellular adhesion molecule-1 expression in dextran sodium sulfate-induced colitis in rats", Vet. Pathol., 34: 598-604, (1997).
Chou, et al., "The Caenorhabditis elegans ord-2 gene encodes a novel Ly-6-related protein required for Olfaction", Genetics, 157: 211-224, (2001).
Dieckgraefe, et al., "Analysis of mucosal gene expression in inflammatory bowel disease by parallel oligonucleotide arrays", Physiol. Genomics, 4: 1-11, (2000).
Dooley, et al., "Regulation of gene expression in inflammatory bowel disease and correlation with IBD drugs", Inflamm. Bowel Dis., vol. 10, No. 1, pp. 1-14, (2004).
Elson, et al., "Experimental models of inflammatory bowel disease reveal innate, adaptive, and regulatory mechanisms of host dialogue with the microbiota", Immunological Reviews, vol. 206, pp. 260-276, (2005).
Fahlgren, et al., "β-defensin-3 and -4 in intestinal epithelial cells display increased mRNA expression in ulcerative colitis", Clin. Exp. Immunol., 137: 379-385, (2004).
Henderson, et al., "Ly-6A.2 expression regulates antigen-specific CD4$^+$ T cell proliferation and cytokine production[1]", The Journal of Immunology, 168: 118-126, (2002).
Hidalgo, et al., "Complete identification of E-selectin ligands on neutrophils reveals distinct functions of PSGL-1, ESL-1, and CD44", Immunity, 26: 477-489, (2007).
Jaakkola, et al., "Ly6c induces clustering of LFA-1 (CD11a/CD18) and is involved in subtype-specific adhesion of CD8 T cells[1]", The Journal of Immunology, 170: 1283-1290, (2003).
Khodadoust, et al., "Complex regulation of Ly-6E gene transcription in T cells by IFNs[1]", The Journal of Immunology, 163: 811-819, (1999).
Lawrance, et al., "Ulcerative colitis and Crohn's disease: distinctive gene expression profiles and novel susceptibility candidate genes", Human Molecular Genetics, vol. 10, No. 5, pp. 445-456, (2001).
Niessner, et al., "Altered Th1/Th2 cytokine profiles in the intestinal mucosa of patients with inflammatory bowel disease as assessed by quantitative reversed transcribed polymerase chain reaction (RT-PCR)", Clin. Exp. Immunol., 101: 428-435, (1995).
Papadakis, "Chemokines in inflammatory bowel disease", Current Allergy and Asthma Reports, 4: 83-89, (2004).
Papadakis, et al., "The role of chemokines and chemokine receptors in mucosal inflammatory", Inflammatory Bowel Diseases, 6(4): 303-313, (2000).

(Continued)

*Primary Examiner*—James Martinell
(74) *Attorney, Agent, or Firm*—Arnold & Porter LLP; Craig Svoboda; Jeffrey P. Bernhardt

(57) ABSTRACT

The present invention provides for a method of detecting the presence of inflammatory bowel disease in gastrointestinal tissues or cells of a mammal by detecting increased expression of LY6 genes in the tissues or cells of the mammal relative to a control.

34 Claims, 53 Drawing Sheets
(12 of 53 Drawing Sheet(s) Filed in Color)

OTHER PUBLICATIONS

Paret, et al., "Ly6 family member C4.4A binds laminins 1 and 5, associates with Galectin-3 and supports cell migration", Int. J. Cancer, 115: 724-733, (2005).

Podolsky, "Inflammatory bowel disease", N. Eng. J. Med., vol. 347, No. 6, pp. 417-429, (2002).

Rock, et al., "The LY-6 locus: A multigene family encoding phosphatodylinositol-Anchored membrane proteins concerned with T-cell activation", Immunological Reviews, No. 111, pp. 195-224, (1989).

Ruiz, et al., "IL-10 gene-deficient mice lack TGF-β/Smad signaling and fail to inhibit proinflammatory gene expression in intestinal epithelial cells after the colonization with colitogenic enterococcus faecalis", The Journal of Immunology, 174: 2990-2999, (2005).

Shao, et al., "Non-classical MHC class 1 molecules on intestinal epithelial cells: mediators of mucosal crosstalk", Immunological Reviews, vol. 206, pp. 160-176, (2005).

Shevach, et al., "Ly-6: a multigene family in search of a function", Immunology Today, vol. 10, No. 6, pp. 195-200, (1989).

Simons, et al., "Cholesterol, lipid rafts, and disease", The Journal of Clinical Investigation, vol. 110, No. 5, pp. 597-603, (2002).

Simons, et al., "Lipid rafts and signal transduction", Nature Reviews, vol. 1, pp. 31-41, (2000).

Singh, et al., "Toll-like receptor-mediated responses of primary intestinal epithelial cells during the development of colitis", Am. J. Physiol. Gastrointest Liver Physiol., 288: G514-G524, (2005).

Snoeck, et al., "The role of enterocytes in the intestinal barrier function and antigen uptake", Microbes and Infection, 7: 997-1004, (2005).

Sunderkotter, et al., "Subpopulations of mouse blood monocytes differ in maturation stage and inflammatory response", The Journal of Immunology, 172: 4410-4417, (2004).

Uguccioni, et al., "Increased expression of IP-10, IL-8, MCP-1, and MCP-3 in ulcerative colitis", American Journal of Pathology, vol. 155, No. 2, pp. 331-336, (1999).

Uthoff, et al., "Identification of candidate genes in ulcerative colitis and Crohn's disease using cDNA array technology", International Journal of Oncology, 19: 803-810, (2001).

Von Tresckow, et al., "Depletion of cellular cholesterol and lipid rafts increases shedding of CD30[1]", The Journal of Immunology, 172: 4324-4331, (2004).

Wolk, et al., "IL-22 induces lipopolysaccharide-binding protein in hepatocytes: A potential systemic role of IL-22 in Crohn's disease", The Journal of Immunology, 178: 5973-5981, (2007).

Z'Graggen, et al., "The C-X-C chemokine ENA-78 is preferentially expressed in intestinal epithelium in inflammatory bowel disease", Gastroenterology, 113: 808-816, (1997).

Zhang, et al., "Ly-6A is critical for the function of double negative regulatory T cells", Eur. J. Immunol., 32: 1584-1592, (2002).

```
cgcgtctgcggctgcgttccccgaaagacgaggctgcgcccggattccggtccgcagggagacc
gaagggcacagctccccgcgccgcgcacgccgcccgagcccggagtgcggacacccccgggatg
cttgcgccccagaggacccgcgccccaagccccgcgccgcccccaggcccacccggagcatgc
tgcctgcagccatgaagggcctcggcctggcgctgctggccgtcctgctgtgctcggcgcccgc
tcatggcctgtggtgccaggactgcaccctgaccaccaactccagccattgcaccccaaagcag
tgccagccgtccgacacggtgtgtgccagtgtccgaatcaccgatcccagcagcagcaggaagg
atcactcggtgaacaagatgtgtgcctcctcctgtgacttcgttaagcgacacttttctcaga
ctatctgatggggtttattaactctgggatcttaaaggtcgacgtggactgctgcgagaaggat
ttgtgcaatggggcggcaggggcagggcacagcccctgggccctggccggggggctcctgctca
gcctggggcctgccctcctctgggctgggccctgatgtctcctccttcccacggggcttctgag
cttgctcccctgagcctgtggctgcctctccccagcctggcgtggctggggctgggggcagcc
ttggcccagctccgtggctgtggcctgtggctctcactcctccccgacgtgaagcctccctgt
ctctccgccagctctgagtcccaggcagctggacatctccaggaaaccaggccatctgggcagg
aggcctggggatgagggtgggggggacccccaggtcccggaggggaagtgaagcaacagccca
gctggaagggcgtcttctgcggag aaataaagtcacttttgagtcctgagaaaaaaaaaa
```

Figure 1A

MLPAAMKGLGLALLAVLLCSAPAHGLWCQDCTLTTNSSHCTPKQCQPSDTVCASVRITDPSSSR
KDHSVNKMCASSCDFVKRHFFSDYLMGFINSGILKVDVDCCEKDLCNGAAGAGHSPWALAGGLL
LSLGPALLWAGP

Figure 1B

```
   1 agggcggtgt caatgcaccc tccagcggtg cgcgcaggcg ggagaaggga gggcggcccg
  61 ggcaagtgag acagttaagg cagtgtcccc accacacccc cacccagatt ggccacgccg
 121 agctggttct tgacagaagg ccttcgcgga ggaagagggg gcacagctgc acaggacacc
 181 ctacggagcc tgcgggcgtg aactttgcc aggcgcacgg gaacgcgcgc ccttcctgtc
 241 agcctcccgg ggcgccaggc tcccgcggcc cgcagcggga cagcctcagt tgtgtgggct
 301 ggacccagtc gctggggtac cgaccagtcc tggaaggcgc agaggacgtg gagtggggag
 361 gctgccttcc tatgtgcgaa gggccagccg ggcacgcagt cctcagaccc tagtccgcac
 421 ccggcaggtc cccacggcac ctgctgcgcc ctcctcgccg ctcccccaac ctccccatct
 481 cagaaaacta ccagttctct cccgccccc ggcgcccctt tcccaggaac gtgcggaggc
 541 gggagaagag gaagacagga aggggtgggg gatgtgaagc gaccgtccca gccttccccg
 601 cccgccaccc ccaccccaac tcggcagccg tcacgtgatg cctggagtgg gaggtgggga
 661 gaaaaggcga gactttgtg ggtgctcccg atcgccagta gttccttcag tctcagccgc
 721 caactccgga ggcgcggtgc tcggcccggg agcgcgagcg ggaggagcag agaccgcag
 781 ccgggagccc gagcgcgggc gatgcaggct ccgcgagcgg cacctgcggc tcctctaagc
 841 tacgaccgtc gtctccgcgg cagcagcgcg ggccccagca gcctcggcag ccacagccgc
 901 tgcagccggg gcagcctccg ctgctgtcgc ctcctctgat gcgcttgccc tctcccggcc
 961 ccgggactcc gggagaatgt gggtcctagg catcgcggca acttttgcg gattgttctt
1021 gcttccaggc tttgcgctgc aaatccagtg ctaccagtgt gaagaattcc agctgaacaa
1081 cgactgctcc tcccccgagt tcattgtgaa ttgcacggtg aacgttcaag acatgtgtca
1141 gaaagaagtg atggagcaaa gtgccgggat catgtaccgc aagtcctgtg catcatcagc
1201 ggcctgtctc atcgcctctg ccgggtacca gtccttctgc tccccaggga aactgaactc
1261 agtttgcatc agctgctgca cacccctct ttgtaacggg ccaaggccca agaaaagggg
1321 aagttctgcc tcggccctca ggccagggct ccgcaccacc atcctgttcc tcaaattagc
1381 cctcttctcg gcacactgct gaagctgaag gagatgccac ccctcctgc attgttcttc
1441 cagccctcgc ccccaacccc ccacctccct gagtgagttt cttctgggtg tccttttatt
1501 ctgggtaggg agcgggagtc cgtgttctct tttgttcctg tgcaaataat gaaagagctc
1561 ggtaaagcat tctgaataaa ttcagcctga ctgaattttc agtatgtact tgaaggaagg
1621 aggtggagtg aaagttcacc cccatgtctg tgtaaccgga gtcaaggcca ggctggcaga
1681 gtcagtcctt agaagtcact gaggtgggca tctgcctttt gtaaagcctc cagtgtccat
1741 tccatccctg atggggcat agtttgagac tgcagagtga gagtgacgtt tccttagggc
1801 tggagggcca gttcccactc aaggctccct cgcttgacat tcaaacttca tgctcctgaa
1861 aaccattctc tgcagcagaa ttggctggtt tcgcgcctga gttgggctct agtgactcga
1921 gactcaatga ctgggactta gactggggct cggcctcgct ctgaaaagtg cttaagaaaa
1981 tcttctcagt tctccttgca gaggactggc gccgggacgc gaagagcaac gggcgctgca
2041 caaagcgggc gctgtcggtg gtggagtgcg catgtacgcg caggcgcttc tcgtggttgg
2101 cgtgctgcag cgacaggcgg cagcacagca cctgcacgaa cacccgccga aactgctgcg
2161 aggacaccgt gtacaggagc gggttgatga ccgagctgag gtagaaaaac gtctccgaga
2221 agggggaggag gatcatgtac gcccggaagt aggacctcgt ccagtcgtgc ttgggtttgg
2281 ccgcagccat gatcctccga atctggttgg gcatccagca tacggccaat gtcacaacaa
2341 tcagccctgg gcagacacga gcaggaggga gagacagaga aaagaaaaac acagcatgag
2401 aacacagtaa atgaataaaa ccataaaata tttagcccct ctgttctgtg cttactggcc
2461 aggaaatggt accaattttt cagtgttgga cttgacagct tcttttgcca caagcaagag
2521 agaatttaac actgtttcaa acccggggga gttggctgtg ttaaagaaag accattaaat
2581 gctttagaca gtgtatttat accagttgat gtctgttaat tttaaaaaaa tgttttcatt
2641 ggtgtttgtt tgcgtatcca gaaagcagtt catgttatcc ata
```

Figure 2A

```
   1 gatgcctgga gtgggaggtg gggagaaaag gcgagacttt tgtgggtgct cccgatcgcc
  61 agtagttcct tcagtctcag ccgccaactc cggaggcgcg gtgctcggcc cgggagcgcg
 121 agcgggagga gcagagaccc gcagccggga gcccgagcgc gggcgatgca ggctccgcga
 181 gcggcacctg cggctcctct aagctacgac cgtcgtctcc gcggcagcag cgcgggcccc
 241 agcagcctcg gcagccacag ccgctgcagc cggggcagcc tccgctgctg tcgcctcctc
 301 tgatgcgctt gccctctccc ggccccggga ctccgggaga atgtgggtcc taggcatcgc
 361 ggcaactttt tgcggattgt tcttgcttcc aggctttgcg ctgcaaatcc agtgctacca
 421 gtgtgaagaa ttccagctga caacgactg ctcctccccc gagttcattg tgaattgcac
 481 ggtgaacgtt caagacatgt gtcagaaaga agtgatggag caaagtgccg ggatcatgta
 541 ccgcaagtcc tgtgcatcat cagcggcctg tctcatcgcc tctgccgggt accagtcctt
 601 ctgctcccca gggaaactga actcagtttg catcagctgc tgcaacaccc ctctttgtaa
 661 cgggccaagg cccaagaaaa ggggaagttc tgcctcggcc tcaggccag ggctccgcac
 721 caccatcctg ttcctcaaat tagccctctt ctcggcacac tgctgaagct gaaggagatg
 781 ccacccccctc ctgcattgtt cttccagccc tcgcccccaa ccccccacct ccctgagtga
 841 gtttcttctg ggtgtccttt tattctgggt aggagcgggg agtccgtgtt tctcttttgtt
 901 cctgtgcaaa taatgaaaga gctcggtaaa gcattctgaa taaattcagc ctgactgaat
 961 tttcagtatg tacttgaagg aaggaggtgg agtgaaagtt caccccccatg tctgtgtaac
1021 cggagtcaag gccaggctgg cagagtcagt ccttagaagt cactgaggtg ggcatctgcc
1081 ttttgtaaag cctccagtgt ccattccatc cctgatgggg gcatagtttg agactgcaga
1141 gtgagagtga cgttttctta ggctggagg ccagttccc actcaaggct ccctcgcttg
1201 acattcaaac ttcatgctcc tgaaaaccat tctctgcagc agaattggct ggtttcgcgc
1261 ctgagttggg ctctagtgac tcgagactca atgactggga cttagactgg ggctcggcct
1321 cgctctgaaa agtgcttaag aaaatcttct cagttctcct tgcagaggac tggcgccggg
1381 acgcgaagag caacgggcgc tgcacaaagc gggcgctgtc ggtggtggag tgcgcatgta
1441 cgcgcaggcg cttctcgtgg ttggcgtgct gcagcgacag gcggcagcac agcacctgca
1501 cgaacacccg ccgaaactgc tgcgagcaca ccgtgtacag gagcgggttg atgaccgagc
1561 tgaggtagaa aaacgtctcc gagaagggga ggaggatcat gtacgcccgg aagtaggacc
1621 tcgtccagtc gtgcttgggt ttggccgcag ccatgatcct ccgaatctgg ttgggcatcc
1681 agcatacggc caatgtcaca acaatcagcc ctgggcagac acgagcagga gggagagaca
1741 gagaaaagaa aaacacagca tgagaacaca gtaaatgaat aaaaccataa aatatttagc
1801 ccctctgttc tgtgcttact ggccaggaaa tggtaccaat ttttcagtgt tggacttgac
1861 agcttctttt gccacaagca agagagaatt taacactgtt tcaaacccgg gggagttggc
1921 tgtgttaaag aaagaccatt aaatgcttta gacagtg
```

Figure 2B

MWVLGIAATFCGLFLLPGFALQIQCYQCEEFQLNNDCSSPEFIVNCTVNVQDMCQKEVMEQSAG
IMYRKSCASSAACLIASAGYQSFCSPGKLNSVCISCCNTPLCNGPRPKKRGSSASALRPGLRTT
ILFLKLALFSAHC

Figure 2C

```
   1 aaggctgggg ttgcctgggg cgaggttact catcctgggc tcaggtaaga gggcccgagc
  61 tcggaggcgg cacatccagg ggggacgcca agggagcagg acggagccat ggaccccgcc
 121 aggaaagcag gtgcccaggc catgatctgg actgcaggct ggctgctgct gctgctgctt
 181 cgcggaggag cgcaggccct ggagtgctac agctgcgtgc agaaagcaga tgacggatgc
 241 tccccgaaca agatgaagac agtgaagtgc cgccggggcg tggacgtctg caccgaggcc
 301 gtgggggcgg tggagaccat ccacggacaa ttctcgctgg cagtgcgggg ttgcggttcg
 361 ggactccccg gcaagaatga ccgcggcctg gatcttcacg ggcttctggc gttcatccag
 421 ctgcagcaat gcgctcagga tcgctgcaac gccaagctca acctcacctc gcgggcgctc
 481 gacccggcag gtaatgagag tgcatacccc cccaacggcg tggagtgcta cagctgtgtg
 541 ggcctgagcc gggaggcgtg ccagggtaca tcgccgccgg tcgtgagctg ctacaacgcc
 601 agcgatcatg tctacaaggg ctgcttcgac ggcaacgtca ccttgacggc agctaatgtg
 661 actgtgtcct tgcctgtccg gggctgtgtc caggatgaat ctgcactcg ggatggagta
 721 acaggcccag ggttcacgct cagtggctcc tgttgccagg ggtcccgctg taactctgac
 781 ctccgcaaca agacctactt ctcccctcga atcccacccc ttgtccggct gccccctcca
 841 gagcccacga ctgtggcctc aaccacatct gtcaccactt ctacctcggc cccagtgaga
 901 cccacatcca ccaccaaacc catgccagcc caaccagtc agactccgag acagggagta
 961 gaacacgagg cctcccggga tgaggagccc aggttgactg gaggcgccgc tggccaccag
1021 gaccgcagca attcagggca gtatcctgca aaagggggc cccagcagcc cataataaa
1081 ggctgtgtgg ctcccacagc tggattggca gcccttctgt tggccgtggc tgctggtgtc
1141 ctactgtgag cttctccacc tggaaatttc cctctcacct acttctctgg ccctgggtac
1201 ccctcttctc atcacttcct gttcccacca ctggactggg ctggcccagc cctgtttt
1261 ccaacattcc ccagtatccc cagcttctgc tgcgctggtt tgcggctttg ggaaataaaa
1321 taccgttgta tatattctgc cagggggtgtt ctagcttttt gaggacagct cctgtatcct
1381 tctcatcctt gtctctccgc ttgtcctctt gtgatgttag acagagtga gagaagtcag
1441 ctgtcacggg gaaggtgaga gagaggatgc taagcttcct actcactttc cctagccag
1501 cctggacttt ggagcgtggg gtgggtggga caatggctcc ccactctaag cactgcctcc
1561 cctactcccc gcatcttttgg ggaatcggtt ccccatatgt cttccttact agactgtgag
1621 ctcctcgagg gcagggaccg tgccttatgt ctgtgtgtga tcagtttctg gcacataaat
1681 gcctcaataa agatttaatt actttgaaaa aaaaaaaaa aaaaaaaaa aaaaaaaaa
1741 aaaaa
```

Figure 3A

MDPARKAGAQAMIWTAGWLLLLLLLRGGAQALECYSCVQKADDGCSPNKMKTVKCAPGVDVCTEA
VGAVETIHGQFSLAVRGCGSGLPGKNDRGLDLHGLLAFIQLQQCAQDRCNAKLNLTSRALDPAG
NESAYPPNGVECYSCVGLSREACQGTSPPVVSCYNASDHVYKGCFDGNVTLTAANVTVSLPVRG
CVQDEFCTRDGVTGPGFTLSGSCCQGSRCNSDLRNKTYFSPRIPPLVRLPPPEPTTVASTTSVT
TSTSAPVRPTSTTKPMPAPTSQTPRQGVEHEASRDEEPRLTGGAAGHQDRSNSGQYPAKGGPQQ
PHNKGCVAPTAGLAALLLAVAAGVLL

Figure 3B

```
   1 gatccgcttt gcgcatccca gtgattcttg ggttccgcgt gtagtttcgg aaggagacat
  61 cgaagcaggg cgaggcgcag agggcgttgc ggactcatgc cccagtcggc agtgcgggt
 121 cccaagccct gcagtgctac agctttgagc acacctactt tggccccttt gacctcaggg
 181 ccatgaagct gcccagcatc tcctgtcctc atgagtgctt tgaggctatc ctgtctctgg
 241 acaccgggta tcgcgcgccg gtgaccctgg tgcggaaggg ctgctggacc gggcctcctg
 301 cgggccagac gcaatcgaac gcggacgcgc tgccgccaga ctactcggtg gtgcgcggct
 361 gcacaactga caaatgcaac gcccacctca tgactcatga cgccctcccc aacctgagcc
 421 aagcacccga cccgccgacg ctcagcggcg ccgagtgcta cgcctgtatc ggggtccacc
 481 aggatgactg cgctatcggc aggtcccgac gagtccagtg tcaccaggac cagaccgcct
 541 gcttccaggg caatggcaga atgacagttg caatttctc agtccctgtg tacatcagaa
 601 cctgccaccg gccctcctgc accaccgagg gcaccaccag ccctggaca gccatcgacc
 661 tccagggctc ctgctgtgag gggtacctct gcaacaggaa atccatgacc cagcccttca
 721 ccagtgcttc agccaccacc cctccccgag cactacaggt cctggccctg ctcctcccag
 781 tcctcctgct ggtggggctc tcagcataga ccgcccctcc aggatgctgg ggacagggct
 841 cacacacctc attcttgctg cttcagcccc tatcacatag ctcactggaa aatgatgtta
 901 aagtaagaat tgcactcctg tccctctggc cttccatctc tcccgccctt gtgccccaca
 961 acctggccaa cagtactgga agaaactgga cacagtcacc agcatccccg gggagggcaa
1021 aacagccatg tcgtgccccg atgaagagca attctgatca cagctgttac tcactgagca
1081 ccagccaggc accaggcacc ccataacacg gcttcctgtg ctctccctcc agagcctgtc
1141 gcagctctag gagggagcta tacaatgatg tctttattag tgtcatcatg agaagcccaa
1201 taagcagtat gccctaacag ttagtaggcc aggctctgga gctaagctgc atgggttcaa
1261 atcccagctc caccattcag cctgcagaga ccatgagcga gttacttaag ccaggctctg
1321 gagctaagct gcatgggttc aaatcccagc tccagcattc agcctacaga gaccatgggt
1381 gagttactta agccaggctc tggagctaag ctgcatgggt tcaaatccca gctccaccat
1441 tcagcctgca gagactgtgg gtgagttact tgagctctct gtgccaatat tttctcacct
1501 ataaggtgga ggtgaaaata aactctataa catgacaaga actacttcac agtagttgca
1561 gtgaggattc aacgagatga acatttagta cttgggacac agcagtggcc cagtgtaaat
1621 gggctacttg tcataagccc taagtcacag gtcaacaaac tgagagcaa aagcacttgg
1681 ttgagcttgt gtatctagtg agtatggatt cagggaccag attcccagcc ccacgaactg
1741 ctaagcaacc ccacctccta aacacatgag tgccgattaa cttcacagaa aaacacacaa
1801 ggcaaagttc agcgaggtga aattctccaa gctataaaga tcagggaaga cttcctggag
1861 gaattcaccc ttgagcaaaa tcctaaagga tcaatagtag ctggcaaaaa gaagcaggag
1921 gaagcgcatt ctaggtagag gagacagcct ggacaaaggt ctgagggagg aaggagcaca
1981 aggagtgcag gacactttca tgagtgcagg acactttcat aactgcatga acttcataga
2041 gatgggatcc tttagcatgt tctctgtgca catgcttgac catgttcttt cacatgcttt
2101 ttgccacttg atctttccag caactcagtg agagaagcaa aaagtaagt tgcatcctgc
2161 tattgtctga atgtttgtgt ctccccaaaa ttcatctttt gaacctaat taccaaagtg
2221 atattactgg gaggtggggc ctttgggagg tggtgagatc atgagggtgg agccccatg
2281 aataggatta gtgcccttat aaaagaggcc ctggagagct gccttgcccc ttccaccaca
2341 tgagaacaca gccagcaggt gcctataagc aagaaagtgg gttctcacca gccatcgaat
2401 ctgctggtgc attgattgca gacttcccag actccagagc tatgagacat aaatttctgt
2461 tgtgtataag ccaaaaaaaa aaaaaaaaa
```

Figure 4A

```
   1 gattcttggg ttccgcgcgt agtttcggaa ggagacatcg aagcagggcg aggcgcagag
  61 ggcgttgcgg actcatgccc cagtcggcag tgcggggtcc caagccctgc agtgctacag
 121 CtttgagCaC acctactttg gcccctttga cctcagggcc atgaagctgc ccagcatctc
 181 ctgtcctcat gagtgctttg aggctatcct gtctctggac accgggtatc gcgcgccggt
 241 gaccctggtg cggaagggct gctggaccgg gcctcctgcg ggccagacgc aatcgaaccc
 301 ggacgcgctg ccgccagact actcggtggt gcgcggctgc acaactgaca aatgcaacgc
 361 ccacctcatg actcatgacg ccctccccaa cctgagccaa gcacccgacc cgccgacgct
 421 cagcggcgcc gagtgctacg cctgtatcgg ggtccaccag gatgactgcg ctatcggcag
 481 gtcccgacga gtccagtgtc accaggacca gaccgcctgc ttccagggca gtggcagaat
 541 gacagttggc aatttctcag tccctgtgta catcagaacc tgccaccggc cctcctgcac
 601 caccgagggc accaccagcc cctggacagc catcgacctc agggctcctg ctgtgaggg
 661 gtacctctgc aacaggaaat ccatgaccca gcccttcacc agtgcttcag ccaccaccc
 721 tccccgagca ctacaggtcc tggccctgct cctcccagtc ctcctgctgg tgggctctc
 781 agcatagacc gccctccag gatgctgggg acagggctca cacacctcat tcttgctgct
 841 tcagccccta tcacatagct cactggaaaa tgatgttaaa gtaagaattg cactcctgtc
 901 cctctggcct tccatctctc ctgcccttgt gccccacaac ctggccaaca gtactggaag
 961 aaactggaca cagtccaccag catcccaggg gagggcaaaa cagccatgtc gtgccctgat
1021 gaagagcaat tctgatcaca gctgttactc actgagcacc agccaggcac caggcacccc
1081 ataacacggc ttcctgtgct ctccttccag agcctgtcgc agctctaggg gggagctata
1141 caatgatgtc tttattagtg tcatcatgag aagcccaata agcagtatgc cctaacagtt
1201 agtaggccag gctctggagc taagctgcat gggttcacat cccagctcca ccattcagcc
1261 tgcagagacc atgagcgagt acttaagcc aggctctgga gctaagctgc atgggttcaa
1321 atcccagctc cagcattcag cctacagaga ccatgggtga gttacttaag ccaggctctg
1381 gagctaagct gcatgggttc aaatcccagc tccaccattc agcctgcaga gactgtgggt
1441 gagttacttg agctctctgt gccaatattt tctcacctat aaggtggagg tgaaaataaa
1501 ctctataaca tgacaagaac tacttcacag tagttgcagt gaggattcaa cgagatgaac
1561 atttagtact tgggacacag cagtggccca gtataaatgg gctacttgtc ataagcccta
1621 agtcacaggt caacaaactg agaggtaaaa gcacttggtt gagcttgtgt atctagtgag
1681 tatggattca gggaccagat tcccagcccc acgaactgct aagcaacccc acctcctaaa
1741 cacatgagtg ccgattaact tcacagaaaa acacacaagg caaagttcag cgaggtgaaa
1801 ttctccaagc tataaagatc agggaagact tcctggagga attcacccctt gagcaaaatc
1861 ctaaaggatc aatagtagct ggcaaaaaga agcagggaa agcacattt aggtagagga
1921 gacagcctgg acaaaggtct gagggaggaa ggaacacaag gagtgcagga cactttcata
1981 actgcatgaa cttcatagag atgggatcct ttagcatgtt ctctgtgcac atgcttgacc
2041 atgttctttc acatgctttt tgccacttga tctttccagc aactcagtga gagaagcaaa
2101 aaagtaagtt gcatcctg
```

Figure 4B

MKLPSISCPHECFEAILSLDTGYRAPVTLVRKGCWTGPPAGQTQSNADALPPDYSVVRGCTTDK
CNAHLMTHDALPNLSQAPDPPTLSGAECYACIGVHQDDCAIGRSRRVQCHQDQTACFQGNGRMT
VGNFSVPVYIRTCHRPSCTTEGTTSPWTAIDLQGSCCEGYLCNRKSMTQPFTSASATTPPRALQ
VLALLLPVLLLVGLSA

Figure 4C

```
  1 gcccacccccc gcccagcccg tgcctataag gccttggcaa tgcaggggcc cgcactgctc
 61 ccagacgaca tcagagatga ggacagcatt gctgctcctt gcagccctgg ctgtggctac
121 agggccagcc cttaccctgc gctgccacgt gtgcaccagc tccagcaact gcaagcattc
181 tgtggtctgc ccggccagct ctcgcttctg caagaccacg aacacagtgg agcctctgag
241 ggggaatctg gtgaagaagg actgtgcgga gtcgtgcaca cccagctaca ccctgcaagg
301 ccaggtcagc agcggcacca gctccaccca gtgctgccag gaggacctgt gcaatgagaa
361 gctgcacaac gctgcaccca cccgcaccgc cctcgcccac agtgccctca gcctggggct
421 ggccctgagc ctcctggccg tcatcttagc ccccagcctg tgaccttccc ccagggaag
481 gccccctcatg cctttccttc cctttctctg gggattccac acctctcttc cccagccgca
541 acggggggtgc caggagcccc aggctgaggg cttccccgaa agtctgggac caggtccagg
601 tgggcatgga atgctgatga cttggagcag gccccacaga ccccacagag gatgaagcca
661 ccccacagag gatgcagccc ccagctgcat ggaaggtgga ggacagaagc cctgtggatc
721 cccggatttc acactccttc tgttttgttg ccgtttattt ttgtactcaa atctctacat
781 ggagataaat gatttaaacc agaaaa
```

Figure 5A

MRTALLLLAALAVATGPALTLRCHVCTSSSNCKHSVVCPASSRFCKTTNTVEPLRGNLVKKDCA
ESCTPSYTLQGQVSSGTSSTQCCQEDLCNEKLHNAAPTRTALAHSALSLGLALSLLAVILAPSL

Figure 5B

```
   1 gctccggcca gccgcggtcc agagcgcgcg aggttcgggg agctccgcca ggctgctggt
  61 acctgcgtcc gcccggcgag caggacaggc tgctttggtt tgtgacctcc aggcaggacg
 121 gccatcctct ccagaatgaa gatcttcttg ccagtgctgc tggctgccct tctgggtgtg
 181 gagcgagcca gctcgctgat gtgcttctcc tgcttgaacc agaagagcaa tctgtactgc
 241 ctgaagccga ccatctgctc cgaccaggac aactactgcg tgactgtgtc tgctagtgcc
 301 ggcattggga atctcgtgac atttggccac agcctgagca agacctgttc cccggcctgc
 361 cccatcccag aaggcgtcaa tgttggtgtg gcttccatgg gcatcagctg ctgccagagc
 421 tttctgtgca atttcagtgc ggccgatggc gggctgcggg caagcgtcac cctgctgggt
 481 gccgggctgc tgctgagcct gctgccggcc ctgctgcggt ttggcccctg accgcccaga
 541 ccctgtcccc cgatccccca gctcaggaag gaaagcccag cccctttctgg atcccacagt
 601 gtatgggagc ccctgactcc tcacgtgcct gatctgtgcc cttggtccca ggtcaggccc
 661 accccctgca cctccacctg ccccagcccc tgcctctgcc caagtgggcc agctgccctc
 721 acttctgggg tggatgatgt gaccttcctt ggggactgc ggaagggacg agggttccct
 781 ggagtcttac ggtccaacat cagaccaagt cccatggaca tgctgacagg gtccccaggg
 841 agaccgtgtc agtagggatg tgtgcctggc tgtgtacgtg ggtgtgcagt gcacgtgaga
 901 gcacgtggcg gcttctgggg gccatgtttg gggaggaggg tgtgccagca gcctggagag
 961 cctcagtccc tgtagccccc tgccctggca cagctgcatg cacttcaagg gcagcctttg
1021 ggggttgggg tttctgccac ttccgggtct aggccctgcc caaatccagc cagtcctgcc
1081 ccagcccacc cccacattgg agccctcctg ctgctttggt gcctcaaata aatacagatg
1141 tcccc
```

Figure 6A

MKIFLPVLLAALLGVERASSLMCFSCLNQKSNLYCLKPTICSDQDNYCVTVSASAGIGNLVTFG
HSLSKTCSPACPIPEGVNVGVASMGISCCQSFLCNFSAADGGLRASVTLLGAGLLLSLLPALLR
FGP

Figure 6B

```
  1 ccagtctgtc gccacctcac ttggtgtctg ctgtccccgc caggcaagcc tggggtgaga
 61 gcacagagga gtgggccggg accatgcggg ggacgcggct ggcgctcctg gcgctggtgc
121 tggctgcctg cggagagctg gcgccggccc tgcgctgcta cgtctgtccg gagcccacag
181 gagtgtcgga ctgtgtcacc atcgccacct gcaccaccaa cgaaaccatg tgcaagacca
241 cactctactc ccgggagata gtgtacccct tccaggggga ctccacggtg accaagtcct
301 gtgccagcaa gtgtaagccc tcggatgtgg atggcatcgg ccagaccctg cccgtgtcct
361 gctgcaatac tgagctgtgc aatgtagacg gggcgcccgc tctgaacagc ctccactgcg
421 gggccctcac gctcctccca ctcttgagcc tccgactgta gagtccccgc ccaccccat
481 ggccctatgc ggcccagccc cgaatgcctt gaagaagtgc cccctgcacc aggaaaaaaa
541 aaaaaaaaaa
```

Figure 7A

MRGTRLALLALVLAACGELAPALRCYVCPEPTGVSDCVTIATCTTNETMCKTTLYSREIVYPFQ
GDSTVTKSCASKCKPSDVDGIGQTLPVSCCNTELCNVDGAPALNSLHCGALTLLPLLSLRL

Figure 7B

```
   1 aagatggcgg cgtgtggacg tgtacggagg atgttccgct tgtcggcggc gctgcatctg
  61 ctgctgctat tcgcggccgg ggccgagaaa ctccccggcc atggcgtcca cagccagggc
 121 cagggtcccg gggccaactt tgtgtccttc gtagggcagg ccggaggcgg cggcccggcg
 181 ggtcagcagc tgccccagct gcttcagtca tcgcagcttc agcagcaaca gcagcagcag
 241 caacagcaac agcagcttca gccgccgcag ccgccttcc cggcgggtgg gcctccggcc
 301 cggcggggag gagcggggc tggtggggc tggaagctgg cggaggaaga gtcctgcagg
 361 gaggacgtga cccgcgtgtg ccctaagcac acctggagca caacctggc ggtgctcgag
 421 tgcctgcagg atgtgaggga gcctgaaaat gaaatttctt cagactgcaa tcatttgttg
 481 tggaattata agctgaacct aactacagat cccaaatttg aatctgtggc cagagaggtt
 541 tgcaaatcta ctataacaga gattaaagaa tgtgctgatg aaccggttgg aaaaggttac
 601 atggtttcct gcttagtgga tcaccgaggc aacatcactg agtatcagtg tcaccagtac
 661 attaccaaga tgacggccat cattttttagt gattaccgtt taatctgtgg cttcatggat
 721 gactgcaaaa atgacatcaa cattctgaaa tgtggcagta ttcggcttgg agaaaaggat
 781 gcacattcac aaggtgaggt ggtatcatgc ttggagaaag gcctggtgaa agaagcagaa
 841 gaaagagaac caagattca agtttctgaa ctctgcaaga aagccattct ccgggtggct
 901 gagctgtcat cggatgactt tcacttagac cggcatttat attttgcttg ccgagatgat
 961 cgggagcgtt tttgtgaaaa tacacaagct ggtgagggca gagtgtataa gtgcctcttt
1021 aaccataaat ttgaagaatc catgagtgaa aagtgtcgag aagcacttac aacccgccaa
1081 aagctgattg cccaggatta taaagtcagt tattcattgg ccaaatcctg taaaagtgac
1141 ttgaagaaat accggtgcaa tgtggaaaac cttccgcgat cgcgtgaagc caggctctcc
1201 tacttgttaa tgtgcctgga gtcagctgta cacagagggc gacaagtcag cagtgagtgc
1261 caggggagaa tgctggatta ccgacgcatg ttgatggaag acttttctct gagccctgag
1321 atcatcctaa gctgtcgggg ggagattgaa caccattgtt ccggattaca tcgaaagggg
1381 cggaccctac actgtctgat gaaagtagtt cgaggggaga aggggaacct tggaatgaac
1441 tgccagcagg cgcttcaaac actgattcag gagactgacc ctggtgcaga ttaccgcatt
1501 gatcgagctt tgaatgaagc ttgtgaatct gtaatccaga cagcctgcaa acatataaga
1561 tctggagacc caatgatctt gtcgtgcctg atggaacatt tatacacaga gaagatggta
1621 gaagactgtg aacaccgtct cttagagctg cagtatttca tctcccggga ttggaagctg
1681 gaccctgtcc tgtaccgcaa gtgccaggga gacgcttctc gtctttgcca cacccacggt
1741 tggaatgaga ccagtgaatt tatgcctcag ggagctgtgt tctcttgttt atacagacac
1801 gcctaccgca ctgaggaaca gggaaggagg ctctcacggg agtgccgagc tgaagtccaa
1861 aggatcctac accagcgtgc catggatgtc aagctggatc ctgccctcca ggataagtgc
1921 ctgattgatc tgggaaaatg gtgcagtgag aaaacagaga ctggacagga gctggagtgc
1981 cttcaggacc atctggatga cttggtggtg gagtgtagag atatagttgg caacctcact
2041 gagttagaat cagaggatat tcaaatagaa gccttgctga tgagagcctg tgagcccata
2101 attcagaact tctgccacga tgtggcagat aaccagatag actctgggga cctgatggag
2161 tgtctgatac agaacaaaca ccagaaggac atgaacgaga gtgtgccat cggagttacc
2221 cacttccagc tggtgcagat gaaggatttt cggttttctt acaagtttaa aatggcctgc
2281 aaggaggacg tgttgaagct tgcccaaac ataaaaaaga aggtggacgt ggtgatctgc
2341 ctgagcacga ccgtgcgcaa tgacactctg caggaagcca aggagcacag ggtgtccctg
2401 aagtgccgca ggcagctccg tgtggaggag ctggagatga cggaggacat ccgcttggag
```

Figure 8A

```
2461 ccagatctat acgaagcctg caagagtgac atcaaaaact tctgttccgc tgtgcaatat
2521 ggcaacgctc agattatcga atgtctgaaa gaaaacaaga agcagctaag cacccgctgc
2581 caccaaaaag tatttaagct gcaggagaca gagatgatgg acccagagct agactacacc
2641 ctcatgaggg tctgcaagca gatgataaag aggttctgtc cggaagcaga ttctaaaacc
2701 atgttgcagt gcttgaagca aaataaaaac agtgaattga tggatcccaa atgcaaacag
2761 atgataacca agcgccagat cacccagaac acagattacc gcttaaaccc catgttaaga
2821 aaagcctgta aagctgacat tcctaaattc tgtcacggta tcctgactaa ggccaaggat
2881 gattcagaat tagaaggaca agtcatctct tgcctgaagc tgagatatgc tgaccagcgc
2941 ctgtcttcag actgtgaaga ccagatccga atcattatcc aggagtccgc cctggactac
3001 cgcctggatc ctcagctcca gctgcactgc tcagacgaga tctccagtct atgtgctgaa
3061 gaagcagcag cccaagagca gacaggtcag gtggaggagt gcctcaaggt caacctgctc
3121 aagatcaaaa cagaattgtg taaaaaggaa gtgctaaaca tgctgaagga agcaaagca
3181 gacatctttg ttgacccggt acttcatact gcttgtgccc tggacattaa acaccactgc
3241 gcagccatca ccctggccg cgggcgtcaa atgtcctgtc tcatggaagc actggaggat
3301 aagcgggtga ggttacagcc cgagtgcaaa aagcgcctca atgaccggat tgagatgtgg
3361 agttacgcag caaaggtggc cccagcagat ggcttctctg atcttgccat gcaagtaatg
3421 acgtctccat ctaagaacta cattctctct gtgatcagtg ggagcatctg tatattgttc
3481 ctgattggcc tgatgtgtgg acggatcacc aagcgagtga cacgagagct caaggacagg
3541 tagagccacc ttgaccacca aggaactac ctatccagtg cccagtttgt acagccctct
3601 tgtatagcat ccccactcac ctcgctcttc tcagaagtga caccaacccc gtgttagagc
3661 attagcagat gtccactgcg ttgtcccatc cagcctccac tcgtgtccat ggtgtcctcc
3721 tcctcctcac cgtgcagcag cagcagctgg tcgctggggt tactgccttt gtttggcaaa
3781 cttgggttta cctgcctgta gacaagtctc tctcatacca acagaacttc cggtacttcc
3841 agaaccaact cacctgacct gcaactcaaa ggcttttta agaaaaccac caaaaaaaaa
3901 a
```

Figure 8B

```
MAACGRVRRMFRLSAALHLLLLFAAGAEKLPGHGVHSQGQGPGANFVSFVGQAGGGGPAGQQLP
QLLQSSQLQQQQQQQQQQQQLQPPQPPFPAGGPPARRGGAGAGGGWKLAEEESCREDVTRVCPK
HTWSNNLAVLECLQDVREPENEISSDCNHLLWNYKLNLTTDPKFESVAREVCKSTITEIKECAD
EPVGKGYMVSCLVDHRGNITEYQCHQYITKMTAIIFSDYRLICGFMDDCKNDINILKCGSIRLG
EKDAHSQGEVVSCLEKGLVKEAEEREPKIQVSELCKKAILRVAELSSDDFHLDRHLYFACRDDR
ERFCENTQAGEGRVYKCLFNHKFEESMSEKCREALTTRQKLIAQDYKVSYSLAKSCKSDLKKYR
CNVENLPRSREARLSYLLMCLESAVHRGRQVSSECQGEMLDYRRMLMEDFSLSPEIILSCRGEI
EHHCSGLHRKGRTLHCLMKVVRGEKGNLGMNCQQALQTLIQETDPGADYRIDRALNEACESVIQ
TACKHIRSGDPMILSCLMEHLYTEKMVEDCEHRLLELQYFISRDWKLDPVLYRKCQGDASRLCH
THGWNETSEFMPQGAVFSCLYRHAYRTEEQGRRLSRECRAEVQRILHQRAMDVKLDPALQDKCL
IDLGKWCSEKTETGQELECLQDHLDDLVVECRDIVGNLTELESEDIQIEALLMRACEPIIQNFC
HDVADNQIDSGDLMECLIQNKHQKDMNEKCAIGVTHFQLVQMKDFRFSYKFKMACKEDVLKLCP
NIKKKVDVVICLSTTVRNDTLQEAKEHRVSLKCRRQLRVEELEMTEDIRLEPDLYEACKSDIKN
FCSAVQYGNAQIIECLKENKKQLSTRCHQKVFKLQETEMMDPELDYTLMRVCKQMIKRFCPEAD
SKTMLQCLKQNKNSELMDPKCKQMITKRQITQNTDYRLNPMLRKACKADIPKFCHGILTKAKDD
SELEGQVISCLKLRYADQRLSSDCEDQIRIIQESALDYRLDPQLQLHCSDEISSLCAEEAAAQ
EQTGQVEECLKVNLLKIKTELCKKEVLNMLKESKADIFVDPVLHTACALDIKHHCAAITPGRGR
QMSCLMEALEDKRVRLQPECKKRLNDRIEMWSYAAKVAPADGFSDLAMQVMTSPSKNYILSVIS
GSICILFLIGLMCGRITKRVTRELKDR
```

Figure 8C

```
   1 gcgtcgagct cgccgcggac tcaagatggc ggcgtgtgga cgtgtacgga ggatgttccg
  61 cttgtcggcg gcgctgcatc tgctgctgct attcgcggcc ggggccgaga aactccccgg
 121 ccagggcgtc cacagccagg gccagggtcc cggggccaac tttgtgtcct tcgtagggca
 181 ggccggaggc ggcggcccgg cgggtcagca gctgccccag ctgcctcagt catcgcagct
 241 tcagcagcaa cagcagcagc agcaacagca cagcagcct cagccgccgc agccgccttt
 301 cccggcgggt gggcctccgg cccggcgggg aggagcgggg gctggtgggg gctggaagct
 361 ggcggaggaa gagtcctgca gggaggacgt gacccgcgtg tgccctaagc acacctggag
 421 caacaacctg gcggtgctcg agtgcctgca ggatgtgagg gagcctgaaa atgaaatttc
 481 ttcagactgc aatcatttgt tgtggaatta taagctgaac ctaactacag atcccaaatt
 541 tgaatctgtg gccagagagg tttgcaaatc tactataaca gagattaaag aatgtgctga
 601 tgaaccggtt ggaaaaggtt acatggtttc ctgcttggtg gatcaccgag caacatcac
 661 tgagtatcag tgtcaccagt acattaccaa gatgacggcc atcattttta gtgattaccg
 721 tttaatctgt ggcttcatgg atgactgcaa aaatgacatc aacattctga atgtggcag
 781 tattcggctt ggagaaaagg atgcacattc acaaggtgag gtggtatcat gcttggagaa
 841 aggcctggtg aaagaagcag aagaaagaga acccaagatt caagtttctg aactctgcaa
 901 gaaagccatt ctccgggtgg ctgagctgtc atcggatgac tttcacttag accggcattt
 961 atattttgct tgccgagatg atcgggagcg ttttgtgaa atacacaag ctggtgaggg
1021 cagagtgtat aagtgcctct ttaaccataa atttgaagaa tccatgagtg aaaagtgtcg
1081 agaagcactt acaacccgcc aaaagctgat tgcccaggat tataaagtca gttattcatt
1141 ggccaaatcc tgtaaaagtg acttgaagaa ataccggtgc aatgtggaaa accttccgcg
1201 atcgcgtgaa gccaggctct cctacttgtt aatgtgcctg gagtcagctg tacacagagg
1261 gcgacaagtc agcagtgagt gccaggggga gatgctggat taccgacgca tgttgatgga
1321 agactttct ctgagccctg agatcatcct aagctgtcgg ggggagattg aacaccattg
1381 ttccggatta catcgaaaag ggcggaccct acactgtctg atgaaagtag tcgagggga
1441 gaaggggaac cttggaatga actgccagca ggcgcttcaa acactgattc aggagactga
1501 ccctggtgca gattaccgca ttgatcgagc tttgaatgaa gcttgtgaat ctgtaatcca
1561 gacagcctgc aaacatataa gatctggaga cccaatgatc ttgtcgtgcc tgatggaaca
1621 tttatacaca gagaagatgg tagaagactg tgaacaccgt ctcttagagc tgcagtattt
1681 catctcccgg gattggaagc tggaccctgt cctgtaccgc aagtgccagg gagacgcttc
1741 tcgtctttgc cacacccacg gttggaatga accagtgaa tttatgcctc agggagctgt
1801 gttctcttgt ttatacagac acgcctaccg cactgaggaa cagggaagga ggctctcacg
1861 ggagtgccga gctgaagtcc aaaggatcct acaccagcgt gccatggatg tcaagctgga
1921 tcctgccctc caggataagt gcctgattga tctggaaaa tggtgcagtg agaaaacaga
1981 gactggacag gagctggagt gccttcagga ccatctggat gacttggtgg tggagtgtag
2041 agatatagtt ggcaacctca ctgagttaga atcagaggat attcaaatag aagccttgct
2101 gatgagagcc tgtgagccca taattcagaa cttctgccac gatgtggcag ataaccagat
2161 agactctggg gacctgatgg agtgtctgat acagaacaaa caccagaagg acatgaacga
2221 gaagtgtgcc atcggagtta cccacttcca gctggtgcag atgaaggatt ttcggttttc
```

Figure 8D

```
2281 ttacaagttt aaaatggcct gcaaggagga cgtgttgaag ctttgcccaa acataaaaaa
2341 gaaggtggac gtggtgatct gcctgagcac gaccgtgcgc aatgacactc tgcaggaagc
2401 caaggagcac agggtgtccc tgaagtgccg caggcagctc cgtgtggagg agctggagat
2461 gacggaggac atccgcttgg agccagatct atacgaagcc tgcaagagtg acatcaaaaa
2521 cttctgttcc gctgtgcaat atggcaacgc tcagattatc gaatgtctga agaaaacaa
2581 gaagcagcta agcacccgct gccaccaaaa agtatttaag ctgcaggaga cagagatgat
2641 ggacccagag ctagactaca ccctcatgag ggtctgcaag cagatgataa agaggttctg
2701 tccggaagca gattctaaaa ccatgttgca gtgcttgaag caaaataaaa acagtgaatt
2761 gatggatccc aaatgcaaac agatgataac caagcgccaa atcacccaga acacagatta
2821 ccgcttaaac cccatgttaa gaaaagcctg taaagctgac attcctaaat tctgtcacgg
2881 tatcctgact aaggccaagg atgattcaga attagaagga caagtcatct cttgcctgaa
2941 gctgagatat gctgaccagc gcctgtcttc agactgtgaa gaccagatcc gaatcattat
3001 ccaggagtcc gccctggact accgcctgga tcctcagctc cagctgcact gctcagacga
3061 gatctccagt ctatgtgctg aagaagcagc agcccaagag cagacaggtc aggtggagga
3121 gtgcctcaag gtcaacctgc tcaagatcaa aacagaattg tgtaaaaagg aagtgctaaa
3181 catgctgaag gaaagcaaag cagacatctt tgttgacccg gtacttcata ctgcttgtgc
3241 cctggacatt aaacaccact gcgcagccat caccctggc cgcgggcgtc aaatgtcctg
3301 tctcatggaa gcactggagg ataagcgggt gaggttacag cccgagtgca aaaagcgcct
3361 caatgaccgg attgagatgt ggagttacgc agcaaaggtg gccccagcag atggcttctc
3421 tgatcttgcc atgcaagtaa tgacgtccc atctaagaac tacattctct ctgtgatcag
3481 tgggagcatc tgtatattgt tcctgattgg cctgatgtgt ggacggatca ccaagcgagt
3541 gacacgagag ctcaaggaca ggctacaata caggtcagag acaatggctt ataaaggttt
3601 agtgtggtct caggatgtga caggcagtcc agcctgacct ttctgcacac tccagacaaa
3661 cttcccagac aagctccttt gtgcctctac gtggagaggg tgtggaaagt tatcacatta
3721 aaagatggag gatttaaaaa aaaaaaaaaa aaaaaaaaaa aaagaaaaaa aaaaaaaaa
```

Figure 8E

```
MAACGRVRRMFRLSAALHLLLLFAAGAEKLPGQGVHSQGQGPGANFVSFVGQAGGGGPAGQQLP
QLPQSSQLQQQQQQQQQQQQQPQPPQPPFPAGGPPARRGGAGAGGGWKLAEEESCREDVTRVCPK
HTWSNNLAVLECLQDVREPENEISSDCNHLLWNYKLNLTTDPKFESVAREVCKSTITEIKECAD
EPVGKGYMVSCLVDHRGNITEYQCHQYITKMTAIIFSDYRLICGFMDDCKNDINILKCGSIRLG
EKDAHSQGEVVSCLEKGLVKEAEEREPKIQVSELCKKAILRVAELSSDDFHLDRHLYFACRDDR
ERFCENTQAGEGRVYKCLFNHKFEESMSEKCREALTTRQKLIAQDYKVSYSLAKSCKSDLKKYR
CNVENLPRSREARLSYLLMCLESAVHRGRQVSSECQGEMLDYRRMLMEDFSLSPEIILSCRGEI
EHHCSGLHRKGRTLHCLMKVVRGEKGNLGMNCQQALQTLIQETDPGADYRIDRALNEACESVIQ
TACKHIRSGDPMILSCLMEHLYTEKMVEDCEHRLLELQYFISRDWKLDPVLYRKCQGDASRLCH
THGWNETSEFMPQGAVFSCLYRHAYRTEEQGRRLSRECRAEVQRILHQRAMDVKLDPALQDKCL
IDLGKWCSEKTETGQELECLQDHLDDLVVECRDIVGNLTELESEDIQIEALLMRACEPIIQNFC
HDVADNQIDSGDLMECLIQNKHQKDMNEKCAIGVTHFQLVQMKDFRFSYKFKMACKEDVLKLCP
NIKKKVDVVICLSTTVRNDTLQFAKEHRVSLKCRRQLRVEELEMTEDIRLEPDLYEACKSDIKN
FCSAVQYGNAQIIECLKENKKQLSTRCHQKVFKLQETEMMDPELDYTLMRVCKQMIKRFCPEAD
SKTMLQCLKQNKNSELMDPKCKQMITKRQITQNTDYRLNPMLRKACKADIPKFCHGILTKAKDD
SELEGQVISCLKLRYADQRLSSDCEDQIRIIIQESALDYRLDPQLQLHCSDEISSLCAEEAAAQ
EQTGQVEECLKVNLLKIKTELCKKEVLNMLKESKADIFVDPVLHTACALDIKHHCAAITPGRGR
QMSCLMEALEDKRVRLQPECKKRLNDRIEMWSYAAKVAPADGFSDLAMQVMTSPSKNYILSVIS
GSICILFLIGLMCGRITKRVTRELKDRLQYRSETMAYKGLVWSQDVTGSPA
```

Figure 8F

```
   1 caaaaacttc tgttccgctg tgcaatatgg caacgctcag attatcgaat gtctgaaaga
  61 aaacaagaag cagctaagca cccgctgcca ccaaaaagta tttaagctgc aggagacaga
 121 gatgatggac ccagagctag actacaccct catgagggtc tgtaagcaga tgataaagag
 181 gttctgtccg gaagcagatt ctaaaaccat gttgcagtgc ttgaagcaaa ataaaaacag
 241 tgaattgatg gatcccaaat gcaaacagat gataaccaag cgccagatca cccagaacac
 301 agattaccgc ttaaaccca tgttaagaaa agcctgtaaa gctgacattc ctaaattctg
 361 tcacggtatc ctgactaagg ccaaggatga ttcagaatta gaaggacaag tcatctcttg
 421 cctgaagctg agatatgctg accagcgcct gtcttcagac tgtgaagacc agatccgaat
 481 cattatccag gagtccgccc tggactaccg cctggatcct cagctccagc tgcactgctc
 541 agacgagatc tccagtctat gtgctgaaga agcagcagcc aagagcaga caggtcaggt
 601 ggaggagtgc ctcaaggtca acctgctcaa gatcaaaaca gaattgtgta aaaggaagt
 661 gctaaacatg ctgaaggaaa gcaaagcaga catctttgtt gacccggtac ttcatactgc
 721 ttgtgccctg gacattaaac accactgcgc agccatcacc cctggccgcg ggcgtcaaat
 781 gtcctgtctc atggaagcac tggaggataa gcgggtgagg ttacagcccg agtgcaaaaa
 841 gcgcctcaat gaccggattg agatgtggag ttacgcagca aggtggccc cagcagatgg
 901 cttctctgat cttgccatgc aagtaatgac gtctccatct aagaactaca ttctctctgt
 961 gatcagtggg agcatctgta tattgttcct gattggcctg atgtgtggac ggatcaccaa
1021 gcgagtgaca cgagagctca aggacaggta gagccacctt gaccaccaaa ggaactacct
1081 atccagtgcc cagtttgtac agccctcttg tatagcatcc ccactcacct cgctcttctc
1141 agaagtgaca ccaaccccgt gttagagcat tagcagatgt ccactgcgtt gtcccatcca
1201 gcctccactc gtgtccatgg tgtcctcctc ctcctcaccg tgcagcagca gcagctggtc
1261 gctggggtta ctgcctttgt ttggcagact tggtttacct gcctgtagtc aagtctctct
1321 cataccaaca gaacttccgg tacttccaga accaactcac ctgacctgca actcaaggc
1381 ttttttaaga aaccaccaa aaaaaaaaat ttttttaaag aaaaaaatgt atatagtaac
1441 gcatctcctc caggcttgat ttgggcaatg gggttatgtc tttcatatga ctgtgtaaaa
1501 caaagacagg acttggaggg gaagcacacc cccagtgtg ccatgactga ggtgtctcgt
1561 tcatctctca gaagcgcctt ggggcctcgc cagggccgtg gtcttaccg aggcgtgggt
1621 gggcagccgt tccccaggct gtgtggggtc ctgctttctt ctgctgagac agtgacgctt
1681 tccagttccc accctaatca gccactgctg gtcacagccc cacagccatg ggtatttctg
1741 tggtctcctc gcttcattga agcaaagcat gagccttcct agacaagggc agctggggag
1801 gggaagggac cggaagtttg tgaagttgaa cagtccatcc atctgcactg agaggctgga
1861 tcctgactcc cgggcagca ggatccagg aaccttcctc ctccagggca gcacaggact
1921 cagccgtgtc tggaccggcc ctgctgaggc tacagtcact ctggaagctc tgcgcttcat
1981 caggaggcag gactgtggcg ggaggggtcc ttgaagatgg gtgtggggag cagtgggtca
2041 ggaagtggga gccagaggtt tgactcactt tgctttattt ttcaggctac aatacaggtc
2101 agagacaatg gcttataaag gtttagtgtg gtctcaggat gtgacaggca gtccagcctg
2161 accttctgc acactccaga caaacttccc agacaagctc ctttgtgcct ctacgtggag
2221 agggtgtgga aagttatcac attaaaagat ggaggattaa aaaaaaaaaa aaaaaaaaa
2281 aaaaaaaa
```

Figure 8G

MMDPELDYTLMRVCKQMIKRFCPEADSKTMLQCLKQNKNSELMDPKCKQMITKRQITQNTDYRL
NPMLRKACKADIPKFCHGILTKAKDDSELEGQVISCLKLRYADQRLSSDCEDQIRIIIQESALD
YRLDPQLQLHCSDEISSLCAEEAAAQEQTGQVEECLKVNLLKIKTELCKKEVLNMLKESKADIF
VDPVLHTACALDIKHHCAAITPGRGRQMSCLMEALEDKRVRLQPECKKRLNDRIEMWSYAAKVA
PADGFSDLAMQVMTSPSKNYILSVISGSICILFLIGLMCGRITKRVTRELKDR

Figure 8H

```
   1 aatttagcca gctgtggtgg cacatacctg taatcccagc tacttgagag actgaggcag
  61 gagaatcact tgaaccggga gatggagttt gcagtgagcc gagatggtgc cactgtactc
 121 cagcctgggt gacagagcaa gactctgtct ccaaaaaaaa aaaaaaaaaa aaaaaaaaga
 181 catttcaagc tggaagattt ggttccctaa ctttgagcct agctctttca ttaaagtaat
 241 aataaaagta gaactctaca tttatataat ggttttgact ttccaaagtg atttcacat
 301 ctcagcagtc ctgtgaagga ctaaataagg tgtttcaggg tagacttggc attgtgtttt
 361 gcaaagaagg tccaaggcca tgcagctatt tggtgacaga attgaaagta aagcctgatt
 421 ctcttgctgc aaggcgactt tgctatctag aagccagggt cactagacaa gatgcagtca
 481 acaaataagt ctccagaaca tatgacatct ccagcctaaa ccaagctcac ctttccatgc
 541 tggctccctc atgcagacgg aggacatccg cttggagcca gatctatacg aagcctgcaa
 601 gagtgacatc aaaaacttct gttccgctgt gcaatatggc aacgctcaga ttatcgaatg
 661 tctgaaagaa aacaagaagc agctaagcac ccgctgccac caaaaagtat ttaagctgca
 721 ggagacagag atgatggacc cagagctaga ctacaccctc atgagggtct gcaagcagat
 781 gataaagagg ttctgtccgg aagcagattc taaaaccatg ttgcagtgct tgaagcaaaa
 841 taaaaacagt gaattgatgg atcccaaatg caaacagatg ataaccaagc gccagatcac
 901 ccagaacaca ggtaagatct tggcttggct ctcctggccc cgtggagtat ctgaaaagga
 961 attcagtggc tgtagagtga cctgctcaaa ctcccagggc tttgttgcct gggaatttta
1021 agggaggagt ctgagtgtaa gcagggcctt cctcctttga ggagcatcca gaaaaatgga
1081 gggagagtca ggggagagag gaggccacaa gaaccagaaa actgccctaa aagaacgttc
1141 agaaggaatc aggccggcag tccttggaaa gaaaaatcta gaattcaat aaaacttcat
1201 gagtgtgcca ggagaatgta cgggtaatct gattcggaac agaaacattt cacctctgag
1261 ttggaagacc tcgtaagtta atggtcacag tgagttggat attgtatttc ttttcagtg
1321 ttctcaaaag tgtctgttat ggggaaggtt gctgatgtcc ccttgatttt tctgaggact
1381 ccttagagta ttggagtctg cacaaaaccc cgcagagtag aaagattcct gaggacctcc
1441 agaagtactc gttaacaagt catattgctg attaaaaaca gtgtagtgag agctcagtaa
1501 atgtttattg aatagataaa tccatggttg tagtcatgat cattgacata atatgctccc
1561 tttaggaagg tggatatcta aaaatgtgtg aatcaggtgg aatgttttgt cacatgctca
1621 ctgctttcta ctctagatta ccgcttaaac cccatgttaa gaaaagcctg taaagctgac
1681 attcctaaat tctgtcacgg tatcctgact aaggccaagg atgattcaga attagaagga
1741 caagtcatct cttgcctgaa gctgagatat gctgaccagc gcctgtcttc agactgtgaa
1801 gaccagatcc gaatcattat ccaggagtcc gccctggact accgcctgga tcctcagctc
1861 cagctgcact gctcagacga ggtgggattt gcgtgcaaaa ctggttacgc acagagctgc
1921 tcagagaagt ttccactgga gaaaagttgt ttactttctc tcccttcagc cgtgaatgat
1981 ctggtgaatt gaaggccatc ttctaggctc tccatggtct gcattcctgt tctttgtaac
2041 actgaattca acttggcatt agtcctgaca ctctaaagcg ttgttccata tttctctgtt
2101 gaacaagggt gttctttcat tatagctctc tgtaaatttg ttcttccctt cttcttattc
2161 tggatggtaa acccaagacc tgccagaaag ataaaagtgc tttcagctgg gcacggtggc
2221 tcacgcctgt aatcccaaca ctttgggagg ccaaggaggg tggatcatct gaggtcagga
2281 gttcaagacc agcctggcta acatggagaa atctgtctct actaaaaata caaaaaatta
2341 gccaggcgtg gtggcgtgca ccagtaatct cagctactca ggaggctgag gcaggagaat
2401 cacttgaacc cgggaggcgg tggttgcagt gagctgagat catgccactg cactccagcc
2461 tgggcgacag aggaagactc tgtctc
```

Figure 8I

MQTEDIRLEPDLYEACKSDIKNFCSAVQYGNAQIIECLKENKKQLSTRCHQKVFKLQETEMMDP
ELDYTLMRVCKQMIKRFCPEADSKTMLQCLKQNKNSELMDPKCKQMITKRQITQNTGKILAWLS
WPRGVSEKEFSGCRVTCSNSQGFVAWEF

Figure 8J

```
  1 ctgagaggaa gttttatctg tgcagccctt ctctgaggat ggacacttct cacactacaa
 61 agtcctgttt gctgattctt cttgtggccc tactgtgtgc agaaagagct cagggactgg
121 agtgttacca gtgctatgga gtcccatttg agacttcttg cccatcaatt acctgcccct
181 accctgatgg agtctgtgtt actcaggagg cagcagttat tgtggattct caaacaagga
241 aagtaaagaa caatctttgc ttacccatct gccctcctaa tattgaaagt atggagatcc
301 tgggtactaa ggtcaacgtg aagacttcct gttgccagga agacctctgc aatgtagcag
361 ttcccaatgg aggcagcacc tggaccatgg cagggtgct tctgttcagc ctgagctcag
421 tcctcctgca gaccttgctc tgatggtcct cccaatgacc tccacccttg tccttttatc
481 ctcatgtgca acaattcttc ctggagccct ctagtgatga attatgagtt atagaagctc
541 caaggtggga gtagtgtgtg aaataccatg ttttgccttt atagcccctg ctgggtaggt
601 aggtgctcta atcctctcta gggctttcaa gtctgtactt cctagaatgt catttgttg
661 tggattgctg ctcatgaccc tggaggcaca cagccagcac agtgaagagg cagaattcca
721 aggtattatg ctatcaccat ccacacataa gtatctgggg tcctgcaatg ttcccacatg
781 tatcctgaat gtcccctgt tgagtccaat aaacccttg ttctcccaaa aaaaaaaaaa
841 aa
```

Figure 9A

MDTSHTTKSCLLILLVALLCAERAQGLECYQCYGVPFETSCPSITCPYPDGVCVTQEAAVIVDS
QTRKVKNNLCLPICPPNIESMEILGTKVNVKTSCCQEDLCNVAVPNGGSTWTMAGVLLFSLSSV
LLQTLL

Figure 9B

```
  1 atctgacaga acttgccact gtgcctgcaa ccttgtctga gaggaaccct tctctgagga
 61 tggacacttc tcacactaca aagtcctgtg tgctcattct tcttgtggcc ctactgtgtg
121 cagaaagagc tcagggactg cagtgctacg agtgctatgg agtgccaatt gagacttcct
181 gcccagcagt tacctgccgc gcctctgatg gattctgcat tgctcaaaac atagaattga
241 ttgaggactc tcaaagaagg aaactaaaga cccgtcagtg cctttctttc tgccctgctg
301 gtgtgccaat cagggatcct aacatcaggg agaggacttc ctgttgcagc gaagacctct
361 gcaatgcagc agttcccact gcaggtagca cctggaccat ggcagggtg cttctgttca
421 gcctgagctc agtcgtcctg cagaccttgc tctgatggtc cttccaatga cccccaccct
481 tttcctttta tcttcatgtg caaccactct ttcctggagt cctctagtga caattatat
541 gttatagaag gtccaatgtg gggatagtgt gtggaacacc ctgtttcacc tttatagccc
601 ctgctgggta agtgcccgac tcctctctag ggctttcaaa tctgtacttc ttgcaatgcc
661 atttagttgt ggatttctat tcttggccct ggaggcatgt ggccagcaca tgcaacaggc
721 agtattccaa ggtattatag tatcaccatc cacacataag tatctggggt cctgcaggt
781 tcccatgtat gcctgtcaat gacccctgtt gagtccaata aaagctttgt tctcccagcc
841 aaaaaaaaaa aaaaaaaaaa aa
```

Figure 10A

MDTSHTTKSCVLILLVALLCAERAQGLQCYECYGVPIETSCPAVTCRASDGFCIAQNIELIEDS
QRRKLKTRQCLSFCPAGVPIRDPNIRERTSCCSEDLCNAAVPTAGSTWTMAGVLLFSLSSVVLQ
TLL

Figure 10B

```
  1 gcccacccccc gcccagcccg tgcctataag gccttggcaa tgcaggggcc cgcactgctc
 61 ccagacgaca tcagagatga ggacagcatt gctgctcctt gcagccctgg ctgtggctac
121 agggccagcc cttaccctgc gctgccacgt gtgcaccagc tccagcaact gcaagcattc
181 tgtggtctgc ccggccagct ctcgcttctg caagaccacg aacacagtgg agcctctgag
241 ggggaatctg gtgaagaagg actgtgcgga gtcgtgcaca cccagctaca ccctgcaagg
301 ccaggtcagc agcggcacca gctccaccca gtgctgccag gaggacctgt gcaatgagaa
361 gctgcacaac gctgcaccca cccgcaccgc cctcgcccac agtgccctca gcctggggct
421 ggccctgagc ctcctggccg tcatcttagc ccccagcctg tgaccttccc cccagggaag
481 gccccctcatg cctttccttc cctttctctg gggattccac acctctcttc cccagccgca
541 acgggggtgc caggagcccc aggctgaggg cttccccgaa agtctgggac caggtccagg
601 tgggcatgga atgctgatga cttggagcag gccccacaga ccccacagag gatgaagcca
661 ccccacagag gatgcagccc ccagctgcat ggaaggtgga ggacagaagc cctgtggatc
721 cccggatttc acactccttc tgttttgttg ccgtttattt ttgtactcaa atctctacat
781 ggagataaat gatttaaacc agaaaa
```

Figure 11A

MRTALLLLAALAVATGPALTLRCHVCTSSSNCKHSVVCPASSRFCKTTNTVEPLRGNLVKKDCA
ESCTPSYTLQGQVSSGTSSTQCCQEDLCNEKLHNAAPTRTALAHSALSLGLALSLLAVILAPSL

Figure 11B

```
   1 gctccggcca gccgcggtcc agagcgcgcg aggttcgggg agctccgcca ggctgctggt
  61 acctgcgtcc gcccggcgag caggacaggc tgctttggtt tgtgacctcc aggcaggacg
 121 gccatcctct ccagaatgaa gatcttcttg ccagtgctgc tggctgccct tctgggtgtg
 181 gagcgagcca gctcgctgat gtgcttctcc tgcttgaacc agaagagcaa tctgtactgc
 241 ctgaagccga ccatctgctc cgaccaggac aactactgcg tgactgtgtc tgctagtgcc
 301 ggcattggga atctcgtgac atttggccac agcctgagca agacctgttc cccggcctgc
 361 cccatcccag aaggcgtcaa tgttggtgtg cttccatgg catcagctg ctgccagagc
 421 tttctgtgca atttcagtgc ggccgatggc gggctgcggg caagcgtcac cctgctgggt
 481 gccggctgc tgctgagcct gctgccggcc ctgctgcggt ttggcccctg accgcccaga
 541 ccctgtcccc cgatccccca gctcaggaag gaaagcccag ccctttctgg atcccacagt
 601 gtatgggagc ccctgactcc tcacgtgcct gatctgtgcc cttggtccca ggtcaggccc
 661 accccctgca cctccacctg ccccagcccc tgcctctgcc aagtgggcc agctgccctc
 721 acttctgggg tggatgatgt gaccttcctt gggggactgc ggaagggacg aggttccct
 781 ggagtcttac ggtccaacat cagaccaagt cccatggaca tgctgacagg gtccccaggg
 841 agaccgtgtc agtagggatg tgtgcctggc tgtgtacgtg ggtgtgcagt gcacgtgaga
 901 gcacgtggcg gcttctgggg gccatgtttg gggagggagg tgtgccagca gcctggagag
 961 cctcagtccc tgtagcccc tgccctggca cagctgcatg cacttcaagg gcagcctttg
1021 ggggttgggg tttctgccac ttccgggtct aggccctgcc caaatccagc cagtcctgcc
1081 ccagcccacc cccacattgg agccctcctg ctgctttggt gcctcaaata aatacagatg
1141 tcccc
```

Figure 12A

MKIFLPVLLAALLGVERASSLMCFSCLNQKSNLYCLKPTICSDQDNYCVTVSASAGIGNLVTFG
HSLSKTCSPACPIPEGVNVGVASMGISCCQSFLCNFSAADGGLRASVTLLGAGLLLSLLPALLR
FGP

Figure 12B

```
  1 actgtgcctg caacctggtc agagaggaag taaggactgg tgtcaggagg gagctgctag
 61 gtttgatctg tgcagccctt ctccaaggat ggacagttgt cacactacaa agtcctgtgt
121 actcatcctt cttgtggtcc tattgtgtgc agaaagagct caggggctgg agtgctataa
181 ctgcctggga gtttcacttg gaattgcctg caaatcaatt acctgcccct accctgatgc
241 agtctgcatt tctcagcagg tagaacttat tgtggactct caaagaagga agtaaagaa
301 caaactctgc tttcctttct gccctgctaa tcttgaaaat atggagatcc tgggtactac
361 tgtcaacgtg aatacttcct gttgcaagga agacctctgc aatgcaccat tttccactgg
421 aggcagcacc tggaccatga caagggtgct tctgttaaat ctgggctcgg tcttcctgca
481 gaccttgctg taaaaggtcc ttcaaggac ctccacccttgttgttttat cctcatttgc
541 aactattcct tcctggagcc ctctagtgat gaattatgag atattgaagc tccaaggtgg
601 gagtagtgtt tgtggaatac gttgtttcaa ctttatagcc cctgcttggt aaatgcccca
661 ctcctctcta ggaatttcaa atatgtactt cctagaatgc catttttgtt ggcttgcta
721 atcttggccc tggaggcccg tggctagcag agggtagagg cagaattcca aggtattaag
781 ccatcaccat ccacacataa gtgtctgagg ttctgcagga ttctcatgta tgcggcttta
841 tgtcccttg ttgagtccaa taaacccttt gttctcc
```

Figure 13A

MDSCHTTKSCVLILLVVLLCAERAQGLECYNCLGVSLGIACKSITCPYPDAVCISQQVELIVDS
QRRKVKNKLCFPFCPANLENMEILGTTVNVNTSCCKEDLCNAPFSTGGSTWTMTRVLLLNLGSV
FLQTLL

Figure 13B

```
  1 ctgcagccag gtctgagagg aagtaaggac tggtgtcagg agggagctgc taggtgacaa
 61 agggaagaac cctcaggata gggctgtggt gggagtgaga ttaggaaaga agagctgggt
121 gggtggtgga tgagagaagt aggcagacat gtattcctca gggaaagctg tgtagagggt
181 tggagggagg gaatattgga tggctgagcc gtgtgagagc ccaggggtgt gatcaggggt
241 ctattaactg gctccaactt ccaaggtttt atctgtgcag cccttctcca aggatggaca
301 cttctcacga gataaagtcc tgtgtgctga tccttcttgt gaccctactc tgtgcagaaa
361 gagctcaggg actggagtgt taccagtgct atggagtccc atttgagact tcttgcccat
421 catttacctg cccctaccct gatggattct gtgttgctca ggaggaagaa tttattgcaa
481 actctcaaag aaagagagta aagagccgtt cttgccatcc tttctgccct gatgaaattg
541 aaaagaagtt tatcctggat cctaacacca agatgaatat ttcctgttgc caggaagacc
601 tctgcaatgc agcagttccc actggaggca gctcctggac cacggcaggg gtgcttctgt
661 tcagcctggg ctcagtcctc ctgcagaccc tgatgtgatg gtccccaccc
```

Figure 14A

MDTSHEIKSCVLILLVTLLCAERAQGLECYQCYGVPFETSCPSFTCPYPDGFCVAQEEEFIANS
QRKRVKSRSCHPFCPDEIEKKFILDPNTKMNISCCQEDLCNAAVPTGGSSWTTAGVLLFSLGSV
LLQTLM

Figure 14B

```
   1 gttatcagag gtgagcccgt gctcttcagc ggagaagatc ccctacctgg ccgccggcca
  61 ctttctgtgg gccgtggggt cctcaaggag acggcccttg ggctcagggg ctgcgtttcc
 121 acacgcgcct ttcccagggc tcccgcgccc gttcctgcct ggccgccggc cgctccaaca
 181 gcagcacaag gcgggactca gaaccggcgt tcaggccgc cagcggccgc gaggccctga
 241 gatgaggctc caaagacccc gacagcccc ggcgggtggg aggcgcgcgc cccggggcgg
 301 gcggggctcc ccctaccggc cagacccggg gagaggcgcg cggaggctgc gaaggttcca
 361 gaagggcggg gaggggcgc cgcgcgctga ccctccctgg gcaccgctgg ggacgatggc
 421 gctgctcgcc ttgctgctgg tcgtggccct accgcgggtg tggacagacg ccaacctgac
 481 tgcgagacaa cgagatccag aggactccca gcgaacggac gagggtgaca atagagtgtg
 541 gtgtcatgtt tgtgagagag aaaacacttt cgagtgccag aacccaagga ggtgcaaatg
 601 gacagagcca tactgcgtta tagcggccgt gaaaatattt ccacgttttt tcatggttgc
 661 gaagcagtgc tccgctggtt gtgcagcgat ggagagaccc aagccagagg agaagcggtt
 721 tctcctggaa gagcccatgc ccttcttta cctcaagtgt tgtaaaattc gctactgcaa
 781 tttagagggg ccacctatca actcatcagt gttcaaagaa tatgctggga catgggtga
 841 gagctgtggt gggctgtggc tggccatcct cctgctgctg gcctccattg cagccggcct
 901 cagcctgtct tgagccacgg gactgccaca gactgagcct tccggagcat ggactcgctc
 961 cagaccgttg tcacctgttg cattaaactt gttttctgtt gattacctct tggtttgact
1021 tcccagggtc ttgggatggg agagtgggga tcaggtgcag ttggctctta accctcaagg
1081 gttctttaac tcacattcag aggaagtcca gatctcctga gtagtgattt tggtgacaag
1141 tttttctctt tgaaatcaaa ccttgtaact catttattgc tgatggccac tctttccctt
1201 gactcccctc tgcctctgag ggcttcagta ttgatgggga gggaggccta agtaccactc
1261 atggagagta tgtgctgaga tgcttccgac ctttcaggtg acgcaggaac actgggggag
1321 tctgaatgat tggggtgaag acatccctgg agtgaaggac tcctcagcat ggggggcagt
1381 ggggcacacg ttagggctgc ccccattcca gtggtggagg cgctgtggat ggctgctttt
1441 cctcaacctt cctaccaga ttccaggagg cagaagataa ctaattgtgt tgaagaaact
1501 tagacttcac ccaccagctg gcacaggtgc acagattcat aaattcccac acgtgtgtgt
1561 tcaacatctg aaacttaggc caagtagaga gcatcagggt aaatggcgtt catttctctg
1621 ttaagatgca gccatccatg gggagctgag aaatcagact caaagttcca ccaaaaacaa
1681 atacaagggg acttcaaaag ttcacgaaaa aattgaatta aagataaaa attaa
```

Figure 15A

MRLQRPRQAPAGGRRAPRGGRGSPYRPDPGRGARRLRRFQKGGEGAPRADPPWAPLGTMALLAL
LLVVALPRVWTDANLTARQRDPEDSQRTDEGDNRVWCHVCERENTFECQNPRRCKWTEPYCVIA
AVKIFPRFFMVAKQCSAGCAAMERPKPEEKRFLLEEPMPFFYLKCCKIRYCNLEGPPINSSVFK
EYAGSMGESCGGLWLAILLLLASIAAGLSLS

Figure 15B

```
   1 ggagagagca ggacacagct atggatgccg ccaggagagg agatacacag ccagtgatgt
  61 ggaccaccgg atggctgttg ctgctgccgc ttctgctgtg tgaaggagcg caagccctgg
 121 agtgctacag ctgcgtgcag aaggcggacg atggatgctc tccgcacagg atgaagacag
 181 tcaaatgtgg tcccggggtg gacgtctgta ccgaggccgt gggagcggta gagaccatcc
 241 acgggcaatt ctctgtggcg gtgcggggct gcggttccgg aatcccgggc aagaacgacc
 301 gcggactgga ccttcacggg ctcctggcct tctttcagct acagcagtgc tccgaggacc
 361 gatgcaacgc caaactcaac ctcactttgc gaggcctcaa ccctgcaggc aatgagagtg
 421 catatgagcc taacggtgca gagtgctaca gctgtgtggg tctgagccgc gagaagtgcc
 481 agggctccat gccgccggtc gtgaactgct acaacgccag tggccgtgtc tacaagggct
 541 gcttcgatgg taacgtcacc ctgacggcag ccaacgtgac cgtgtcctta cctgtccgag
 601 gctgcgtcca ggacgagacc tgcacccggg atggggtgac gggtccagga ttcacactca
 661 gcggctcttg ctgtcaggc ccccgctgta acgccgacct tcgcaacaag acctatttct
 721 cccctcgaat cccaccccta gtcctgctgc ccctccaac caccgcagcc ccatccactc
 781 gggcccagaa ctcctccagc acgacctcta cagcagcccc aaccacgacc acctccatca
 841 tcaagcccac cacagcccaa gccagccaca cttctcccca tgaaatggat ctcgaagtca
 901 tacaggaaga gggggcgtcg ttgagtggag gtgctgcggg ccatggaggt actgcgggcc
 961 atggaggtgc tgcgggccac caagaccgca gcaatatgga aagtatcca ggaaagggtg
1021 gggcccagat cccagctaaa ggaggctctg gcactctagg gtcctggttg tctgcagttc
1081 tgttgactgt ggttgctggc gcgatgctgt gaatgtctca tctcgaaaag tccatctcac
1141 tttgtttccc tggccccgtg gtaccaactc tttccatttc tcacttgact ggactggctc
1201 cgcccccatc cttcagcatt ctcagttccg actgcactgg tttgcagctt cggaaaacag
1261 tcctctgttg taaatattcc gctcgggtgg ccctacttt ttgatgcggc cacagcattc
1321 cccctgatgg tgaccaggac agaggaaga gacgtctact ggctgagaga ggcccagaga
1381 gtccacggca agcctcctct tccgttttc ctgaccaggc tggaagatga ccaggcaggt
1441 agacaatgga tccatcctcc gagcactgtg cttgcctggc acattgtgcg gaaatctggt
1501 cgcctgtctt ccttaggaga ctgtgaacaa ctctacaaca gggtcttgtc tctggcctct
1561 ctatgtgttc tgtctggcac aggaaggtgt caataaagat ttagttactt tgtatagtga
1621 gttaactaaa aaaaaaaaaa aaaaaaaaa aaaaaaaa
```

Figure 16A

MDAARRGDTQPVMWTTGWLLLLPLLLCEGAQALECYSCVQKADDGCSPHRMKTVKCGPGVDVCT
EAVGAVETIHGQFSVAVRGCGSGIPGKNDRGLDLHGLLAFFQLQQCSEDRCNAKLNLTLRGLNP
AGNESAYEPNGAECYSCVGLSREKCQGSMPPVVNCYNASGRVYKGCFDGNVTLTAANVTVSLPV
RGCVQDETCTRDGVTGPGFTLSGSCCQGPRCNADLRNKTYFSPRIPPLVLLPPPTTAAPSTRAQ
NSSSTTSTAAPTTTTSIIKPTTAQASHTSPHEMDLEVIQEEGASLSGGAAGHGGTAGHGGAAGH
QDRSNMEKYPGKGGAQIPAKGGSGTLGSWLSAVLLTVVAGAML

Figure 16B

```
  1 tcgctccccg cgccgtgccc gccgctgagc ccggagtgcg acacacccag ggatgcctgc
 61 gccccagagg accccccgcct gcagccccccg cgcctctttc aggccctatc ggagcatgct
121 gcctgcagcc atgaagagcc tcggtctggc gctgctggcc ttgcttctct gcccctcgcc
181 ggcccatggc ctgtggtgcc aggactgcac cctggccaat tccagccatt gcgctccgaa
241 gcagtgccag cccaccgata ccgtttgtgc cagcgtgcgg atcaccgacc ccagcagcag
301 caggaaggat cattctgtga acaagatgtg tgcttcctcc tgcgacttcg ttaagcggca
361 cttttctca gactatctga tggggttcat taactctggg atcttaaaag tcgacgtgga
421 ctgctgcgag aaagatttgt gcaacgggc atcggtcgca ggacgcagcc cctgggccct
481 ggctggggg ctcctgctca gcctggggcc tgctcttctc tgggctgggc cctaagaccc
541 ctccctccct cctgctgggc tttgagcttt gtcccctaag cctgttgctg ccctccccca
601 gcctggcctg gctggggctg ggacagcaag ggtttggcat caaggtctga ggctctcaac
661 ctccctagat gtgagtgagc cttctccgtt tctccaccag ctccatatcc caagcagctg
721 aatatctcca ggagtccaga catcctggca ggaagctggg gtaggggga ggggagggc
781 aagggactga gaccctccag gtctccaagg ggagggaggt caagccaggg acagcccaac
841 agcctggcct gagggcatt aactacagag aaataaagtc acttctgagt cttgtgaaaa
901 aaaaaaaaaa aaaaaaaaa aaaaaaaaaa aaaa
```

Figure 17A

MPAPQRTPACSPRASFRPYRSMLPAAMKSLGLALLALLLCPSPAHGLWCQDCTLANSSHCAPKQ
CQPTDTVCASVRITDPSSSRKDHSVNKMCASSCDFVKRHFFSDYLMGFINSGILKSRRGLLRER
FVQRGIGRRTQPLGPGWGAPVQLGAWLFFGLGPKTPPSLLVGFGACPLSLLVPLPSLAWLGLGQ
QGFGIKV

Figure 17B

```
   1 agaagaggcg agacttttt  gggtgctccg gatcgccagt agttcttcaa gcctcagcag
  61 ccaactcctc cggaggcgct cgcgctccgcc ccagggagcg cgaatccaag gagcctggga
 121 ccagcctctg ggagccccg  cgcgggcga  tgcgggcgcc gcgggcgaca cctgcggctc
 181 ctctcggtgg cagccgtcgc ttgggcggca gcagcgcgag cctcggcagc ctcggcagct
 241 actgtcgccg cggccagaac agcctccgct gcggtcgtgg tctctgatgc tcttgcccgc
 301 tcccggccct gccgatccgg gaggatgtgg gttctcggca tcgcagcaac tttttgcgga
 361 ttgttctggc ttccagggct ggcgctgcaa attcagtgct accagtgtga agaattccag
 421 ctgaacaacg attgctcatc ccctgagttc atcgtaaatt gcaccgtgaa cgttcaagac
 481 atgtgtcaga agaagtgat  ggagcaaagt gctgggatca tgtaccggaa gtcgtgtgca
 541 tcgtcagcag cctgtctcat tgcttcagct gggtaccagt ccttctgttc ccctgggaaa
 601 ctgaactccg tgtgcatcag ctgctgcaac ccctctttt gcaatgggcc gaggcccaag
 661 aagagaggca gctctgcctc ggccatcagg ccagggcttc tcaccactct cctgttcttc
 721 cacttagccc tctgcttggc acactgctga agctaaagga gatgccaacc cctgctgcct
 781 cacctgtctg gcccttcgtc tctcaccttc ccgagtctct tctgggtgtc cttttattct
 841 gggtagacaa gggagtcttt ttgttccctc ctttcaagta acgcaagatt gccgtgcaca
 901 aatactttg  taagctctga accaattcat tctgaatttc tgtgtgtagt tgaagaaaaa
 961 agcatggagc agaaagtcca gaccctccca tcccaatctg gttaaccacc gccaaggcta
1021 gcctggaaga accagccctt agaagtcatt gagatacgca tctgcctttc ccaaagcctt
1081 gagcttccat tctgtcccag taggagtcac agtctattca gagactgctg ctgcgtgaag
1141 gtaactttgc ttttgcggga gggagagcc  agtttcggct caaggcttct gaacttgcca
1201 ttcatacttc ctgctcctgt aaactatttt ctggggtgga cccagctggt ttggtctctg
1261 agccagtctg tggtgactca ggactcaagg gctgggcttt agcctctcca ggcttggcct
1321 cagtctgaaa agtgcttaag aaaaccttgt tagttctcct ggaggaagag ttactgcgcc
1381 gggaggctag gaagatgagg gggctgcggg ctgagctggt gctgtccttg gtggagatga
1441 agcgggcacg ctggcgtttc tcttggttgg catgctgcag agtcaggcgg cagcagagca
1501 cctgccagaa caccttccgg aactgctgag aggcacgtt  gtagaggaga gggttgacca
1561 cagagctgag gtagaagaag gtatcagaga agggcaggag gatcatgtat gccctgaagt
1621 acgttctggt ccagtcatgt ttgggttttg ctgcagccat gatccgtcgg atctgattgg
1681 gcatccaaca cacggccaac gtcaccacaa tcagtcctgg caggcaagaa caggagagaa
1741 aaggagacgg ggagagaaac agcatgagaa caaaaataaa taataaaaa  cccataaaat
1801 attaagcccc ttggttctgt tgcttactgg ccgagaaacg gtaccaatct ttcagctctg
1861 tgcttgtcgg cttcttttg  ccactggcaa aggagaattt aatgctgctt caagctcagg
1921 ggacttggct atgttaaaaa gcgttaaatg ctttcgacag tgtatttata cttacggctg
1981 cctgttaatt ttcaaaatgt tttcattgtt gctcgtgtat ccagaaaata tctcacgttg
2041 gccaaaa
```

Figure 18A

MWVLGIAATFCGLFWLPGLALQIQCYQCEEFQLNNDCSSPEFIVNCTVNVQDMCQKEVMEQSAG
IMYRKSCASSAACLIASAGYQSFCSPGKLNSVCISCCNTPLCNGPRPKKRGSSASAIRPGLLTT
LLFFHLALCLAHC

Figure 18B

```
  1 ggcaggcctg agtgaggacc tcgaccatgc aggggacctg gatggtgctg ttggcactga
 61 tattgggcac cttcggggag cttgctatgg ccttacagtg ctacacctgt gcgaatcctg
121 tgagtgcatc caactgtgtc accaccaccc actgccacat caatgaaacc atgtgcaaga
181 ctacgctcta ctccctggag attgttttcc ctttcctggg ggactccacg gtgaccaagt
241 cctgcgccag caagtgtgag ccttcggatg tggatggcat tgggcaaacc cggccagtgt
301 cctgctgcaa ttctgaccta tgcaacgtgg atggggcacc cagcctgggc agtcctggtg
361 gcctgctcct tgccctggca cttttcttgc tcttgggtgt cctgctgtaa agccatggcc
421 atctagctcc actcccttgt ccctgacatc ccagttccct aatgcctaga agaaatacaa
481 tggccatctg caaaaaaaaa aaaaaaaaaa aaaaaa
```

Figure 19A

MQGTWMVLLALILGTFGELAMALQCYTCANPVSASNCVTTTHCHINETMCKTTLYSLEIVFPFL
GDSTVTKSCASKCEPSDVDGIGQTRPVSCCNSDLCNVDGAPSLGSPGGLLLALALFLLLGVLL

Figure 19B

```
  1 atgcttttta tggcaggccc tgcagccagc tggtccctga ggcccctggg actccatggc
 61 gtcccccaag ccttgtgtgc tgtcctctta acagtgctgg tcatgaagac cttggttctc
121 ggtgatacca agctcgagga ccttcaccct cagtccctcc cactaaacaa gtacctgaat
181 tgctaccgat gtctgctgga gaccgaagag ctggggtgcc tcctggggtc tgacacctgc
241 ctgacacctc tgggcagcag ctgtgtcacc ctgcacataa agaacagcag cggttttaat
301 gtcatggtga gcgactgcta cagcaaggag cagatggtcc attgttcata tacccgtgct
361 tccccggtgt ttggcttttg gatattctat cagtgttgct cctggatttc tgcaacaat
421 ccggacaaca gaaagaatag catgcactag
```

Figure 20A

MLFMAGPAASWSLRPLGLHGVPQALCAVLLTVLVMKTLVLGDTKLEDLHPQSLPLNKYLNCYRC
LLETEELGCLLGSDTCLTPLGSSCVTLHIKNSSGFNVMVSDCYSKEQMVHCSYTRASPVFGFWI
FYQCCFLDFCNNPDNRKNSMH

Figure 20B

```
  1 agagctggag acctgggaat ctgctgtcaa ctgctggggc tgtggacatt ctcaggaccc
 61 tcaccatgaa acacctcctg ttgctcaccc tgtctgccct actctactgc tgggtctcag
121 ctgatactcg atgtcactcc tgctacaaag tccctgtgct gggctgtgtg gatcgccagt
181 cctgccgcct ggagccgggc cacaaatgcc tgacaacaaa cgtgtacctt gggaagatgt
241 gggttttctc taacctgcgc tgcggcacac cagaagagcc ttgtcgggag gtcttcaacg
301 aaaccaacca taagctgggc ctgaactaca acaccacctg ctgtgacaag ataactgta
361 acagcccggc tccacggccc acaccccgcac tggccctcat ctccctcacc tccttggctg
421 gcctcggcct ctggttattg cattgagact agctccatgg ctacaatctt accacctgct
481 atagcctgag cctttctccc tgtgtcctca gagctccagc tttccagaat cttctctcct
541 cccaccccct tcttctgaag atcatgtccc tagtcctata ccatttattt catgggactg
601 tacctggagt ggcctttcta gccaccgctc ctctccctca cttgtcacct tccactccat
661 tccacccaca cacagacaca cagacacaca gacacaaaga cacacacaca cacacacaca
721 cacacacaca cccagtcctt tccatttcc ttctagaaca ctctacctcc tccactggcc
781 actgaaaggc tcccctcctt ggacgcacac tgctgtgcct ctgggatcta agtctggaag
841 aactcctgtc ttgtctccag ggagtgattc caaaaggcgc tggcctcatt gcatgggcct
901 ggcttaccag accctctgct tgtccccttc tatcttgaga aataaacatc agtgtctaat
```

Figure 21A

MKHLLLLTLSALLYCWVSADTRCHSCYKVPVLGCVDRQSCRLEPGHKCLTTNVYLGKMWVFSNL
RCGTPEEPCREVFNETNHKLGLNYNTTCCDKDNCNSPAPRPTPALALISLTSLAGLGLWLLH

Figure 21B

```
   1 gcctacttgg cctgcctgcg atgcggtacc aacaccgcac gaagtgtgta cagattccca
  61 gttagacagc aggagggacc tgggagcggc caggggatg ttttatctct aagagaccaa
 121 gagctcaggc agggcttctg tgccctgctt cctccctggc ttgagctgga tcctggacca
 181 gctgctgacc tcctgttcac tctggcactg ccctcacgtc tccgtcatga cccatctgct
 241 cacagtgttc ctggtggccc tgatgggcct gcctgtggcc caggctctgg agtgccacgt
 301 gtgtgcctac aatggagaca actgcttcaa acccatgcgc tgcccagcca tggccaccta
 361 ctgtatgacc acacgaactt acttcacccc ataccggatg aaggtgagga agtcctgtgt
 421 ccccagctgc tttgaaaccg tgtacgatgg ctattccaag catgcatctg ccacctcctg
 481 ttgccagtac tacctctgca acggtgctgg ctttgctacc ccggtgacct tggccctggt
 541 cccagcactc ctagctacct tctggagctt gctgtaaagc tcggttcccc aagccagatc
 601 cactcaaacg caacactctc aaaaaacaca gtttccctct ctctcccaat tcactccacc
 661 caacgctctt ccttctgaca ctcctcaact accacgaggt cccatggcta cctacgaaag
 721 aactgatggc atccagatac ctcactccaa ggtcattttc agaaggctga catgtggacc
 781 tgtaatgtgc ccacccatgg gtggggcagg ctgggcttct cctctaccca agatcagggg
 841 catctgggag aatgtttatg gaggagggt catcactcaa gtcaaggagc actgatttga
 901 tagaattagt agccaaactc caccttcaga accctgcctc agtctaccca gtagaggatg
 961 ggtctgctag aggtgagggg aggagagcgg cggagaataa cgagctggct agaagcagag
1021 aaagactcag cagggctgtc tccgaagatc agcgcggctt gccagagcaa atgtgatgtg
1081 gaagccatgt gaggaagccc tttgtcattt ccacttatct gaggaactct gccagacctg
1141 atgttgggat agccattggc caagggttcc tagcaacggc gtcatttcca taggccactg
1201 aaatccctcc agcccagct cagcaggccc cttgacctcc actacagtcc ttcattcaca
1261 caccagctgc tgggccttga agttggcagg gacttgggag caggtgaccc atgctatttt
1321 ttgtctggcc tgttattctg ggcatggcaa gaagggatca gacgcaggtc agagcagggc
1381 agtagggcga ctgagacagg gaaacagact tcagccagtg gcttcccagg tcccgtaggc
1441 agctcctaca tccttcagtc tcttgttaca ttcccgggag acaaatatac agggagccaa
1501 gccgagtgct aggtgatgac tgcctgtgaa gtctattgtg ccacagact gctgggtacc
1561 aagtctcagg agaacccagc ctagatttag gagacacaga tctgcctttc atgcagtgta
1621 gctgtccttg ggagccttac catgctctct aactagtacc tcaactcaca tgtcactgag
1681 gaaccccta acactggccc agcccagggg tcgggatgct ggccaatgtc catggagtgg
1741 gactacccat ggagagtcct tgggtcatca atcacaaat gttttattcc aacctcccag
1801 tggtgagagc tcggacaca aagtccatc ctgggaccct tcttcctggt tctaggcaga
1861 cctgaactct gtctgctgct agagctgatg tggttttccg cctcagtttc ctcctccggg
1921 gataggccac cggaggattt gggagggtgg ggagggcatc ctgctgatgg gctcgccgag
1981 gttctcagga acaggaacgg gcggggcttt agtacacagg tgagttgggt gggaactggc
2041 ccggagctga ggagacactg actgggcaga gggaagatga gtctcaaggg agggcaggaa
2101 aagggagggg gagcgcgcat gcacatgtgc actcagtgca ggctacagag cccaaaaggc
2161 agcactggct gtggtgtccc ctgaggccca ggcaagatgc taggaggaag ccaatgctgc
2221 ccccacctga gctcacatgg aacatgcaca ccaccagcag cagcagcaag cattgagact
2281 gacctgtgga cgccataggg cactggcaag gagggtcaga ggcgggtccc tgactcagtg
2341 ggtgaggccc gggaaacatt atcctgttac cctgcgtgtg caagatcatt gtccccagct
```

Figure 22A

```
2401 agatggcgtc ctcaaccaaa actgagagga gccccagttc aggtcctccc tcctaccaca
2461 aggggtggt gtggaggagg cttgattgcc cttggagaag caccggtact gcagagctgg
2521 gggccagctt ctttcatctg tgtctagaca ccgaccagat aggccccaca gtggcaacac
2581 tgccacacag ccctacaaga agccctgtgc ctagctagca cagagcccca aaaggtgctc
2641 aattaataca gggccaagcc tgccagtggg ggggatgcag attaggggaa cagacccaga
2701 tggcctgtcc tgaaccctgt ctgggtggt gtgatgagca tctgtctagc ccactgcagg
2761 tggctctaca cactccacaa cagttctgca aaagtgtatg aggtggtcat tactgcgccc
2821 ctctcacagg taaaggcact gaggcacgga ggagtgaggc acttcatttt cctgggccat
2881 tcaactttcc aggaccaaca cattcaacta tgggtactac tccaatagct ggggttcttt
2941 gaggctgggc cccctgaaga tgatagtggc ttcatcaacc agagaatttc agagtgcagt
3001 gttgtaggag cctatgaacc tgaaatgtca gaactggagg tttgaggggc tgaggggtag
3061 gccagggtg tctggcccct tgtgtggaga cagagagaga gggaacatgg gatgggtag
3121 tagagagaag tgcaaggag cgtcagcctt tctcagggct aatgctgtca gggacgaggg
3181 ctcaagcctg tgagtgttct cacactgtga taaacagtgg cccctcaaca cagacggtgt
3241 ccagagtggc cggcagtggt tatctagagt tgcaatctgg aagcctcttg gtagtcactg
3301 gagagaggcc gcttgatggg acagcaccaa atgtgtgtgc ttctgtggga tgtgaggaag
3361 ctgggtcagc gcatgaagcc aaagcgtcct tcagagcaga ggggtggctg gtctagtcca
3421 ccagagacaa gctatccagt gagagtcata ctctgccacc gtctctgtga ttaccttacc
3481 ccaaagcaga cggggacggg atgcagagca cccgtgtctt catcttctgc ggcaagcacg
3541 tgagttcaca ttctgaaact ctagaaagat ttccaggagt ggggtgtgcc tttgctttgg
3601 tgcatggtta cttcctggca agcaccgtgg catcccgcag cactgagtga cctgggctcc
3661 tcaagccatc tcattggtga atgacagtg ccagtaccct ctcagctggc tcttggaggc
3721 ctgtgcatgg ggtctgcaca gaggaggccc ccaaactatg catggacgga cacgtgatgc
3781 ctagcacttc ccttggttgt gtctctgcca accccaggct ctcacccagc aaggaaatga
3841 aatccacttt tatgacacat ctccctcccc cagccagctc cattcaccta tatgccaggg
3901 tggtcccttt caatgtctgt cccccattgg atgaataaac aagcgaagga ca
```

Figure 22B

```
MTHLLTVFLVALMGLPVAQALECHVCAYNGDNCFKPMRCPAMATYCMTTRTYFTPYRMKVRKSC
VPSCFETVYDGYSKHASATSCCQYYLCNGAGFATPVTLALVPALLATFWSLL
```

Figure 22C

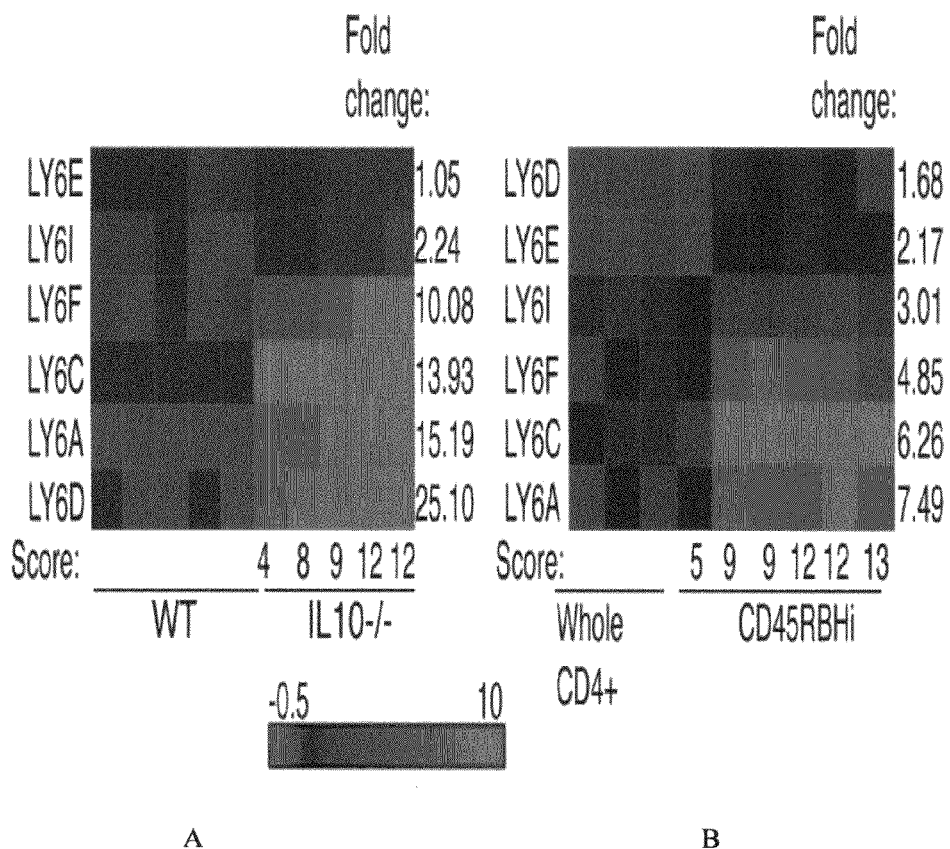
Figure 23 A-B

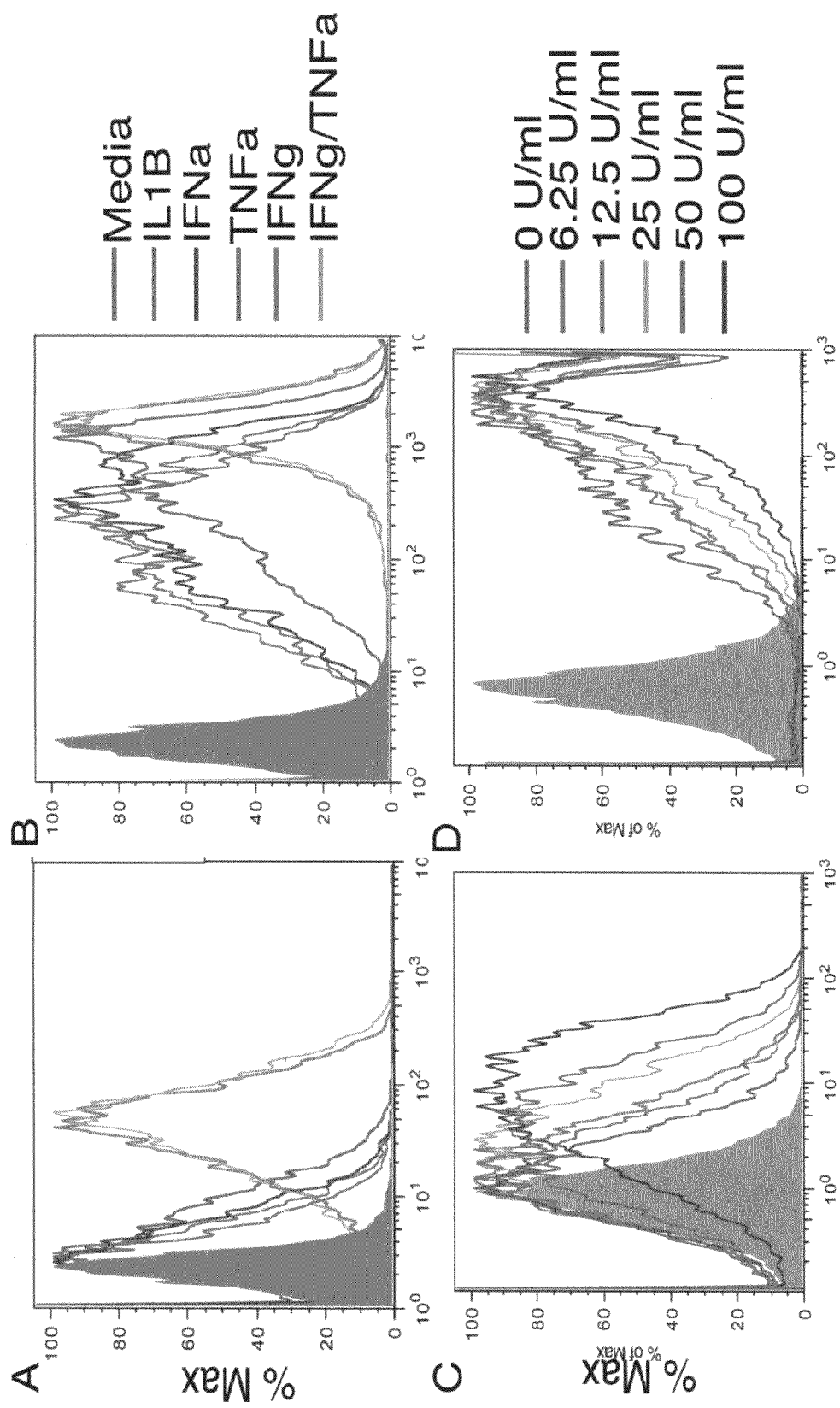
Figure 25A-D

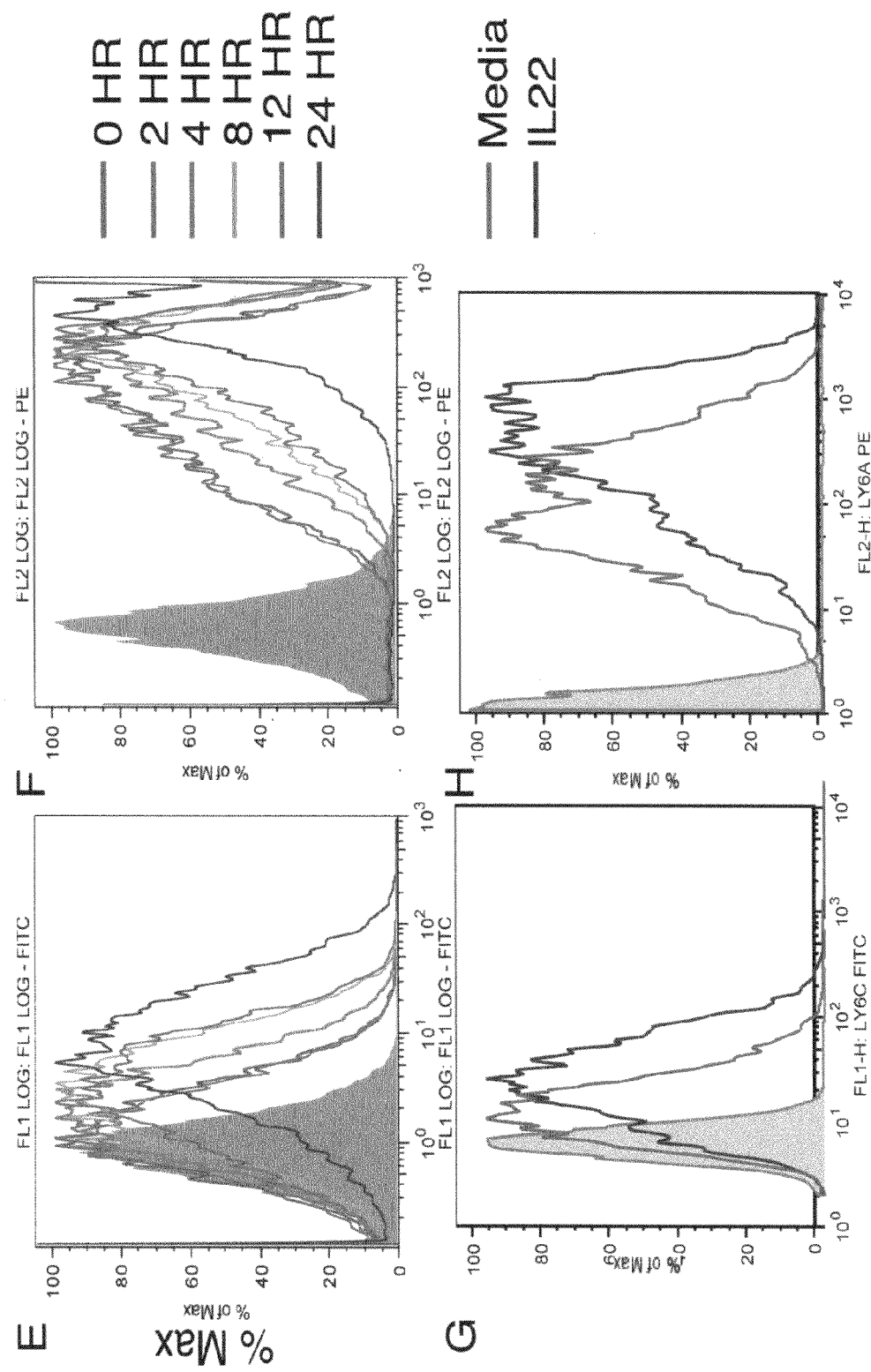
Figure 25 E-H

A 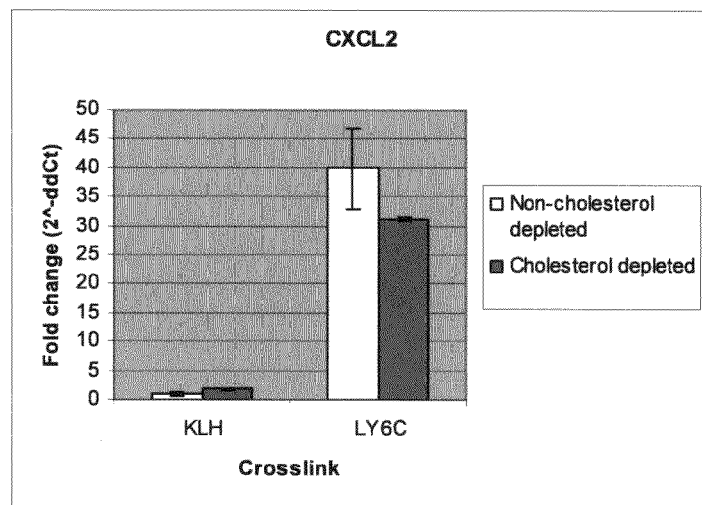
B 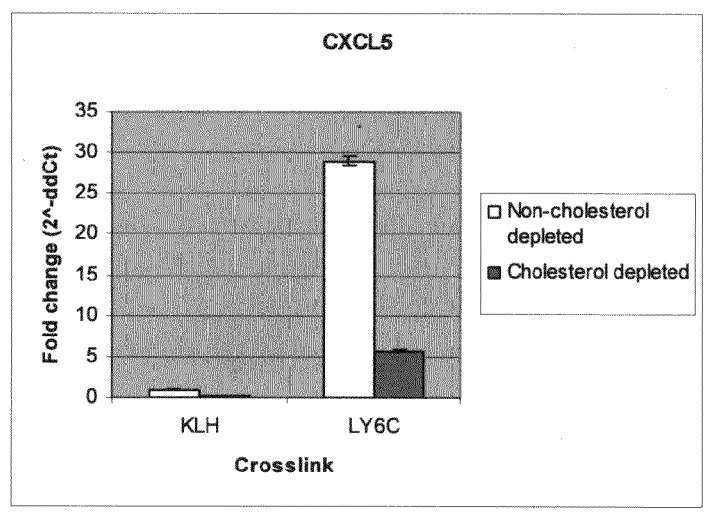
C 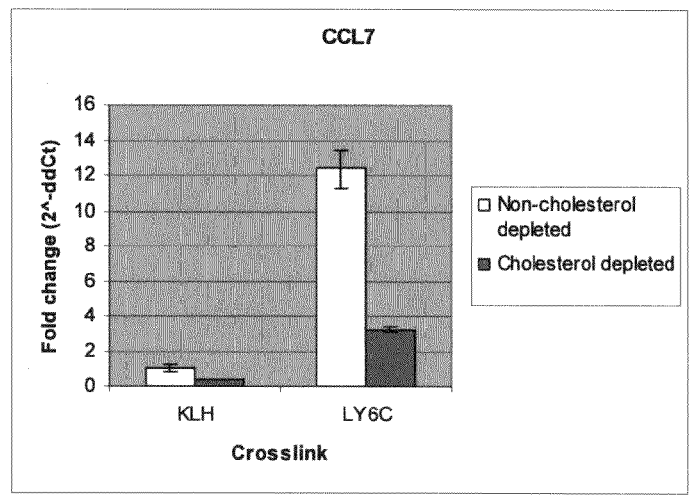
Figure 26 A-C

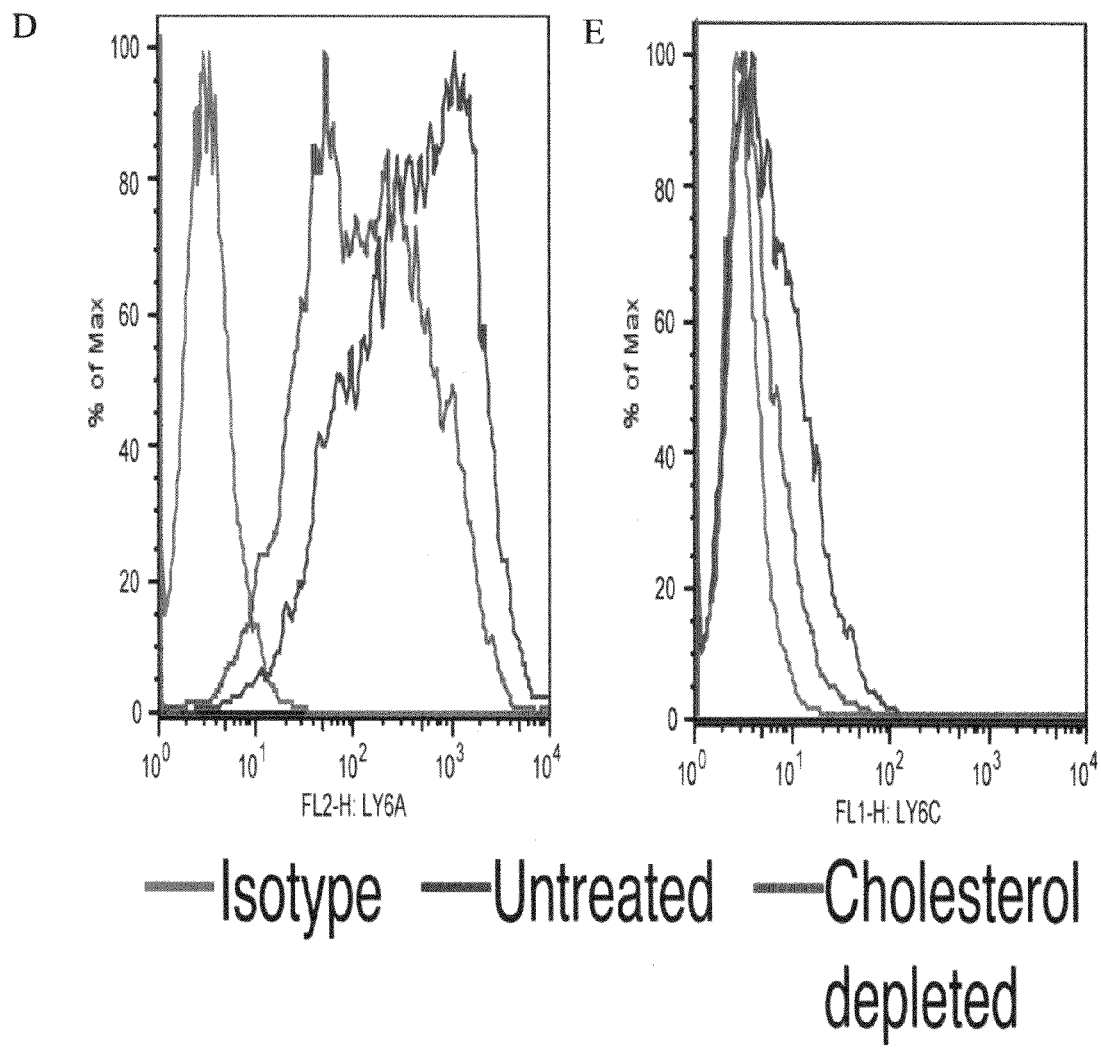
Figure 26D-E

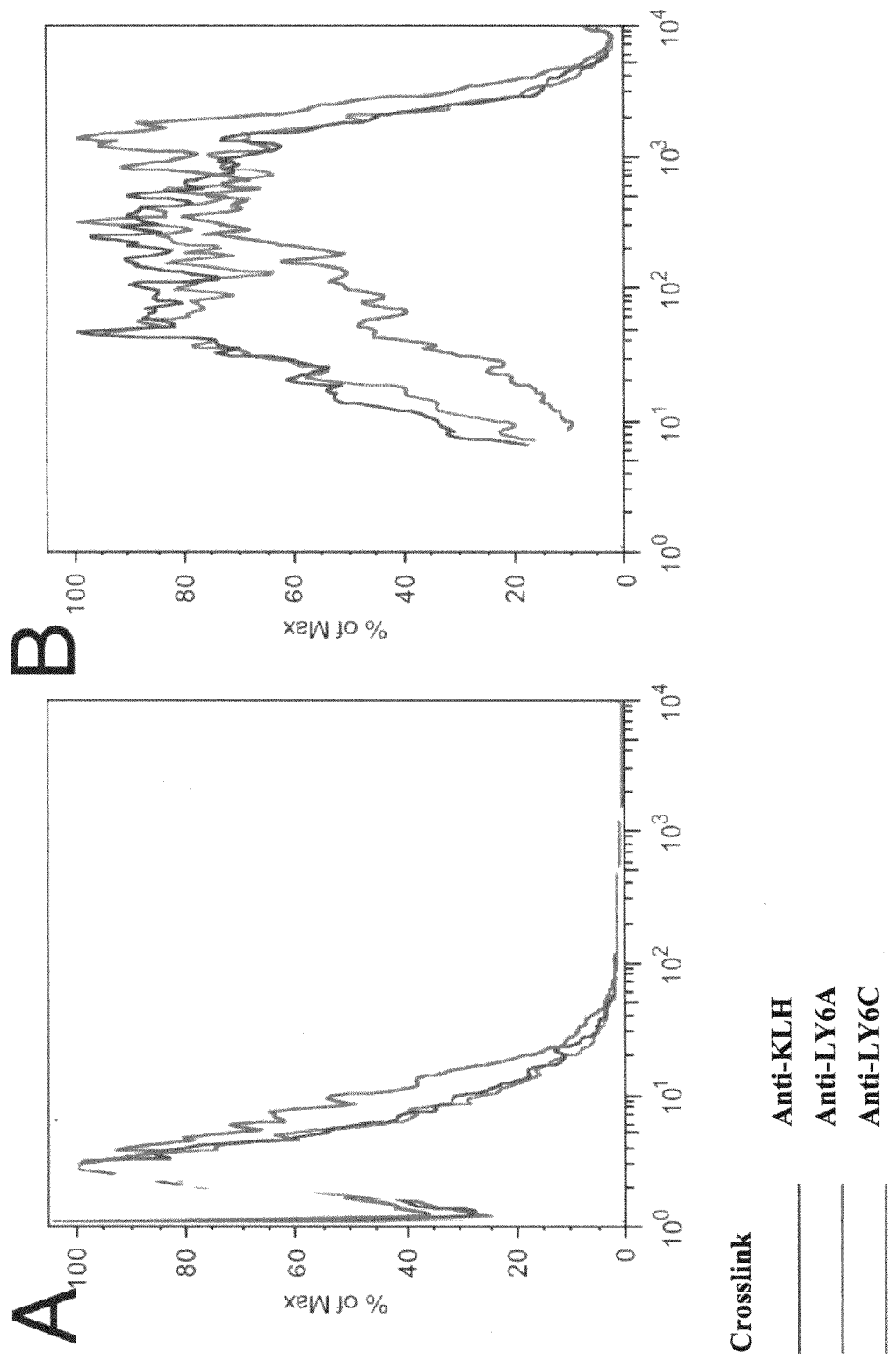
Figure 27 A-B

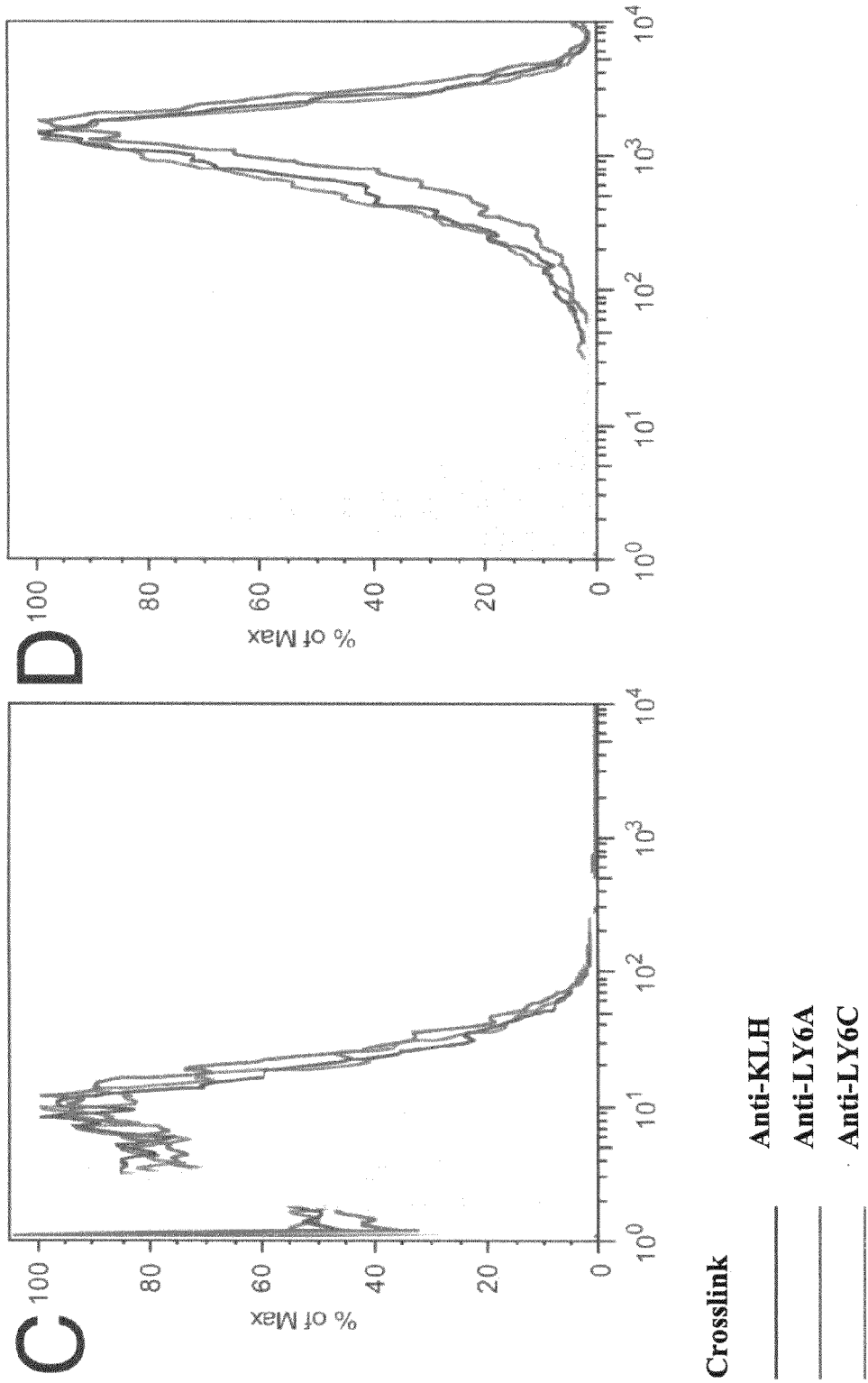
Figure 27 C-D

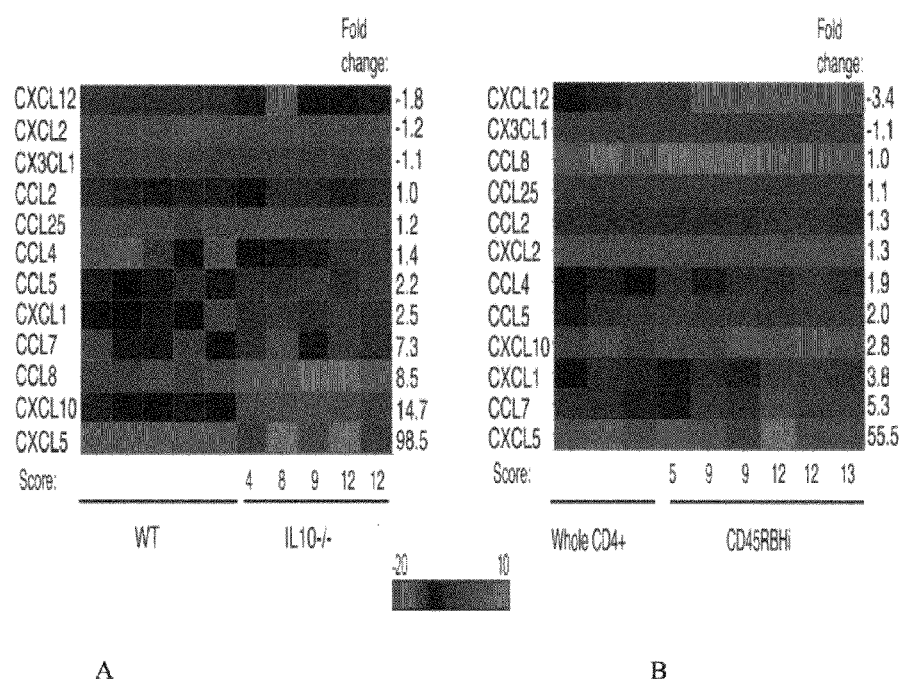
Figure 29 A-B

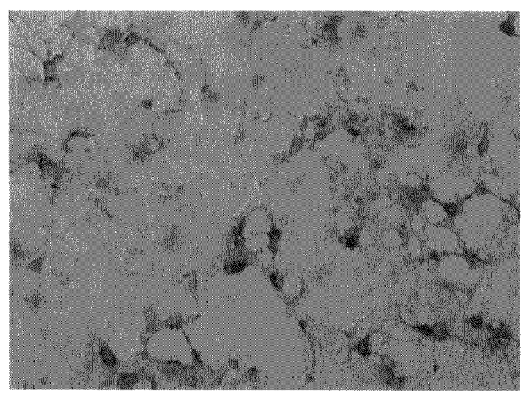
A
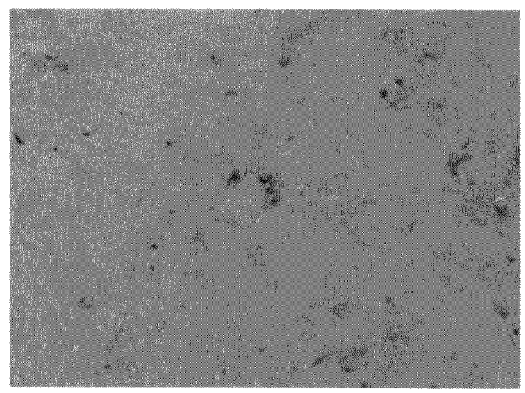
B
Figure 32 A-B

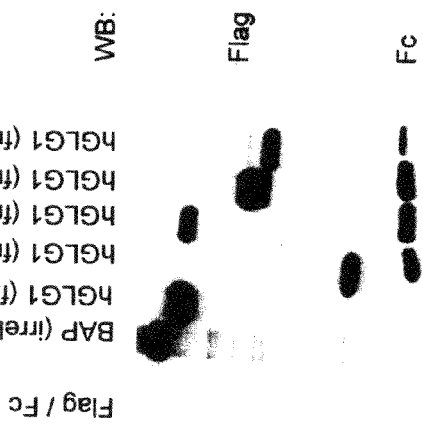
Figure 33A
Figure 33B

```
cgttgctgtc gctctgcacg cacctatgtg gaaactaaag cccagagaga aagtctgact
tgccccacag ccagtgagtg actgcagcag caccagaatc tggtctgttt cctgtttggc
tcttctacca ctacggcttg ggatctcggg catggtggct ttgccaatgg tccttgtttt
gctgctggtc ctgagcagag gtgagagtga attggacgcc aagatcccat ccacagggga
tgccacagaa tggcggaatc ctcacctgtc catgctgggg tcctgccagc cagcccctc
ctgccagaag tgcatcctct cacacccag ctgtgcatgg tgcaagcaac tgaacttcac
cgcgtcggga gaggcggagg cgcggcgctg cgcccgacga gaggagctgc tggctcgagg
ctgcccgctg gaggagctgg aggagccccg cggccagcag gaggtgctgc aggaccagcc
gctcagccag ggcgcccgcg gagagggtgc cacccagctg gcgccgcagc gggtccgggt
cacgctgcgg cctggggagc cccagcagct ccaggtccgc ttccttcgtg ctgaggata
cccggtggac ctgtactacc ttatggacct gagctactcc atgaaggacg acctggaacg
cgtgcgccag ctcgggcacg ctctgctggt ccggctgcag gaagtcaccc attctgtgcg
cattggtttt ggttcctttg tggacaaaac ggtgctgccc tttgtgagca cagtaccctc
caaactgcgc caccctgcc ccacccggct ggagcgctgc cagtcaccat tcagctttca
ccatgtgctg tccctgacgg gggacgcaca agccttcgag cgggaggtgg ggcgccagag
tgtgtccggc aatctggact cgcctgaagg tggcttcgat gccattctgc aggctgcact
ctgccaggag cagattggct ggagaaatgt gtcccggctg ctggtgttca cttcagacga
cacattccat acagctgggg acgggaagtt gggcggcatt ttcatgccca gtgatgggca
ctgccacttg gacagcaatg gcctctacag tcgcagcaca gagtttgact acccttctgt
gggtcaggta gcccaggccc tctctgcagc aaatatccag cccatctttg ctgtcaccag
tgccgcactg cctgtctacc aggagctgag taaactgatt cctaagtctg cagttgggga
gctgagtgag gactccagca acgtggtaca gctcatcatg gatgcttata atagcctgtc
ttccaccgtg accctttgaac actcttcact ccctcctggg gtccacattt cttacgaatc
ccagtgtgag ggtcctgaga agagggaggg taaggctgag gatcgaggac agtgcaacca
cgtccgaatc aaccagacgg tgactttctg ggtttctctc caagccaccc actgcctccc
agagccccat ctcctgaggc tccgggccct tggcttctca gaggagctga ttgtggagtt
gcacacgctg tgtgactgta attgcagtga cacccagccc caggctcccc actgcagtga
tggccaggga cacctacaat gtggtgtatg cagctgtgcc cctggccgcc taggtcggct
ctgtgagtgc tctgtggcag agctgtcctc cccagacctg gaatctgggt gccgggctcc
caatggcaca gggcccctgt gcagtggaaa gggtcactgt caatgtggac gctgcagctg
cagtggacag agctctgggc atctgtgcga gtgtgacgat gccagctgtg agcgacatga
gggcatcctc tgcggaggct ttggtcgctg ccaatgtgga gtatgtcact gtcatgccaa
ccgcacgggc agagcatgcg aatgcagtgg ggacatggac agttgcatca gtcccgaggg
agggctctgc agtgggcatg gacgctgcaa atgcaaccgc tgccagtgct tggacggcta
ctatggtgct ctatgcgacc aatgcccagg ctgcaagaca ccatgcgaga gacaccggga
ctgtgcagag tgtggggcct tcaggactgg cccactggcc accaactgca gtacagcttg
tgcccatacc aatgtgaccc tggccttggc ccctatcttg gatgatggct ggtgcaaaga
gcggaccctg gacaaccagc tgttcttctt cttggtggag gatgacgcca gaggcacggt
cgtgctcaga gtgagacccc aagaaaaggg agcagaccac acgcaggcca ttgtgctggg
ctgcgtaggg ggcatcgtgg cagtggggct ggggctggtc ctggcttacc ggctctcggt
ggaaatctat gaccgccggg aatacagtcg ctttgagaag gagcagcaac aactcaactg
gaagcaggac agtaatcctc tctacaaaag tgccatcacg accaccatca atcctcgctt
tcaagaggca gacagtccca ctctctgaag gagggaggga cacttaccca aggctcttct
ccttggagga cagtgggaac tggagggtga gaggaagggt gggtctgtaa gaccttggta
ggggactaat tcactggcga ggtgcggcca ccacctact tcatttcag agtgacaccc
aagagggctg cttcccatgc ctgcaacctt gcatccatct gggctacccc acccaagtat
acaataaagt cttacctcag aaaaaaaaaa aaaaaaaa
```

Figure 36A

```
MVALPMVLVLLLVLSRGESELDAKIPSTGDATEWRNPHLSMLGSCQPAPSCQKCILSHPSCAWC
KQLNFTASGEAEARRCARREELLARGCPLEELEEPRGQQEVLQDQPLSQGARGEGATQLAPQRV
RVTLRPGEPQQLQVRFLRAEGYPVDLYYLMDLSYSMKDDLERVRQLGHALLVRLQEVTHSVRIG
FGSFVDKTVLPFVSTVPSKLRHPCPTRLERCQSPFSFHHVLSLTGDAQAFEREVGRQSVSGNLD
SPEGGFDAILQAALCQEQIGWRNVSRLLVFTSDDTFHTAGDGKLGGIFMPSDGHCHLDSNGLYS
RSTEFDYPSVGQVAQALSAANIQPIFAVTSAALPVYQELSKLIPKSAVGELSEDSSNVVQLIMD
AYNSLSSTVTLEHSSLPPGVHISYESQCEGPEKREGKAEDRGQCNHVRINQTVTFWVSLQATHC
LPEPHLLRLRALGFSEELIVELHTLCDCNCSDTQPQAPHCSDGQGHLQCGVCSCAPGRLGRLCE
CSVAELSSPDLESGCRAPNGTGPLCSGKGHCQCGRCSCSGQSSGHLCECDDASCERHEGILCGG
FGRCQCGVCHCANRTGRACECSGDMDSCISPEGGLCSGHGRCKCNRCQCLDGYYGALCDQCPG
CKTPCERHRDCAECGAFRTGPLATNCSTACAHTNVTLALAPILDDGWCKERTLDNQLFFFLVED
DARGTVVLRVRPQEKGADHTQAIVLGCVGGIVAVGLGLVLAYRLSVEIYDRREYSRFEKEQQQL
NWKQDSNPLYKSAITTTINPRFQEADSPTL
```

Figure 36B

SEQUENCE LISTING

<160> NUMBER OF SEQ ID NOS: 69

<210> SEQ ID NO 1
<211> LENGTH: 957
<212> TYPE: DNA
<213> ORGANISM: Homo Sapiens

<400> SEQUENCE: 1

```
cgcgtctgcg gctgcgttcc ccgaaagacg aggctgcgcc cggattccgg tccgcaggga      60
gaccgaaggg cacagctccc cgcgccgcgc acgccgcccg agcccggagt gcggacaccc     120
ccgggatgct tgcgccccag aggacccgcg ccccaagccc ccgcgccgcc cccaggccca     180
cccggagcat gctgcctgca gccatgaagg gcctcggcct ggcgctgctg gccgtcctgc     240
tgtgctcggc gcccgctcat ggcctgtggt gccaggactg cacccctgacc accaactcca     300
gccattgcac cccaaagcag tgccagccgt ccgacacggt gtgtgccagt gtccgaatca     360
ccgatcccag cagcagcagg aaggatcact cggtgaacaa gatgtgtgcc tcctcctgtg     420
acttcgttaa gcgacacttt ttctcagact atctgatggg gtttattaac tctgggatct     480
taaaggtcga cgtggactgc tgcgagaagg atttgtgcaa tggggcggca ggggcagggc     540
acagcccctg ggcctggcc gggggctcc tgctcagcct ggggcctgcc ctcctctggg     600
ctgggccctg atgtctcctc cttcccacgg ggcttctgag cttgctcccc tgagcctgtg     660
gctgccctct ccccagcctg gcgtggctgg ggctgggggc agccttggcc cagctccgtg     720
gctgtggcct gtggctctca ctcctccccc gacgtgaagc ctccctgtct ctccgccagc     780
tctgagtccc aggcagctgg acatctccag gaaaccaggc catctgggca ggaggcctgg     840
ggatgagggt ggggggggac ccccaggtcc cggagggaa gtgaagcaac agcccagctg     900
gaagggcgtc ttctgcggag aaataaagtc acttttgagt cctgagaaaa aaaaaaa      957
```

<210> SEQ ID NO 2
<211> LENGTH: 140
<212> TYPE: PRT
<213> ORGANISM: Homo Sapiens

<400> SEQUENCE: 2

```
Met Leu Pro Ala Ala Met Lys Gly Leu Gly Leu Ala Leu Leu Ala Val
 1               5                  10                  15

Leu Leu Cys Ser Ala Pro Ala His Gly Leu Trp Cys Gln Asp Cys Thr
            20                  25                  30

Leu Thr Thr Asn Ser Ser His Cys Thr Pro Lys Gln Cys Gln Pro Ser
        35                  40                  45

Asp Thr Val Cys Ala Ser Val Arg Ile Thr Asp Pro Ser Ser Ser Arg
    50                  55                  60
```

```
Lys Asp His Ser Val Asn Lys Met Cys Ala Ser Ser Cys Asp Phe Val
 65                  70                  75                  80

Lys Arg His Phe Phe Ser Asp Tyr Leu Met Gly Phe Ile Asn Ser Gly
                 85                  90                  95

Ile Leu Lys Val Asp Val Asp Cys Cys Glu Lys Asp Leu Cys Asn Gly
            100                 105                 110

Ala Ala Gly Ala Gly His Ser Pro Trp Ala Leu Ala Gly Gly Leu Leu
        115                 120                 125

Leu Ser Leu Gly Pro Ala Leu Leu Trp Ala Gly Pro
    130                 135                 140

<210> SEQ ID NO 3
<211> LENGTH: 2683
<212> TYPE: DNA
<213> ORGANISM: Homo Sapiens

<400> SEQUENCE: 3
agggcggtgt caatgcaccc tccagcggtg cgcgcaggcg ggagaaggga gggcggcccg      60
ggcaagtgag acagttaagg cagtgtcccc accacacccc cacccagatt ggccacgccg     120
agctggttct tgacagaagg ccttcgcgga ggaagagggg gcacagctgc acaggacacc     180
ctacggagcc tgcgggcgtg gaactttgcc aggcgcacgg gaacgcgcgc ccttcctgtc     240
agcctcccgg ggcgccaggc tcccgcggcc cgcagcggga cagcctcagt tgtgtgggct     300
ggacccagtc gctggggtac cgaccagtcc tggaaggcgc agaggacgtg gagtggggag     360
gctgccttcc tatgtgcgaa gggccagccg ggcacgcagt cctcagaccc tagtccgcac     420
ccggcaggtc cccacggcac ctgctgcgcc ctcctcgccg ctcccccaac ctccccatct     480
cagaaaacta ccagttctct cccgcccccc ggcgcccctt tcccaggaac gtgcggaggc     540
gggagaagag gaagacagga aggggtgggg gatgtgaagc gaccgtccca gccttccccg     600
cccgccaccc ccaccccaac tcggcagccg tcacgtgatg cctggagtgg aggtggggga     660
gaaaaggcga acttttgtgt ggtgctcccg atcgccagta gttccttcag tctcagccgc     720
caactccgga ggcgcggtgc tcggcccggg agcgcgagcg ggaggagcag agacccgcag     780
ccgggagccc gagcgcgggc gatgcaggct ccgcgagcgg cacctgcggc tcctctaagc     840
tacgaccgtc gtctccgcgg cagcagcgcg ggccccagca gcctcggcag ccacagccgc     900
tgcagccggg gcagcctccg ctgctgtcgc ctcctctgat gcgcttgccc tctcccggcc     960
ccgggactcc gggagaatgt gggtcctagg catcgcggca actttttgcg gattgttctt    1020
gcttccaggc tttgcgctgc aaatccagtg ctaccagtgt gaagaattcc agctgaacaa    1080
cgactgctcc tcccccgagt tcattgtgaa ttgcacggtg aacgttcaag acatgtgtca    1140
gaaagaagtg atggagcaaa gtgccgggat catgtaccgc aagtcctgtg catcatcagc    1200
ggcctgtctc atcgcctctg ccgggtacca gtccttctgc tccccaggga aactgaactc    1260
agtttgcatc agctgctgca acacccctct ttgtaacggg ccaaggccca agaaaagggg    1320
aagttctgcc tcggccctca ggccagggct ccgcaccacc atcctgttcc tcaaattagc    1380
cctcttctcg gcacactgct gaagctgaag gagatgccac ccctcctgc attgttcttc    1440 cagccctcgc ccccaacccc ccactccct gagtgagttt cttctgggtg tccttttatt    1500
ctgggtaggg agcgggagtc cgtgttctct tttgttcctg tgcaaataat gaaagagctc    1560
ggtaaagcat tctgaataaa ttcagcctga ctgaattttc agtatgtact tgaaggaagg    1620
aggtggagtg aaagttcacc cccatgtctg tgtaaccgga gtcaaggcca ggctggcaga    1680
```

```
gtcagtcctt agaagtcact gaggtgggca tctgccttt  gtaaagcctc cagtgtccat    1740
tccatccctg atgggggcat agtttgagac tgcagagtga gagtgacgtt ttcttagggc    1800
tggagggcca gttcccactc aaggctccct cgcttgacat tcaaacttca tgctcctgaa    1860
aaccattctc tgcagcagaa ttggctggtt tcgcgcctga gttgggctct agtgactcga    1920
gactcaatga ctgggactta actgggggct cggcctcgct ctgaaaagtg cttaagaaaa    1980
tcttctcagt tctccttgca gaggactggc gccgggacgc gaagagcaac gggcgctgca    2040
caaagcgggc gctgtcggtg gtggagtgcg catgtacgcg caggcgcttc tcgtggttgg    2100
cgtgctgcag cgacaggcgg cagcacagca cctgcacgaa caccccgccga aactgctgcg    2160 aggacaccgt gtacaggagc gggttgatga ccgagctgag gtagaaaaac gtctccgaga    2220
aggggaggag gatcatgtac gcccggaagt aggacctcgt ccagtcgtgc ttgggtttgg    2280
ccgcagccat gatcctccga atctggttgg gcatccagca tacggccaat gtcacaacaa    2340
tcagccctgg gcagacacga gcaggaggga gagacagaga aaagaaaaac acagcatgag    2400
aacacagtaa atgaataaaa ccataaaata tttagcccct ctgttctgtg cttactggcc    2460
aggaaatggt accaattttt cagtgttgga cttgacagct tcttttgcca caagcaagag    2520
agaatttaac actgtttcaa acccgggga  gttggctgtg ttaaagaaag accattaaat    2580
gctttagaca gtgtatttat accagttgat gtctgttaat tttaaaaaaa tgttttcatt    2640
ggtgtttgtt tgcgtatcca gaaagcagtt catgttatcc ata                      2683

<210> SEQ ID NO 4
<211> LENGTH: 1959
<212> TYPE: DNA
<213> ORGANISM: Homo Sapiens

<400> SEQUENCE: 4
gatgcctgga gtgggaggtg gggagaaaag gcgagacttt tgtgggtgct cccgatcgcc      60
agtagttcct tcagtctcag ccgccaactc cggaggcgcg gtgctcggcc cgggagcgcg     120
agcgggagga gcagagaccc gcagccggga gcccgagcgc gggcgatgca ggctccgcga     180
gcggcacctg cggctcctct aagctacgac cgtcgtctcc gcggcagcag cgcgggcccc     240
agcagcctcg gcagccacag ccgctgcagc cggggcagcc tccgctgctg tcgcctcctc     300
tgatgcgctt gccctctccc ggccccggga ctccgggaga atgtgggtcc taggcatcgc     360
ggcaactttt tgcggattgt tcttgcttcc aggctttgcg ctgcaaatcc agtgctacca     420
gtgtgaagaa ttccagctga caacgactg  ctcctccccc gagttcattg tgaattgcac     480
ggtgaacgtt caagacatgt gtcagaaaga agtgatggag caaagtgccg ggatcatgta     540
ccgcaagtcc tgtgcatcat cagcggcctg tctcatcgcc tctgccgggt accagtcctt     600
ctgctcccca gggaaactga actcagtttg catcagctgc tgcaacaccc ctctttgtaa     660
cgggccaagg cccaagaaaa ggggaagttc tgcctcggcc ctcaggccag gctccgcac     720 caccatcctg ttcctcaaat tagccctctt ctcggcacac tgctgaagct gaaggagatg    780 ccacccctc  ctgcattgtt cttccagccc tcgcccccaa ccccccacct ccctgagtga    840
gtttcttctg ggtgtccttt tattctgggt agggagcggg agtccgtgtt ctcttttgtt    900
cctgtgcaaa taatgaaaga gctcggtaaa gcattctgaa taaattcagc tgactgaat    960 tttcagtatg tacttgaagg aaggaggtgg agtgaaagtt cacccccatg tctgtgtaac   1020
cggagtcaag gccaggctgg cagagtcagt ccttagaagt cactgaggtg gcatctgcc    1080 ttttgtaaag cctccagtgt ccattccatc cctgatgggg gcatagtttg agactgcaga   1140
```

```
gtgagagtga cgttttctta gggctggagg gccagttccc actcaaggct ccctcgcttg   1200
acattcaaac ttcatgctcc tgaaaaccat tctctgcagc agaattggct ggtttcgcgc   1260
ctgagttggg ctctagtgac tcgagactca atgactggga cttagactgg ggctcggcct   1320
cgctctgaaa agtgcttaag aaaatcttct cagttctcct gcagaggac tggcgccggg    1380 acgcgaagag caacgggcgc tgcacaaagc gggcgctgtc ggtggtggag tgcgcatgta   1440
cgcgcaggcg cttctcgtgg ttggcgtgct gcagcgacag gcggcagcac agcacctgca   1500
cgaacacccg ccgaaactgc tgcgaggaca ccgtgtacag gagcgggttg atgaccgagc   1560
tgaggtagaa aaacgtctcc gagaagggga ggaggatcat gtacgcccgg aagtaggacc   1620
tcgtccagtc gtgcttgggt ttggccgcag ccatgatcct ccgaatctgg ttgggcatcc   1680
agcatacggc caatgtcaca acaatcagcc ctgggcagac acgagcagga gggagagaca   1740
gagaaaagaa aaacacagca tgagaacaca gtaaatgaat aaaaccataa aatatttagc   1800
ccctctgttc tgtgcttact ggccaggaaa tggtaccaat ttttcagtgt tggacttgac   1860
agcttctttt gccacaagca agagagaatt taacactgtt tcaaacccgg gggagttggc   1920
tgtgttaaag aaagaccatt aaatgcttta gacagtgta                          1959
```

<210> SEQ ID NO 5
<211> LENGTH: 141
<212> TYPE: PRT
<213> ORGANISM: Homo Sapiens

<400> SEQUENCE: 5

```
Met Trp Val Leu Gly Ile Ala Ala Thr Phe Cys Gly Leu Phe Leu Leu
  1               5                  10                  15

Pro Gly Phe Ala Leu Gln Ile Gln Cys Tyr Gln Cys Glu Glu Phe Gln
             20                  25                  30

Leu Asn Asn Asp Cys Ser Ser Pro Glu Phe Ile Val Asn Cys Thr Val
         35                  40                  45

Asn Val Gln Asp Met Cys Gln Lys Glu Val Met Glu Gln Ser Ala Gly
     50                  55                  60

Ile Met Tyr Arg Lys Ser Cys Ala Ser Ser Ala Ala Cys Leu Ile Ala
 65                  70                  75                  80

Ser Ala Gly Tyr Gln Ser Phe Cys Ser Pro Gly Lys Leu Asn Ser Val
                 85                  90                  95

Cys Ile Ser Cys Cys Asn Thr Pro Leu Cys Asn Gly Pro Arg Pro Lys
            100                 105                 110

Lys Arg Gly Ser Ser Ala Ser Ala Leu Arg Pro Gly Leu Arg Thr Thr
        115                 120                 125

Ile Leu Phe Leu Lys Leu Ala Leu Phe Ser Ala His Cys
    130                 135                 140
```

<210> SEQ ID NO 6
<211> LENGTH: 1745
<212> TYPE: DNA
<213> ORGANISM: Homo Sapiens

<400> SEQUENCE: 6

```
aaggctgggg ttgcctgggg cgaggttact catcctgggc tcaggtaaga gggcccgagc     60
tcggaggcgg cacatccagg ggggacgcca agggagcagg acggagccat ggaccccgcc    120
aggaaagcag gtgcccaggc catgatctgg actgcaggct ggctgctgct gctgctgctt    180
cgcggaggag cgcaggccct ggagtgctac agctgcgtgc agaaagcaga tgacggatgc    240
```

-continued

```
tccccgaaca agatgaagac agtgaagtgc gcgccgggcg tggacgtctg caccgaggcc    300
gtggggcgg tggagaccat ccacggacaa ttctcgctgg cagtgcgggg ttgcggttcg    360
ggactccccg gcaagaatga ccgcggcctg gatcttcacg ggcttctggc gttcatccag    420
ctgcagcaat gcgctcagga tcgctgcaac gccaagctca acctcacctc gcgggcgctc    480
gacccggcag gtaatgagag tgcatacccg cccaacggcg tggagtgcta cagctgtgtg    540
ggcctgagcc gggaggcgtg ccagggtaca tcgccgccgg tcgtgagctg ctacaacgcc    600
agcgatcatg tctacaaggg ctgcttcgac ggcaacgtca ccttgacggc agctaatgtg    660
actgtgtcct tgcctgtccg gggctgtgtc caggatgaat tctgcactcg ggatggagta    720
acaggcccag ggttcacgct cagtggctcc tgttgccagg ggtcccgctg taactctgac    780
ctccgcaaca agacctactt ctcccctcga atcccacccc ttgtccggct gccccctcca    840
gagcccacga ctgtggcctc aaccacatct gtcaccactt ctacctcggc ccagtgaga    900
cccacatcca ccaccaaacc catgccagcg ccaaccagtc agactccgag acagggagta    960
gaacacgagg cctcccggga tgaggagccc aggttgactg gaggcgccgc tggccaccag    1020
gaccgcagca attcagggca gtatcctgca aagggggggc cccagcagcc ccataataaa    1080
ggctgtgtgg ctcccacagc tggattggca gcccttctgt tggccgtggc tgctggtgtc    1140
ctactgtgag cttctccacc tggaaatttc cctctcacct acttctctgg ccctgggtac    1200
ccctcttctc atcacttcct gttcccacca ctggactggg ctggcccagc ccctgttttt    1260
ccaacattcc ccagtatccc cagcttctgc tgcgctggtt tgcggctttg ggaaataaaa    1320
taccgttgta tatattctgc caggggtgtt ctagcttttt gaggacagct cctgtatcct    1380
tctcatcctt gtctctccgc ttgtcctctt gtgatgttag acagagtga gagaagtcag    1440
ctgtcacggg gaaggtgaga gagaggatgc taagcttcct actcactttc tcctagccag    1500
cctggacttt ggagcgtggg gtgggtggga caatggctcc ccactctaag cactgcctcc    1560
cctactcccc gcatctttgg ggaatcggtt ccccatatgt cttccttact agactgtgag    1620
ctcctcgagg gcagggaccg tgccttatgt ctgtgtgtga tcagtttctg gcacataaat    1680
gcctcaataa agatttaatt actttgaaaa aaaaaaaaaa aaaaaaaaa aaaaaaaaa    1740
aaaaa                                                              1745
```

<210> SEQ ID NO 7
<211> LENGTH: 346
<212> TYPE: PRT
<213> ORGANISM: Homo Sapiens

<400> SEQUENCE: 7

```
Met Asp Pro Ala Arg Lys Ala Gly Ala Gln Ala Met Ile Trp Thr Ala
 1               5                  10                  15

Gly Trp Leu Leu Leu Leu Leu Leu Arg Gly Gly Ala Gln Ala Leu Glu
            20                  25                  30

Cys Tyr Ser Cys Val Gln Lys Ala Asp Asp Gly Cys Ser Pro Asn Lys
        35                  40                  45

Met Lys Thr Val Lys Cys Ala Pro Gly Val Asp Val Cys Thr Glu Ala
    50                  55                  60

Val Gly Ala Val Glu Thr Ile His Gly Gln Phe Ser Leu Ala Val Arg
65                  70                  75                  80

Gly Cys Gly Ser Gly Leu Pro Gly Lys Asn Asp Arg Gly Leu Asp Leu
                85                  90                  95
```

```
His Gly Leu Leu Ala Phe Ile Gln Leu Gln Gln Cys Ala Gln Asp Arg
            100                 105                 110
Cys Asn Ala Lys Leu Asn Leu Thr Ser Arg Ala Leu Asp Pro Ala Gly
        115                 120                 125
Asn Glu Ser Ala Tyr Pro Pro Asn Gly Val Glu Cys Tyr Ser Cys Val
    130                 135                 140
Gly Leu Ser Arg Glu Ala Cys Gln Gly Thr Ser Pro Pro Val Val Ser
145                 150                 155                 160
Cys Tyr Asn Ala Ser Asp His Val Tyr Lys Gly Cys Phe Asp Gly Asn
                165                 170                 175
Val Thr Leu Thr Ala Ala Asn Val Thr Val Ser Leu Pro Val Arg Gly
            180                 185                 190
Cys Val Gln Asp Glu Phe Cys Thr Arg Asp Gly Val Thr Gly Pro Gly
        195                 200                 205
Phe Thr Leu Ser Gly Ser Cys Cys Gln Gly Ser Arg Cys Asn Ser Asp
    210                 215                 220
Leu Arg Asn Lys Thr Tyr Phe Ser Pro Arg Ile Pro Pro Leu Val Arg
225                 230                 235                 240
Leu Pro Pro Pro Glu Pro Thr Thr Val Ala Ser Thr Thr Ser Val Thr
                245                 250                 255
Thr Ser Thr Ser Ala Pro Val Arg Pro Thr Ser Thr Thr Lys Pro Met
            260                 265                 270
Pro Ala Pro Thr Ser Gln Thr Pro Arg Gln Gly Val Glu His Glu Ala
        275                 280                 285
Ser Arg Asp Glu Glu Pro Arg Leu Thr Gly Gly Ala Ala Gly His Gln
    290                 295                 300
Asp Arg Ser Asn Ser Gly Gln Tyr Pro Ala Lys Gly Gly Pro Gln Gln
305                 310                 315                 320
Pro His Asn Lys Gly Cys Val Ala Pro Thr Ala Gly Leu Ala Ala Leu
                325                 330                 335
Leu Leu Ala Val Ala Ala Gly Val Leu Leu
            340                 345

<210> SEQ ID NO 8
<211> LENGTH: 2490
<212> TYPE: DNA
<213> ORGANISM: Homo Sapiens

<400> SEQUENCE: 8
gatccgcttt gcgcatccca gtgattcttg ggttccgcgt gtagtttcgg aaggagacat    60
cgaagcaggg cgaggcgcag agggcgttgc ggactcatgc cccagtcggc agtgcggggt   120
cccaagccct gcagtgctac agctttgagc acacctactt tggccccttt gacctcaggg   180
ccatgaagct gcccagcatc tcctgtcctc atgagtgctt tgaggctatc ctgtctctgg   240
acaccgggta tcgcgcgccg gtgaccctgg tgcggaaggg ctgctggacc gggcctcctg   300
cgggccagac gcaatcgaac gcggacgcgc tgccgccaga ctactcggtg gtgcgcggct   360
gcacaactga caaatgcaac gcccacctca tgactcatga cgccctcccc aacctgagcc   420
aagcacccga cccgccgacg ctcagcggcg ccgagtgcta cgcctgtatc ggggtccacc   480
aggatgactg cgctatcggc aggtcccgac gagtccagtg tcaccaggac agaccgcct   540 gcttccaggg caatggcaga atgacagttg caatttctc agtccctgtg tacatcagaa   600
cctgccaccg gccctcctgc accaccgagg caccaccag ccctggaca gccatcgacc   660 tccagggctc ctgctgtgag gggtaccctct gcaacaggaa atccatgacc cagcccttca   720
```

```
ccagtgcttc agccaccacc cctcccgag cactacaggt cctggccctg ctcctcccag     780
tcctcctgct ggtggggctc tcagcataga ccgcccctcc aggatgctgg ggacagggct     840
cacacacctc attcttgctg cttcagcccc tatcacatag ctcactggaa atgatgttaa    900
aagtaagaat tgcactcctg tccctctggc cttccatctc tcccgccctt gtgccccaca    960
acctggccaa cagtactgga agaaactgga cacagtcacc agcatcccg gggagggcaa   1020
aacagccatg tcgtgccccg atgaagagca attctgatca cagctgttac tcactgagca   1080
ccagccaggc accaggcacc ccataacacg gcttcctgtg ctctccctcc agagcctgtc   1140
gcagctctag gagggagcta acaatgatg tctttattag tgtcatcatg agaagcccaa   1200
taagcagtat gccctaacag ttagtaggcc aggctctgga gctaagctgc atgggttcaa   1260
atcccagctc caccattcag cctgcagaga ccatgagcga gttacttaag ccaggctctg   1320
gagctaagct gcatgggttc aaatcccagc tccagcattc agcctacaga gccatgggt   1380
gagttactta agccaggctc tggagctaag ctgcatgggt tcaaatccca gctccaccat   1440
tcagcctgca gagactgtgg gtgagttact tgagctctct gtgccaatat tttctcacct   1500
ataaggtgga ggtgaaaata aactctataa catgacaaga actacttcac agtagttgca   1560
gtgaggattc aacgagatga acatttagta cttgggacac agcagtggcc cagtgtaaat   1620
gggctacttg tcataagccc taagtcacag gtcaacaaac tgagaggcaa aagcacttgg   1680
ttgagcttgt gtatctagtg agtatggatt cagggaccag attcccagcc ccacgaactg   1740
ctaagcaacc ccacctccta aacacatgag tgccgattaa cttcacagaa aaacacacaa   1800
ggcaaagttc agcgaggtga aattctccaa gctataaaga tcagggaaga cttcctggag   1860
gaattcaccc ttgagcaaaa tcctaaagga tcaatagtag ctggcaaaaa gaagcaggag   1920
gaagcgcatt ctaggtagag gagacagcct ggacaaaggt ctgagggagg aaggagcaca   1980
aggagtgcag gacactttca tgagtgcagg acactttcat aactgcatga acttcataga   2040
gatgggatcc tttagcatgt tctctgtgca catgcttgac catgttcttt cacatgcttt   2100
ttgccacttg atctttccag caactcagtg agagaagcaa aaaagtaagt tgcatcctgc   2160
tattgtctga atgtttgtgt ctccccaaaa ttcatctttt gaaacctaat taccaaagtg   2220
atattactgg gaggtgggc ctttgggagg tggtgagatc atgagggtgg agcccccatg   2280
aataggatta gtgcccttat aaaagaggcc ctggagagct gccttgcccc ttccaccaca   2340
tgagaacaca gccagcaggt gcctataagc aagaaagtgg gttctcacca gccatcgaat   2400
ctgctggtgc attgattgca gacttcccag actccagagc tatgagacat aaatttctgt   2460
tgtgtataag ccaaaaaaaa aaaaaaaaa                                      2490
```

<210> SEQ ID NO 9
<211> LENGTH: 2118
<212> TYPE: DNA
<213> ORGANISM: Homo Sapiens

<400> SEQUENCE: 9

```
gattcttggg ttccgcgcgt agtttcggaa ggagacatcg aagcagggcg aggcgcagag      60
ggcgttgcgg actcatgccc cagtcggcag tgcgggtcc caagccctgc agtgctacag    120
ctttgagcac acctactttg gccctttga cctcagggcc atgaagctgc ccagcatctc    180
ctgtcctcat gagtgctttg aggctatcct gtctctggac accgggtatc gcgcgccggt    240
gaccctggtg cggaagggct gctggaccgg gcctcctgcg ggccagacgc aatcgaaccc    300
```

```
ggacgcgctg ccgccagact actcggtggt gcgcggctgc acaactgaca aatgcaacgc    360
ccacctcatg actcatgacg ccctccccaa cctgagccaa gcacccgacc cgccgacgct    420
cagcggcgcc gagtgctacg cctgtatcgg ggtccaccag gatgactgcg ctatcggcag    480
gtcccgacga gtccagtgtc accaggacca gaccgcctgc ttccagggca gtggcagaat    540
gacagttggc aatttctcag tccctgtgta catcagaacc tgccaccggc cctcctgcac    600
caccgagggc accaccagcc cctggacagc catcgacctc cagggctcct gctgtgaggg    660
gtacctctgc aacaggaaat ccatgaccca gcccttcacc agtgcttcag ccaccacccc    720
tccccgagca ctacaggtcc tggccctgct cctcccagtc ctcctgctgg tggggctctc    780
agcatagacc gcccctccag gatgctgggg acagggctca cacacctcat tcttgctgct    840
tcagccccta tcacatagct cactggaaaa tgatgttaaa gtaagaattg cactcctgtc    900
cctctggcct tccatctctc ctgcccttgt gccccacaac ctggccaaca gtactggaag    960
aaactggaca cagtcaccag catcccaggg gagggcaaaa cagccatgtc gtgccctgat   1020
gaagagcaat tctgatcaca gctgttactc actgagcacc agccaggcac caggcacccc   1080
ataacacggc ttcctgtgct ctccttccag agcctgtcgc agctctaggg gggagctata   1140
caatgatgtc tttattagtg tcatcatgag aagcccaata agcagtatgc cctaacagtt   1200
agtaggccag gctctggagc taagctgcat gggttcacat cccagctcca ccattcagcc   1260
tgcagagacc atgagcgagt tacttaagcc aggctctgga gctaagctgc atgggttcaa   1320
atcccagctc cagcattcag cctacagaga ccatgggtga gttacttaag ccaggctctg   1380
gagctaagct gcatgggttc aaatcccagc tccaccattc agcctgcaga gactgtgggt   1440
gagttacttg agctctctgt gccaatattt tctcacctat aaggtggagg tgaaaataaa   1500
ctctataaca tgacaagaac tacttcacag tagttgcagt gaggattcaa cgagatgaac   1560
atttagtact tgggacacag cagtggccca gtataaatgg gctacttgtc ataagcccta   1620
agtcacaggt caacaaactg agaggtaaaa gcacttggtt gagcttgtgt atctagtgag   1680
tatggattca gggaccagat tcccagcccc acgaactgct aagcaacccc acctcctaaa   1740
cacatgagtg ccgattaact tcacagaaaa acacacaagg caaagttcag cgaggtgaaa   1800
ttctccaagc tataaagatc agggaagact tcctggagga attcaccctt gagcaaaatc   1860
ctaaaggatc aatagtagct ggcaaaaaga agcaggagga agcacatttt aggtagagga   1920
gacagcctgg acaaaggtct gagggaggaa ggaacacaag gagtgcagga cactttcata   1980
actgcatgaa cttcatagag atgggatcct ttagcatgtt ctctgtgcac atgcttgacc   2040
atgttctttc acatgctttt tgccacttga tctttccagc aactcagtga gagaagcaaa   2100
aaagtaagtt gcatcctg                                                 2118
```

<210> SEQ ID NO 10
<211> LENGTH: 208
<212> TYPE: PRT
<213> ORGANISM: Homo Sapiens

<400> SEQUENCE: 10

```
Met Lys Leu Pro Ser Ile Ser Cys Pro His Glu Cys Phe Glu Ala Ile
 1               5                   10                  15

Leu Ser Leu Asp Thr Gly Tyr Arg Ala Pro Val Thr Leu Val Arg Lys
             20                  25                  30

Gly Cys Trp Thr Gly Pro Pro Ala Gly Gln Thr Gln Ser Asn Ala Asp
         35                  40                  45
```

```
Ala Leu Pro Pro Asp Tyr Ser Val Val Arg Gly Cys Thr Thr Asp Lys
     50                  55                  60

Cys Asn Ala His Leu Met Thr His Asp Ala Leu Pro Asn Leu Ser Gln
 65                  70                  75                  80

Ala Pro Asp Pro Thr Leu Ser Gly Ala Glu Cys Tyr Ala Cys Ile
                 85                  90                  95

Gly Val His Gln Asp Asp Cys Ala Ile Gly Arg Ser Arg Val Gln
            100                 105                 110

Cys His Gln Asp Gln Thr Ala Cys Phe Gln Gly Asn Gly Arg Met Thr
            115                 120                 125

Val Gly Asn Phe Ser Val Pro Val Tyr Ile Arg Thr Cys His Arg Pro
    130                 135                 140

Ser Cys Thr Thr Glu Gly Thr Thr Ser Pro Trp Thr Ala Ile Asp Leu
145                 150                 155                 160

Gln Gly Ser Cys Cys Glu Gly Tyr Leu Cys Asn Arg Lys Ser Met Thr
                165                 170                 175

Gln Pro Phe Thr Ser Ala Ser Ala Thr Thr Pro Pro Arg Ala Leu Gln
            180                 185                 190

Val Leu Ala Leu Leu Leu Pro Val Leu Leu Val Gly Leu Ser Ala
    195                 200                 205

<210> SEQ ID NO 11
<211> LENGTH: 806
<212> TYPE: DNA
<213> ORGANISM: Homo Sapiens

<400> SEQUENCE: 11
gcccaccccc gcccagcccg tgcctataag gccttggcaa tgcaggggcc cgcactgctc      60
ccagacgaca tcagagatga ggacagcatt gctgctcctt gcagccctgg ctgtggctac     120
agggccagcc cttaccctgc gctgccacgt gtgcaccagc tccagcaact gcaagcattc     180
tgtggtctgc ccggccagct ctcgcttctg caagaccacg aacacagtgg agcctctgag     240
ggggaatctg gtgaagaagg actgtgcgga gtcgtgcaca cccagctaca ccctgcaagg     300
ccaggtcagc agcggcacca gctccaccca gtgctgccag gaggacctgt gcaatgagaa     360
gctgcacaac gctgcacccc ccgcaccgc cctcgcccac agtgccctca gcctggggct     420
ggccctgagc ctcctggccg tcatcttagc ccccagcctg tgaccttccc ccagggaag     480 gccctcatg cctttccttc cctttctctg gggattccac acctctcttc cccagccgca     540 acggggtgc caggagcccc aggctgaggg cttccccgaa agtctgggac caggtccagg     600
tgggcatgga atgctgatga cttggagcag gccccacaga ccccacagag gatgaagcca     660
ccccacagag gatgcagccc ccagctgcat ggaaggtgga ggacagaagc cctgtggatc     720
cccggatttc acactccttc tgttttgttg ccgtttattt ttgtactcaa atctctacat     780
ggagataaat gatttaaacc agaaaa                                          806

<210> SEQ ID NO 12
<211> LENGTH: 128
<212> TYPE: PRT
<213> ORGANISM: Homo Sapiens

<400> SEQUENCE: 12

Met Arg Thr Ala Leu Leu Leu Ala Ala Leu Ala Val Ala Thr Gly
  1               5                  10                  15

Pro Ala Leu Thr Leu Arg Cys His Val Cys Thr Ser Ser Ser Asn Cys
                 20                  25                  30
```

```
Lys His Ser Val Val Cys Pro Ala Ser Ser Arg Phe Cys Lys Thr Thr
            35                  40                  45
Asn Thr Val Glu Pro Leu Arg Gly Asn Leu Val Lys Lys Asp Cys Ala
 50                  55                  60
Glu Ser Cys Thr Pro Ser Tyr Thr Leu Gln Gly Gln Val Ser Ser Gly
 65                  70                  75                  80
Thr Ser Ser Thr Gln Cys Cys Gln Glu Asp Leu Cys Asn Glu Lys Leu
                 85                  90                  95
His Asn Ala Ala Pro Thr Arg Thr Ala Leu Ala His Ser Ala Leu Ser
            100                 105                 110
Leu Gly Leu Ala Leu Ser Leu Leu Ala Val Ile Leu Ala Pro Ser Leu
            115                 120                 125
```

<210> SEQ ID NO 13
<211> LENGTH: 1145
<212> TYPE: DNA
<213> ORGANISM: Homo Sapiens

<400> SEQUENCE: 13

```
gctccggcca gccgcggtcc agagcgcgcg aggttcgggg agctccgcca ggctgctggt    60
acctgcgtcc gcccggcgag caggacaggc tgctttggtt tgtgacctcc aggcaggacg   120
gccatcctct ccagaatgaa gatcttcttg ccagtgctgc tggctgccct tctgggtgtg   180
gagcgagcca gctcgctgat gtgcttctcc tgcttgaacc agaagagcaa tctgtactgc   240
ctgaagccga ccatctgctc cgaccaggac aactactgcg tgactgtgtc tgctagtgcc   300
ggcattggga tctcgtgac atttggccac agcctgagca agacctgttc ccggcctgc    360
cccatcccag aaggcgtcaa tgttggtgtg gcttccatgg gcatcagctg ctgccagagc   420
tttctgtgca atttcagtgc ggccgatggc gggctgcggg caagcgtcac cctgctgggt   480
gccgggctgc tgctgagcct gctgccggcc ctgctgcggt ttggcccctg accgccaga    540
ccctgtcccc cgatccccca gctcaggaag gaaagcccag ccctttctgg atcccacagt   600
gtatgggagc cctgactcc tcacgtgcct gatctgtgcc cttggtccca ggtcaggccc    660
accccctgca cctccacctg ccccagcccc tgcctctgcc caagtgggcc agctgccctc   720
acttctgggg tggatgatgt gaccttcctt gggggactgc ggaagggacg agggttccct   780
ggagtcttac ggtccaacat cagaccaagt cccatggaca tgctgacagg gtccccaggg   840
agaccgtgtc agtagggatg tgtgcctggc tgtgtacgtg ggtgtgcagt gcacgtgaga   900
gcacgtggcg gcttctgggg gccatgtttg gggagggagg tgtgccagca gcctggagag   960
cctcagtccc tgtagccccc tgccctggca cagctgcatg cacttcaagg gcagcctttg  1020
ggggttgggg tttctgccac ttccgggtct aggccctgcc caaatccagc cagtcctgcc  1080
ccagcccacc cccacattgg agccctcctg ctgctttggt gcctcaaata aatacagatg  1140
tcccc                                                              1145
```

<210> SEQ ID NO 14
<211> LENGTH: 131
<212> TYPE: PRT
<213> ORGANISM: Homo Sapiens

<400> SEQUENCE: 14

```
Met Lys Ile Phe Leu Pro Val Leu Leu Ala Ala Leu Leu Gly Val Glu
  1               5                  10                  15
Arg Ala Ser Ser Leu Met Cys Phe Ser Cys Leu Asn Gln Lys Ser Asn
```

```
                 20                  25                  30
Leu Tyr Cys Leu Lys Pro Thr Ile Cys Ser Asp Gln Asp Asn Tyr Cys
             35                  40                  45

Val Thr Val Ser Ala Ser Ala Gly Ile Gly Asn Leu Val Thr Phe Gly
 50                  55                  60

His Ser Leu Ser Lys Thr Cys Ser Pro Ala Cys Pro Ile Pro Glu Gly
 65                  70                  75                  80

Val Asn Val Gly Val Ala Ser Met Gly Ile Ser Cys Cys Gln Ser Phe
                 85                  90                  95

Leu Cys Asn Phe Ser Ala Ala Asp Gly Gly Leu Arg Ala Ser Val Thr
                100                 105                 110

Leu Leu Gly Ala Gly Leu Leu Leu Ser Leu Leu Pro Ala Leu Leu Arg
            115                 120                 125

Phe Gly Pro
        130

<210> SEQ ID NO 15
<211> LENGTH: 550
<212> TYPE: DNA
<213> ORGANISM: Homo Sapiens

<400> SEQUENCE: 15
ccagtctgtc gccacctcac ttggtgtctg ctgtccccgc caggcaagcc tggggtgaga      60
gcacagagga gtgggccggg accatgcggg ggacgcggct ggcgctcctg cgctggtgc     120 tggctgcctg cggagagctg gcgccggccc tgcgctgcta cgtctgtccg agcccacag     180 gagtgtcgga ctgtgtcacc atcgccacct gcaccaccaa cgaaaccatg tgcaagacca     240
cactctactc ccgggagata gtgtacccct tccaggggga ctccacggtg accaagtcct     300
gtgccagcaa gtgtaagccc tcggatgtgg atggcatcgg ccagaccctg ccgtgtcct     360 gctgcaatac tgagctgtgc aatgtagacg gggcgcccgc tctgaacagc ctccactgcg     420
gggccctcac gctcctccca ctcttgagcc tccgactgta gagtccccgc caccccat     480 ggccctatgc ggcccagccc cgaatgcctt gaagaagtgc ccctgcacc aggaaaaaaa     540 aaaaaaaaaa                                                            550

<210> SEQ ID NO 16
<211> LENGTH: 125
<212> TYPE: PRT
<213> ORGANISM: Homo Sapiens

<400> SEQUENCE: 16

Met Arg Gly Thr Arg Leu Ala Leu Leu Ala Leu Val Leu Ala Ala Cys
  1               5                  10                  15

Gly Glu Leu Ala Pro Ala Leu Arg Cys Tyr Val Cys Pro Glu Pro Thr
             20                  25                  30

Gly Val Ser Asp Cys Val Thr Ile Ala Thr Cys Thr Thr Asn Glu Thr
             35                  40                  45

Met Cys Lys Thr Thr Leu Tyr Ser Arg Glu Ile Val Tyr Pro Phe Gln
 50                  55                  60

Gly Asp Ser Thr Val Thr Lys Ser Cys Ala Ser Lys Cys Lys Pro Ser
 65                  70                  75                  80

Asp Val Asp Gly Ile Gly Gln Thr Leu Pro Val Ser Cys Cys Asn Thr
                 85                  90                  95

Glu Leu Cys Asn Val Asp Gly Ala Pro Ala Leu Asn Ser Leu His Cys
                100                 105                 110
```

-continued

Gly Ala Leu Thr Leu Leu Pro Leu Leu Ser Leu Arg Leu
        115                 120                 125

<210> SEQ ID NO 17
<211> LENGTH: 3901
<212> TYPE: DNA
<213> ORGANISM: Homo Sapiens

<400> SEQUENCE: 17

| | | | | | |
|---|---|---|---|---|---|
| aagatggcgg | cgtgtggacg | tgtacggagg | atgttccgct | tgtcggcggc | gctgcatctg | 60 |
| ctgctgctat | tcgcggccgg | ggccgagaaa | ctccccggcc | atggcgtcca | cagccagggc | 120 |
| cagggtcccg | gggccaactt | tgtgtccttc | gtagggcagg | ccggaggcgg | cggcccggcg | 180 |
| ggtcagcagc | tgccccagct | gcttcagtca | tcgcagcttc | agcagcaaca | gcagcagcag | 240 |
| caacagcaac | agcagcttca | gccgccgcag | ccgccttttc | cggcgggtgg | gcctccggcc | 300 |
| cggcggggag | gagcggggc | tggtggggc | tggaagctgg | cggaggaaga | gtcctgcagg | 360 |
| gaggacgtga | cccgcgtgtg | ccctaagcac | acctggagca | caacctggc | ggtgctcgag | 420 |
| tgcctgcagg | atgtgaggga | gcctgaaaat | gaaatttctt | cagactgcaa | tcatttgttg | 480 |
| tggaattata | agctgaacct | aactacagat | cccaaatttg | aatctgtggc | cagagaggtt | 540 |
| tgcaaatcta | ctataacaga | gattaaagaa | tgtgctgatg | aaccggttgg | aaaaggttac | 600 |
| atggtttcct | gcttagtgga | tcaccgaggc | aacatcactg | agtatcagtg | tcaccagtac | 660 |
| attaccaaga | tgacggccat | cattttagt | gattaccgtt | taatctgtgg | cttcatggat | 720 |
| gactgcaaaa | atgacatcaa | cattctgaaa | tgtggcagta | ttcggcttgg | agaaaaggat | 780 |
| gcacattcac | aaggtgaggt | ggtatcatgc | ttggagaaag | gcctggtgaa | agaagcagaa | 840 |
| gaaagagaac | ccaagattca | agtttctgaa | ctctgcaaga | aagccattct | ccgggtggct | 900 |
| gagctgtcat | cggatgactt | tcacttagac | cggcatttat | attttgcttg | ccgagatgat | 960 |
| cgggagcgtt | tttgtgaaaa | tacacaagct | ggtgagggca | gagtgtataa | gtgcctcttt | 1020 |
| aaccataaat | ttgaagaatc | catgagtgaa | aagtgtcgag | aagcacttac | aacccgccaa | 1080 |
| aagctgattg | cccaggatta | taaagtcagt | tattcattgg | ccaaatcctg | taaaagtgac | 1140 |
| ttgaagaaat | accggtgcaa | tgtggaaaac | cttccgcgat | cgcgtgaagc | caggctctcc | 1200 |
| tacttgttaa | tgtgcctgga | gtcagctgta | cacagagggc | gacaagtcag | cagtgagtgc | 1260 |
| caggggagga | tgctggatta | ccgacgcatg | ttgatgaag | actttctct | gagccctgag | 1320 |
| atcatcctaa | gctgtcgggg | ggagattgaa | caccattgtt | ccggattaca | tcgaaaaggg | 1380 |
| cggaccctac | actgtctgat | gaaagtagtt | cgaggggaga | agggaacct | tggaatgaac | 1440 |
| tgccagcagg | cgcttcaaac | actgattcag | gagactgacc | ctggtgcaga | ttaccgcatt | 1500 |
| gatcgagctt | tgaatgaagc | ttgtgaatct | gtaatccaga | cagcctgcaa | acatataaga | 1560 |
| tctggagacc | caatgatctt | gtcgtgcctg | atggaacatt | tatacacaga | gaagatggta | 1620 |
| gaagactgtg | aacaccgtct | cttagagctg | cagtatttca | tctcccggga | ttggaagctg | 1680 |
| gaccctgtcc | tgtaccgcaa | gtgccaggga | gacgcttctc | gtctttgcca | cccccacggt | 1740 |
| tggaatgaga | ccagtgaatt | tatgcctcag | ggagctgtgt | tctcttgttt | atacagacac | 1800 |
| gcctaccgca | ctgaggaaca | gggaaggagg | ctctcacggg | agtgccgagc | tgaagtccaa | 1860 |
| aggatcctac | accagcgtgc | catggatgtc | aagctggatc | ctgccctcca | ggataagtgc | 1920 |
| ctgattgatc | tggaaaaatg | gtgcagtgag | aaaacagaga | ctggacagga | gctggagtgc | 1980 |
| cttcaggacc | atctggatga | cttggtggtg | gagtgtagag | atatagttgg | caacctcact | 2040 |

-continued

```
gagttagaat cagaggatat tcaaatagaa gccttgctga tgagagcctg tgagcccata        2100
attcagaact tctgccacga tgtggcagat aaccagatag actctgggga cctgatggag        2160
tgtctgatac agaacaaaca ccagaaggac atgaacgaga agtgtgccat cggagttacc        2220
cacttccagc tggtgcagat gaaggatttt cggttttctt acaagtttaa aatggcctgc        2280
aaggaggacg tgttgaagct ttgcccaaac ataaaaaaga aggtggacgt ggtgatctgc        2340
ctgagcacga ccgtgcgcaa tgacactctg caggaagcca aggagcacag ggtgtccctg        2400
aagtgccgca ggcagctccg tgtggaggag ctggagatga cggaggacat ccgcttggag        2460
ccagatctat acgaagcctg caagagtgac atcaaaaact tctgttccgc tgtgcaatat        2520
ggcaacgctc agattatcga atgtctgaaa gaaaacaaga agcagctaag cacccgctgc        2580
caccaaaaag tatttaagct gcaggagaca gagatgatgg acccagagct agactacacc        2640
ctcatgaggg tctgcaagca gatgataaag aggttctgtc cggaagcaga ttctaaaacc        2700
atgttgcagt gcttgaagca aaataaaaac agtgaattga tggatcccaa atgcaaacag        2760
atgataacca agcgccagat cacccagaac acagattacc gcttaaaccc catgttaaga        2820
aaagcctgta aagctgacat tcctaaattc tgtcacggta tcctgactaa ggccaaggat        2880
gattcagaat tagaaggaca agtcatctct tgcctgaagc tgagatatgc tgaccagcgc        2940
ctgtcttcag actgtgaaga ccagatccga atcattatcc aggagtccgc cctggactac        3000
cgcctggatc ctcagctcca gctgcactgc tcagacgaga tctccagtct atgtgctgaa        3060
gaagcagcag cccaagagca gacaggtcag gtggaggagt gcctcaaggt caacctgctc        3120
aagatcaaaa cagaattgtg taaaaaggaa gtgctaaaca tgctgaagga agcaaagca         3180 gacatctttg ttgacccggt acttcatact gcttgtgccc tggacattaa acaccactgc        3240
gcagccatca cccctggccg cgggcgtcaa atgtcctgtc tcatggaagc actggaggat        3300
aagcgggtga ggttacagcc cgagtgcaaa aagcgcctca tgaccggat tgagatgtgg         3360 agttacgcag caaaggtggc cccagcagat ggcttctctg atcttgccat gcaagtaatg        3420
acgtctccat ctaagaacta cattctctct gtgatcagtg ggagcatctg tatattgttc        3480
ctgattggcc tgatgtgtgg acggatcacc aagcgagtga cacgagagct caaggacagg        3540
tagagccacc ttgaccacca aaggaactac ctatccagtg cccagtttgt acagccctct        3600
tgtatagcat ccccactcac ctcgctcttc tcagaagtga caccaacccc gtgttagagc        3660
attagcagat gtccactgcg ttgtcccatc cagcctccac tcgtgtccat ggtgtcctcc        3720
tcctcctcac cgtgcagcag cagcagctgg tcgctggggt tactgccttt gtttggcaaa        3780
cttgggttta cctgcctgta gacaagtctc tctcatacca acagaacttc cggtacttcc        3840
agaaccaact cacctgacct gcaactcaaa ggcttttta agaaaaccac caaaaaaaaa         3900
a                                                                        3901
```

<210> SEQ ID NO 18
<211> LENGTH: 1179
<212> TYPE: PRT
<213> ORGANISM: Homo Sapiens

<400> SEQUENCE: 18

```
Met Ala Ala Cys Gly Arg Val Arg Arg Met Phe Arg Leu Ser Ala Ala
 1               5                  10                  15

Leu His Leu Leu Leu Phe Ala Ala Gly Ala Glu Lys Leu Pro Gly
            20                  25                  30
```

```
His Gly Val His Ser Gln Gly Gln Gly Pro Gly Ala Asn Phe Val Ser
         35                  40                  45
Phe Val Gly Gln Ala Gly Gly Gly Pro Ala Gly Gln Gln Leu Pro
    50                  55                  60
Gln Leu Leu Gln Ser Ser Gln Leu Gln Gln Gln Gln Gln Gln Gln Gln
65                  70                  75                  80
Gln Gln Gln Gln Leu Gln Pro Pro Gln Pro Phe Pro Ala Gly Gly
                85                  90                  95
Pro Pro Ala Arg Arg Gly Gly Ala Gly Gly Gly Trp Lys Leu
            100                 105                 110
Ala Glu Glu Glu Ser Cys Arg Glu Asp Val Thr Arg Val Cys Pro Lys
            115                 120                 125
His Thr Trp Ser Asn Asn Leu Ala Val Leu Glu Cys Leu Gln Asp Val
    130                 135                 140
Arg Glu Pro Glu Asn Glu Ile Ser Ser Asp Cys Asn His Leu Leu Trp
145                 150                 155                 160
Asn Tyr Lys Leu Asn Leu Thr Thr Asp Pro Lys Phe Glu Ser Val Ala
                165                 170                 175
Arg Glu Val Cys Lys Ser Thr Ile Thr Glu Ile Lys Glu Cys Ala Asp
            180                 185                 190
Glu Pro Val Gly Lys Gly Tyr Met Val Ser Cys Leu Val Asp His Arg
    195                 200                 205
Gly Asn Ile Thr Glu Tyr Gln Cys His Gln Tyr Ile Thr Lys Met Thr
    210                 215                 220
Ala Ile Ile Phe Ser Asp Tyr Arg Leu Ile Cys Gly Phe Met Asp Asp
225                 230                 235                 240
Cys Lys Asn Asp Ile Asn Ile Leu Lys Cys Gly Ser Ile Arg Leu Gly
                245                 250                 255
Glu Lys Asp Ala His Ser Gln Gly Glu Val Val Ser Cys Leu Glu Lys
            260                 265                 270
Gly Leu Val Lys Glu Ala Glu Arg Glu Pro Lys Ile Gln Val Ser
    275                 280                 285
Glu Leu Cys Lys Lys Ala Ile Leu Arg Val Ala Glu Leu Ser Ser Asp
290                 295                 300
Asp Phe His Leu Asp Arg His Leu Tyr Phe Ala Cys Arg Asp Asp Arg
305                 310                 315                 320
Glu Arg Phe Cys Glu Asn Thr Gln Ala Gly Glu Gly Arg Val Tyr Lys
                325                 330                 335
Cys Leu Phe Asn His Lys Phe Glu Glu Ser Met Ser Glu Lys Cys Arg
            340                 345                 350
Glu Ala Leu Thr Thr Arg Gln Lys Leu Ile Ala Gln Asp Tyr Lys Val
            355                 360                 365
Ser Tyr Ser Leu Ala Lys Ser Cys Lys Ser Asp Leu Lys Lys Tyr Arg
    370                 375                 380
Cys Asn Val Glu Asn Leu Pro Arg Ser Arg Glu Ala Arg Leu Ser Tyr
385                 390                 395                 400
Leu Leu Met Cys Leu Glu Ser Ala Val His Arg Gly Arg Gln Val Ser
                405                 410                 415
Ser Glu Cys Gln Gly Glu Met Leu Asp Tyr Arg Arg Met Leu Met Glu
            420                 425                 430
Asp Phe Ser Leu Ser Pro Glu Ile Ile Leu Ser Cys Arg Gly Glu Ile
            435                 440                 445
Glu His His Cys Ser Gly Leu His Arg Lys Gly Arg Thr Leu His Cys
```

-continued

```
            450                 455                 460
Leu Met Lys Val Arg Gly Glu Lys Gly Asn Leu Gly Met Asn Cys
465                 470                 475                 480

Gln Gln Ala Leu Gln Thr Leu Ile Gln Glu Thr Asp Pro Gly Ala Asp
                485                 490                 495

Tyr Arg Ile Asp Arg Ala Leu Asn Glu Ala Cys Glu Ser Val Ile Gln
                500                 505                 510

Thr Ala Cys Lys His Ile Arg Ser Gly Asp Pro Met Ile Leu Ser Cys
                515                 520                 525

Leu Met Glu His Leu Tyr Thr Glu Lys Met Val Glu Asp Cys Glu His
                530                 535                 540

Arg Leu Leu Glu Leu Gln Tyr Phe Ile Ser Arg Asp Trp Lys Leu Asp
545                 550                 555                 560

Pro Val Leu Tyr Arg Lys Cys Gln Gly Asp Ala Ser Arg Leu Cys His
                565                 570                 575

Thr His Gly Trp Asn Glu Thr Ser Glu Phe Met Pro Gln Gly Ala Val
                580                 585                 590

Phe Ser Cys Leu Tyr Arg His Ala Tyr Arg Thr Glu Glu Gln Gly Arg
                595                 600                 605

Arg Leu Ser Arg Glu Cys Arg Ala Glu Val Gln Arg Ile Leu His Gln
                610                 615                 620

Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
                660                 665                 670

Asp Ile Val Gly Asn Leu Thr Glu Leu Glu Ser Glu Asp Ile Gln Ile
                675                 680                 685

Glu Ala Leu Leu Met Arg Ala Cys Glu Pro Ile Ile Gln Asn Phe Cys
                690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
                725                 730                 735

Gly Val Thr His Phe Gln Leu Val Gln Met Lys Asp Phe Arg Phe Ser
                740                 745                 750

Tyr Lys Phe Lys Met Ala Cys Lys Glu Asp Val Leu Lys Leu Cys Pro
                755                 760                 765

Asn Ile Lys Lys Lys Val Asp Val Val Ile Cys Leu Ser Thr Thr Val
770                 775                 780

Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
                805                 810                 815

Arg Leu Glu Pro Asp Leu Tyr Glu Ala Cys Lys Ser Asp Ile Lys Asn
                820                 825                 830

Phe Cys Ser Ala Val Gln Tyr Gly Asn Ala Gln Ile Ile Glu Cys Leu
                835                 840                 845

Lys Glu Asn Lys Lys Gln Leu Ser Thr Arg Cys His Gln Lys Val Phe
                850                 855                 860

Lys Leu Gln Glu Thr Glu Met Met Asp Pro Glu Leu Asp Tyr Thr Leu
865                 870                 875                 880
```

Met Arg Val Cys Lys Gln Met Ile Lys Arg Phe Cys Pro Glu Ala Asp
            885                 890                 895
Ser Lys Thr Met Leu Gln Cys Leu Lys Gln Asn Lys Asn Ser Glu Leu
        900                 905                 910
Met Asp Pro Lys Cys Lys Gln Met Ile Thr Lys Arg Gln Ile Thr Gln
    915                 920                 925
Asn Thr Asp Tyr Arg Leu Asn Pro Met Leu Arg Lys Ala Cys Lys Ala
930                 935                 940
Asp Ile Pro Lys Phe Cys His Gly Ile Leu Thr Lys Ala Lys Asp Asp
945                 950                 955                 960
Ser Glu Leu Glu Gly Gln Val Ile Ser Cys Leu Lys Leu Arg Tyr Ala
            965                 970                 975
Asp Gln Arg Leu Ser Ser Asp Cys Glu Asp Gln Ile Arg Ile Ile Ile
        980                 985                 990
Gln Glu Ser Ala Leu Asp Tyr Arg Leu Asp Pro Gln Leu Gln Leu His
    995                 1000                1005
Cys Ser Asp Glu Ile Ser Ser Leu Cys Ala Glu Glu Ala Ala Ala Gln
    1010                1015                1020
Glu Gln Thr Gly Gln Val Glu Glu Cys Leu Lys Val Asn Leu Leu Lys
1025                1030                1035                1040
Ile Lys Thr Glu Leu Cys Lys Lys Glu Val Leu Asn Met Leu Lys Glu
            1045                1050                1055
Ser Lys Ala Asp Ile Phe Val Asp Pro Val Leu His Thr Ala Cys Ala
            1060                1065                1070
Leu Asp Ile Lys His His Cys Ala Ala Ile Thr Pro Gly Arg Gly Arg
            1075                1080                1085
Gln Met Ser Cys Leu Met Glu Ala Leu Glu Asp Lys Arg Val Arg Leu
            1090                1095                1100
Gln Pro Glu Cys Lys Lys Arg Leu Asn Asp Arg Ile Glu Met Trp Ser
1105                1110                1115                1120
Tyr Ala Ala Lys Val Ala Pro Ala Asp Gly Phe Ser Asp Leu Ala Met
            1125                1130                1135
Gln Val Met Thr Ser Pro Ser Lys Asn Tyr Ile Leu Ser Val Ile Ser
            1140                1145                1150
Gly Ser Ile Cys Ile Leu Phe Leu Ile Gly Leu Met Cys Gly Arg Ile
            1155                1160                1165
Thr Lys Arg Val Thr Arg Glu Leu Lys Asp Arg
            1170                1175

<210> SEQ ID NO 19
<211> LENGTH: 3779
<212> TYPE: DNA
<213> ORGANISM: Homo Sapiens

<400> SEQUENCE: 19
gcgtcgagct cgccgcggac tcaagatggc ggcgtgtgga cgtgtacgga ggatgttccg       60
cttgtcggcg gcgctgcatc tgctgctgct attcgcggcc ggggccgaga aactccccgg      120
ccagggcgtc cacagccagg gccagggtcc cggggccaac tttgtgtcct tcgtagggca      180
ggccggaggc ggcggcccgg cgggtcagca gctgccccag ctgcctcagt catcgcagct      240
tcagcagcaa cagcagcagc agcaacagca acagcagcct cagccgccgc agccgccttt      300
cccggcgggt gggcctccgg cccggcgggg aggagcgggg gctggtgggg gctgaaagct      360
ggcggaggaa gagtcctgca ggaggacgt gacccgcgtg tgccctaagc acacctggag      420

-continued

```
caacaacctg gcggtgctcg agtgcctgca ggatgtgagg gagcctgaaa atgaaatttc      480
ttcagactgc aatcatttgt tgtggaatta taagctgaac ctaactacag atcccaaatt      540
tgaatctgtg gccagagagg tttgcaaatc tactataaca gagattaaag aatgtgctga      600
tgaaccggtt ggaaaaggtt acatggtttc ctgcttggtg gatcaccgag gcaacatcac      660
tgagtatcag tgtcaccagt acattaccaa gatgacggcc atcattttta gtgattaccg      720
tttaatctgt ggcttcatgg atgactgcaa aaatgacatc aacattctga atgtggcag       780 tattcggctt ggagaaaagg atgcacattc acaaggtgag gtggtatcat gcttggagaa      840
aggcctggtg aaagaagcag aagaaagaga acccaagatt caagtttctg aactctgcaa      900
gaaagccatt ctccgggtgg ctgagctgtc atcggatgac tttcacttag accggcattt      960
atattttgct tgccgagatg atcgggagcg tttttgtgaa aatacacaag ctggtgaggg     1020
cagagtgtat aagtgcctct ttaaccataa atttgaagaa tccatgagtg aaaagtgtcg     1080
agaagcactt acaacccgcc aaaagctgat tgcccaggat tataaagtca gttattcatt     1140
ggccaaatcc tgtaaaagtg acttgaagaa ataccggtgc aatgtggaaa accttccgcg     1200
atcgcgtgaa gccaggctct cctacttgtt aatgtgcctg gagtcagctg tacacagagg     1260
gcgacaagtc agcagtgagt gccaggggga gatgctggat taccgacgca tgttgatgga     1320
agactttcct ctgagccctg agatcatcct aagctgtcgg ggggagattg aacaccattg     1380
ttccggatta catcgaaaag gccggaccct acactgtctg atgaaagtag ttcgagggga     1440
gaaggggaac cttggaatga actgccagca ggcgcttcaa acactgattc aggagactga     1500
ccctggtgca gattaccgca ttgatcgagc tttgaatgaa gcttgtgaat ctgtaatcca     1560
gacagcctgc aaacatataa gatctggaga cccaatgatc ttgtcgtgcc tgatggaaca     1620
tttatacaca gagaagatgg tagaagactg tgaacaccgt ctcttagagc tgcagtattt     1680
catctcccgg gattggaagc tggaccctgt cctgtaccgc aagtgccagg agacgcttc      1740 tcgtctttgc cacacccacg gttggaatga gaccagtgaa tttatgcctc agggagctgt     1800
gttctcttgt ttatacagac acgcctaccg cactgaggaa cagggaagga ggctctcacg     1860
ggagtgccga gctgaagtcc aaaggatcct acaccagcgt gccatggatg tcaagctgga     1920
tcctgccctc caggataagt gcctgattga tctgggaaaa tggtgcagtg agaaaacaga     1980
gactggacag gagctggagt gccttcagga ccatctggat gacttggtgg tggagtgtag     2040
agatatagtt ggcaacctca ctgagttaga atcagaggat attcaaatag aagccttgct     2100
gatgagagcc tgtgagccca taattcagaa cttctgccac gatgtggcag ataaccagat     2160
agactctggg gacctgatgg agtgtctgat acagaacaaa caccagaagg acatgaacga     2220
gaagtgtgcc atcggagtta cccacttcca gctggtgcag atgaaggatt ttcggttttc     2280
ttacaagttt aaaatggcct gcaaggagga cgtgttgaag cttttgccca acataaaaaa     2340
gaaggtggac gtggtgatct gcctgagcac gaccgtgcgc aatgacactc tgcaggaagc     2400
caaggagcac agggtgtccc tgaagtgccg caggcagctc cgtgtggagg agctggagat     2460
gacggaggac atccgcttgg agccagatct atacgaagcc tgcaagagtg acatcaaaaa     2520
cttctgttcc gctgtgcaat atggcaacgc tcagattatc gaatgtctga agaaaacaa      2580 gaagcagcta agcacccgct gccaccaaaa agtatttaag ctgcaggaga cagagatgat     2640
ggacccagag ctagactaca ccctcatgag ggtctgcaag cagatgataa agaggttctg     2700
tccggaagca gattctaaaa ccatgttgca gtgcttgaag caaaataaaa acagtgaatt     2760
```

-continued

```
gatggatccc aaatgcaaac agatgataac caagcgccag atcacccaga acacagatta    2820
ccgcttaaac cccatgttaa gaaaagcctg taaagctgac attcctaaat tctgtcacgg    2880
tatcctgact aaggccaagg atgattcaga attagaagga caagtcatct cttgcctgaa    2940
gctgagatat gctgaccagc gcctgtcttc agactgtgaa gaccagatcc gaatcattat    3000
ccaggagtcc gccctggact accgcctgga tcctcagctc cagctgcact gctcagacga    3060
gatctccagt ctatgtgctg aagaagcagc agcccaagag cagacaggtc aggtggagga    3120
gtgcctcaag gtcaacctgc tcaagatcaa aacagaattg tgtaaaaagg aagtgctaaa    3180
catgctgaag gaaagcaaag cagacatctt tgttgacccg gtacttcata ctgcttgtgc    3240
cctggacatt aaacaccact gcgcagccat caccctggc cgcgggcgtc aaatgtcctg    3300
tctcatggaa gcactggagg ataagcgggt gaggttacag cccgagtgca aaagcgcct    3360 caatgaccgg attgagatgt ggagttacgc agcaaaggtg gccccagcag atggcttctc    3420
tgatcttgcc atgcaagtaa tgacgtctcc atctaagaac tacattctct ctgtgatcag    3480
tgggagcatc tgtatattgt tcctgattgg cctgatgtgt ggacggatca ccaagcgagt    3540
gacacgagag ctcaaggaca ggctacaata caggtcagac acaatggctt ataaaggttt    3600
agtgtggtct caggatgtga caggcagtcc agcctgacct ttctgcacac tccagacaaa    3660
cttcccagac aagctccttt gtgcctctac gtggagaggg tgtggaaagt tatcacatta    3720
aaagatggag gatttaaaaa aaaaaaaaaa aaaaaaaaaa aaagaaaaaa aaaaaaaaa     3779
```

<210> SEQ ID NO 20
<211> LENGTH: 1203
<212> TYPE: PRT
<213> ORGANISM: Homo Sapiens

<400> SEQUENCE: 20

```
Met Ala Ala Cys Gly Arg Val Arg Arg Met Phe Arg Leu Ser Ala Ala
 1               5                  10                  15

Leu His Leu Leu Leu Leu Phe Ala Ala Gly Ala Glu Lys Leu Pro Gly
                20                  25                  30

Gln Gly Val His Ser Gln Gly Gln Gly Pro Gly Ala Asn Phe Val Ser
            35                  40                  45

Phe Val Gly Gln Ala Gly Gly Gly Pro Ala Gly Gln Gln Leu Pro
        50                  55                  60

Gln Leu Pro Gln Ser Ser Gln Leu Gln Gln Gln Gln Gln Gln Gln
 65                  70                  75                  80

Gln Gln Gln Gln Pro Gln Pro Pro Gln Pro Phe Pro Ala Gly Gly
                85                  90                  95

Pro Pro Ala Arg Arg Gly Gly Ala Gly Gly Gly Gly Trp Lys Leu
            100                 105                 110

Ala Glu Glu Glu Ser Cys Arg Glu Asp Val Thr Arg Val Cys Pro Lys
            115                 120                 125

His Thr Trp Ser Asn Asn Leu Ala Val Leu Glu Cys Leu Gln Asp Val
        130                 135                 140

Arg Glu Pro Glu Asn Glu Ile Ser Ser Asp Cys Asn His Leu Leu Trp
145                 150                 155                 160

Asn Tyr Lys Leu Asn Leu Thr Thr Asp Pro Lys Phe Glu Ser Val Ala
                165                 170                 175

Arg Glu Val Cys Lys Ser Thr Ile Thr Glu Ile Lys Glu Cys Ala Asp
            180                 185                 190

Glu Pro Val Gly Lys Gly Tyr Met Val Ser Cys Leu Val Asp His Arg
```

-continued

```
              195                 200                 205
Gly Asn Ile Thr Glu Tyr Gln Cys His Gln Tyr Ile Thr Lys Met Thr
            210                 215                 220
Ala Ile Ile Phe Ser Asp Tyr Arg Leu Ile Cys Gly Phe Met Asp Asp
225                 230                 235                 240
Cys Lys Asn Asp Ile Asn Ile Leu Lys Cys Gly Ser Ile Arg Leu Gly
                245                 250                 255
Glu Lys Asp Ala His Ser Gln Gly Glu Val Val Ser Cys Leu Glu Lys
            260                 265                 270
Gly Leu Val Lys Glu Ala Glu Arg Glu Pro Lys Ile Gln Val Ser
            275                 280                 285
Glu Leu Cys Lys Lys Ala Ile Leu Arg Val Ala Glu Leu Ser Ser Asp
        290                 295                 300
Asp Phe His Leu Asp Arg His Leu Tyr Phe Ala Cys Arg Asp Asp Arg
305                 310                 315                 320
Glu Arg Phe Cys Glu Asn Thr Gln Ala Gly Glu Gly Arg Val Tyr Lys
                325                 330                 335
Cys Leu Phe Asn His Lys Phe Glu Glu Ser Met Ser Glu Lys Cys Arg
                340                 345                 350
Glu Ala Leu Thr Thr Arg Gln Lys Leu Ile Ala Gln Asp Tyr Lys Val
            355                 360                 365
Ser Tyr Ser Leu Ala Lys Ser Cys Lys Ser Asp Leu Lys Lys Tyr Arg
        370                 375                 380
Cys Asn Val Glu Asn Leu Pro Arg Ser Arg Glu Ala Arg Leu Ser Tyr
385                 390                 395                 400
Leu Leu Met Cys Leu Glu Ser Ala Val His Arg Gly Arg Gln Val Ser
                405                 410                 415
Ser Glu Cys Gln Gly Glu Met Leu Asp Tyr Arg Arg Met Leu Met Glu
            420                 425                 430
Asp Phe Ser Leu Ser Pro Glu Ile Ile Leu Ser Cys Arg Gly Glu Ile
        435                 440                 445
Glu His His Cys Ser Gly Leu His Arg Lys Gly Arg Thr Leu His Cys
    450                 455                 460
Leu Met Lys Val Val Arg Gly Glu Lys Gly Asn Leu Gly Met Asn Cys
465                 470                 475                 480
Gln Gln Ala Leu Gln Thr Leu Ile Gln Glu Thr Asp Pro Gly Ala Asp
                485                 490                 495
Tyr Arg Ile Asp Arg Ala Leu Asn Glu Ala Cys Glu Ser Val Ile Gln
                500                 505                 510
Thr Ala Cys Lys His Ile Arg Ser Gly Asp Pro Met Ile Leu Ser Cys
            515                 520                 525
Leu Met Glu His Leu Tyr Thr Glu Lys Met Val Glu Asp Cys Glu His
        530                 535                 540
Arg Leu Leu Glu Leu Gln Tyr Phe Ile Ser Arg Asp Trp Lys Leu Asp
545                 550                 555                 560
Pro Val Leu Tyr Arg Lys Cys Gln Gly Asp Ala Ser Arg Leu Cys His
                565                 570                 575
Thr His Gly Trp Asn Glu Thr Ser Glu Phe Met Pro Gln Gly Ala Val
            580                 585                 590
Phe Ser Cys Leu Tyr Arg His Ala Tyr Arg Thr Glu Glu Gln Gly Arg
        595                 600                 605
Arg Leu Ser Arg Glu Cys Arg Ala Glu Val Gln Arg Ile Leu His Gln
    610                 615                 620
```

```
Arg Ala Met Asp Val Lys Leu Asp Pro Ala Leu Gln Asp Lys Cys Leu
625                 630                 635                 640

Ile Asp Leu Gly Lys Trp Cys Ser Glu Lys Thr Glu Thr Gly Gln Glu
                645                 650                 655

Leu Glu Cys Leu Gln Asp His Leu Asp Asp Leu Val Val Glu Cys Arg
            660                 665                 670

Asp Ile Val Gly Asn Leu Thr Glu Leu Glu Ser Glu Asp Ile Gln Ile
                675                 680                 685

Glu Ala Leu Leu Met Arg Ala Cys Glu Pro Ile Ile Gln Asn Phe Cys
690                 695                 700

His Asp Val Ala Asp Asn Gln Ile Asp Ser Gly Asp Leu Met Glu Cys
705                 710                 715                 720

Leu Ile Gln Asn Lys His Gln Lys Asp Met Asn Glu Lys Cys Ala Ile
                725                 730                 735

Gly Val Thr His Phe Gln Leu Val Gln Met Lys Asp Phe Arg Phe Ser
                740                 745                 750

Tyr Lys Phe Lys Met Ala Cys Lys Glu Asp Val Leu Lys Leu Cys Pro
            755                 760                 765

Asn Ile Lys Lys Val Asp Val Val Ile Cys Leu Ser Thr Thr Val
770                 775                 780

Arg Asn Asp Thr Leu Gln Glu Ala Lys Glu His Arg Val Ser Leu Lys
785                 790                 795                 800

Cys Arg Arg Gln Leu Arg Val Glu Glu Leu Glu Met Thr Glu Asp Ile
                805                 810                 815

Arg Leu Glu Pro Asp Leu Tyr Glu Ala Cys Lys Ser Asp Ile Lys Asn
                820                 825                 830

Phe Cys Ser Ala Val Gln Tyr Gly Asn Ala Gln Ile Ile Glu Cys Leu
            835                 840                 845

Lys Glu Asn Lys Lys Gln Leu Ser Thr Arg Cys His Gln Lys Val Phe
850                 855                 860

Lys Leu Gln Glu Thr Glu Met Met Asp Pro Glu Leu Asp Tyr Thr Leu
865                 870                 875                 880

Met Arg Val Cys Lys Gln Met Ile Lys Arg Phe Cys Pro Glu Ala Asp
                885                 890                 895

Ser Lys Thr Met Leu Gln Cys Leu Lys Gln Asn Lys Asn Ser Glu Leu
            900                 905                 910

Met Asp Pro Lys Cys Lys Gln Met Ile Thr Lys Arg Gln Ile Thr Gln
            915                 920                 925

Asn Thr Asp Tyr Arg Leu Asn Pro Met Leu Arg Lys Ala Cys Lys Ala
    930                 935                 940

Asp Ile Pro Lys Phe Cys His Gly Ile Leu Thr Lys Ala Lys Asp Asp
945                 950                 955                 960

Ser Glu Leu Glu Gly Gln Val Ile Ser Cys Leu Lys Leu Arg Tyr Ala
                965                 970                 975

Asp Gln Arg Leu Ser Ser Asp Cys Glu Asp Gln Ile Arg Ile Ile Ile
            980                 985                 990

Gln Glu Ser Ala Leu Asp Tyr Arg Leu Asp Pro Gln Leu Gln Leu His
            995                 1000                1005

Cys Ser Asp Glu Ile Ser Ser Leu Cys Ala Glu Ala Ala Ala Gln
    1010                1015                1020

Glu Gln Thr Gly Gln Val Glu Glu Cys Leu Lys Val Asn Leu Leu Lys
1025                1030                1035                1040
```

Ile Lys Thr Glu Leu Cys Lys Lys Glu Val Leu Asn Met Leu Lys Glu
             1045                1050                1055

Ser Lys Ala Asp Ile Phe Val Asp Pro Val Leu His Thr Ala Cys Ala
             1060                1065                1070

Leu Asp Ile Lys His His Cys Ala Ala Ile Thr Pro Gly Arg Gly Arg
         1075                1080                1085

Gln Met Ser Cys Leu Met Glu Ala Leu Glu Asp Lys Arg Val Arg Leu
         1090                1095                1100

Gln Pro Glu Cys Lys Lys Arg Leu Asn Asp Arg Ile Glu Met Trp Ser
1105                1110                1115                1120

Tyr Ala Ala Lys Val Ala Pro Ala Asp Gly Phe Ser Asp Leu Ala Met
             1125                1130                1135

Gln Val Met Thr Ser Pro Ser Lys Asn Tyr Ile Leu Ser Val Ile Ser
             1140                1145                1150

Gly Ser Ile Cys Ile Leu Phe Leu Ile Gly Leu Met Cys Gly Arg Ile
             1155                1160                1165

Thr Lys Arg Val Thr Arg Glu Leu Lys Asp Arg Leu Gln Tyr Arg Ser
         1170                1175                1180

Glu Thr Met Ala Tyr Lys Gly Leu Val Trp Ser Gln Asp Val Thr Gly
1185                1190                1195                1200

Ser Pro Ala

<210> SEQ ID NO 21
<211> LENGTH: 2288
<212> TYPE: DNA
<213> ORGANISM: Homo Sapiens

<400> SEQUENCE: 21

```
caaaaacttc tgttccgctg tgcaatatgg caacgctcag attatcgaat gtctgaaaga      60
aaacaagaag cagctaagca cccgctgcca ccaaaaagta tttaagctgc aggagacaga     120
gatgatggac ccagagctag actacaccct catgagggtc tgtaagcaga tgataaagag     180
gttctgtccg gaagcagatt ctaaaaccat gttgcagtgc ttgaagcaaa ataaaaacag     240
tgaattgatg gatcccaaat gcaaacagat gataaccaag cgccagatca cccagaacac     300
agattaccgc ttaaacccca tgttaagaaa agcctgtaaa gctgacattc ctaaattctg     360
tcacggtatc ctgactaagg ccaaggatga ttcagaatta gaaggacaag tcatctcttg     420
cctgaagctg agatatgctg accagcgcct gtcttcagac tgtgaagacc agatccgaat     480
cattatccag gagtccgccc tggactaccg cctggatcct cagctccagc tgcactgctc     540
agacgagatc tccagtctat gtgctgaaga agcagcagcc aagagcaga caggtcaggt     600
ggaggagtgc ctcaaggtca acctgctcaa gatcaaaaca gaattgtgta aaaaggaagt     660
gctaaacatg ctgaaggaaa gcaaagcaga catctttgtt gacccggtac ttcatactgc     720
ttgtgccctg gacattaaac accactgcgc agccatcacc cctggccgcg ggcgtcaaat     780
gtcctgtctc atggaagcac tggaggataa gcgggtgagg ttacagcccg agtgcaaaaa     840
gcgcctcaat gaccggattg agatgtggag ttacgcagca aaggtggccc cagcagatgg     900
cttctctgat cttgccatgc aagtaatgac gtctccatct aagaactaca ttctctctgt     960
gatcagtggg agcatctgta tattgttcct gattggcctg atgtgtggac ggatcaccaa    1020
gcgagtgaca cgagagctca aggacaggta gagccacctt gaccaccaaa ggaactacct    1080
atccagtgcc cagtttgtac agccctcttg tatagcatcc ccactcacct cgctcttctc    1140
agaagtgaca ccaaccccgt gttagagcat tagcagatgt ccactgcgtt gtcccatcca    1200
```

-continued

```
gcctccactc gtgtccatgg tgtcctcctc ctcctcaccg tgcagcagca gcagctggtc     1260
gctggggtta ctgcctttgt ttggcagact tggtttacct gcctgtagtc aagtctctct     1320
cataccaaca gaacttccgg tacttccaga accaactcac ctgacctgca actcaaaggc     1380
ttttttaaga aaaccaccaa aaaaaaaaat tttttaaag aaaaaaatgt atatagtaac      1440
gcatctcctc caggcttgat ttgggcaatg gggttatgtc tttcatatga ctgtgtaaaa     1500
caaagacagg acttggaggg aagcacacc acccagtgtg ccatgactga ggtgtctcgt     1560
tcatctctca gaagcgcctt ggggcctcgc cagggccgtg gtcttcaccg aggcgtgggt     1620
gggcagccgt tccccaggct gtgtggggtc ctgctttctt ctgctgagac agtgacgctt     1680
tccagtttcc accctaatca gccactgctg gtcacagccc cacagccatg ggtatttctg     1740
tggtctcctc gcttcattga agcaaagcat gagccttcct agacaagggc agctggggag     1800
gggaagggac cggaagtttg tgaagttgaa cagtccatcc atctgcactg agaggctgga     1860
tcctgagtcc cggggcagca ggatcccagg aaccttcctc ctccagggca gcacaggact     1920
cagccgtgtc tggaccggcc ctgctgaggc tacagtcact ctggaagctc tgcgcttcat     1980
caggaggcag gactgtggcg ggaggggtcc ttgaagatgg gtgtggggag cagtgggtca     2040
ggaagtggga gccagaggtt tgactcactt tgctttattt ttcaggctac aatacaggtc     2100
agagacaatg gcttataaag gtttagtgtg gtctcaggat gtgacaggca gtccagcctg     2160 accttctgc acactccaga caaacttccc agacaagctc ctttgtgcct ctacgtggag      2220
agggtgtgga aagttatcac attaaaagat ggaggattaa aaaaaaaaaa aaaaaaaaa     2280 aaaaaaaa                                                             2288
```

<210> SEQ ID NO 22
<211> LENGTH: 309
<212> TYPE: PRT
<213> ORGANISM: Homo Sapiens

<400> SEQUENCE: 22

```
Met Met Asp Pro Glu Leu Asp Tyr Thr Leu Met Arg Val Cys Lys Gln
  1               5                  10                  15

Met Ile Lys Arg Phe Cys Pro Glu Ala Asp Ser Lys Thr Met Leu Gln
             20                  25                  30

Cys Leu Lys Gln Asn Lys Asn Ser Glu Leu Met Asp Pro Lys Cys Lys
         35                  40                  45

Gln Met Ile Thr Lys Arg Gln Ile Thr Gln Asn Thr Asp Tyr Arg Leu
     50                  55                  60

Asn Pro Met Leu Arg Lys Ala Cys Lys Ala Asp Ile Pro Lys Phe Cys
 65                  70                  75                  80

His Gly Ile Leu Thr Lys Ala Lys Asp Asp Ser Glu Leu Glu Gly Gln
                 85                  90                  95

Val Ile Ser Cys Leu Lys Leu Arg Tyr Ala Asp Gln Arg Leu Ser Ser
            100                 105                 110

Asp Cys Glu Asp Gln Ile Arg Ile Ile Gln Glu Ser Ala Leu Asp
        115                 120                 125

Tyr Arg Leu Asp Pro Gln Leu Gln Leu His Cys Ser Asp Glu Ile Ser
    130                 135                 140

Ser Leu Cys Ala Glu Glu Ala Ala Gln Glu Gln Thr Gly Gln Val
145                 150                 155                 160

Glu Glu Cys Leu Lys Val Asn Leu Leu Lys Ile Lys Thr Glu Leu Cys
                165                 170                 175
```

```
Lys Lys Glu Val Leu Asn Met Leu Lys Glu Ser Lys Ala Asp Ile Phe
            180                 185                 190
Val Asp Pro Val Leu His Thr Ala Cys Ala Leu Asp Ile Lys His His
        195                 200                 205
Cys Ala Ala Ile Thr Pro Gly Arg Gly Arg Gln Met Ser Cys Leu Met
    210                 215                 220
Glu Ala Leu Glu Asp Lys Arg Val Arg Leu Gln Pro Glu Cys Lys Lys
225                 230                 235                 240
Arg Leu Asn Asp Arg Ile Glu Met Trp Ser Tyr Ala Ala Lys Val Ala
                245                 250                 255
Pro Ala Asp Gly Phe Ser Asp Leu Ala Met Gln Val Met Thr Ser Pro
            260                 265                 270
Ser Lys Asn Tyr Ile Leu Ser Val Ile Ser Gly Ser Ile Cys Ile Leu
        275                 280                 285
Phe Leu Ile Gly Leu Met Cys Gly Arg Ile Thr Lys Arg Val Thr Arg
    290                 295                 300
Glu Leu Lys Asp Arg
305

<210> SEQ ID NO 23
<211> LENGTH: 2486
<212> TYPE: DNA
<213> ORGANISM: Homo Sapiens

<400> SEQUENCE: 23
aatttagcca gctgtggtgg cacatacctg taatcccagc tacttgagag actgaggcag      60
gagaatcact tgaaccggga gatggagttt gcagtgagcc gagatggtgc cactgtactc     120
cagcctgggt gacagagcaa gactctgtct ccaaaaaaaa aaaaaaaaa aaaaaaaga      180 catttcaagc tggaagattt ggttccctaa ctttgagcct agctctttca ttaaagtaat     240
aataaaagta gaactctaca tttatataat ggttttgact ttccaaagtg attttcacat     300
ctcagcagtc ctgtgaagga ctaaataagg tgtttcaggg tagacttggc attgtgtttt     360
gcaaagaagg tccaaggcca tgcagctatt tggtgacaga attgaaagta aagcctgatt     420
ctcttgctgc aaggcgactt tgctatctag aagccagggt cactagacaa gatgcagtca     480
acaaataagt ctccagaaca tatgacatct ccagcctaaa ccaagctcac ctttccatgc     540
tggctccctc atgcagacgg aggacatccg cttggagcca gatctatacg aagcctgcaa     600
gagtgacatc aaaaacttct gttccgctgt gcaatatggc aacgctcaga ttatcgaatg     660
tctgaaagaa aacaagaagc agctaagcac ccgctgccac caaaaagtat ttaagctgca     720
ggagacagag atgatggacc cagagctaga ctacaccctc atgagggtct gcaagcagat     780
gataaagagg ttctgtccgg aagcagattc taaaaccatg ttgcagtgct gaagcaaaa     840 taaaacagt gaattgatgg atcccaaatg caaacagatg ataaccaagc gccagatcac     900
ccagaacaca ggtaagatct tggcttggct ctcctggccc cgtggagtat ctgaaaagga     960
attcagtggc tgtagagtga cctgctcaaa ctcccagggc tttgttgcct gggaattta    1020 agggaggagt ctgagtgtaa gcagggcctt cctcctttga ggagcatcca gaaaaatgga    1080
gggagagtca gggagagag gaggccacaa gaaccagaaa actgccctaa agaacgttc    1140 agaaggaatc aggccggcag tccttggaaa gaaaaatcta gaattcaat aaaacttcat    1200 gagtgtgcca ggagaatgta cgggtaatct gattcggaac agaaacattt cacctctgag    1260
ttggaagacc tcgtaagtta atggtcacag tgagttggat attgtatttc ttttcagtg    1320
```

-continued

```
ttctcaaaag tgtctgttat ggggaaggtt gctgatgtcc ccttgatttt tctgaggact   1380
ccttagagta ttggagtctg cacaaaaccc cgcagagtag aaagattcct gaggacctcc   1440
agaagtactc gttaacaagt catattgctg attaaaaaca gtgtagtgag agctcagtaa   1500
atgtttattg aatagataaa tccatggttg tagtcatgat cattgacata atatgctccc   1560
tttaggaagg tggatatcta aaaatgtgtg aatcaggtgg aatgttttgt cacatgctca   1620
ctgctttcta ctctagatta ccgcttaaac cccatgttaa gaaaagcctg taaagctgac   1680
attcctaaat tctgtcacgg tatcctgact aaggccaagg atgattcaga attagaagga   1740
caagtcatct cttgcctgaa gctgagatat gctgaccagc gcctgtcttc agactgtgaa   1800
gaccagatcc gaatcattat ccaggagtcc gccctggact accgcctgga tcctcagctc   1860
cagctgcact gctcagacga ggtgggattt gcgtgcaaaa ctggttacgc acagagctgc   1920
tcagagaagt ttccactgga gaaagttgt ttactttctc tcccttcagc cgtgaatgat   1980
ctggtgaatt gaaggccatc ttctaggctc tccatggtct gcattcctgt tctttgtaac   2040
actgaattca acttggcatt agtcctgaca ctctaaagcg ttgttccata tttctctgtt   2100
gaacaagggt gttctttcat tatagctctc tgtaaatttg ttcttccctt cttcttattc   2160
tggatggtaa acccaagacc tgccagaaag ataaaagtgc tttcagctgg gcacggtggc   2220
tcacgcctgt aatcccaaca ctttgggagg ccaaggaggg tggatcatct gaggtcagga   2280
gttcaagacc agcctggcta acatggagaa atctgtctct actaaaaata caaaaaatta   2340
gccaggcgtg gtggcgtgca ccagtaatct cagctactca ggaggctgag gcaggagaat   2400
cacttgaacc cggggaggcgg tggttgcagt gagctgagat catgccactg cacccccagcc   2460 tgggcgacag aggaagactc tgtctc                                       2486
```

<210> SEQ ID NO 24
<211> LENGTH: 156
<212> TYPE: PRT
<213> ORGANISM: Homo Sapiens

<400> SEQUENCE: 24

```
Met Gln Thr Glu Asp Ile Arg Leu Glu Pro Asp Leu Tyr Glu Ala Cys
  1               5                  10                  15

Lys Ser Asp Ile Lys Asn Phe Cys Ser Ala Val Gln Tyr Gly Asn Ala
             20                  25                  30

Gln Ile Ile Glu Cys Leu Lys Glu Asn Lys Lys Gln Leu Ser Thr Arg
         35                  40                  45

Cys His Gln Lys Val Phe Lys Leu Gln Glu Thr Glu Met Met Asp Pro
     50                  55                  60

Glu Leu Asp Tyr Thr Leu Met Arg Val Cys Lys Gln Met Ile Lys Arg
 65                  70                  75                  80

Phe Cys Pro Glu Ala Asp Ser Lys Thr Met Leu Gln Cys Leu Lys Gln
                 85                  90                  95

Asn Lys Asn Ser Glu Leu Met Asp Pro Lys Cys Lys Gln Met Ile Thr
            100                 105                 110

Lys Arg Gln Ile Thr Gln Asn Thr Gly Lys Ile Leu Ala Trp Leu Ser
        115                 120                 125

Trp Pro Arg Gly Val Ser Glu Lys Glu Phe Ser Gly Cys Arg Val Thr
    130                 135                 140

Cys Ser Asn Ser Gln Gly Phe Val Ala Trp Glu Phe
145                 150                 155
```

<210> SEQ ID NO 25
<211> LENGTH: 842
<212> TYPE: DNA
<213> ORGANISM: Mus musculus

<400> SEQUENCE: 25

```
ctgagaggaa gttttatctg tgcagcccctt ctctgaggat ggacacttct cacactacaa      60
agtcctgttt gctgattctt cttgtggccc tactgtgtgc agaaagagct cagggactgg     120
agtgttacca gtgctatgga gtcccatttg agacttcttg cccatcaatt acctgcccct     180
accctgatgg agtctgtgtt actcaggagg cagcagttat tgtggattct caaacaagga     240
aagtaaagaa caatctttgc ttacccatct gccctcctaa tattgaaagt atggagatcc     300
tgggtactaa ggtcaacgtg aagacttcct gttgccagga agacctctgc aatgtagcag     360
ttcccaatgg aggcagcacc tggaccatgg caggggtgct tctgttcagc ctgagctcag     420
tcctcctgca gaccttgctc tgatggtcct cccaatgacc tccacccttg tccttttatc     480
ctcatgtgca acaattcttc ctggagccct ctagtgatga attatgagtt atagaagctc     540
caaggtggga gtagtgtgtg aaataccatg ttttgccttt atagcccctg ctgggtaggt     600
aggtgctcta atcctctcta gggctttcaa gtctgtactt cctagaatgt catttttgttg     660
tggattgctg ctcatgaccc tggaggcaca cagccagcac agtgaagagg cagaattcca     720
aggtattatg ctatcaccat ccacacataa gtatctgggg tcctgcaatg ttcccacatg     780
tatcctgaat gtccccctgt tgagtccaat aaacccttg ttctcccaaa aaaaaaaaa     840
aa                                                                   842
```

<210> SEQ ID NO 26
<211> LENGTH: 134
<212> TYPE: PRT
<213> ORGANISM: Mus musculus

<400> SEQUENCE: 26

```
Met Asp Thr Ser His Thr Thr Lys Ser Cys Leu Leu Ile Leu Leu Val
  1               5                  10                  15

Ala Leu Leu Cys Ala Glu Arg Ala Gln Gly Leu Glu Cys Tyr Gln Cys
                 20                  25                  30

Tyr Gly Val Pro Phe Glu Thr Ser Cys Pro Ser Ile Thr Cys Pro Tyr
             35                  40                  45

Pro Asp Gly Val Cys Val Thr Gln Glu Ala Ala Val Ile Val Asp Ser
         50                  55                  60

Gln Thr Arg Lys Val Lys Asn Asn Leu Cys Leu Pro Ile Cys Pro Pro
 65                  70                  75                  80

Asn Ile Glu Ser Met Glu Ile Leu Gly Thr Lys Val Asn Val Lys Thr
                 85                  90                  95

Ser Cys Cys Gln Glu Asp Leu Cys Asn Val Ala Val Pro Asn Gly Gly
                100                 105                 110

Ser Thr Trp Thr Met Ala Gly Val Leu Leu Phe Ser Leu Ser Ser Val
            115                 120                 125

Leu Leu Gln Thr Leu Leu
        130
```

<210> SEQ ID NO 27
<211> LENGTH: 862
<212> TYPE: DNA
<213> ORGANISM: Mus musculus

<400> SEQUENCE: 27

```
atctgacaga acttgccact gtgcctgcaa ccttgtctga gaggaaccct tctctgagga      60
tggacacttc tcacactaca aagtcctgtg tgctcattct tcttgtggcc ctactgtgtg     120
cagaaagagc tcagggactg cagtgctacg agtgctatgg agtgccaatt gagacttcct    180
gcccagcagt tacctgccgc gcctctgatg gattctgcat tgctcaaaac atagaattga    240
ttgaggactc tcaaagaagg aaactaaaga cccgtcagtg cctttctttc tgccctgctg    300
gtgtgccaat cagggatcct aacatcaggg agaggacttc ctgttgcagc gaagacctct    360
gcaatgcagc agttcccact gcaggtagca cctggaccat ggcaggggtg cttctgttca    420
gcctgagctc agtcgtcctg cagaccttgc tctgatggtc cttccaatga cccccaccct    480
tttccttta tcttcatgtg caaccactct ttcctggagt cctctagtga caaattatat    540
gttatagaag gtccaatgtg gggatagtgt gtggaacacc ctgtttcacc tttatagccc    600
ctgctgggta agtgcccgac tcctctctag ggctttcaaa tctgtacttc ttgcaatgcc    660
atttagttgt ggatttctat tcttggccct ggaggcatgt ggccagcaca tgcaacaggc    720
agtattccaa ggtattatag tatcaccatc cacacataag tatctggggt cctgcagggt    780
tcccatgtat gcctgtcaat gaccccctgtt gagtccaata aaagctttgt tctcccagcc    840
aaaaaaaaaa aaaaaaaaaa aa                                              862
```

<210> SEQ ID NO 28
<211> LENGTH: 131
<212> TYPE: PRT
<213> ORGANISM: Mus musculus

<400> SEQUENCE: 28

```
Met Asp Thr Ser His Thr Thr Lys Ser Cys Val Leu Ile Leu Leu Val
 1               5                  10                  15

Ala Leu Leu Cys Ala Glu Arg Ala Gln Gly Leu Gln Cys Tyr Glu Cys
            20                  25                  30

Tyr Gly Val Pro Ile Glu Thr Ser Cys Pro Ala Val Thr Cys Arg Ala
        35                  40                  45

Ser Asp Gly Phe Cys Ile Ala Gln Asn Ile Glu Leu Ile Glu Asp Ser
    50                  55                  60

Gln Arg Arg Lys Leu Lys Thr Arg Gln Cys Leu Ser Phe Cys Pro Ala
65                  70                  75                  80

Gly Val Pro Ile Arg Asp Pro Asn Ile Arg Glu Arg Thr Ser Cys Cys
                85                  90                  95

Ser Glu Asp Leu Cys Asn Ala Ala Val Pro Thr Ala Gly Ser Thr Trp
            100                 105                 110

Thr Met Ala Gly Val Leu Leu Phe Ser Leu Ser Ser Val Leu Gln
        115                 120                 125

Thr Leu Leu
    130
```

<210> SEQ ID NO 29
<211> LENGTH: 806
<212> TYPE: DNA
<213> ORGANISM: Mus musculus

<400> SEQUENCE: 29

```
gcccaccccc gcccagcccg tgcctataag gccttggcaa tgcaggggcc cgcactgctc      60
ccagacgaca tcagagatga ggacagcatt gctgctcctt gcagccctgg ctgtggctac    120
```

```
agggccagcc cttaccctgc gctgccacgt gtgcaccagc tccagcaact gcaagcattc      180
tgtggtctgc ccggccagct ctcgcttctg caagaccacg aacacagtgg agcctctgag      240
ggggaatctg gtgaagaagg actgtgcgga gtcgtgcaca cccagctaca ccctgcaagg      300
ccaggtcagc agcggcacca gctccaccca gtgctgccag gaggacctgt gcaatgagaa      360
gctgcacaac gctgcaccca cccgcaccgc cctcgcccac agtgccctca gcctggggct      420
ggccctgagc ctcctggccg tcatcttagc ccccagcctg tgaccttccc cccagggaag      480 gccccctcatg cctttccttc cctttctctg gggattccac acctctcttc cccagccgca      540 acggggggtgc caggagcccc aggctgaggg cttccccgaa agtctgggac caggtccagg      600
tgggcatgga atgctgatga cttggagcag gccccacaga ccccacagag gatgaagcca      660
ccccacagag gatgcagccc ccagctgcat ggaaggtgga ggacagaagc cctgtggatc      720
cccggatttc acactccttc tgttttgttg ccgtttattt ttgtactcaa atctctacat      780
ggagataaat gatttaaacc agaaaa                                          806
```

<210> SEQ ID NO 30
<211> LENGTH: 128
<212> TYPE: PRT
<213> ORGANISM: Mus musculus

<400> SEQUENCE: 30

```
Met Arg Thr Ala Leu Leu Leu Ala Ala Leu Ala Val Ala Thr Gly
 1               5                  10                  15

Pro Ala Leu Thr Leu Arg Cys His Val Cys Thr Ser Ser Ser Asn Cys
                20                  25                  30

Lys His Ser Val Val Cys Pro Ala Ser Ser Arg Phe Cys Lys Thr Thr
            35                  40                  45

Asn Thr Val Glu Pro Leu Arg Gly Asn Leu Val Lys Lys Asp Cys Ala
        50                  55                  60

Glu Ser Cys Thr Pro Ser Tyr Thr Leu Gln Gly Gln Val Ser Ser Gly
65                  70                  75                  80

Thr Ser Ser Thr Gln Cys Cys Gln Glu Asp Leu Cys Asn Glu Lys Leu
                85                  90                  95

His Asn Ala Ala Pro Thr Arg Thr Ala Leu Ala His Ser Ala Leu Ser
            100                 105                 110

Leu Gly Leu Ala Leu Ser Leu Leu Ala Val Ile Leu Ala Pro Ser Leu
        115                 120                 125
```

<210> SEQ ID NO 31
<211> LENGTH: 1145
<212> TYPE: DNA
<213> ORGANISM: Mus musculus

<400> SEQUENCE: 31

```
gctccggcca gccgcggtcc agagcgcgcg aggttcgggg agctccgcca ggctgctggt       60
acctgcgtcc gcccggcgag caggacaggc tgctttggtt tgtgacctcc aggcaggacg      120
gccatcctct ccagaatgaa gatcttcttg ccagtgctgc tggctgccct tctgggtgtg      180
gagcgagcca gctcgctgat gtgcttctcc tgcttgaacc agaagagcaa tctgtactgc      240
ctgaagccga ccatctgctc cgaccaggac aactactgcg tgactgtgtc tgctagtgcc      300
ggcattggga atctcgtgac atttggccac agcctgagca agacctgttc cccggcctgc      360
cccatcccag aaggcgtcaa tgttggtgtg cttccatgg catcagctg ctgccagagc      420 tttctgtgca atttcagtgc ggccgatggc gggctgcggg caagcgtcac cctgctggt      480
```

```
gccgggctgc tgctgagcct gctgccggcc ctgctgcggt ttggcccctg accgcccaga    540
ccctgtcccc cgatccccca gctcaggaag gaaagcccag ccctttctgg atcccacagt    600
gtatgggagc ccctgactcc tcacgtgcct gatctgtgcc cttggtccca ggtcaggccc    660
accccctgca cctccacctg ccccagcccc tgcctctgcc caagtgggcc agctgccctc    720
acttctgggg tggatgatgt gaccttcctt gggggactgc ggaagggacg agggttccct    780
ggagtcttac ggtccaacat cagaccaagt cccatggaca tgctgacagg gtccccaggg    840
agaccgtgtc agtagggatg tgtgcctggc tgtgtacgtg ggtgtgcagt gcacgtgaga    900
gcacgtggcg gcttctgggg gccatgtttg gggagggagg tgtgccagca gcctggagag    960
cctcagtccc tgtagccccc tgccctggca cagctgcatg cacttcaagg gcagcctttg   1020
ggggttgggg tttctgccac ttccgggtct aggccctgcc caaatccagc cagtcctgcc   1080
ccagcccacc cccacattgg agccctcctg ctgctttggt gcctcaaata aatacagatg   1140
tcccc                                                               1145
```

<210> SEQ ID NO 32
<211> LENGTH: 131
<212> TYPE: PRT
<213> ORGANISM: Mus Musculus

<400> SEQUENCE: 32

```
Met Lys Ile Phe Leu Pro Val Leu Leu Ala Ala Leu Leu Gly Val Glu
  1               5                  10                  15

Arg Ala Ser Ser Leu Met Cys Phe Ser Cys Leu Asn Gln Lys Ser Asn
             20                  25                  30

Leu Tyr Cys Leu Lys Pro Thr Ile Cys Ser Asp Gln Asp Asn Tyr Cys
         35                  40                  45

Val Thr Val Ser Ala Ser Ala Gly Ile Gly Asn Leu Val Thr Phe Gly
     50                  55                  60

His Ser Leu Ser Lys Thr Cys Ser Pro Ala Cys Pro Ile Pro Glu Gly
 65                  70                  75                  80

Val Asn Val Gly Val Ala Ser Met Gly Ile Ser Cys Cys Gln Ser Phe
                 85                  90                  95

Leu Cys Asn Phe Ser Ala Ala Asp Gly Gly Leu Arg Ala Ser Val Thr
            100                 105                 110

Leu Leu Gly Ala Gly Leu Leu Leu Ser Leu Leu Pro Ala Leu Leu Arg
        115                 120                 125

Phe Gly Pro
    130
```

<210> SEQ ID NO 33
<211> LENGTH: 877
<212> TYPE: DNA
<213> ORGANISM: Mus musculus

<400> SEQUENCE: 33

```
actgtgcctg caacctggtc agagaggaag taaggactgg tgtcaggagg gagctgctag     60
gtttgatctg tgcagcccct tctccaaggat ggacagttgt cacactacaa agtcctgtgt    120
actcatcctt cttgtggtcc tattgtgtgc agaaagagct caggggctgg agtgctataa    180
ctgcctggga gtttcacttg gaattgcctg caaatcaatt acctgcccct accctgatgc    240
agtctgcatt tctcagcagg tagaacttat tgtggactct caaagaagga agtaaagaa    300 caaactctgc tttcctttct gccctgctaa tcttgaaaat atggagatcc tgggtactac    360
```

```
tgtcaacgtg aatacttcct gttgcaagga agacctctgc aatgcaccat tttccactgg    420
aggcagcacc tggaccatga caagggtgct tctgttaaat ctgggctcgg tcttcctgca    480
gaccttgctg taaaaggtcc ttccaaggac ctccacccct gttgttttat cctcatttgc    540
aactattcct tcctggagcc ctctagtgat gaattatgag atattgaagc tccaaggtgg    600
gagtagtgtt tgtggaatac gttgtttcaa ctttatagcc cctgcttggt aaatgcccca    660
ctcctctcta ggaatttcaa atatgtactt cctagaatgc cattttgttg tggcttgcta    720
atcttggccc tggaggcccg tggctagcag agggtagagg cagaattcca aggtattaag    780
ccatcaccat ccacacataa gtgtctgagg ttctgcagga ttctcatgta tgcggcttta    840
tgtccccttg ttgagtccaa taaaccctt gttctcc                             877
```

<210> SEQ ID NO 34
<211> LENGTH: 134
<212> TYPE: PRT
<213> ORGANISM: Mus musculus

<400> SEQUENCE: 34

```
Met Asp Ser Cys His Thr Thr Lys Ser Cys Val Leu Ile Leu Leu Val
 1               5                  10                  15

Val Leu Leu Cys Ala Glu Arg Ala Gln Gly Leu Glu Cys Tyr Asn Cys
            20                  25                  30

Leu Gly Val Ser Leu Gly Ile Ala Cys Lys Ser Ile Thr Cys Pro Tyr
        35                  40                  45

Pro Asp Ala Val Cys Ile Ser Gln Gln Val Glu Leu Ile Val Asp Ser
    50                  55                  60

Gln Arg Arg Lys Val Lys Asn Lys Leu Cys Phe Pro Phe Cys Pro Ala
65                  70                  75                  80

Asn Leu Glu Asn Met Glu Ile Leu Gly Thr Thr Val Asn Val Asn Thr
                85                  90                  95

Ser Cys Cys Lys Glu Asp Leu Cys Asn Ala Pro Phe Ser Thr Gly Gly
            100                 105                 110

Ser Thr Trp Thr Met Thr Arg Val Leu Leu Leu Asn Leu Gly Ser Val
        115                 120                 125

Phe Leu Gln Thr Leu Leu
    130
```

<210> SEQ ID NO 35
<211> LENGTH: 710
<212> TYPE: DNA
<213> ORGANISM: Mus musculus

<400> SEQUENCE: 35

```
ctgcagccag gtctgagagg aagtaaggac tggtgtcagg agggagctgc taggtgacaa     60
agggaagaac cctcaggata gggctgtggt gggagtgaga ttaggaaaga agagctgggt    120
gggtggtgga tgagagaagt aggcagacat gtattcctca gggaaagctg tgtagagggt    180
tggagggagg gaatattgga tggctgagcc gtgtgagagc ccaggggtgt gatcagggg    240 ctattaactg gctccaactt ccaaggtttt atctgtgcag cccttctcca aggatggaca    300
cttctcacga gataaagtcc tgtgtgctga tccttcttgt gaccctactc tgtgcagaaa    360
gagctcaggg actggagtgt taccagtgct atggagtccc atttgagact tcttgcccat    420
catttacctg cccctacct gatggattct gtgttgctca ggaggaagaa tttattgcaa    480
actctcaaag aaagagagta aagagccgtt cttgccatcc tttctgccct gatgaaattg    540
```

```
aaaagaagtt tatcctggat cctaacacca agatgaatat ttcctgttgc caggaagacc    600
tctgcaatgc agcagttccc actggaggca gctcctggac cacggcaggg gtgcttctgt    660
tcagcctggg ctcagtcctc ctgcagaccc tgatgtgatg gtccccaccc              710
```

<210> SEQ ID NO 36
<211> LENGTH: 134
<212> TYPE: PRT
<213> ORGANISM: Mus musculus

<400> SEQUENCE: 36

```
Met Asp Thr Ser His Glu Ile Lys Ser Cys Val Leu Ile Leu Leu Val
 1               5                  10                  15

Thr Leu Leu Cys Ala Glu Arg Ala Gln Gly Leu Glu Cys Tyr Gln Cys
            20                  25                  30

Tyr Gly Val Pro Phe Glu Thr Ser Cys Pro Ser Phe Thr Cys Pro Tyr
        35                  40                  45

Pro Asp Gly Phe Cys Val Ala Gln Glu Glu Glu Phe Ile Ala Asn Ser
    50                  55                  60

Gln Arg Lys Arg Val Lys Ser Arg Ser Cys His Pro Phe Cys Pro Asp
65                  70                  75                  80

Glu Ile Glu Lys Lys Phe Ile Leu Asp Pro Asn Thr Lys Met Asn Ile
                85                  90                  95

Ser Cys Cys Gln Glu Asp Leu Cys Asn Ala Ala Val Pro Thr Gly Gly
            100                 105                 110

Ser Ser Trp Thr Thr Ala Gly Val Leu Leu Phe Ser Leu Gly Ser Val
        115                 120                 125

Leu Leu Gln Thr Leu Met
    130
```

<210> SEQ ID NO 37
<211> LENGTH: 1735
<212> TYPE: DNA
<213> ORGANISM: Mus musculus

<400> SEQUENCE: 37

```
gttatcagag gtgagcccgt gctcttcagc ggagaagatc ccctacctgg ccgccggcca    60
ctttctgtgg gccgtggggt cctcaaggag acggcccttg ggctcagggg ctgcgtttcc    120
acacgcgcct ttcccagggc tcccgcgccc gttcctgcct ggccgccggc cgctccaaca    180
gcagcacaag gcgggactca gaaccggcgt tcagggccgc cagcggccgc gaggccctga    240
gatgaggctc caaagacccc gacaggcccc ggcgggtggg aggcgcgcgc cccggggcgg    300
gcggggctcc ccctaccggc cagacccggg gagaggcgcg cggaggctgc gaaggttcca    360
gaagggcggg gaggggcgc cgcgcgctga ccctccctgg caccgctggg gacgatggc     420 gctgctcgcc ttgctgctgg tcgtggccct accgcgggtg tggacagacg ccaacctgac    480
tgcgagacaa cgagatccag aggactccca gcgaacggac gagggtgaca atagagtgtg    540
gtgtcatgtt tgtgagagag aaaacacttt cgagtgccag aacccaagga ggtgcaaatg    600
gacagagcca tactgcgtta tagcggccgt gaaaatattt ccacgttttt tcatggttgc    660
gaagcagtgc tccgctggtt gtgcagcgat ggagagaccc aagccagagg agaagcggtt    720
tctcctggaa gagcccatgc ccttctttta cctcaagtgt tgtaaaattc gctactgcaa    780
tttagagggg ccacctatca actcatcagt gttcaaagaa tatgctggga gcatgggtga    840
gagctgtggt gggctgtggc tggccatcct cctgctgctg gcctccattg cagccggcct    900
```

```
cagcctgtct tgagccacgg gactgccaca gactgagcct tccggagcat ggactcgctc    960
cagaccgttg tcacctgttg cattaaactt gttttctgtt gattacctct tggtttgact   1020
tcccagggtc ttgggatggg agagtgggga tcaggtgcag ttggctctta accctcaagg   1080 gttcttaac tcacattcag aggaagtcca gatctcctga gtagtgattt tggtgacaag    1140
tttttctctt tgaaatcaaa ccttgtaact catttattgc tgatggccac tcttttcctt   1200
gactcccctc tgcctctgag ggcttcagta ttgatgggga gggaggccta agtaccactc   1260
atggagagta tgtgctgaga tgcttccgac ctttcaggtg acgcaggaac actgggggag   1320
tctgaatgat tggggtgaag acatccctgg agtgaaggac tcctcagcat gggggggcagt 1380 ggggcacacg ttagggctgc ccccattcca gtggtggagg cgctgtggat ggctgctttt   1440
cctcaacctt tcctaccaga ttccaggagg cagaagataa ctaattgtgt tgaagaaact   1500
tagacttcac ccaccagctg gcacaggtgc acagattcat aaattcccac acgtgtgtgt   1560
tcaacatctg aaacttaggc caagtagaga gcatcagggt aaatggcgtt catttctctg   1620
ttaagatgca gccatccatg gggagctgag aaatcagact caaagttcca ccaaaaacaa   1680
atacaagggg acttcaaaag ttcacgaaaa aattgaatta aagataaaaa attaa         1735
```

<210> SEQ ID NO 38
<211> LENGTH: 223
<212> TYPE: PRT
<213> ORGANISM: Mus musculus

<400> SEQUENCE: 38

```
Met Arg Leu Gln Arg Pro Arg Gln Ala Pro Ala Gly Gly Arg Arg Ala
 1               5                  10                  15

Pro Arg Gly Gly Arg Gly Ser Pro Tyr Arg Pro Asp Pro Gly Arg Gly
             20                  25                  30

Ala Arg Arg Leu Arg Arg Phe Gln Lys Gly Gly Glu Gly Ala Pro Arg
         35                  40                  45

Ala Asp Pro Pro Trp Ala Pro Leu Gly Thr Met Ala Leu Leu Ala Leu
     50                  55                  60

Leu Leu Val Val Ala Leu Pro Arg Val Trp Thr Asp Ala Asn Leu Thr
 65                  70                  75                  80

Ala Arg Gln Arg Asp Pro Glu Asp Ser Gln Arg Thr Asp Glu Gly Asp
                 85                  90                  95

Asn Arg Val Trp Cys His Val Cys Glu Arg Glu Asn Thr Phe Glu Cys
            100                 105                 110

Gln Asn Pro Arg Arg Cys Lys Trp Thr Glu Pro Tyr Cys Val Ile Ala
        115                 120                 125

Ala Val Lys Ile Phe Pro Arg Phe Phe Met Val Ala Lys Gln Cys Ser
    130                 135                 140

Ala Gly Cys Ala Ala Met Glu Arg Pro Lys Pro Glu Glu Lys Arg Phe
145                 150                 155                 160

Leu Leu Glu Glu Pro Met Pro Phe Phe Tyr Leu Lys Cys Cys Lys Ile
                165                 170                 175

Arg Tyr Cys Asn Leu Glu Gly Pro Pro Ile Asn Ser Ser Val Phe Lys
            180                 185                 190

Glu Tyr Ala Gly Ser Met Gly Glu Ser Cys Gly Gly Leu Trp Leu Ala
        195                 200                 205

Ile Leu Leu Leu Leu Ala Ser Ile Ala Ala Gly Leu Ser Leu Ser
    210                 215                 220
```

```
<210> SEQ ID NO 39
<211> LENGTH: 20
<212> TYPE: DNA
<213> ORGANISM: Artificial Sequence
<220> FEATURE:
<223> OTHER INFORMATION: Artificial Sequence

<400> SEQUENCE: 39
cttacccatc tgccctccta                                                   20

<210> SEQ ID NO 40
<211> LENGTH: 20
<212> TYPE: DNA
<213> ORGANISM: Artificial Sequence
<220> FEATURE:
<223> OTHER INFORMATION: Artificial Sequence

<400> SEQUENCE: 40
cctccattgg gaactgctac                                                   20

<210> SEQ ID NO 41
<211> LENGTH: 24
<212> TYPE: DNA
<213> ORGANISM: Artificial Sequence
<220> FEATURE:
<223> OTHER INFORMATION: Artificial Sequence

<400> SEQUENCE: 41
tcctgttgcc aggaagacct ctgc                                              24

<210> SEQ ID NO 42
<211> LENGTH: 20
<212> TYPE: DNA
<213> ORGANISM: Artificial Sequence
<220> FEATURE:
<223> OTHER INFORMATION: Artificial Sequence

<400> SEQUENCE: 42
acttcctgcc cagcagttac                                                   20

<210> SEQ ID NO 43
<211> LENGTH: 20
<212> TYPE: DNA
<213> ORGANISM: Artificial Sequence
<220> FEATURE:
<223> OTHER INFORMATION: Artificial Sequence

<400> SEQUENCE: 43
ggcactgacg ggtctttagt                                                   20

<210> SEQ ID NO 44
<211> LENGTH: 20
<212> TYPE: DNA
<213> ORGANISM: Artificial Sequence
<220> FEATURE:
<223> OTHER INFORMATION: Artificial Sequence

<400> SEQUENCE: 44
ctgccgcgcc tctgatggat                                                   20

<210> SEQ ID NO 45
<211> LENGTH: 1659
<212> TYPE: DNA
<213> ORGANISM: mus musculus

<400> SEQUENCE: 45
```

-continued

```
ggagagagca ggacacagct atggatgccg ccaggagagg agatacacag ccagtgatgt      60
ggaccaccgg atggctgttg ctgctgccgc ttctgctgtg tgaaggagcg caagccctgg     120
agtgctacag ctgcgtgcag aaggcggacg atggatgctc ccgcacagg atgaagacag      180
tcaaatgtgg tcccggggtg gacgtctgta ccgaggccgt gggagcggta gagaccatcc     240
acgggcaatt ctctgtggcg gtgcggggct gcggttccgg aatcccgggc aagaacgacc     300
gcggactgga ccttcacggg ctcctggcct tctttcagct acagcagtgc tccgaggacc     360
gatgcaacgc caaactcaac ctcactttgc gaggcctcaa ccctgcaggc aatgagagtg     420
catatgagcc taacggtgca gagtgctaca gctgtgtggg tctgagccgc gagaagtgcc     480
agggctccat gccgccggtc gtgaactgct acaacgccag tggccgtgtc tacaagggct     540
gcttcgatgg taacgtcacc ctgacggcag ccaacgtgac cgtgtcctta cctgtccgag     600
gctgcgtcca ggacgagacc tgcacccggg atggggtgac gggtccagga ttcacactca     660
gcggctcttg ctgtcagggc cccgctgtat acgccgacct tcgcaacaag acctatttct     720
cccctcgaat cccacccta gtcctgctgc cccctccaac caccgcagcc ccatccactc      780
gggcccagaa ctcctccagc acgacctcta cagcagcccc aaccacgacc acctccatca     840
tcaagcccac cacagcccaa gccagccaca cttctcccca tgaaatggat ctcgaagtca     900
tacaggaaga gggggcgtcg ttgagtggag gtgctgcggg ccatggaggt actgcgggcc     960
atggaggtgc tgcgggccac caagaccgca gcaatatgga gaagtatcca ggaaagggtg    1020
gggcccagat cccagctaaa ggaggctctg gcactctagg gtcctggttg tctgcagttc    1080
tgttgactgt ggttgctggc gcgatgctgt gaatgtctca tctcgaaaag tccatctcac    1140
tttgtttccc tggccccgtg gtaccaactc tttccatttc tcacttgact ggactggctc    1200
cgcccccatc cttcagcatt ctcagttccg actgcactgg tttgcagctt cggaaaacag    1260
tcctctgttg taaatattcc gctcgggtgg ccctactttt tgatgcggc cacagcattc     1320
cccctgatgg tgaccaggac agagggaaga gacgtctact ggctgagaga ggcccagaga    1380
gtccacggca agcctcctct tcccgttttc ctgaccaggc tggaagatga ccaggcaggt    1440
agacaatgga tccatcctcc gagcactgtg cttgcctggc acattgtgcg gaaatctggt    1500
cgcctgtctt ccttaggaga ctgtgaacaa ctctacaaca gggtcttgtc tctgcctct     1560
ctatgtgttc tgtctggcac aggaaggtgt caataaagat ttagttactt tgtatagtga    1620
gttaactaaa aaaaaaaaaa aaaaaaaaaa aaaaaaaa                             1659
```

<210> SEQ ID NO 46
<211> LENGTH: 363
<212> TYPE: PRT
<213> ORGANISM: mus musculus

<400> SEQUENCE: 46

```
Met Asp Ala Ala Arg Gly Asp Thr Gln Pro Val Met Trp Thr Thr
  1               5                  10                  15

Gly Trp Leu Leu Leu Leu Pro Leu Leu Leu Cys Glu Gly Ala Gln Ala
                 20                  25                  30

Leu Glu Cys Tyr Ser Cys Val Gln Lys Ala Asp Asp Gly Cys Ser Pro
             35                  40                  45

His Arg Met Lys Thr Val Lys Cys Gly Pro Gly Val Asp Val Cys Thr
         50                  55                  60

Glu Ala Val Gly Ala Val Glu Thr Ile His Gly Gln Phe Ser Val Ala
 65                  70                  75                  80
```

```
Val Arg Gly Cys Gly Ser Gly Ile Pro Gly Lys Asn Asp Arg Gly Leu
                85                  90                  95

Asp Leu His Gly Leu Leu Ala Phe Phe Gln Leu Gln Gln Cys Ser Glu
            100                 105                 110

Asp Arg Cys Asn Ala Lys Leu Asn Leu Thr Leu Arg Gly Leu Asn Pro
        115                 120                 125

Ala Gly Asn Glu Ser Ala Tyr Glu Pro Asn Gly Ala Glu Cys Tyr Ser
    130                 135                 140

Cys Val Gly Leu Ser Arg Glu Lys Cys Gln Gly Ser Met Pro Pro Val
145                 150                 155                 160

Val Asn Cys Tyr Asn Ala Ser Gly Arg Val Tyr Lys Gly Cys Phe Asp
                165                 170                 175

Gly Asn Val Thr Leu Thr Ala Ala Asn Val Thr Val Ser Leu Pro Val
            180                 185                 190

Arg Gly Cys Val Gln Asp Glu Thr Cys Thr Arg Asp Gly Val Thr Gly
        195                 200                 205

Pro Gly Phe Thr Leu Ser Gly Ser Cys Cys Gln Gly Pro Arg Cys Asn
    210                 215                 220

Ala Asp Leu Arg Asn Lys Thr Tyr Phe Ser Pro Arg Ile Pro Pro Leu
225                 230                 235                 240

Val Leu Leu Pro Pro Thr Thr Ala Ala Pro Ser Thr Arg Ala Gln
                245                 250                 255

Asn Ser Ser Ser Thr Thr Ser Thr Ala Ala Pro Thr Thr Thr Thr Ser
            260                 265                 270

Ile Ile Lys Pro Thr Thr Ala Gln Ala Ser His Thr Ser Pro His Glu
        275                 280                 285

Met Asp Leu Glu Val Ile Glu Glu Gly Ala Ser Leu Ser Gly Gly
    290                 295                 300

Ala Ala Gly His Gly Gly Thr Ala Gly His Gly Gly Ala Ala Gly His
305                 310                 315                 320

Gln Asp Arg Ser Asn Met Glu Lys Tyr Pro Gly Lys Gly Gly Ala Gln
                325                 330                 335

Ile Pro Ala Lys Gly Gly Ser Gly Thr Leu Gly Ser Trp Leu Ser Ala
            340                 345                 350

Val Leu Leu Thr Val Val Ala Gly Ala Met Leu
            355                 360

<210> SEQ ID NO 47
<211> LENGTH: 934
<212> TYPE: DNA
<213> ORGANISM: mus musculus

<400> SEQUENCE: 47 tcgctcccccg cgccgtgccc gccgctgagc ccggagtgcg acacccccag ggatgcctgc      60
gccccagagg accccccgcct gcagccccccg cgcctctttc aggccctatc ggagcatgct    120
gcctgcagcc atgaagagcc tcggtctggc gctgctggcc ttgcttctct gccccctcgcc    180 ggcccatggc ctgtggtgcc aggactgcac cctggccaat tccagccatt gcgctccgaa    240
gcagtgccag cccaccgata ccgtttgtgc cagcgtgcgg atcaccgacc ccagcagcag    300
caggaaggat cattctgtga acaagatgtg tgcttcctcc tgcgacttcg ttaagcggca    360 cttttttctca gactatctga tggggttcat taactctggg atcttaaaag tcgacgtgga    420
ctgctgcgag aaagatttgt gcaacggggc atcggtcgca ggacgcagcc cctgggccct    480
```

-continued

| | |
|---|---|
| ggctgggggg ctcctgctca gcctggggcc tgctcttctc tgggctgggc cctaagaccc | 540 |
| ctccctccct cctgctgggc tttggagctt gtccctaag cctgttgctg ccctcccca | 600 |
| gcctggcctg gctggggctg ggacagcaag ggtttggcat caaggtctga ggctctcaac | 660 |
| ctccctagat gtgagtgagc cttctccgtt tctccaccag ctccatatcc caagcagctg | 720 |
| aatatctcca ggagtccaga catcctggca ggaagctggg gtagggggga ggggagggc | 780 |
| aagggactga gaccctccag gtctccaagg ggagggaggt caagccaggg acagcccaac | 840 |
| agcctggcct gagggggcatt aactacagag aaataaagtc acttctgagt cttgtgaaaa | 900 |
| aaaaaaaaaa aaaaaaaaaa aaaaaaaaaa aaaa | 934 |

<210> SEQ ID NO 48
<211> LENGTH: 160
<212> TYPE: PRT
<213> ORGANISM: mus musculus

<400> SEQUENCE: 48

```
Met Pro Ala Pro Gln Arg Thr Pro Ala Cys Ser Pro Arg Ala Ser Phe
1               5                   10                  15
Arg Pro Tyr Arg Ser Met Leu Pro Ala Ala Met Lys Ser Leu Gly Leu
            20                  25                  30
Ala Leu Leu Ala Leu Leu Leu Cys Pro Ser Pro Ala His Gly Leu Trp
        35                  40                  45
Cys Gln Asp Cys Thr Leu Ala Asn Ser Ser His Cys Ala Pro Lys Gln
    50                  55                  60
Cys Gln Pro Thr Asp Thr Val Cys Ala Ser Val Arg Ile Thr Asp Pro
65                  70                  75                  80
Ser Ser Ser Arg Lys Asp His Ser Val Asn Lys Met Cys Ala Ser Ser
                85                  90                  95
Cys Asp Phe Val Lys Arg His Phe Phe Ser Asp Tyr Leu Met Gly Phe
            100                 105                 110
Ile Asn Ser Gly Ile Leu Lys Val Asp Val Asp Cys Cys Glu Lys Asp
        115                 120                 125
Leu Cys Asn Gly Ala Ser Val Ala Gly Arg Ser Pro Trp Ala Leu Ala
    130                 135                 140
Gly Gly Leu Leu Leu Ser Leu Gly Pro Ala Leu Leu Trp Ala Gly Pro
145                 150                 155                 160
```

<210> SEQ ID NO 49
<211> LENGTH: 2047
<212> TYPE: DNA
<213> ORGANISM: mus musculus

<400> SEQUENCE: 49

| | |
|---|---|
| agaagaggcg agactttttt gggtgctccg gatcgccagt agttcttcaa gcctcagcag | 60 |
| ccaactcctc cggaggcgct gcgctccgcc ccagggagcg cgaatccaag gagcctggga | 120 |
| ccagcctctg ggagcccccg gcgcgggcga tgcgggcgcc gcgggcgaca cctgcggctc | 180 |
| ctctcggtgg cagccgtcgc ttgggcggca gcagcgcgag cctcggcagc tcggcagct | 240 |
| actgtcgccg cggccagaac agcctccgct gcggtcgtgg tctctgatgc tcttgcccgc | 300 |
| tcccggccct gccgatccgg gaggatgtgg gttctcggca tcgcagcaac ttttttgcgga | 360 |
| ttgttctggc ttccagggct ggcgctgcaa attcagtgct accagtgtga agaattccag | 420 |
| ctgaacaacg attgctcatc ccctgagttc atcgtaaatt gcaccgtgaa cgttcaagac | 480 |
| atgtgtcaga agaagtgat ggagcaaagt gctgggatca tgtaccggaa gtcgtgtgca | 540 |

```
tcgtcagcag cctgtctcat tgcttcagct gggtaccagt ccttctgttc ccctgggaaa      600
ctgaactccg tgtgcatcag ctgctgcaac acccctcttt gcaatgggcc gaggcccaag      660
aagagaggca gctctgcctc ggccatcagg ccaggcttc tcaccactct cctgttcttc       720
cacttagccc tctgcttggc acactgctga agctaaagga gatgccaacc cctgctgcct     780
cacctgtctg gcccttcgtc tctcaccttc ccgagtctct tctgggtgtc cttttattct     840
gggtagacaa gggagtcttt ttgttccctc ctttcaagta acgcaagatt gccgtgcaca     900 aatactttg taagctctga accaattcat tctgaattc tgtgtgtagt tgaagaaaaa       960
agcatggagc agaaagtcca gaccctccca tcccaatctg gttaaccacc gccaaggcta    1020
gcctggaaga accagccctt agaagtcatt gagatacgca tctgcctttc ccaaagcctt    1080
gagcttccat tctgtcccag taggagtcac agtctattca gagactgctg ctgcgtgaag    1140
gtaactttgc ttttgcggga ggggagagcc agtttcggct caaggcttct gaacttgcca    1200
ttcatacttc ctgctcctgt aaactatttt ctggggtgga cccagctggt ttggtctctg    1260
agccagtctg tggtgactca ggactcaagg gctgggcctt agcctctcca ggcttggcct    1320
cagtctgaaa agtgcttaag aaaaccttgt tagttctcct ggaggaagag ttactgcgcc    1380
gggaggctag gaagatgagg gggctgcggg ctgagctggt gctgtccttg gtggagatga    1440
agcgggcacg ctggcgtttc tcttggttgg catgctgcag agtcaggcgg cagcagagca    1500
cctgccagaa caccttccgg aactgctgag aggacacgtt gtagaggaga gggttgacca    1560
cagagctgag gtagaagaag gtatcagaga agggcaggag gatcatgtat gccctgaagt    1620
acgttctggt ccagtcatgt ttgggtttttg ctgcagccat gatccgtcgg atctgattgg    1680
gcatccaaca cacggccaac gtcaccacaa tcagtcctgg caggcaagaa caggagagaa    1740
aaggagacgg ggagagaaac agcatgagaa caaaaataaa taataaaaa cccataaaat      1800 attaagcccc ttggttctgt tgcttactgg ccgagaaacg gtaccaatct ttcagctctg    1860
tgcttgtcgg cttctttttg ccactggcaa aggagaattt aatgctgctt caagctcagg    1920
ggacttggct atgttaaaaa gcgttaaatg ctttcgacag tgtatttata cttacggctg    1980
cctgttaatt ttcaaaatgt tttcattgtt gctcgtgtat ccagaaaata tctcacgttg    2040
gccaaaa                                                              2047
```

<210> SEQ ID NO 50
<211> LENGTH: 141
<212> TYPE: PRT
<213> ORGANISM: mus musculus

<400> SEQUENCE: 50

```
Met Trp Val Leu Gly Ile Ala Ala Thr Phe Cys Gly Leu Phe Trp Leu
 1               5                  10                  15

Pro Gly Leu Ala Leu Gln Ile Gln Cys Tyr Gln Cys Glu Glu Phe Gln
            20                  25                  30

Leu Asn Asn Asp Cys Ser Ser Pro Glu Phe Ile Val Asn Cys Thr Val
        35                  40                  45

Asn Val Gln Asp Met Cys Gln Lys Glu Val Met Glu Gln Ser Ala Gly
    50                  55                  60

Ile Met Tyr Arg Lys Ser Cys Ala Ser Ala Ala Cys Leu Ile Ala
65                  70                  75                  80

Ser Ala Gly Tyr Gln Ser Phe Cys Ser Pro Gly Lys Leu Asn Ser Val
                85                  90                  95
```

```
Cys Ile Ser Cys Cys Asn Thr Pro Leu Cys Asn Gly Pro Arg Pro Lys
            100                 105                 110

Lys Arg Gly Ser Ser Ala Ser Ala Ile Arg Pro Gly Leu Leu Thr Thr
        115                 120                 125

Leu Leu Phe Phe His Leu Ala Leu Cys Leu Ala His Cys
    130                 135                 140

<210> SEQ ID NO 51
<211> LENGTH: 516
<212> TYPE: DNA
<213> ORGANISM: mus musculus

<400> SEQUENCE: 51
ggcaggcctg agtgaggacc tcgaccatgc aggggacctg gatggtgctg ttggcactga      60
tattgggcac cttcggggag cttgctatgg ccttacagtg ctacacctgt gcgaatcctg     120
tgagtgcatc caactgtgtc accaccaccc actgccacat caatgaaacc atgtgcaaga     180
ctacgctcta ctccctggag attgttttcc ctttcctggg ggactccacg gtgaccaagt     240
cctgcgccag caagtgtgag ccttcggatg tggatggcat tgggcaaacc cggccagtgt     300
cctgctgcaa ttctgaccta tgcaacgtgg atggggcacc cagcctgggc agtcctggtg     360
gcctgctcct tgccctggca ctttcttgc tcttgggtgt cctgctgtaa agccatggcc     420
atctagctcc actcccttgt ccctgacatc ccagttccct aatgcctaga gaaatacaa     480 tggccatctg caaaaaaaaa aaaaaaaaaa aaaaaa                              516

<210> SEQ ID NO 52
<211> LENGTH: 127
<212> TYPE: PRT
<213> ORGANISM: mus musculus

<400> SEQUENCE: 52

Met Gln Gly Thr Trp Met Val Leu Leu Ala Leu Ile Leu Gly Thr Phe
 1               5                  10                  15

Gly Glu Leu Ala Met Ala Leu Gln Cys Tyr Thr Cys Ala Asn Pro Val
            20                  25                  30

Ser Ala Ser Asn Cys Val Thr Thr Thr His Cys His Ile Asn Glu Thr
        35                  40                  45

Met Cys Lys Thr Thr Leu Tyr Ser Leu Glu Ile Val Phe Pro Phe Leu
    50                  55                  60

Gly Asp Ser Thr Val Thr Lys Ser Cys Ala Ser Lys Cys Glu Pro Ser
65                  70                  75                  80

Asp Val Asp Gly Ile Gly Gln Thr Arg Pro Val Ser Cys Cys Asn Ser
                85                  90                  95

Asp Leu Cys Asn Val Asp Gly Ala Pro Ser Leu Gly Ser Pro Gly Gly
            100                 105                 110

Leu Leu Leu Ala Leu Ala Leu Phe Leu Leu Gly Val Leu Leu
        115                 120                 125

<210> SEQ ID NO 53
<211> LENGTH: 450
<212> TYPE: DNA
<213> ORGANISM: mus musculus

<400> SEQUENCE: 53 atgctttta tggcaggccc tgcagccagc tggtccctga ggcccctggg actccatggc       60
gtcccccaag cctgtgtgc tgtcctctta acagtgctgg tcatgaagac cttggttctc     120
```

```
ggtgatacca agctcgagga ccttcaccct cagtccctcc cactaaacaa gtacctgaat    180
tgctaccgat gtctgctgga gaccgaagag ctggggtgcc tcctggggtc tgacacctgc    240
ctgacacctc tgggcagcag ctgtgtcacc ctgcacataa agaacagcag cggttttaat    300
gtcatggtga gcgactgcta cagcaaggag cagatggtcc attgttcata tacccgtgct    360
tccccggtgt ttggcttttg gatattctat cagtgttgct tcctggattt ctgcaacaat    420
ccggacaaca gaaagaatag catgcactag                                     450
```

```
<210> SEQ ID NO 54
<211> LENGTH: 149
<212> TYPE: PRT
<213> ORGANISM: mus musculus

<400> SEQUENCE: 54
```

```
Met Leu Phe Met Ala Gly Pro Ala Ala Ser Trp Ser Leu Arg Pro Leu
 1               5                  10                  15

Gly Leu His Gly Val Pro Gln Ala Leu Cys Ala Val Leu Leu Thr Val
            20                  25                  30

Leu Val Met Lys Thr Leu Val Leu Gly Asp Thr Lys Leu Glu Asp Leu
        35                  40                  45

His Pro Gln Ser Leu Pro Leu Asn Lys Tyr Leu Asn Cys Tyr Arg Cys
    50                  55                  60

Leu Leu Glu Thr Glu Glu Leu Gly Cys Leu Leu Gly Ser Asp Thr Cys
65                  70                  75                  80

Leu Thr Pro Leu Gly Ser Ser Cys Val Thr Leu His Ile Lys Asn Ser
                85                  90                  95

Ser Gly Phe Asn Val Met Val Ser Asp Cys Tyr Ser Lys Glu Gln Met
            100                 105                 110

Val His Cys Ser Tyr Thr Arg Ala Ser Pro Val Phe Gly Phe Trp Ile
        115                 120                 125

Phe Tyr Gln Cys Cys Phe Leu Asp Phe Cys Asn Asn Pro Asp Asn Arg
    130                 135                 140

Lys Asn Ser Met His
145
```

```
<210> SEQ ID NO 55
<211> LENGTH: 960
<212> TYPE: DNA
<213> ORGANISM: mus musculus

<400> SEQUENCE: 55
```

```
agagctggag acctgggaat ctgctgtcaa ctgctggggc tgtggacatt ctcaggaccc     60
tcaccatgaa acacctcctg ttgctcaccc tgtctgccct actctactgc tgggtctcag    120
ctgatactcg atgtcactcc tgctacaaag tccctgtgct gggctgtgtg atcgccagt     180 cctgccgcct ggagccgggc cacaaatgcc tgacaacaaa cgtgtacctt gggaagatgt    240
gggttttctc taacctgcgc tgcggcacac cagaagagcc ttgtcgggag gtcttcaacg    300
aaaccaacca taagctgggc ctgaactaca caccacctg ctgtgacaag ataactgta     360 acagcccggc tccacggccc acacccgcac tggccctcat ctccctcacc tccttggctg    420
gcctcggcct ctggttattg cattgagact agctccatgg ctacaatctt accacctgct    480
atagcctgag cctttctccc tgtgtcctca gagctccagc tttccagaat cttctctcct    540 cccacccccct tcttctgaag atcatgtccc tagtcctata ccatttattt catgggactg    600
tacctggagt ggcctttcta gccaccgctc ctctccctca cttgtcacct tccactccat    660
```

```
tccacccaca cacagacaca cagacacaca gacacaaaga cacacacaca cacacacaca       720
cacacacaca cccagtcctt tcccatttcc ttctagaaca ctctacctcc tccactggcc       780
actgaaaggc tcccctcctt ggacgcacac tgctgtgcct ctgggatcta agtctggaag       840
aactcctgtc ttgtctccag ggagtgattc caaaaggcgc tggcctcatt gcatgggcct       900
ggcttaccag accctctgct tgtccccttc tatcttgaga aataaacatc agtgtctaat       960
```

<210> SEQ ID NO 56
<211> LENGTH: 126
<212> TYPE: PRT
<213> ORGANISM: mus musculus

<400> SEQUENCE: 56

```
Met Lys His Leu Leu Leu Thr Leu Ser Ala Leu Leu Tyr Cys Trp
  1               5                  10                  15

Val Ser Ala Asp Thr Arg Cys His Ser Cys Tyr Lys Val Pro Val Leu
             20                  25                  30

Gly Cys Val Asp Arg Gln Ser Cys Arg Leu Glu Pro Gly His Lys Cys
         35                  40                  45

Leu Thr Thr Asn Val Tyr Leu Gly Lys Met Trp Val Phe Ser Asn Leu
     50                  55                  60

Arg Cys Gly Thr Pro Glu Glu Pro Cys Arg Glu Val Phe Asn Glu Thr
 65                  70                  75                  80

Asn His Lys Leu Gly Leu Asn Tyr Asn Thr Thr Cys Cys Asp Lys Asp
                 85                  90                  95

Asn Cys Asn Ser Pro Ala Pro Arg Pro Thr Pro Ala Leu Ala Leu Ile
            100                 105                 110

Ser Leu Thr Ser Leu Ala Gly Leu Gly Leu Trp Leu Leu His
        115                 120                 125
```

<210> SEQ ID NO 57
<211> LENGTH: 3952
<212> TYPE: DNA
<213> ORGANISM: mus musculus

<400> SEQUENCE: 57

```
gcctacttgg cctgcctgcg atgcggtacc aacaccgcac gaagtgtgta cagattccca        60
gttagacagc aggagggacc tgggagcggc caggggatg ttttatctct aagagaccaa       120
gagctcaggc agggcttctg tgccctgctt cctccctggc ttgagctgga tcctggacca       180
gctgctgacc tcctgttcac tctggcactg ccctcacgtc tccgtcatga cccatctgct       240
cacagtgttc ctggtggccc tgatgggcct gctgtggcc caggctctgg agtgccacgt       300
gtgtgcctac aatggagaca actgcttcaa acccatgcgc tgcccagcca tggccaccta       360
ctgtatgacc acacgaactt acttcacccc ataccggatg aaggtgagga agtcctgtgt       420
ccccagctgc tttgaaaccg tgtacgatgg ctattccaag catgcatctg ccacctcctg       480
ttgccagtac tacctctgca acggtgctgg cttttgctac ccggtgacct tggccctggt       540
cccagcactc ctagctacct tctggagctt gctgtaaagc tcggttcccc aagccagatc       600
cactcaaacg caaacactctc aaaaaacaca gtttccctct ctctcccaat tcactccacc       660
caacgctctt ccttctgaca ctcctcaact accacgaggt cccatggcta cctacgaaag       720
aactgatggc atccagatac ctcactccaa ggtcattttc agaaggctga catgtggacc       780
tgtaatgtgc ccaccccatgg gtggggcagg ctgggcttct cctctaccca agatcagggg       840
```

-continued

```
catctgggag aatgtttatg gaggaggggt catcactcaa gtcaaggagc actgatttga    900
tagaattagt agccaaactc caccttcaga accctgcctc agtctaccca gtagaggatg    960
ggtctgctag aggtgagggg aggagagcgg cggagaataa cgagctggct agaagcagag   1020
aaagactcag cagggctgtc tccgaagatc agcgcggctt gccagagcaa atgtgatgtg   1080
gaagccatgt gaggaagccc tttgtcattt ccacttatct gaggaactct gccagacctg   1140
atgttgggat agccattggc caagggttcc tagcaacggc gtcatttcca taggccactg   1200
aaatccctcc agcccagct cagcaggccc cttgacctcc actacagtcc ttcattcaca   1260
caccagctgc tgggccttga agttggcagg gacttgggag caggtgaccc atgctatttt   1320
ttgtctggcc tgttattctg ggcatggcaa gagggatca gacgcaggtc agagcagggc    1380
agtagggcga ctgagacagg gaaacagact tcagccagtg gcttcccagg tcccgtaggc   1440
agctcctaca tccttcagtc tcttgttaca ttcccgggag acaaatatac agggagccaa   1500
gccgagtgct aggtgatgac tgcctgtgaa gtcattgtg ccacagact gctgggtacc    1560 aagtctcagg agaacccagc ctagatttag gagacacaga tctgcctttc atgcagtgta   1620
gctgtccttg ggagccttac catgctctct aactagtacc tcaactcaca tgtcactgag   1680 gaaccccta acactggccc agcccagggg tcgggatgct ggccaatgtc catggagtgg    1740
gactacccat ggagagtcct tgggtcatca catcacaaat gttttattcc aacctcccag   1800
tggtgagagc tcgggacaca aaggtccatc ctggggacct tcttcctggt tctaggcaga   1860
cctgaactct gtctgctgct agagctgatg tggttttccg cctcagtttc ctcctccggg   1920
gataggccac cggaggattt gggagggtgg ggagggcatc ctgctgatgg gctcgccgag   1980
gttctcagga acaggaacgg gcggggcttt agtacacagg tgagttgggt gggaactggc   2040
ccggagctga ggagacactg actgggcaga gggaagatga gtctcaaggg agggcaggaa   2100 aagggaggg gagcgcgcat gcacatgtgc actcagtgca ggctacagag cccaaaaggc    2160
agcactggct gtggtgtccc ctgaggccca ggcaagatgc taggaggaag ccaatgctgc   2220
ccccacctga gctcacatgg aacatgcaca ccaccagcag cagcagcaag cattgagact   2280
gacctgtgga cgccataggg cactggcaag gagggtcaga ggcgggtccc tgactcagtg   2340
ggtgaggccc gggaaacatt atcctgttac cctgcgtgtg caagatcatt gtccccagct   2400
agatggcgtc ctcaaccaaa actgagagga gccccagttc aggtcctccc tcctaccaca   2460 aggggtggt gtgaggagg cttgattgcc cttggagaag caccggtact gcagagctgg    2520
gggccagctt ctttcatctg tgtctagaca ccgaccagat aggccccaca gtggcaacac   2580
tgccacacag ccctcaagaa agccctgtgc ctagctagca cagagcccca aaaggtgctc   2640
aattaataca gggccaagcc tgccagtggg ggggatgcag attaggggaa cagacccaga   2700
tggcctgtcc tgaaccctgt ctggggtggt gtgatgagca tctgtctagc ccactgcagg   2760
tggctctaca cactccacaa cagttctgca aaagtgtatg aggtggtcat tactgcgccc   2820
ctctcacagg taaaggcact gaggcacgga ggagtgaggc acttcatttt cctgggccat   2880
tcaactttcc aggaccaaca cattcaacta tgggtactac tccaatagct ggggttcttt   2940
gaggctgggc ccctgaaga tgatagtggc ttcatcaacc agagaatttc agagtgcagt   3000
gttgtaggag cctatgaacc tgaaatgtca gaactggagg tttgagggc tgaggggtag    3060 gccaggggtg tctggcccct tgtgtggaga cagagagaga gggaacatgg gatggggtag   3120
tagagagaag tgcaaaggag cgtcagccct tctcagggct aatgctgtca gggacgaggg   3180
ctcaagcctg tgagtgttct cacactgtga taaacagtgg cccctcaaca cagacggtgt   3240
```

-continued

```
ccagagtggc cggcagtggt tatctagagt tgcaatctgg aagcctcttg gtagtcactg    3300
gagagaggcc gcttgatggg acagcaccaa atgtgtgtgc ttctgtggga tgtgaggaag    3360
ctgggtcagc gcatgaagcc aaagcgtcct tcagagcaga ggggtggctg gtctagtcca    3420
ccagagacaa gctatccagt gagagtcata ctctgccacc gtctctgtga ttaccttacc    3480
ccaaagcaga cggggacggg atgcagagca cccgtgtctt catcttctgc ggcaagcacg    3540
tgagttcaca ttctgaaact ctagaaagat ttccaggagt ggggtgtgcc tttgctttgg    3600
tgcatggtta cttcctggca agcaccgtgg catcccgcag cactgagtga cctgggctcc    3660
tcaagccatc tcattggtga atgacagtg ccagtaccct ctcagctggc tcttggaggc     3720
ctgtgcatgg ggtctgcaca gaggaggccc ccaaactatg catggacgga cacgtgatgc    3780
ctagcacttc ccttggttgt gtctctgcca accccaggct ctcacccagc aaggaaatga    3840
aatccacttt tatgacacat ctccctcccc cagccagctc cattcaccta tatgccaggg    3900
tggtcccttt caatgtctgt cccccattgg atgaataaac aagcgaagga ca            3952
```

<210> SEQ ID NO 58
<211> LENGTH: 116
<212> TYPE: PRT
<213> ORGANISM: mus musculus

<400> SEQUENCE: 58

```
Met Thr His Leu Leu Thr Val Phe Leu Val Ala Leu Met Gly Leu Pro
 1               5                  10                  15

Val Ala Gln Ala Leu Glu Cys His Val Cys Ala Tyr Asn Gly Asp Asn
             20                  25                  30

Cys Phe Lys Pro Met Arg Cys Pro Ala Met Ala Thr Tyr Cys Met Thr
         35                  40                  45

Thr Arg Thr Tyr Phe Thr Pro Tyr Arg Met Lys Val Arg Lys Ser Cys
     50                  55                  60

Val Pro Ser Cys Phe Glu Thr Val Tyr Asp Gly Tyr Ser Lys His Ala
 65                  70                  75                  80

Ser Ala Thr Ser Cys Cys Gln Tyr Tyr Leu Cys Asn Gly Ala Gly Phe
                 85                  90                  95

Ala Thr Pro Val Thr Leu Ala Leu Val Pro Ala Leu Leu Ala Thr Phe
            100                 105                 110

Trp Ser Leu Leu
        115
```

<210> SEQ ID NO 59
<211> LENGTH: 20
<212> TYPE: DNA
<213> ORGANISM: Artificial Sequence
<220> FEATURE:
<223> OTHER INFORMATION: Artificial Sequence

<400> SEQUENCE: 59

```
catgatcctc cgaatctggt                                                  20
```

<210> SEQ ID NO 60
<211> LENGTH: 20
<212> TYPE: DNA
<213> ORGANISM: Artificial Sequence
<220> FEATURE:
<223> OTHER INFORMATION: Artificial Sequence

<400> SEQUENCE: 60

-continued agcacagaac agagggggcta                                        20

<210> SEQ ID NO 61
<211> LENGTH: 20
<212> TYPE: DNA
<213> ORGANISM: Artificial Sequence
<220> FEATURE:
<223> OTHER INFORMATION: Artificial Sequence

<400> SEQUENCE: 61
atacggccaa tgtcacaaca                                         20

<210> SEQ ID NO 62
<211> LENGTH: 20
<212> TYPE: DNA
<213> ORGANISM: Artificial Sequence
<220> FEATURE:
<223> OTHER INFORMATION: Artificial Sequence

<400> SEQUENCE: 62
acttcctgtt cccaccactg                                         20

<210> SEQ ID NO 63
<211> LENGTH: 20
<212> TYPE: DNA
<213> ORGANISM: Artificial Sequence
<220> FEATURE:
<223> OTHER INFORMATION: Artificial Sequence

<400> SEQUENCE: 63
agaggacaag cggagagaca                                         20

<210> SEQ ID NO 64
<211> LENGTH: 20
<212> TYPE: DNA
<213> ORGANISM: Artificial Sequence
<220> FEATURE:
<223> OTHER INFORMATION: Artificial Sequence

<400> SEQUENCE: 64
ttctggcagg ggtgttctag                                         20

<210> SEQ ID NO 65
<211> LENGTH: 18
<212> TYPE: DNA
<213> ORGANISM: Artificial Sequence
<220> FEATURE:
<223> OTHER INFORMATION: Artificial Sequence

<400> SEQUENCE: 65
agcagcagca ggaaggat                                           18

<210> SEQ ID NO 66
<211> LENGTH: 20
<212> TYPE: DNA
<213> ORGANISM: Artificial Sequence
<220> FEATURE:
<223> OTHER INFORMATION: Artificial Sequence

<400> SEQUENCE: 66
aaaagtgccg cttaacgaag                                         20

<210> SEQ ID NO 67
<211> LENGTH: 24
<212> TYPE: DNA
<213> ORGANISM: Artificial Sequence

```
<220> FEATURE:
<223> OTHER INFORMATION: Artificial Sequence

<400> SEQUENCE: 67
caagatgtgt gcttcctcct gcga                                          24

<210> SEQ ID NO 68
<211> LENGTH: 2798
<212> TYPE: DNA
<213> ORGANISM: Homo Sapiens

<400> SEQUENCE: 68
cgttgctgtc gctctgcacg cacctatgtg gaaactaaag cccagagaga aagtctgact    60
tgccccacag ccagtgagtg actgcagcag caccagaatc tggtctgttt cctgtttggc   120
tcttctacca ctacggcttg ggatctcggg catggtggct ttgccaatgg tccttgtttt   180
gctgctggtc ctgagcagag gtgagagtga attggacgcc aagatcccat ccacagggga   240
tgccacagaa tggcggaatc ctcacctgtc catgctgggg tcctgccagc agccccctc    300
ctgccagaag tgcatcctct cacacccag ctgtgcatgg tgcaagcaac tgaacttcac    360
cgcgtcggga gaggcggagg cgcggcgctg cgcccgacga gaggagctgc tggctcgagg   420
ctgcccgctg gaggagctgg aggagccccg cggccagcag gaggtgctgc aggaccagcc   480
gctcagccag ggcgcccgcg gagagggtgc cacccagctg gcgccgcagc gggtccgggt   540
cacgctgcgg cctggggagc ccagcagct ccaggtccgc ttccttcgtg ctgagggata    600
cccggtggac ctgtactacc ttatggacct gagctactcc atgaaggacg acctggaacg   660
cgtgcgccag ctcgggcacg ctctgctggt ccggctgcag gaagtcaccc attctgtgcg   720
cattggtttt ggttcctttg tggacaaaac ggtgctgccc tttgtgagca cagtaccctc   780
caaactgcgc caccctgcc cacccggct ggagcgctgc cagtcaccat tcagctttca    840
ccatgtgctg tccctgacgg gggacgcaca agccttcgag cgggaggtgg ggcgccagag   900
tgtgtccggc aatctggact cgcctgaagg tggcttcgat gccattctgc aggctgcact   960
ctgccaggag cagattggct ggagaaatgt gtcccggctg ctggtgttca cttcagacga  1020
cacattccat acagctgggg acgggaagtt gggcggcatt ttcatgccca gtgatgggca  1080
ctgccacttg gacagcaatg gcctctacag tcgcagcaca gagtttgact acccttctgt  1140
gggtcaggta gcccaggccc tctctgcagc aaatatccag cccatctttg ctgtcaccag  1200
tgccgcactg cctgtctacc aggagctgag taaactgatt cctaagtctg cagttgggga  1260
gctgagtgag gactccagca acgtggtaca gctcatcatg gatgcttata atagcctgtc  1320
ttccaccgtg acccttgaac actcttcact ccctcctggg gtccacattt cttacgaatc  1380
ccagtgtgag ggtcctgaga agagggaggg taaggctgag gatcgaggac agtgcaacca  1440
cgtccgaatc aaccagacgg tgactttctg ggtttctctc caagccaccc actgcctccc  1500
agagccccat ctcctgaggc tccgggccct tggcttctca gaggagctga ttgtggagtt  1560
gcacacgctg tgtgactgta attgcagtga cacccagccc caggctcccc actgcagtga  1620
tggccaggga cacctacaat gtggtgtatg cagctgtgcc cctggccgcc taggtcggct  1680
ctgtgagtgc tctgtggcag agctgtcctc cccagacctg gaatctgggt gccgggctcc  1740
caatggcaca gggcccctgt gcagtggaaa gggtcactgt caatgtggac gctgcagctg  1800
cagtggacag agctctggc atctgtgcga gtgtgacgat gccagctgtg agcgacatga   1860
gggcatcctc tgcggaggct ttggtcgctg ccaatgtgga gtatgtcact gtcatgccaa   1920
```

-continued

```
ccgcacgggc agagcatgcg aatgcagtgg ggacatggac agttgcatca gtcccgaggg    1980
agggctctgc agtgggcatg gacgctgcaa atgcaaccgc tgccagtgct tggacggcta    2040
ctatggtgct ctatgcgacc aatgcccagg ctgcaagaca ccatgcgaga cacccggga     2100
ctgtgcagag tgtggggcct tcaggactgg cccactggcc accaactgca gtacagcttg    2160
tgcccatacc aatgtgaccc tggccttggc ccctatcttg atgatggct ggtgcaaaga     2220
gcggaccctg acaaccagc tgttcttctt cttggtggag gatgacgcca gaggcacggt     2280
cgtgctcaga gtgagacccc aagaaaaggg agcagaccac acgcaggcca ttgtgctggg    2340
ctgcgtaggg ggcatcgtgg cagtgggggct ggggctggtc ctggcttacc ggctctcggt    2400
ggaaatctat gaccgccggg aatacagtcg ctttgagaag gagcagcaac aactcaactg    2460
gaagcaggac agtaatcctc tctacaaaag tgccatcacg accaccatca atcctcgctt    2520
tcaagaggca gacagtccca ctctctgaag gagggaggga cacttaccca aggctcttct    2580
ccttggagga cagtgggaac tggagggtga aggaagggt gggtctgtaa gaccttggta     2640
ggggactaat tcactggcga ggtgcggcca ccaccctact tcattttcag agtgacaccc    2700
aagagggctg cttcccatgc ctgcaacctt gcatccatct gggctacccc acccaagtat    2760
acaataaagt cttacctcag aaaaaaaaaa aaaaaaaa                            2798
```

<210> SEQ ID NO 69
<211> LENGTH: 798
<212> TYPE: PRT
<213> ORGANISM: Homo Sapiens

<400> SEQUENCE: 69

```
Met Val Ala Leu Pro Met Val Leu Val Leu Leu Val Leu Ser Arg
  1               5                  10                  15

Gly Glu Ser Glu Leu Asp Ala Lys Ile Pro Ser Thr Gly Asp Ala Thr
                 20                  25                  30

Glu Trp Arg Asn Pro His Leu Ser Met Leu Gly Ser Cys Gln Pro Ala
             35                  40                  45

Pro Ser Cys Gln Lys Cys Ile Leu Ser His Pro Ser Cys Ala Trp Cys
         50                  55                  60

Lys Gln Leu Asn Phe Thr Ala Ser Gly Glu Ala Glu Ala Arg Arg Cys
 65                  70                  75                  80

Ala Arg Arg Glu Glu Leu Leu Ala Arg Gly Cys Pro Leu Glu Glu Leu
                 85                  90                  95

Glu Glu Pro Arg Gly Gln Gln Glu Val Leu Gln Asp Gln Pro Leu Ser
            100                 105                 110

Gln Gly Ala Arg Gly Glu Gly Ala Thr Gln Leu Ala Pro Gln Arg Val
        115                 120                 125

Arg Val Thr Leu Arg Pro Gly Glu Pro Gln Gln Leu Gln Val Arg Phe
    130                 135                 140

Leu Arg Ala Glu Gly Tyr Pro Val Asp Leu Tyr Tyr Leu Met Asp Leu
145                 150                 155                 160

Ser Tyr Ser Met Lys Asp Asp Leu Glu Arg Val Arg Gln Leu Gly His
                165                 170                 175

Ala Leu Leu Val Arg Leu Gln Glu Val Thr His Ser Val Arg Ile Gly
            180                 185                 190

Phe Gly Ser Phe Val Asp Lys Thr Val Leu Pro Phe Val Ser Thr Val
        195                 200                 205

Pro Ser Lys Leu Arg His Pro Cys Pro Thr Arg Leu Glu Arg Cys Gln
    210                 215                 220
```

-continued

```
Ser Pro Phe Ser Phe His His Val Leu Ser Leu Thr Gly Asp Ala Gln
225                 230                 235                 240

Ala Phe Glu Arg Glu Val Gly Arg Gln Ser Val Ser Gly Asn Leu Asp
            245                 250                 255

Ser Pro Glu Gly Gly Phe Asp Ala Ile Leu Gln Ala Ala Leu Cys Gln
            260                 265                 270

Glu Gln Ile Gly Trp Arg Asn Val Ser Arg Leu Leu Val Phe Thr Ser
            275                 280                 285

Asp Asp Thr Phe His Thr Ala Gly Asp Gly Lys Leu Gly Gly Ile Phe
    290                 295                 300

Met Pro Ser Asp Gly His Cys His Leu Asp Ser Asn Gly Leu Tyr Ser
305                 310                 315                 320

Arg Ser Thr Glu Phe Asp Tyr Pro Ser Val Gly Gln Val Ala Gln Ala
                325                 330                 335

Leu Ser Ala Ala Asn Ile Gln Pro Ile Phe Ala Val Thr Ser Ala Ala
            340                 345                 350

Leu Pro Val Tyr Gln Glu Leu Ser Lys Leu Ile Pro Lys Ser Ala Val
        355                 360                 365

Gly Glu Leu Ser Glu Asp Ser Ser Asn Val Val Gln Leu Ile Met Asp
370                 375                 380

Ala Tyr Asn Ser Leu Ser Ser Thr Val Thr Leu Glu His Ser Ser Leu
385                 390                 395                 400

Pro Pro Gly Val His Ile Ser Tyr Glu Ser Gln Cys Glu Gly Pro Glu
                405                 410                 415

Lys Arg Glu Gly Lys Ala Glu Asp Arg Gly Gln Cys Asn His Val Arg
            420                 425                 430

Ile Asn Gln Thr Val Thr Phe Trp Val Ser Leu Gln Ala Thr His Cys
        435                 440                 445

Leu Pro Glu Pro His Leu Leu Arg Leu Arg Ala Leu Gly Phe Ser Glu
    450                 455                 460

Glu Leu Ile Val Glu Leu His Thr Leu Cys Asp Cys Asn Cys Ser Asp
465                 470                 475                 480

Thr Gln Pro Gln Ala Pro His Cys Ser Asp Gly Gln Gly His Leu Gln
                485                 490                 495

Cys Gly Val Cys Ser Cys Ala Pro Gly Arg Leu Gly Arg Leu Cys Glu
            500                 505                 510

Cys Ser Val Ala Glu Leu Ser Ser Pro Asp Leu Glu Ser Gly Cys Arg
        515                 520                 525

Ala Pro Asn Gly Thr Gly Pro Leu Cys Ser Gly Lys Gly His Cys Gln
530                 535                 540

Cys Gly Arg Cys Ser Cys Ser Gly Gln Ser Ser Gly His Leu Cys Glu
545                 550                 555                 560

Cys Asp Asp Ala Ser Cys Glu Arg His Glu Gly Ile Leu Cys Gly Gly
                565                 570                 575

Phe Gly Arg Cys Gln Cys Gly Val Cys His Cys His Ala Asn Arg Thr
            580                 585                 590

Gly Arg Ala Cys Glu Cys Ser Gly Asp Met Asp Ser Cys Ile Ser Pro
        595                 600                 605

Glu Gly Gly Leu Cys Ser Gly His Gly Arg Cys Lys Cys Asn Arg Cys
610                 615                 620

Gln Cys Leu Asp Gly Tyr Tyr Gly Ala Leu Cys Asp Gln Cys Pro Gly
625                 630                 635                 640
```

```
                            -continued
Cys Lys Thr Pro Cys Glu Arg His Arg Asp Cys Ala Glu Cys Gly Ala
            645                 650             655

Phe Arg Thr Gly Pro Leu Ala Thr Asn Cys Ser Thr Ala Cys Ala His
            660                 665             670

Thr Asn Val Thr Leu Ala Leu Ala Pro Ile Leu Asp Asp Gly Trp Cys
        675                 680             685

Lys Glu Arg Thr Leu Asp Asn Gln Leu Phe Phe Phe Leu Val Glu Asp
        690                 695             700

Asp Ala Arg Gly Thr Val Val Leu Arg Val Arg Pro Gln Glu Lys Gly
705                 710                 715                 720

Ala Asp His Thr Gln Ala Ile Val Leu Gly Cys Val Gly Gly Ile Val
            725                 730             735

Ala Val Gly Leu Gly Leu Val Leu Ala Tyr Arg Leu Ser Val Glu Ile
            740                 745             750

Tyr Asp Arg Arg Glu Tyr Ser Arg Phe Glu Lys Glu Gln Gln Gln Leu
            755                 760             765

Asn Trp Lys Gln Asp Ser Asn Pro Leu Tyr Lys Ser Ala Ile Thr Thr
    770                 775             780

Thr Ile Asn Pro Arg Phe Gln Glu Ala Asp Ser Pro Thr Leu
785                 790                 795
```

METHODS FOR DETECTING INFLAMMATORY BOWEL DISEASE

CROSS-REFERENCE TO RELATED APPLICATIONS

This application claims priority under Section 119(e) and the benefit of U.S. Provisional Application Ser. No. 60/891,196 filed Feb. 22, 2007, U.S. Provisional Application Ser. No. 60/987,752 filed Nov. 13, 2007, and U.S. Provisional Application Ser. No. 61/024,170 filed Jan. 28, 2008, the entire disclosures of which are incorporated herein by reference in their entirety.

FIELD OF THE INVENTION

The present invention relates to gene expression profiles in inflammatory bowel disease pathogenesis. This discovery finds use in the detection and diagnosis of inflammatory bowel disease.

BACKGROUND OF THE INVENTION

Inflammatory bowel disease (IBD), a chronic inflammatory disorder of the gastrointestinal tract suffered by approximately one million patients in the United States, is made up of two major disease groups: ulcerative colitis (UC) and Crohn's Disease (CD). In both forms of IBD, intestinal microbes may initiate the disease in genetically susceptible individuals. UC is often restricted to the colon, while CD typically occurs in the ileum of the small intestine and in the colon. (Podolsky, D. K., N. Engl. J. Med. 347:417-429 (2002). Gene expression profiling of tissue from IBD patients has provided some insight into possible targets for therapy and/or diagnosis (see, for example, Dieckgraefe, B. K. et al., Physiol. Genomics 4:1-11 (2000); Lawrance I. C. et al., Hum Mol. Genet. 10:445-456 (2001); Dooley T. P. et al., Inflamm. Bowel Dis. 10:1-14 (2004); and Uthoff S. M., Int J Oncol. 19:803-810 (2001)). Further investigations of gene dysregulation in patients experiencing inflammatory bowel disease include, or example, Lawrance, I. C. et al., who disclosed distinctive gene expression profiles for several genes in UC and CD (Lawrance, I. C. et al., Human Mol. Genetics 10(5):445-456 (2001)). Uthoff, S. M. S. et al. disclosed the identification of candidate genes for UC and CD using micro array analysis (Uthoff, S. M. S. et al., Int'l. J. Oncology 19:803-810 (2001). Dooley, T. P. et al. disclosed correlation of gene expression in IBD with drug treatment for the disorder (Dooley, T. P. et al., Inflamm. Bowel Dis. 10(1):1-14 (2004).

There is a need for the identification of additional biological markers of inflammatory bowel disease for use in diagnosis of this chronic disease. The present disclosure fills that need.

The entire contents of all references cited herein are hereby incorporated by reference.

SUMMARY OF THE INVENTION

Disclosed herein is the unique finding that members of the LY6 superfamily of genes are upregulated on the surface of intestinal epithelial cells (IEC) in models of murine colitis and in intestinal tissue of human patients experiencing IBD, which genes are not expressed on healthy IEC. The majority of LY6 family members are GPI-anchored cell surface glycoproteins with broad distribution on cells of hematopoietic origin, and more limited expression on non-hematopoietic cells. Though widely used as markers of differentiation of immune cells (Sunderkotter, C. et al., J. Immunol. 172:4410-4417 (2004)), the functions that the LY6 family possesses have been difficult to elucidate (Shevach, E. M. and P. E. Korty, Immunol. Today 10: 195-200 (1989)). Reports have shown that LY6 molecules are involved in a diverse array of functions including T cell activation (Zhang, Z. X. et al., Eur. J. Immunol. 32:1584-1592 (2002) and Henderson, S. C. et al., J. Immunol. 168:118-126 (2002), olfaction (Chou, J. H. et al., Genetics 157:211-224 (2001) and cellular adhesion (Jaakkola, I. et al., J. Immunol. 170:1283-1290 (2003)).

In the broadest sense, the invention provides for a method of detecting increased expression of genes of the human LY6 gene family in intestinal tissue in intestinal tissue from a first mammal experiencing an intestinal disorder relative to a control mammal. In a more directed sense, the method is expected to be applicable to the diagnosis of disorders related to intestinal disorders associated with human LY6H, LYPD1, LYPD3, and LYPD5 expression, which disorders include without limitation inflammatory bowel disease (IBD), such as ulcerative colitis (UC) and Crohn's Disease (CD). In one embodiment, the method of the invention is useful to detect responders and nonresponders of IBD therapeutic treatment. In one embodiment, the IBD is ulcerative colitis (UC). In one embodiment, the IBD is Crohn's Disease (CD). In one embodiment, the intestinal tissue is colon tissue. In one embodiment, the colon tissue is sigmoid colon. In one embodiment, LY6H, LYPD1, LYPD3 and/or LYPD5 gene expression is increased in intestinal tissue (such as colon tissue) in an IBD, UC or CD mammal relative to normal intestinal (such as normal colon tissue) of a mammal not experiencing IBD, CD or UC. In an embodiment, the LY6H gene comprises the nucleic acid of SEQ ID NO:1 and encodes the LY6H polypeptide comprising SEQ ID NO:2. In an embodiment, the LYPD1 gene comprises the nucleic acid of SEQ ID NOS:3 or 4 and encodes the LYPD1 polypeptide comprising SEQ ID NO:5. In an embodiment, the LYPD3 gene comprises the nucleic acid of SEQ ID NO:6 and encodes the LYPD3 polypeptide comprising SEQ ID NO:7. In an embodiment, the LYPD5 gene comprises the nucleic acid of SEQ ID NOS:8 or 9 and encodes the LYPD5 polypeptide comprising SEQ ID NO:10.

In one embodiment, the method of the invention comprises obtaining a tissue sample from a test mammal suspected of experiencing an intestinal disorder, contacting the tissue with a detectable agent that interacts with LY6H, LYPD1, LYPD3 and/or LYPD5 protein or with nucleic acid encoding LY6H, LYPD1, LYPD3 and/or LYPD5 and determining the level of LY6H, LYPD1, LYPD3 and/or LYPD5 expression relative to a control tissue. In one embodiment increased expression of LY6H, LYPD1, LYPD3 and/or LYPD5 relative to control is indicative of IBD in the test mammal. In one embodiment, increased expression of LY6H, LYPD1, LYPD3 and/or LYPD5 in test intestinal tissue relative to control intestinal tissue is indicative of UC in the test mammal. In one embodiment, increased expression of LY6H, LYPD1, LYPD3 and/or LYPD5 in test intestinal tissue relative to control intestinal tissue is indicative of CD in the test mammal. In one embodiment the tissue or cells from the test and control mammal are from the colon.

In one embodiment, LY6H, LYPD1, LYPD3 and/or LYPD5 expression is determine by detection of gene expression, such as by detection of mRNA encoding LY6H, LYPD1, LYPD3 and/or LYPD5 in a tissue sample or cells. In an embodiment, a control sample is a sample of tissue or cells of the same tissue or cell type obtained from a mammal known not to be experiencing a gastrointestinal disorder, such as IBD, UC or CD. In an embodiment, a control sample is a universal standard comprising RNA from several normal tissues or from multiple cell lines. In microarray analysis, such universal standards are useful for monitoring and controlling intra- and inter-experimental variation. In one embodiment, a universal standard (or Universal Reference RNA (URR) is prepared as provided in Novoradovskaya, N. et al., (2004) BMC Genomics 5:20, which reference is hereby incorporated by reference in its entirety. In one embodiment, for use as a control in microarray analysis of mouse RNA, the URR is a Universal Mouse Reference RNA from Stratagene® (catalog #740100, Stratagene®, La Jolla, Calif.). In one embodiment, for use as a control in microarray analysis of human RNA, the URR is a Universal Human Reference RNA from Stratagene® (catalog #740000). In one embodiment, for use as a control in microarray analysis of rat RNA, the URR is a Universal Rat Reference RNA from Stratagene® (catalog #740200). In one embodiment, where the RNA is mouse RNA, the cell lines from which total RNA is extracted comprise cell lines derived from embryo, embryo fibroblast, kidney, liver hepatocyte, lung alveolar macrophage, B-lymphocyte, T-lymphocyte (thymus), mammary gland, muscle myoblast, skin, and testis. In one embodiment, where the RNA is human RNA, the cell lines from which total RNA is extracted comprise cell lines derived from mammary gland adenocarcinoma, liver hepatoblastoma, cervix adenocarcinoma, embryonal carcinoma or testis, brain glioblastoma, melanoma, liposarcoma, histiocytic lymphoma (macrophage, histiocyte), T lymphoblast lymphoblastic leukemia, B lymphocyte plasmacytoma melanoma. In one embodiment where the RNA is rat RNA, the cell lines from which total RNA is extracted comprise cell lines derived from blood basophilic leukemia, blood T-lymphocyte lymphoma, blood B-lymphoblast hybridoma, brain glioma, embryo yolk sac carcinoma, embryo normal fibroblast, normal kidney, liver hepatoma, lung normal alveolar macrophage, lung normal alveolar type II, mammary gland adenocarcinoma, muscle myoblast, normal skin, and testis leydig cell tumor.

In one aspect, the invention concerns an article of manufacture comprising a container and a composition of matter contained within the container, wherein the composition of matter comprises a nucleic acid encoding LY6H, LYPD1, LYPD3 and/or LYPD5 or their complements, and/or an anti-LY6H, LYPD1, LYPD3 and/or LYPD5 antibody or antibodies, or anti-LY6H-, LYPD1-, LYPD3- and/or LYPD5-binding fragment thereof, wherein the nucleic acids and/or antibodies are detectable. In one embodiment, the composition of matter comprises detecting agents for detecting nucleic acid binding, such as without limitation LY6H-, LYPD1-, LYPD3- and/or LYPD5-encoding nucleic acids or their complements, to LY6H, LYPD1, LYPD3 and/or LYPD5 nucleic acid in a tissue sample of a test mammal suspected of experiencing an intestinal disorder. In one embodiment, the compositions of matter comprises detecting agents for detecting antibody binding to, for example, LY6H, LYPD1, LYPD3 and/or LYPD5 in a tissue sample of a test mammal suspected of experiencing an intestinal disorder. In one embodiment, the antibody of the composition is detectably labeled. In one embodiment, the antibody of the composition is detectable by a second antibody, which second antibody is detectable or detectably labeled. The article may further optionally comprise a label affixed to the container, or a package insert included with the container, that refers to the use the LY6H, LYPD1, LYPD3 and/or LYPD5 nucleic acid or its complement and/or the anti-LY6H, anti-LYPD1, anti-LYPD3 and/or anti-LYPD5 antibody or LY6H, LYPD1, LYPD3 and/or LYPD5 binding fragment thereof in the detection of increased expression of LY6H, LYPD1, LYPD3 and/or LYPD5 in intestinal tissue, including without limitation, colon tissue. In an embodiment, the intestinal disorder is IBD. In an embodiment the intestinal disorder is UC or CD. In an embodiment the LYPD1 polypeptide and the anti-LYPD1 antibody is an antibody as disclosed in U.S. Pat. No. 7,157,558 and U.S. Pat. No. 7,144,990, respectively.

In one aspect, the present invention concerns a method of diagnosing the presence of an intestinal disorder in a mammal, comprising detecting the level of expression of a gene encoding LY6H, LYPD1, LYPD3 and/or LYPD5 polypeptide (a) in a test sample of tissue or cells obtained from said mammal, and (b) in a control sample of known normal cells from a mammal not experiencing an intestinal disorder of the same tissue origin or type, wherein a higher level of expression of the LY6H, LYPD1, LYPD3 and/or LYPD5 polypeptide in the test sample, as compared to the control sample, is indicative of the presence of an intestinal disorder in the mammal from which the test sample was obtained. In an embodiment, the intestinal disorder in IBD. In an embodiment, the IBD is UC. In an embodiment, the IBD is CD. In an embodiment, the detecting is by contacting an antibody to LY6H, LYPD1, LYPD3 and/or LYPD5 polypeptide, or binding fragment of the antibody, with the test and control samples and determining the relative amount of antibody-polypeptide complex formation. A higher level of antibody-polypeptide complex formation in the test sample relative of the control sample is indicative of intestinal disorder, such as IBD, UC or CD, in the test mammal. The antibody of the invention is detectably labeled or, alternatively, the antibody is detected by subsequent binding of a second antibody which is detectable.

In yet a further embodiment, the present invention concerns a method of diagnosing the presence of an intestinal disorder in a mammal, comprising (a) contacting a test sample comprising tissue or cells obtained from the test mammal with an oligonucleotide that hybridizes at high stringency to LY6H, LYPD1, LYPD3 and/or LYPD5 nucleic acid (or its complement) or an antibody that binds specifically to LY6H, LYPD1, LYPD3 and/or LYPD5 polypeptide and (b) detecting the formation of a complex between the oligonucleotide or antibody and the LY6H, LYPD1, LYPD3 and/or LYPD5 nucleic acid (or its complement) or LY6H, LYPD1, LYPD3 and/or LYPD5 polypeptide, respectively, in the test sample, wherein the formation of more of such complex in the test sample relative to a control sample is indicative of the presence of an intestinal disorder (such as IBD, UC or CD) in the test mammal. In one embodiment, the intestinal disorder is IBD. In one embodiment, the disorder is UC. In one embodiment the disorder is CD. In one embodiment the tissue of the test and control mammals is colon tissue. Optionally, the LY6H, LYPD1, LYPD3 and/or LYPD5 polypeptide binding antibody or LY6H, LYPD1, LYPD3 and/or LYPD5 gene hybridizing oligonucleotide employed by the method of the invention is detecable, detectably labeled, attached to a solid support, or the like, and/or the test sample of tissue or cells is obtained from an individual suspected of experiencing an intestinal disorder, wherein the disorder is IBD, such as without limitation, UC or CD.

In yet a further embodiment, the present invention concerns the use of (a) a LY6H, LYPD1, LYPD3 and/or LYPD5 polypeptide, (b) a nucleic acid encoding a LY6H, LYPD1, LYPD3 and/or LYPD5 polypeptide or a vector or host cell comprising the nucleic acid of (a), (c) an anti-LY6H, LYPD1, LYPD3 and/or LYPD5 polypeptide antibody, or (d) a LY6H, LYPD1, LYPD3 and/or LYPD5-binding oligopeptide, in the preparation of a medicament useful for the diagnostic detection of an intestinal disorder, including without limitation, IBD CD or UC, in an intestinal tissue of a mammal, including without limitation colon tissue.

In one aspect, the invention comprises a method of detecting a therapeutic drug response in a mammal treated with an IBD therapeutic agent, wherein the method comprises determining LY6H, LYPD1, LYPD3 and/or LYPD5 expression in gastrointestinal tissue of a test mammal relative to a control gastrointestinal tissue of a control mammal, where a higher level of expression of LY6H, LYPD1, LYPD3 and/or LYPD5 in a test tissue relative to a control tissue indicates a disease state or continuation of the disease state. A difference in LY6H, LYPD1, LYPD3 and/or LYPD5 expression in the test tissue that is not significantly higher than normal control expression levels or are within a range of normal expression levels for LY6H, LYPD1, LYPD3 and/or LYPD5 in a population of mammals indicates improvement or resolution of the intestinal disorder, which improvement or resolution may be attributed to the therapeutic agent. In one embodiment, a therapeutic response is determined when the levels of expression of LY6H, LYPD1, LYPD3 and/or LYPD5 in gastrointestinal or colon tissues or cells of the mammal treated with a therapeutic agent are different (expression is more similar to normal control, i.e., LY6H, LYPD1, LYPD3 and/or LYPD5 levels are lower than LY6H, LYPD1, LYPD3 and/or LYPD5 expression levels were in the mammal prior to treatment.

Yet further embodiments of the present invention will be evident to the skilled artisan upon a reading of the present specification.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B depict the nucleic acid sequence (SEQ ID NO:1) encoding human LY6H polypeptide and the amino acid sequence of human LY6H polypeptide (SEQ ID NO:2).

FIGS. 2A and 2B depict nucleic acid sequences (SEQ ID NOS:3 and 4) encoding the human LYPD1 polypeptide and the amino acid sequence of human LYPD1 polypeptide shown in FIG. 2C (SEQ ID NO:5).

FIGS. 3A and 3B depict the nucleic acid sequence (SEQ ID NO:6) encoding human LYPD3 polypeptide and the amino acid sequence of human LYPD3 polypeptide (SEQ ID NO:7).

FIGS. 4A and 4B depict nucleic acid sequences (SEQ ID NOS:8 and 9) encoding human LYPD5 polypeptide and the amino acid sequence of human LYPD5 polypeptide shown in FIG. 4C (SEQ ID NO:10).

FIGS. 5A and 5B depict the nucleic acid sequence (SEQ ID NO:11) encoding human LY6D polypeptide and the amino acid sequence of human LY6D polypeptide (SEQ ID NO:12).

FIGS. 6A and 6B depict the nucleic acid sequence (SEQ ID NO:13) encoding human LY6E polypeptide and the amino acid sequence of human LY6E polypeptide (SEQ ID NO:14).

FIGS. 7A and 7B depict the nucleic acid sequence (SEQ ID NO:15) encoding human LYPD2 polypeptide and the amino acid sequence of human LYPD2 polypeptide (SEQ ID NO:16).

FIGS. 8A-8J depict sequences of GLG-1 (ESL-1) molecules:
(A-C) - Accession No. U64791, nucleic acid sequence (SEQ ID NO:17) (8A-B) encoding human GLG-1 (ESL-1) polypeptide (SEQ ID NO:18) (8C);
(D-F) - Accession No. NM_012201, nucleic acid sequence (SEQ ID NO:19) (8D-E) encoding human GLG-1 (ESL-1) polypeptide (SEQ ID NO:20) (8F);
(G-H) - Accession No. AK172806, nucleic acid sequence (SEQ ID NO:21) (8G) encoding human GLG-1 (ESL-1) polypeptide (SEQ ID NO:22) (8H); and
(I-J) - Accession No. AK131501, nucleic acid sequence (SEQ ID NO:23) (8I) encoding human GLG-1 (ESL-1) polypeptide (SEQ ID NO:24) (8J).

FIGS. 9A and 9B depict the nucleic acid sequence (SEQ ID NO:25) encoding murine LY6A polypeptide and the amino acid sequence of murine LY6A polypeptide (SEQ ID NO:26).

FIGS. 10A and 10B depict the nucleic acid sequence (SEQ ID NO:27) encoding murine LY6C polypeptide and the amino acid sequence of murine LY6C polypeptide (SEQ ID NO:28).

FIGS. 11A and 11B depict the nucleic acid sequence (SEQ ID NO:29) encoding murine LY6D polypeptide and the amino acid sequence of murine LY6D polypeptide (SEQ ID NO:30).

FIGS. 12A and 12B depict the nucleic acid sequence (SEQ ID NO:31) encoding murine LY6E polypeptide and the amino acid sequence of murine LY6E polypeptide (SEQ ID NO:32).

FIGS. 13A and 13B depict the nucleic acid sequence (SEQ ID NO:33) encoding murine LY6F polypeptide and the amino acid sequence of murine LY6F polypeptide (SEQ ID NO:34).

FIGS. 14A and 14B depict the nucleic acid sequence (SEQ ID NO:35) encoding murine LY6I polypeptide and the amino acid sequence of murine LY6I polypeptide (SEQ ID NO:36).

FIGS. 15A and 15B depict the nucleic acid sequence (SEQ ID NO:37) encoding murine LY6K polypeptide and the amino acid sequence of murine LY6K polypeptide (SEQ ID NO:38).

FIGS. 16A and 16B depict the nucleic acid sequence (SEQ ID NO:45) encoding murine LYPD3 polypeptide and the amino acid sequence of murine LYPD3 polypeptide (SEQ ID NO:46).

FIGS. 17A and 17B depict the nucleic acid sequence (SEQ ID NO:47) encoding murine LY6H polypeptide and the amino acid sequence of murine LY6H polypeptide (SEQ ID NO:48).

FIGS. 18A and 18B depict the nucleic acid sequence (SEQ ID NO:49) encoding murine LYPD1 polypeptide and the amino acid sequence of murine LYPD1 polypeptide (SEQ ID NO:50).

FIGS. 19A and 19B depict the nucleic acid sequence (SEQ ID NO:51) encoding murine LYPD2 polypeptide and the amino acid sequence of murine LYPD2 polypeptide (SEQ ID NO:52).

FIGS. 20A and 20B depict the nucleic acid sequence (SEQ ID NO:53) encoding murine LY6g5c polypeptide and the amino acid sequence of murine LY6g5c polypeptide (SEQ ID NO:54).

FIGS. 21A and 21B depict the nucleic acid sequence (SEQ ID NO:55) encoding murine LY6g6c polypeptide and the amino acid sequence of murine LY6g6c polypeptide (SEQ ID NO:56).

FIGS. 22A-C depict the nucleic acid sequence (SEQ ID NO:57) (22A-B) encoding murine SLURP2/LYNX1 polypeptide and the amino acid sequence of murine SLURP2/LYNX1 polypeptide (SEQ ID NO:58) (22C).

FIG. 23A-B shows that LY6 family members are upregulated in EC in murine models of colitis. EC in both the IL10$^{-/-}$ (FIG. 23A) and CD45RB$^{Hi}$ transfer colitis model (FIG. 23B) were isolated by LCM and RNA was purified. Microarray analysis was performed and analyzed as described in the Examples. Numbers represent the mean of the fold change compared to a universal standard RNA of colitic mice over healthy mice. Numbers below the heatmap indicate the inflammation score of the individual mouse.

FIGS. 26A-26E Lipid raft depletion results in an inhibition of LY6C-mediated chemokine production. Cholesterol depleted (dark bars) or non-depleted (open bars) YAMC cells were incubated with plate-bound nati-KLH or anti-LY6C as indicated for 15 hours. RNA was collected and expression levels of CXCL2, CXCL5, and CCL7 were determined (FIGS. 26A-26C). Surface levels of LY6A (FIG. 26D) and LY6C (FIG. 26E) where decreased in response to cholesterol depletion.

FIGS. 27A-27D show that crosslinking of LY6C, but not LY6A, induces upregulation of surface expression of LY6A and LY6C. YAMC cells were incubated for 24 hours on plates coated with anti-KLH control, anti-LY6A or anti-LY6C and analyzed by flow cytometry for expression of LY6C (FIG. 27A) or LY6A (FIG. 27B). Cells were pretreated for 12 hours with 100 U/ml of IFNγ and similarly plated on antibody coated plates and analyzed for expression of LY6C (FIG. 27C) or LY6A (FIG. 27D).

FIG. 28A: YAMC cells were preincubated or not, as indicated, with 100 U/ml of IFNγ for 15 hours and cultured on plates coated with 10 μg/ml of anti-LY6A (black bars) or anti-LY6C (hatched bars) or anti-KLH control (open bars). RNA was isolated at 24 (left), 48 (center) and 72 (right) hours and analyzed for expression of CXCL5 or CCL7 (A). Data indicates mean±SD of the fold change (as determined by $2^{-\Delta\Delta Ct}$ method) compared to untreated, isotype crosslinked cells. FIG. 28B: Supernatants were collected at 48 hours in cells crosslinked, as above, with 1, 5 or 10 μg/ml (as indicated) of antibody and CXCL5 secretion into the supernatant was determined by ELISA. *<0.05. FIG. 28C: Levels of both CXCL5 and CXCL2 in response to LY6C crosslinking were diminished when LY6C levels were knocked down with siRNA.

FIGS. 29A-29B show that IEC in colitis possess a similar chemokine gene expression pattern. IEC in both the IL10$^{-/-}$ (FIG. 29A) and CD45RBHi transfer colitis model (FIG. 29B) were isolated by LCM and RNA was purified. Microarray analysis was performed and analyzed as described in the Examples. Numbers represent the mean of the fold change compared to the universal standard RNA of colitic mice over healthy mice. Numbers below the heatmap indicate the inflammation score of the individual mouse.

FIGS. 32A and 32B shows (A) untransfected COS cells, and (B) COS cells transfected with GLG-1 (ESL-1) polypeptide and stained with LYPD5-Fc protein.

FIG. 33A depicts the structure of GLG-1 or ESL-1 and various fragments suitable for characterizing the binding of LYPD5 and FIG. 33B shows the results of a co-immunoprecipitation study characterizing the binding of LYPD5 and an LYPD5 ligand.

FIGS. 36A and 36B depict the nucleic acid sequence (SEQ ID NO: 68) encoding human integrin, beta 7, and the amino acid sequence of human integrin, beta 7 polypeptide (SEQ ID NO: 69).

DETAILED DESCRIPTION OF THE INVENTION

Definitions

Figure 24:
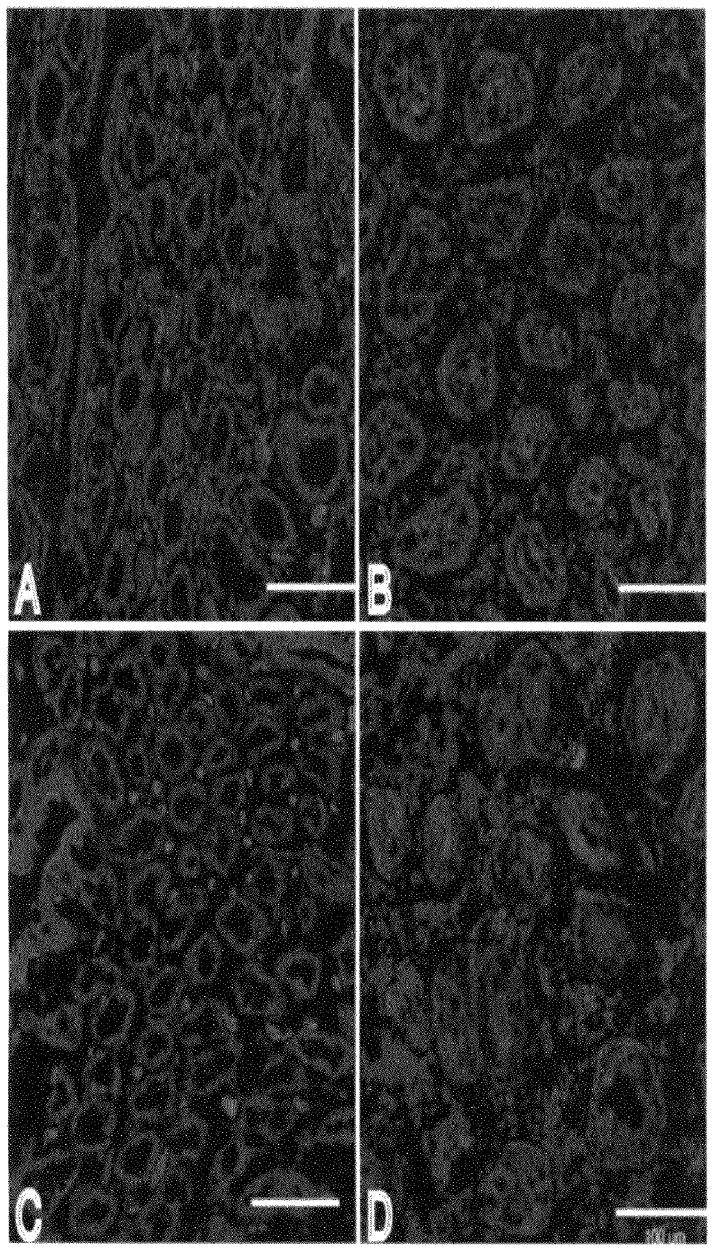
FIGS. 24A-24D show that surface expression of LY6 molecules is upregulated on IEC in the IL10−/− model of colitis. Wild type (FIG. 24A) or L10 −/− mice (FIG. 24B) were stained for surface expression of LY6A (green, with DAPI counterstain). Similarly, wild type (FIG. 24C) or IL10 −/− mice (FIG. 24D) were stained for surface expression of LY6C.

"Inflammatory Bowel Disease" or "IBD" is used interchangeably herein to refer to diseases of the bowel that cause inflammation and/or ulceration and includes without limitation Crohn's disease and ulcerative colitis.

"Crohn's disease (CD)" or "ulcerative colitis (UC)" are chronic inflammatory bowel diseases of unknown etiology. Crohn's disease, unlike ulcerative colitis, can affect any part of the bowel. The most prominent feature Crohn's disease is the granular, reddish-purple edmatous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

Anti-inflammatory drugs sulfasalazine and 5-aminosalisylic acid (5-ASA) are useful for treating mildly active colonic Crohn's disease and is commonly prescribed to maintain remission of the disease. Metroidazole and ciprofloxacin are similar in efficacy to sulfasalazine and appear to be particularly useful for treating perianal disease. In more severe cases, corticosteroids are effective in treating active exacerbations and can even maintain remission. Azathioprine and 6-mercaptopurine have also shown success in patients who require chronic administration of cortico steroids. It is also possible that these drugs may play a role in the long-term prophylaxis. Unfortunately, there can be a very long delay (up to six months) before onset of action in some patients.

Antidiarrheal drugs can also provide symptomatic relief in some patients. Nutritional therapy or elemental diet can improve the nutritional status of patients and induce symptomatic improvement of acute disease, but it does not induce sustained clinical remissions. Antibiotics are used in treating secondary small bowel bacterial overgrowth and in treatment of pyogenic complications.

"Ulcerative colitis (UC)" afflicts the large intestine. The course of the disease may be continuous or relapsing, mild or severe. The earliest lesion is an inflammatory infiltration with abscess formation at the base of the crypts of Lieberkühn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

Treatment for UC includes sulfasalazine and related salicylate-containing drugs for mild cases and corticosteroid drugs in severe cases. Topical administration of either salicylates or corticosteroids is sometimes effective, particularly when the disease is limited to the distal bowel, and is associated with decreased side effects compared with systemic use. Supportive measures such as administration of iron and antidiarrheal agents are sometimes indicated. Azathioprine, 6-mercaptopurine and methotrexate are sometimes also prescribed for use in refractory corticosteroid-dependent cases.

As used herein, "LY6 gene family member" or "LY6 gene superfamily member" is used interchangeably herein to refer to a gene having homology to members of the LY6 gene family, the majority of which gene family members are GPI-anchored cell surface glycoproteins with broad distribution on cells of hematopoietic origin and more limited expression on non-hematopoietic cells. Members of this gene family are used as markers of differentiation of immune cells (Sunderkotter, C. et al., J. Immunol. 172:4410-4417 (2004)). Genes of the LY6 family have been examined (Shevach, E. M. and P. E. Korty, Immunol. Today 10:195-200 (1989)) and functions include T cell activation (Zhang, Z. X. et al., Eur. J. Immunol. 32:1584-1592 (2002) and Henderson, S. C. et al., J. Immunol. 168:118-126 (2002), olfaction (Chou, J. H. et al., Genetics 157:211-224 (2001) and cellular adhesion (Jaakkola, I. et al., J. Immunol. 170:1283-1290 (2003)). Members of the LY6 gene family include without limitation members of the mammalian LY6 gene family, such as the LY6 family genes of mouse or human. As use here, "LY6 gene" refers to a LY6 gene family member and "LY6 polypeptide" refers to the polypeptide encoded by a LY6 gene. Murine LY6 gene family members include, without limitation, LY6A (NM_010738, nucleic acid SEQ ID NO:25 which encodes polypeptide SEQ ID NO:26), LY6C(NM_010741, nucleic acid SEQ ID NO:27 which encodes polypeptide SEQ ID NO:28), LY6D (NM_003695, nucleic acid SEQ ID NO:29 which encodes polypeptide SEQ ID NO:30), LY6E (NM_002346, nucleic acid SEQ ID NO:31 which encodes polypeptide SEQ ID NO:32), LY6F (NM_008530, nucleic acid SEQ ID NO:33 which encodes polypeptide SEQ ID NO:34), LY6I (NM_020498, nucleic acid SEQ ID NO:35 which encodes polypeptide SEQ ID NO:36), and LY6K (NM_017527, nucleic acid SEQ ID NO:37 which encodes polypeptide SEQ ID NO:38). Human LY6 gene family members include, without limitation, LY6H (NM_002347, nucleic acid SEQ ID NO:1 which encodes polypeptide SEQ ID NO:2), LYPD1 (NM_144586, nucleic acid SEQ ID NOS:3 or 4 which encodes polypeptide SEQ ID NO:5), LYPD3 (NM_014400, nucleic acid SEQ ID NO:6 which encodes polypeptide SEQ ID NO:7), LYPD5 (NM_182573, nucleic acid SEQ ID NOS:8 or 9 which encodes polypeptide SEQ ID NO:10), LY6D (NM_003695, nucleic acid SEQ ID NO:11 which encodes polypeptide SEQ ID NO:12), LY6E (NMNM_002346, nucleic acid SEQ ID NO:13 which encodes polypeptide SEQ ID NO:14), LYPD2 (NM_205545, nucleic acid SEQ ID NO:15 which encodes polypeptide SEQ ID NO:16). In embodiments, the polynucleotide of each LY6 gene family member disclosed herein comprises at least 15, at least 25, at least, at least 50, at least 100, at least 250, at least 500, at least 750, at least 1000, at least 1250, at least 1500, at least 1750, at least 2000, or at least 2040 contiguous nucleotides of SEQ ID NOs:1, 3, 4, 6, 8, 9, 11, 13, 15, 25, 27, 29, 31, 33, 35, 37, 45, 47, 49, 51, 53, 55, or 57, or the LY6 gene family member polynucleotide comprises SEQ ID NOS:1, 3, 4, 6, 8, 9, 11, 13, 15, 25, 27, 29, 31, 33, 35, 37, 45, 47, 49, 51, 53, 55, or 57. In one embodiment, a polynucleotide that binds a LY6 gene family member polynucleotide (SEQ ID NOs:1, 3, 4, 6, 8, 9, 11, 13, 15, 25, 27, 29, 31, 33, 35, 37, 45, 47, 49, 51, 53, 55, or 57), or fragment thereof, has at least 75%, at least 80%, at least 85%, at least 90%, at least 95%, at least 97%, at least 99% or 100% sequence identity with the LY6 polypeptide or fragment thereof. In one embodiment, the LY6 gene family member polypeptide comprises at least 10, at least 25, at least 50, at least 75, at least 100, at least 125, at least 150, at least 175, at least 200, at least 225, at least 250, at least 275, at least 300, or at least 325, at least contiguous amino acids of SEQ ID NOs:2, 5, 7, 10, 12, 14, 26, 28, 30, 32, 34, 36, 38, 46, 48, 50, 52, 54, 56, or 58, or the LY6 gene family polypeptide comprises SEQ ID NOs:2, 5, 7, 10, 12, 14, 26, 28, 30, 32, 34, 36, 38, 46, 48, 50, 52, 54, 56, or 58).

A "native sequence polypeptide" of any of the LY6 gene family members comprises a polypeptide having the same amino acid sequence as the corresponding LY6 gene family member polypeptide derived from nature. Such native sequence LY6 polypeptides can be isolated from nature or can be produced by recombinant or synthetic means. The term "native sequence LY6 polypeptide" specifically encompasses naturally-occurring truncated or secreted forms of the specific LY6 polypeptide (e.g., an extracellular domain sequence), naturally-occurring variant forms (e.g., alternatively spliced forms) and naturally-occurring allelic variants of the polypeptide. In one specific aspect, the native sequence LY6 polypeptides disclosed herein are mature or full-length native sequence polypeptides corresponding to the sequences in FIGS. 1-7 and SEQ ID NOs:2, 5, 7, 10, 12, 14, 26, 28, 30, 32, 34, 36, 38, 46, 48, 50, 52, 54, 56, or 58.

As used herein, a "LY6 polypeptide variant" means a LY6 polypeptide, preferably biologically active forms thereof, as defined herein, having at least about 80% amino acid sequence identity with a full-length native sequence LY6 polypeptide sequence, as disclosed herein, and variant forms thereof lacking the signal peptide, an extracellular domain, or any other fragment of a full length native sequence LY6 polypeptide such as those referenced herein. Such variant polypeptides include, for instance, polypeptides wherein one or more amino acid residues are added, or deleted, at the N- or C-terminus of the full-length native amino acid sequence. In a specific aspect, such variant polypeptides will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence LY6 polypeptide sequence polypeptide, as disclosed herein, and variant forms thereof lacking a signal peptide, an extracellular domain, or any other fragment of a full length native sequence LY6 polypeptide such as those disclosed herein.

"Percent (%) amino acid sequence identity" with respect to a LY6 polypeptide sequence identified herein is defined as the percentage of amino acid residues in a candidate sequence that are identical with the amino acid residues in the specific LY6 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

As used herein "LY6 variant polynucleotide" or "LY6 variant nucleic acid sequence," or "LY6 gene" refers to a nucleic acid molecule which encodes a LY6 gene family member polypeptide, preferably biologically active forms thereof, as defined herein, and which have at least about 80% nucleic acid sequence identity with a nucleic acid sequence encoding a full-length native sequence LY6 polypeptide sequence identified herein, or any other fragment of the respective full-length LY6 polypeptide sequence as identified herein (such as those encoded by a nucleic acid that represents only a portion of the complete coding sequence for a full-length LY6 polypeptide). Ordinarily, such variant polynucleotides will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding the respective full-length native sequence LY6 polypeptide sequence or any other fragment of the respective full-length LY6 polypeptide sequence identified herein. Such variant polynucleotides do not encompass the native nucleotide sequence.

Ordinarily, such variant polynucleotides vary at least about 50 nucleotides in length from the native sequence polypeptide, alternatively the variance can be at least about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to a LY6 gene polypeptide-encoding nucleic acid sequences identified herein is defined as the percentage of nucleotides in a candidate sequence that are identical with the nucleotides in the LY6 gene nucleic acid sequence of interest, respectively, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

$$100 \text{ times the fraction } W/Z$$

where W is the number of nucleotides scored as identical matches by the sequence alignment program ALIGN-2 in that program=s alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "REF-DNA", wherein "REF-DNA" represents a hypothetical LY6 gene-encoding nucleic acid sequence of interest, "Comparison DNA" represents the nucleotide sequence of a nucleic acid molecule against which the "REF-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, LY6 gene variant polynucleotides are nucleic acid molecules that encode LY6 polypeptide, respectively, and which are capable of hybridizing, preferably under stringent hybridization and wash conditions, to nucleotide sequences encoding a full-length LY6 polypeptide, respectively, as disclosed herein. Such variant polypeptides may be those that are encoded by such variant polynucleotides.

"Isolated", when used to describe the various LY6 polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, such polypeptides will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Such isolated polypeptides includes the corresponding polypeptides in situ within recombinant cells, since at least one component of the LY6 polypeptide from its natural environment will not be present. Ordinarily, however, such isolated polypeptides will be prepared by at least one purification step.

An "isolated" LY6 polypeptide-encoding nucleic acid is a nucleic acid molecule that is identified and separated from at least one contaminant nucleic acid molecule with which it is ordinarily associated in the natural source of the polypeptide-encoding nucleic acid. Any of the above such isolated nucleic acid molecule is other than in the form or setting in which it is found in nature. Any such nucleic acid molecules therefore are distinguished from the specific polypeptide-encoding nucleic acid molecule as it exists in natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein "expression" as applied to gene expression, refers to transcription of a gene encoding a protein to produce mRNA as well as translation of the mRNA to produce the protein encoded by the gene. Thus, increased or decreased expression refers to increased or decreased transcription of a gene and/or increased or decreased translation of mRNA resulting from transcription.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50EC; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42EC; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt=s solution, sonicated salmon sperm DNA (50 μg/ml), 0.1% SDS, and 10% dextran sulfate at 42EC, with a 10 minute wash at 42EC in 0.2×SSC (sodium chloride/sodium citrate) followed by a 10 minute high-stringency wash consisting of 0.1×SSC containing EDTA at 55EC.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37EC in a solution comprising: 20% formamide, 5×SSC (150 mM NaCl, 15 mM trisodium citrate), 50 mM sodium phosphate (pH 7.6), 5×Denhardt=s solution, 10% dextran sulfate, and 20 mg/ml denatured sheared salmon sperm DNA, followed by washing the filters in 1×SSC at about 37-50EC. The ordinarily skilled artisan will recognize how to adjust the temperature, ionic strength, etc. as necessary to accommodate factors such as probe length and the like.

The term "epitope tagged" when used herein refers to a chimeric polypeptide comprising an LY6 polypeptide, or LY6 polypeptide binding agent fused to a "tag polypeptide". The tag polypeptide has enough residues to provide an epitope against which an antibody can be made, yet is short enough such that it does not interfere with the activity of the polypeptide to which it is fused. The tag polypeptide preferably also is sufficiently unique so that such antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of polypeptides which retain a biological and/or an immunological activity of native or naturally-occurring polypeptide, wherein "biological" activity refers to a biological function (either inhibitory or stimulatory) caused by a native or naturally-occurring polypeptide other than the ability to induce the production of an antibody against an antigenic epitope possessed by a native or naturally-occurring polypeptide, and an "immunological" activity refers to the ability to induce the production of an antibody against an antigenic epitope possessed by a native or naturally-occurring polypeptide. An active polypeptide, as used herein, is an antigen that is differentially expressed, either from a qualitative or quantitative perspective, in IBD tissue, relative to its expression on similar tissue that is not afflicted with IBD.

The term "antagonist" is used in the broadest sense, and includes any molecule that partially or fully blocks, inhibits, or neutralizes a biological activity of a native polypeptide disclosed herein. Suitable antagonist molecules specifically include antagonist antibodies or antibody fragments, fragments or amino acid sequence variants of native polypeptides, peptides, antisense oligonucleotides, small organic molecules, etc. Methods for identifying antagonists may comprise contacting such a polypeptide, including a cell expressing it, with a candidate agonist or antagonist molecule and measuring a detectable change in one or more biological activities normally associated with such polypeptide.

"Treating" or "treatment" or "alleviation" refers to both therapeutic treatment and prophylactic or preventative measures, wherein the object is to prevent or slow down (lessen) the progression of a disease. Treatment may also refer the modification of the progression of an IBD.

"Diagnosing" refers to the process of identifying or determining the distinguishing characteristics of a disease including without limitation IBD, UC and/or Crohn's Disease. The process of diagnosing is sometimes also expressed as staging or disease classification based on severity or disease progression as well as on location (such as, for example, location within or along the gastrointestinal tract at which inflammation and/or altered gene expression is found).

Subjects in need of diagnosis include those already experiencing with aberrant LY6 expression as well as those prone to having or those in whom aberrant LY6 expression is to be prevented. Accordingly, an aspect of the invention is the detection of a therapeutic drug response in a mammal treated with a therapeutic agent for the treatment of IBD, wherein the method comprises determining Ih LY6 expression in gastrointestinal tissue of a test mammal relative to a control and determining that the LY6 expression levels are within not significantly different from normal control expression levels. In one embodiment, a therapeutic response is determined when the levels of expression of LY6 of the mammal treated with a therapeutic agent are different (expression is more similar to normal control, i.e., LY6 expression levels are lower than LY6 expression levels were in the mammal prior to treatment).

The above parameters for assessing successful treatment and improvement in the disease are readily measurable by routine procedures familiar to a physician. For IBD therapy, efficacy can be measured, for example, by assessing the time to disease progression (TTP) and/or determining the response rate (RR). Biopsies may be taken to assess gene expression and observe histopathology of gastrointestinal tissue from the patient. The invention described herein relating to the process of prognosing and/or diagnosing involves the determination and evaluation of LY6 gene expression upregulation.

"Mammal" or "mammalian subject" for purposes of the treatment of, alleviating the symptoms of or diagnosis of a IBD refers to any animal classified as a mammal, including humans, domestic and farm animals, and zoo, sports, or pet animals, such as dogs, cats, cattle, horses, sheep, pigs, goats, rabbits, ferrets, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN7, polyethylene glycol (PEG), and PLURONICS7.

By "solid phase" or "solid support" is meant a non-aqueous matrix to which a polypeptide, nucleic acid, antibody or LY6 binding agent can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes.

A "small molecule" or "small organic molecule" is defined herein to have a molecular weight below about 500 Daltons.

An "effective amount" of an antagonist agent is an amount sufficient to bring about a physiological effect, such as without limitation to inhibit, partially or entirely, function of gene or its encoded protein. An "effective amount" may be determined empirically and in a routine manner, in relation to this purpose.

The term "therapeutically effective amount" refers to an antagonist or other drug effective to "treat" a disease or disorder in a subject or mammal. In the case of IBD, the therapeutically effective amount of the drug will restore aberrant LY6 expression to normal physiological levels; reduce gastrointestinal inflammation; reduce the number of gastrointestinal lesions; and/or relieve to some extent one or more of the symptoms associated with IBD, UC and/or CD. See the definition herein of "treating".

A "growth inhibitory amount" of an antagonist is an amount capable of inhibiting the growth of a cell, especially tumor, e.g., cancer cell, either in vitro or in vivo. For purposes of inhibiting neoplastic cell growth, such an amount may be determined empirically and in a routine manner.

A "cytotoxic amount" of an antagonist is an amount capable of causing the destruction of a cell, especially a proliferating cell, e.g., cancer cell, either in vitro or in vivo. For purposes of inhibiting neoplastic cell growth may be determined empirically and in a routine manner.

The term "antibody" is used in the broadest sense and specifically covers, for example, anti-LY6 monoclonal antibodies (including antagonist and neutralizing antibodies), anti-LY6 antibody compositions with polyepitopic specificity, polyclonal antibodies, single chain anti-LY6 antibodies, multispecific antibodies (e.g., bispecific) and antigen binding fragments (see below) of all of the above enumerated antibodies as long as they exhibit the desired biological or immunological activity. The term "immunoglobulin" (Ig) is used interchangeably with antibody herein.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the approximately 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about Kabat residues 24-34 (L1), 50-56 (L2) and 89-97 (L3) in the $V_L$, and around about Kabat residues 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. around about Chothia residues 26-32 (L1), 50-52 (L2) and 91-96 (L3) in the $V_L$, and 26-32 (H1), 52A-55 (H2) and 96-101 (H3) in the $V_H$ (Chothia and Lesk J. Mol. Biol. 196:901-917 (1987)).

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816, 567), phage display technologies (see, e.g., Clackson et al., Nature, 352:624-628 (1991); Marks et al., J. Mol. Biol., 222: 581-597 (1991); Sidhu et al., J. Mol. Biol. 338(2):299-310 (2004); Lee et al., J. Mol. Biol. 340(5):1073-1093 (2004); Fellouse, Proc. Nat. Acad. Sci. USA 101(34):12467-12472 (2004); and Lee et al. J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569,825; 5,625,126; 5,633,425; and 5,661,016; Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). Humanized antibody as used herein is a subset of chimeric antibodies.

"Humanized" forms of non-human (e.g., murine) antibodies are chimeric antibodies which contain minimal sequence derived from non-human immunoglobulin. For the most part, humanized antibodies are human immunoglobulins (recipient or acceptor antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence although the FR regions may include one or more amino acid substitutions that improve binding affinity. The number of these amino acid substitutions in the FR are typically no more than 6 in the H chain, and in the L chain, no more than 3. The humanized antibody optionally also will comprise at least a portion of an immunoglobulin constant region (Fc), typically that of a human immunoglobulin. For further details, see Jones et al., Nature 321:522-525 (1986); Reichmann et al., Nature 332:323-329 (1988); and Presta, Curr. Op. Struct. Biol. 2:593-596 (1992).

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab=fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

As used herein "LY6 binding polypeptide" is an oligopeptide that binds, preferably specifically, to a LY6 polypeptide, ligand or signaling component, respectively, or a LY6 binding portion or fragment thereof. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. Proc. Natl. Acad. Sci. USA, 87:6378 (1990); Lowman, H. B. et al. Biochemistry, 30:10832 (1991); Clackson, T. et al. Nature, 352: 624 (1991); Marks, J. D. et al., J. Mol. Biol., 222:581 (1991); Kang, A. S. et al. Proc. Natl. Acad. Sci. USA, 88:8363 (1991), and Smith, G. P., Current Opin. Biotechnol., 2:668 (1991).

An LY6 antagonist (e.g., antibody, polypeptide, oligopeptide or small molecule) "which binds" a target antigen of interest, e.g. LY6 is one that binds the target with sufficient affinity so as to be a useful diagnostic, prognostic and/or therapeutic agent, in targeting a cell or tissue expressing the antigen, and does not significantly cross-react with other proteins. The extent of binding to a non-desired marker polypeptide will be less than about 10% of the binding to the particular desired target, as determinable by common techniques such as fluorescence activated cell sorting (FACS) analysis or radioimmunoprecipitation (RIA).

Moreover, the term "specific binding" or "specifically binds to" or is "specific for" a particular LY6 polypeptide or an epitope on a particular LY6 polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. In one embodiment, such terms refer to binding where a molecule binds to a particular polypeptide or epitope on a particular polypeptide without substantially binding to any other polypeptide or polypeptide epitope. Alternatively, such terms can be described by a molecule having a Kd for the target of at least about $10^{-4}$ M, $10^{-5}$ M, $10^{-6}$ M, $10^{-7}$ M, $10^{-8}$ M, $10^{-9}$ M, $10^{-10}$ M, $10^{-11}$ M, $10^{-12}$ M, or greater.

A gastrointestinal cell or tissue that "overexpresses" LY6 if that cell or tissue is shown to have increased nucleic acid encoding LY6 in a cells or if that cell or tissue over produces and secretes LY6 protein, compared to a normal gastrointestinal cell or tissue of the same tissue type. Such overexpression may result from gene amplification or by increased transcription or translation. Various diagnostic or prognostic assays are known that measure altered expression levels resulting in increased or decreased levels at the cell surface or increased or decreased levels of secreted protein and include without limitation immunohistochemistry assay using anti-LY6 antibodies, FACS analysis, etc. Alternatively, the levels of LY6 encoding nucleic acid or mRNA can be measured in the cell, e.g., via fluorescent in situ hybridization using a nucleic acid based probe corresponding to a LY6-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). Alternatively, LY6 polypeptide overexpression is determinable by measuring shed antigen in a biological fluid such as serum, e.g., using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). In addition to the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the therapeutic agent.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" or "therapeutic agent" is a chemical compound useful in the treatment of a disorder or disease. Examples of chemotherapeutic or therapeutic agents for the treatment of IBD include without limitation anti-inflammatory drugs sulfasalazine and 5-aminosalisylic acid (5-ASA); metroidazole and ciprofloxacin are similar in efficacy to sulfasalazine and appear to be particularly useful for treating perianal disease; in more severe cases, corticosteroids are effective in treating active exacerbations and can even maintain remission; azathioprine, 6-mercaptopurine, and methotrexate have also shown success in patients who require chronic administration of cortico steroids; antidiarrheal drugs can also provide symptomatic relief in some patients; nutritional therapy or elemental diet can improve the nutritional status of patients and induce symtomatic improvement of acute disease; antibiotics are used in treating secondary small bowel bacterial overgrowth and in treatment of pyogenic complications. IBD chemotherapeutic agents further include biologicals and other agents as follows: anti-beta7 antibodies (see, for example, WO2006026759), anti-alpha4 antibodies (such as ANTEGEN®), anti-TNF antibody (REMICADE®)) or non-protein compounds including without limitation 5-ASA compounds ASACOL®, PENTASA™, ROWASA™, COLAZAL™, and other compounds such as Purinethol and steroids such as prednisone. Examples of chemotherapeutic agents for the treatment of cancer include hydroxyureataxanes (such as paclitaxel and doxetaxel) and/or anthracycline antibiotics; alkylating agents such as thiotepa and CYTOXAN7 cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL7); beta-lapachone; lapachol; colchicines; betulinic acid; a camptothecin (including the synthetic analogue topotecan (HYCAMTIN7), CPT-11 (irinotecan, CAMPTOSAR7), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN7 doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK7 polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE7, FILDESIN7); dacarbazine; mannomustine; mitobronitol; mitolactol; pipobroman; gacytosine; arabinoside ("Ara-C"); thiotepa; taxoids, e.g., TAXOL7 paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE7 doxetaxel (Rhône-Poulenc Rorer, Antony, France); chloranbucil; gemcitabine (GEMZAR7); 6-thioguanine; mercaptopurine; methotrexate; platinum analogs such as cis-platin and carboplatin; vinblastine (VELBAN7); platinum; etoposide (VP-16); ifosfamide; mitoxantrone; vincristine (ONCOVIN7); oxaliplatin; leucovovin; vinorelbine (NAVELBIE7); novantrone; edatrexate; daunomycin; aminopterin; ibandronate; topoisomerase inhibitor RFS 2000; difluoromethylornithine (DMFO); retinoids such as retinoic acid; capecitabine (XELODA7); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-1, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

"Epithelia," "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithelial tissue includes: olfactory epithelium—the pseudostratified epithelium lining the olfactory region of the nasal cavity, and containing the receptors for the sense of smell; glandular epithelium—the epithelium composed of secreting cells squamous epithelium; squamous epithelium—the epithelium comprising one or more cell layers, the most superficial of which is comosed of flat, scalelike or platelike cells. Epithelium can also refer to transitional epithelium, like that which is characteristically found lining hollow organs that are subject to great mechanical change due to contraction and distention, e.g., tissue which represents a transition between stratified squamous and columnar epithelium.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "LY6" or "LY6 polypeptide" is used herein to refer generically to any of the mammalian homologs of the mammalian LY6 gene family. The term "LY6" may be used to describe protein or nucleic acid.

The term "overexpression" as used herein, refers to cellular gene expression levels of a tissue that is higher than the normal expression levels for that tissue. The term "underexpression" as used herein, refers to cellular gene expression levels of a tissue that is lower than the normal expression levels for that tissue. In either case, the higher or lower expression is significantly different from normal expression under controlled conditions of the study.

A "control" includes a sample obtained for use in determining base-line or normal expression or activity in a mammal that is not experiencing IBD. Accordingly, a control sample may be obtained by a number of means including from tissue or cells not affected by inflammation and/or IBD, UC or CD (as determined by standard techniques); non-IBD cells or tissue e.g., from cells of a subject not experiencing IBD; from subjects not having an IBD, Crohn's disease, or ulcerative colitis disorder; from subjects not suspected of being at risk for an IBD, CD or UC; or from cells or cell lines derived from such subjects. A control also includes a previously established standard. For assays, such as mRNA assays, including microarray assays, a control may be a universal control. Such universal control refers to RNA expression information of a particular LY6 gene obtained from RNA isolated from a mixture of healthy tissues or from a mixture of cell lines derived from various tissues such as, without limitation, universal reference RNAs disclosed herein. Accordingly, any test or assay conducted according to the invention may be compared with the established standard and it may not be necessary to obtain a control sample for comparison each time.

TABLE 1

```
/*
 *
 * C-C increased from 12 to 15
 * Z is average of EQ
 * B is average of ND
 * match with stop is __M; stop-stop = 0; J (joker) match = 0
 */
#define __M      -8       /* value of a match with a stop */
int      __day[26][26] = {
/*       A B C D E F G H I J K L M N O P Q R S T U V W X Y Z */
/* A */   { 2, 0,-2, 0, 0,-4, 1,-1,-1, 0,-1,-2,-1, 0,__M, 1, 0,-2, 1, 1, 0, 0,-6, 0,-3, 0},
/* B */   { 0, 3,-4, 3, 2,-5, 0, 1,-2, 0, 0,-3,-2, 2,__M,-1, 1, 0, 0, 0, 0,-2,-5, 0,-3, 1},
/* C */   {-2,-4,15,-5,-5,-4,-3,-3,-2, 0,-5,-6,-5,-4,__M,-3,-5,-4, 0,-2, 0,-2,-8, 0, 0,-5},
/* D */   { 0, 3,-5, 4, 3,-6, 1, 1,-2, 0, 0,-4,-3, 2,__M,-1, 2,-1, 0, 0, 0,-2,-7, 0,-4, 2},
/* E */   { 0, 2,-5, 3, 4,-5, 0, 1,-2, 0, 0,-3,-2, 1,__M,-1, 2,-1, 0, 0, 0,-2,-7, 0,-4, 3},
/* F */   {-4,-5,-4,-6,-5, 9,-5,-2, 1, 0,-5, 2, 0,-4,__M,-5,-5,-4,-3,-3, 0,-1, 0, 0, 7,-5},
/* G */   { 1, 0,-3, 1, 0,-5, 5,-2,-3, 0,-2,-4,-3, 0,__M,-1,-1,-3, 1, 0, 0,-1,-7, 0,-5, 0},
/* H */   {-1, 1,-3, 1, 1,-2,-2, 6,-2, 0, 0,-2,-2, 2,__M, 0, 3, 2,-1,-1, 0,-2,-3, 0, 0, 2},
/* I */   {-1,-2,-2,-2,-2, 1,-3,-2, 5, 0,-2, 2, 2,-2,__M,-2,-2,-2,-1, 0, 0, 4,-5, 0,-1,-2},
/* J */   { 0, 0, 0, 0, 0, 0, 0, 0, 0, 0,__M, 0, 0, 0, 0, 0, 0, 0, 0, 0, 0, 0, 0, 0, 0, 0},
/* K */   {-1, 0,-5, 0, 0,-5,-2, 0,-2, 0, 5,-3, 0, 1,__M,-1, 1, 3, 0, 0, 0,-2,-3, 0,-4, 0},
/* L */   {-2,-3,-6,-4,-3, 2,-4,-2, 2, 0,-3, 6, 4,-3,__M,-3,-2,-3,-3,-1, 0, 2,-2, 0,-1,-2},
/* M */   {-1,-2,-5,-3,-2, 0,-3,-2, 2, 0, 0, 4, 6,-2,__M,-2,-1, 0,-2,-1, 0, 2,-4, 0,-2,-1},
/* N */   { 0, 2,-4, 2, 1,-4, 0, 2,-2, 0, 1,-3,-2, 2,__M,-1, 1, 0, 1, 0, 0,-2,-4, 0,-2, 1},
/* O */   {__M,__M,__M,__M,__M,__M,__M,__M,__M,__M,__M,__M,__M,__M,__M,
```

TABLE 1-continued

```
                0,_M,_M,_M,_M,_M,_M,_M,_M,_M,_M,_M},
/* P */         { 1,-1,-3,-1,-1,-5,-1, 0,-2, 0,-1,-3,-2,-1,_M, 6, 0, 0, 1, 0, 0,-1,-6, 0,-5, 0},
/* Q */         { 0, 1,-5, 2, 2,-5,-1, 3,-2, 0, 1,-2,-1, 1,_M, 0, 4, 1,-1,-1, 0,-2,-5, 0,-4, 3},
/* R */         {-2, 0,-4,-1,-1,-4,-3, 2,-2, 0, 3,-3, 0, 0,_M, 0, 1, 6, 0,-1, 0,-2, 2, 0,-4, 0},
/* S */         { 1, 0, 0, 0, 0,-3, 1,-1,-1, 0, 0,-3,-2, 1,_M, 1,-1, 0, 2, 1, 0,-1,-2, 0,-3, 0},
/* T */         { 1, 0,-2, 0, 0,-3, 0,-1, 0, 0, 0,-1,-1, 0,_M, 0,-1,-1, 1, 3, 0, 0,-5, 0,-3, 0},
/* U */         { 0, 0, 0, 0, 0, 0, 0, 0, 0, 0, 0, 0, 0, 0,_M, 0, 0, 0, 0, 0, 0, 0, 0, 0, 0, 0},
/* V */         { 0,-2,-2,-2,-2,-1,-1,-2, 4, 0,-2, 2, 2,-2,_M,-1,-2,-2,-1, 0, 0, 4,-6, 0,-2,-2},
/* W */         {-6,-5,-8,-7,-7, 0,-7,-3,-5, 0,-3,-2,-4,-4,_M,-6,-5, 2,-2,-5, 0,-6,17, 0, 0,-6},
/* X */         { 0, 0, 0, 0, 0, 0, 0, 0, 0, 0, 0, 0, 0, 0,_M, 0, 0, 0, 0, 0, 0, 0, 0, 0, 0, 0},
/* Y */         {-3,-3, 0,-4,-4, 7,-5, 0,-1, 0,-4,-1,-2,-2,_M,-5,-4,-4,-3,-3, 0,-2, 0, 0,10,-4},
/* Z */         { 0, 1,-5, 2, 3,-5, 0, 2,-2, 0, 0,-2,-1, 1,_M, 0, 3, 0, 0, 0, 0,-2,-6, 0,-4, 4}
};
/*
*/
#include <stdio.h>
#include <ctype.h>
#define MAXJMP      16       /* max jumps in a diag */
#define MAXGAP      24       /* don't continue to penalize gaps larger than this */
#define JMPS        1024     /* max jmps in an path */
#define MX          4        /* save if there's at least MX-1 bases since last jmp */
#define DMAT        3        /* value of matching bases */
#define DMIS        0        /* penalty for mismatched bases */
#define DINS0       8        /* penalty for a gap */
#define DINS1       1        /* penalty per base */
#define PINS0       8        /* penalty for a gap */
#define PINS1       4        /* penalty per residue */
struct jmp {
        short       n[MAXJMP];      /* size of jmp (neg for dely) */
        unsigned short x[MAXJMP];   /* base no. of jmp in seq x */
};                                  /* limits seq to 2^16 -1 */
struct diag {
        int         score;          /* score at last jmp */
        long        offset;         /* offset of prev block */
        short       ijmp;           /* current jmp index */
        struct      jmp jp;         /* list of jmps */
};
struct path {
        int         spc;            /* number of leading spaces */
        short       n[JMPS];        /* size of jmp (gap) */
        int         x[JMPS];        /* loc of jmp (last elem before gap) */
};
char            *ofile;             /* output file name */
char            *namex[2];          /* seq names: getseqs( ) */
char            *prog;              /* prog name for err msgs */
char            *seqx[2];           /* seqs: getseqs( ) */
int             dmax;               /* best diag: nw( ) */
int             dmax0;              /* final diag */
int             dna;                /* set if dna: main( ) */
int             endgaps;            /* set if penalizing end gaps */
int             gapx, gapy;         /* total gaps in seqs */
int             len0, len1;         /* seq lens */
int             ngapx, ngapy;       /* total size of gaps */
int             smax;               /* max score: nw( ) */
int             *xbm;               /* bitmap for matching */
long            offset;             /* current offset in jmp file */
struct  diag    *dx;                /* holds diagonals */
struct  path    pp[2];              /* holds path for seqs */
char            *calloc( ), *malloc( ), *index( ), *strcpy( );
char            *getseq( ), *g_calloc( );
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
#include "nw.h"
#include "day.h"
static   _dbval[26] = {
        1,14,2,13,0,0,4,11,0,0,12,0,3,15,0,0,0,5,6,8,8,7,9,0,10,0
};
static   _pbval[26] = {
```

TABLE 1-continued

```
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};
main(ac, av)                                                                                    main
        int       ac;
        char      *av[ ];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;
        endgaps = 0;                      /* 1 to penalize endgaps */
        ofile = "align.out";              /* output file */
        nw( );                            /* fill in the matrix, get the possible jmps */
        readjmps( );                      /* get the actual jmps */
        print( );                         /* print stats, alignment */
        cleanup(0);                       /* unlink any tmp files */
}
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                                                           nw
{
        char      *px, *py;               /* seqs and ptrs */
        int       *ndely, *dely;          /* keep track of dely */
        int       ndelx, delx;            /* keep track of delx */
        int       *tmp;                   /* for swapping row0, row1 */
        int       mis;                    /* score for each type */
        int       ins0, ins1;             /* insertion penalties */
        register  id;                     /* diagonal index */
        register  ij;                     /* jmp index */
        register  *col0, *col1;           /* score for curr, last row */
        register  xx, yy;                 /* index into seqs */
        dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;              /* Waterman Bull Math Biol 84 */
        }
        else
                for (yy = 1; yy <= len1; yy++)
                        dely[yy] = -ins0;
        /* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
```

TABLE 1-continued

```
                else {
                        col1[0] = 0;
                        delx = -ins0;
                        ndelx = 0;
                }
        }                                                                                       ...nw
        for (py = seqx[1], yy = 1; yy <= len1; py++, yy++) {
                mis = col0[yy-1];
                if (dna)
                        mis += (xbm[*px-'A']&xbm[*py-'A'])? DMAT : DMIS;
                else
                        mis += _day[*px-'A'][*py-'A'];
                /* update penalty for del in x seq;
                 * favor new del over ongong del
                 * ignore MAXGAP if weighting endgaps
                 */
                if (endgaps || ndely[yy] < MAXGAP) {
                        if (col0[yy] - ins0 >= dely[yy]) {
                                dely[yy] = col0[yy] - (ins0+ins1);
                                ndely[yy] = 1;
                        } else {
                                dely[yy] -= ins1;
                                ndely[yy]++;
                        }
                } else {
                        if (col0[yy] - (ins0+ins1) >= dely[yy]) {
                                dely[yy] = col0[yy] - (ins0+ins1);
                                ndely[yy] = 1;
                        } else
                                ndely[yy]++;
                }
                /* update penalty for del in y seq;
                 * favor new del over ongong del
                 */
                if (endgaps || ndelx < MAXGAP) {
                        if (col1[yy-1] - ins0 >= delx) {
                                delx = col1[yy-1] - (ins0+ins1);
                                ndelx = 1;
                        } else {
                                delx -= ins1;
                                ndelx++;
                        }
                } else {
                        if (col1[yy-1] - (ins0+ins1) >= delx) {
                                delx = col1[yy-1] - (ins0+ins1);
                                ndelx = 1;
                        } else
                                ndelx++;
                }
                /* pick the maximum score; we're favoring
                 * mis over any del and delx over dely
                 */
                id = xx - yy + len1 - 1;                                                        ...nw
                if (mis >= delx && mis >= dely[yy])
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                             && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
                if (dx[id].jp.n[0] && (!dna || (ndely[yy] >= MAXJMP
                             && xx > dx[id].jp.x[ij]+MX) || mis > dx[id].score+DINS0)) {
                                dx[id].ijmp++;
                                if (++ij >= MAXJMP) {
```

TABLE 1-continued

```
                              writejmps(id);
                              ij = dx[id].ijmp = 0;
                              dx[id].offset = offset;
                              offset += sizeof(struct jmp) + sizeof(offset);
                          }
                      }
                      dx[id].jp.n[ij] = −ndely[yy];
                      dx[id].jp.x[ij] = xx;
                      dx[id].score = dely[yy];
                  }
                  if (xx == len0 && yy < len1) {
                      /* last col
                      */
                      if (endgaps)
                              col1[yy] −= ins0+ins1*(len1−yy);
                      if (col1[yy] > smax) {
                              smax = col1[yy];
                              dmax = id;
                      }
                  }
              }
              if (endgaps && xx < len0)
                      col1[yy−1] −= ins0+ins1*(len0−xx);
              if (col1[yy−1] > smax) {
                      smax = col1[yy−1];
                      dmax = id;
              }
              tmp = col0; col0 = col1; col1 = tmp;
          }
          (void) free((char *)ndely);
          (void) free((char *)dely);
          (void) free((char *)col0);
          (void) free((char *)col1);
}
/*
*
* print( ) -- only routine visible outside this module
*
* static:
* getmat( ) -- trace back best path, count matches: print( )
* pr_align( ) -- print alignment of described in array p[ ]: print( )
* dumpblock( ) -- dump a block of lines with numbers, stars: pr_align( )
* nums( ) -- put out a number line: dumpblock( )
* putline( ) -- put out a line (name, [num], seq, [num]): dumpblock( )
* stars( ) - -put a line of stars: dumpblock( )
* stripname( ) -- strip any path and prefix from a seqname
*/
#include "nw.h"
#define SPC         3
#define P_LINE      256     /* maximum output line */
#define P_SPC       3       /* space between name or num and seq */
extern    _day[26][26];
int       olen;             /* set output line length */
FILE      *fx;              /* output file */
print( )                                                                      print
{
          int     lx, ly, firstgap, lastgap;     /* overlap */
          if ((fx = fopen(ofile, "w")) == 0) {
                  fprintf(stderr,"%s: can't write %s\n", prog, ofile);
                  cleanup(1);
          }
          fprintf(fx, "<first sequence: %s (length = %d)\n", namex[0], len0);
          fprintf(fx, "<second sequence: %s (length = %d)\n", namex[1], len1);
          olen = 60;
          lx = len0;
          ly = len1;
          firstgap = lastgap = 0;
          if (dmax < len1 − 1) {           /* leading gap in x */
                  pp[0].spc = firstgap = len1 − dmax − 1;
                  ly −= pp[0].spc;
          }
          else if (dmax > len1 − 1) { /* leading gap in y */
                  pp[1].spc = firstgap = dmax − (len1 − 1);
                  lx −= pp[1].spc;
          }
          if (dmax0 < len0 − 1) {          /* trailing gap in x */
                  lastgap = len0 − dmax0 −1;
                  lx −= lastgap;
          }
```

TABLE 1-continued

```
                else if (dmax0 > len0 - 1) {        /* trailing gap in y */
                        lastgap = dmax0 - (len0 - 1);
                        ly -= lastgap;
                }
                getmat(lx, ly, firstgap, lastgap);
                pr_align( );
        }
}
/*
* trace back the best path, count matches
*/
static
getmat(lx, ly, firstgap, lastgap)                                                              getmat
        int         lx, ly;                         /* "core" (minus endgaps) */
        int         firstgap, lastgap;              /* leading trailing overlap */
{
        int            nm, i0, i1, siz0, siz1;
        char           outx[32];
        double         pct;
        register       n0, n1;
        register char  *p0, *p1;
        /* get total matches, score
        */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
        * if penalizing endgaps, base is the shorter seq
        * else, knock off overhangs and take shorter core
        */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx);                                       ...getmat
        if (gapx) {
                (void) sprintf(outx, " (%d %s%s)",
                        ngapx, (dna)? "base":"residue", (ngapx == 1)? "":"s");
                fprintf(fx,"%s", outx);
        }
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
```

TABLE 1-continued

```
                                "\n<score: %d (Dayhoff PAM 250 matrix, gap penalty = %d + %d per residue)\n",
                                smax, PINS0, PINS1);
                if (endgaps)
                                fprintf(fx,
                                "<endgaps penalized. left endgap: %d %s%s, right endgap: %d %s%s\n",
                                firstgap, (dna)? "base" : "residue", (firstgap == 1)? "" : "s",
                                lastgap, (dna)? "base" : "residue", (lastgap == 1)? "" : "s");
                else
                                fprintf(fx, "<endgaps not penalized\n");
}
static          nm;                             /* matches in core -- for checking */
static          lmax;                           /* lengths of stripped file names */
static          ij[2];                          /* jmp index for a path */
static          nc[2];                          /* number at start of current line */
static          ni[2];                          /* current elem number -- for gapping */
static          siz[2];
static char     *ps[2];                         /* ptr to current element */
static char     *po[2];                         /* ptr to next output char slot */
static char     out[2][P_LINE];                 /* output line */
static char     star[P_LINE];                   /* set by stars( ) */
/*
* print alignment of described in struct path pp[ ]
*/
static
pr_align( )                                                                                                     pr_align
{
                int             nn;             /* char count */
                int             more;
                register        i;
                for (i = 0, lmax = 0; i < 2; i++) {
                                nn = stripname(namex[i]);
                                if (nn > lmax)
                                                lmax = nn;
                                nc[i] = 1;
                                ni[i] = 1;
                                siz[i] = ij[i] = 0;
                                ps[i] = seqx[i];
                                po[i] = out[i];
                }
                for (nn = nm = 0, more = 1; more; ) {                                                           ...pr_align
                                for (i = more = 0; i < 2; i++) {
                                                /*
                                                * do we have more of this sequence?
                                                */
                                                if (!*ps[i])
                                                                continue;
                                                more++;
                                                if (pp[i].spc) { /* leading space */
                                                                *po[i]++ = ' ';
                                                                pp[i].spc--;
                                                }
                                                else if (siz[i]) { /* in a gap */
                                                                *po[i]++ = '-';
                                                                siz[i]--;
                                                }
                                                else {          /* we're putting a seq element
                                                                */
                                                                *po[i] = *ps[i];
                                                                if (islower(*ps[i]))
                                                                                *ps[i] = toupper(*ps[i]);
                                                                po[i]++;
                                                                ps[i]++;
                                                                /*
                                                                * are we at next gap for this seq?
                                                                */
                                                                if (ni[i] == pp[i].x[ij[i]]) {
                                                                                /*
                                                                                * we need to merge all gaps
                                                                                * at this location
                                                                                */
                                                                                siz[i] = pp[i].n[ij[i]++];
                                                                                while (ni[i] == pp[i].x[ij[i]])
                                                                                                siz[i] += pp[i].n[ij[i]++];
                                                                }
                                                                ni[i]++;
                                                }
                                }
                                if (++nn == olen || !more && nn) {
                                                dumpblock( );
```

TABLE 1-continued

```
                        for (i = 0; i < 2; i++)
                                po[i] = out[i];
                        nn = 0;
                }
        }
}
/*
* dump a block of lines, including numbers, stars: pr_align( )
*/
static
dumpblock( )                                                                    dumpblock
{
        register i;
        for (i = 0; i < 2; i++)
                *po[i]-- = '\0';
                                                                             ...dumpblock
        (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars( );
                        putline(i);
                        if (i == 0 && *out[1])
                                fprintf(fx, star);
                        if (i == 1)
                                nums(i);
                }
        }
}
/*
* put out a number line: dumpblock( )
*/
static
nums(ix)                                                                        nums
        int     ix;      /* index in out[ ] holding seq line */
{
        char            nline[P_LINE];
        register        i, j;
        register        char *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
* put out a line (name, [num], seq, [num]): dumpblock( )
*/
static
putline(ix)                                                                     putline
        int                             ix;
{
        int             i;                                                   ...putline
        register char   *px;
        for (px = namex[ix], i = 0; *px && *px != ':'; px++, i++)
                (void) putc(*px, fx);
        for (; i < lmax+P_SPC; i++)
                (void) putc(' ', fx);
        /* these count from 1:
```

TABLE 1-continued

```
         * ni[ ] is current element (from 1)
         * nc[ ] is number at start of current line
         */
         for (px = out[ix]; *px; px++)
                  (void) putc(*px&0x7F, fx);
         (void) putc('\n', fx);
}
/*
* put a line of stars (seqs always in out[0], out[1]): dumpblock( )
*/
static
stars( )                                                                                    stars
{
         int             i;
         register char   *p0, *p1, cx, *px;
         if (!*out[0] || (*out[0] == ' ' && *(po[0]) == ' ') ||
            !*out[1] || (*out[1] == ' ' && *(po[1]) == ' '))
                  return;
         px = star;
         for (i = lmax+P_SPC; i; i--)
                  *px++ = ' ';
         for (p0 = out[0], p1 = out[1]; *p0 && *p1; p0++, p1++) {
                  if (isalpha(*p0) && isalpha(*p1)) {
                           if (xbm[*p0-'A']&xbm[*p1-'A']) {
                                    cx = '*';
                                    nm++;
                           }
                           else if (!dna && __day[*p0-'A'][*p1-'A'] > 0)
                                    cx = '.';
                           else
                                    cx = ' ';
                  }
                  else
                           cx = ' ';
                  *px++ = cx;
         }
         *px++ = '\n';
         *px = '\0';
}
/*
* strip path or prefix from pn, return len: pr_align( )
*/
static
stripname(pn)                                                                               stripname
         char     *pn;      /* file name (may be path) */
{
         register char   *px, *py;
         py = 0;
         for (px = pn; *px; px++)
                  if (*px == '/')
                           py = px + 1;
         if (py)
                  (void) strcpy(pn, py);
         return(strlen(pn));
}
/*
* cleanup( ) -- cleanup any tmp file
* getseq( ) -- read in seq, set dna, len, maxlen
* g_calloc( ) -- calloc( ) with error checkin
* readjmps( ) -- get the good jmps, from tmp file if necessary
* writejmps( ) -- write a filled array of jmps to a tmp file: nw( )
*/
#include "nw.h"
#include <sys/file.h>
char     *jname = "/tmp/homgXXXXXX";                 /* tmp file for jmps */
FILE     *fj;
int      cleanup( );                                 /* cleanup tmp file */
long     lseek( );
/*
* remove any tmp file if we blow
*/
cleanup(i)                                                                                  cleanup
         int     i;
{
         if (fj)
                  (void) unlink(jname);
         exit(i);
}
/*
```

TABLE 1-continued

```
* read, return ptr to seq, set dna, len, maxlen
* skip lines starting with ';', '<', or '>'
* seq in upper or lower case
*/
char      *
getseq(file, len)                                                                              getseq
          char      *file;     /* file name */
          int       *len;      /* seq len */
{
          char              line[1024], *pseq;
          register char     *px, *py;
          int               natgc, tlen;
          FILE              *fp;
          if ((fp = fopen(file,"r")) == 0) {
                    fprintf(stderr,"%s: can't read %s\n", prog, file);
                    exit(1);
          }
          tlen = natgc = 0;
          while (fgets(line, 1024, fp)) {
                    if (*line == ';' || *line == '<' || *line == '>')
                              continue;
                    for (px = line; *px != '\n'; px++)
                              if (isupper(*px) || islower(*px))
                                        tlen++;
          }
          if ((pseq = malloc((unsigned)(tlen+6))) == 0) {
                    fprintf(stderr,"%s: malloc( ) failed to get %d bytes for %s\n", prog, tlen+6, file);
                    exit(1);
          }
          pseq[0] = pseq[1] = pseq[2] = pseq[3] = '\0';
                                                                                               ...getseq
          py = pseq + 4;
          *len = tlen;
          rewind(fp);
          while (fgets(line, 1024, fp)) {
                    if (*line == ';' || *line == '<' || *line == '>')
                              continue;
                    for (px = line; *px != '\n'; px++) {
                              if (isupper(*px))
                                        *py++ = *px;
                              else if (islower(*px))
                                        *py++ = toupper(*px);
                              if (index("ATGCU",*(py−1)))
                                        natgc++;
                    }
          }
          *py++ = '\0';
          *py = '\0';
          (void) fclose(fp);
          dna = natgc > (tlen/3);
          return(pseq+4);
}
char *
g_calloc(msg, nx, sz)                                                                          g_calloc
          char      *msg;      /* program, calling routine */
          int       nx, sz;    /* number and size of elements */
{
          char              *px, *calloc( );
          if ((px = calloc((unsigned)nx, (unsigned)sz)) == 0) {
                    if (*msg) {
                              fprintf(stderr, "%s: g_calloc( ) failed %s (n=%d, sz=%d)\n", prog, msg, nx, sz);
                              exit(1);
                    }
          }
          return(px);
}
/*
* get final jmps from dx[ ] or tmp file, set pp[ ], reset dmax: main( )
*/
readjmps( )                                                                                    readjmps
{
          int               fd = −1;
          int               siz, i0, i1;
          register i, j, xx;
          if (fj) {
                    (void) fclose(fj);
                    if ((fd = open(jname, O_RDONLY, 0)) < 0) {
                              fprintf(stderr, "%s: can't open( ) %s\n", prog, jname);
                              cleanup(1);
```

TABLE 1-continued

```
                        }
                }
                for (i = i0 = i1 = 0, dmax0 = dmax, xx = len0; ; i++) {
                        while (1) {
                                for (j = dx[dmax].ijmp; j >= 0 && dx[dmax].jp.x[j] >= xx; j--)
                                        ;
                                                                                                        ...readjmps
                                if (j < 0 && dx[dmax].offset && fj) {
                                        (void) lseek(fd, dx[dmax].offset, 0);
                                        (void) read(fd, (char *)&dx[dmax].jp, sizeof(struct jmp));
                                        (void) read(fd, (char *)&dx[dmax].offset, sizeof(dx[dmax].offset));
                                        dx[dmax].ijmp = MAXJMP-1;
                                }
                                else
                                        break;
                        }
                        if (i >= JMPS) {
                                fprintf(stderr, "%s: too many gaps in alignment\n", prog);
                                cleanup(1);
                        }
                        if (j >= 0) {
                                siz = dx[dmax].jp.n[j];
                                xx = dx[dmax].jp.x[j];
                                dmax += siz;
                                if (siz < 0) {                          /* gap in second seq */
                                        pp[1].n[i1] = -siz;
                                        xx += siz;
                                        /* id = xx - yy + len1 - 1
                                         */
                                        pp[1].x[i1] = xx - dmax + len1 - 1;
                                        gapy++;
                                        ngapy -= siz;
/* ignore MAXGAP when doing endgaps */
                                        siz = (-siz < MAXGAP || endgaps)? -siz : MAXGAP;
                                        i1++;
                                }
                                else if (siz > 0) {     /* gap in first seq */
                                        pp[0].n[i0] = siz;
                                        pp[0].x[i0] = xx;
                                        gapx++;
                                        ngapx += siz;
/* ignore MAXGAP when doing endgaps */
                                        siz = (siz < MAXGAP || endgaps)? siz : MAXGAP;
                                        i0++;
                                }
                        }
                        else
                                break;
                }
                /* reverse the order of jmps
                 */
                for (j = 0, i0--; j < i0; j++, i0--) {
                        i = pp[0].n[j]; pp[0].n[j] = pp[0].n[i0]; pp[0].n[i0] = i;
                        i = pp[0].x[j]; pp[0].x[j] = pp[0].x[i0]; pp[0].x[i0] = i;
                }
                for (j = 0, i1--; j < i1; j++, i1--) {
                        i = pp[1].n[j]; pp[1].n[j] = pp[1].n[i1]; pp[1].n[i1] = i;
                        i = pp[1].x[j]; pp[1].x[j] = pp[1].x[i1]; pp[1].x[i1] = i;
                }
                if (fd >= 0)
                        (void) close(fd);
                if (fj) {
                        (void) unlink(jname);
                        fj = 0;
                        offset = 0;
                }
/*
 * write a filled jmp struct offset of the prev one (if any): nw( )
 */
writejmps(ix)                                                                                           writejmps
        int     ix;
{
        char    *mktemp( );
        if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
```

TABLE 1-continued

```
            fprintf(stderr, "%s: can't write %s\n", prog, jname);
            exit(1);
        }
    }
    (void) fwrite((char *)&dx[ix].jp, sizeof(struct jmp), 1, fj);
    (void) fwrite((char *)&dx[ix].offset, sizeof(dx[ix].offset), 1, fj);
}
```

TABLE 2

| Reference | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the reference polypeptide) = 5 divided by 15 = 33.3%

TABLE 3

| Reference | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the reference polypeptide) = 5 divided by 10 = 50%

TABLE 4

| Reference-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the reference-DNA nucleic acid sequence) = 6 divided by 14 = 42.9%

TABLE 5

| Reference-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the reference-DNA nucleic acid sequence) = 4 divided by 12 = 33.3%

Diagnostic Methods of the Invention

It is further contemplated that use of therapeutic agents for IBD may be specifically targeted to disorders where the affected tissue and/or cells exhibit increased LY6 expression relative to control. Accordingly, it is contemplated that the detection of increased LY6 expression may be used to detect IBD, such as CD or UC, in the gastrointestinal tissue of a mammal and/or to identify tissues and disorders that will particularly benefit from treatment with an IBD therapeutic agent, including a chemotherapeutic agent, useful in ameliorating IBD, UC and/or CD in a human patient.

In preferred embodiments, LY6 expression levels are detected, either by direct detection of the gene transcript or by detection of protein levels or activity. Transcripts may be detected using any of a wide range of techniques that depend primarily on hybridization or probes to the LY6 mRNA transcripts, to cDNAs synthesized therefrom, or to DNA where LY6 gene amplification is present. Well known techniques include Northern blotting, reverse-transcriptase PCR and microarray analysis of transcript levels. Methods for detecting LY6 protein levels include Western blotting, immunoprecipitation, two-dimensional polyacrylamide gel electrophoresis (2D SDS-PAGE—preferably compared against a standard wherein the position of the LY6 proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification, etc. LY6 activity may also be assessed by analyzing binding to substrate DNA or in vitro transcriptional activation of target promoters. Gel shift assay, DNA footprinting assays and DNA-protein crosslinking assays are all methods that may be used to assess the presence of a protein capable of binding to Gli binding sites on DNA. J Mol. Med. 77(6):459-68 (1999); Cell 100(4): 423-34 (2000); Development 127(19): 4923-4301 (2000).

In certain embodiments, LY6 transcript levels are measured, and diseased or disordered tissues showing significantly elevated LY6 levels relative to control are treated with an IBD therapeutic compound. Accordingly, LY6 expression levels are a powerful diagnostic measure for determining whether a patient is experiencing IBD and whether that patient should receive an IBD therapeutic agent.

Antibody Compositions for Use in the Methods of the Invention

A. Anti-LY6 Antibodies

In one embodiment, the present invention provides the use of anti-LY6 antibodies, which may find use herein as therapeutic, diagnostic and/or prognostic agents in determining the existence, severity of and/or prognosing the disease course of an inflammatory bowel disease such as UC. Exemplary antibodies that may be used for such purposes include polyclonal, monoclonal, humanized, bispecific, and heteroconjugate antibodies. The term "antibodies" sometimes also include antigen-binding fragments. Anti-LY6 antibodies are available commercially, such as for example, from R&D Systems, Minneapolis, Minn. Antibodies that bind specifically to LY6 as antigen may be obtained commercially or prepared by standard methods known in the art of antibody and protein chemistry for use in the method of the invention. Antibodies to LYPD1 are disclosed, for example in U.S. Pat. No. 7,144, 990, the disclosure patent is hereby incorporated by reference in its entirety.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, J. Immunol., 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.* 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., Proc. Natl. Acad. Sci. USA, 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-LY6 antibodies useful in the practice of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., J. Immunol. 151:2296 (1993); Chothia et al., J. Mol. Biol., 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol. 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-LY6 antibody antibodies are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno. 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., *Nature* 348:552-553 (1990) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, while retaining similar antigen binding specificity of the corresponding full length molecule, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and scFv antibody fragments can all be expressed in and secreted from E. coli, thus allowing the facile production of large amounts of these fragments. Antibody fragments can be isolated from the antibody phage libraries discussed above. Alternatively, Fab'-SH fragments can be directly recovered from E. coli and chemically coupled to form $F(ab')_2$ fragments (Carter et al., Bio/Technology 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind separate antigens or bind to two different epitopes of a particular LY6 polypeptide described herein. Other such antibodies may combine the above LY6 binding site with a binding site for another protein. Where the bispecific antibody is useful in the diagnostic method of the invention, the second antibody arm may bind a detectable polypeptide. Bispecific antibodies can be prepared as full length antibodies or antibody fragments (e.g., $F(ab')_2$ bispecific antibodies).

Methods for making bispecific antibodies are known in the art. Traditional production of full length bispecific antibodies is based on the co-expression of two immunoglobulin heavy chain-light chain pairs, where the two chains have different specificities (Millstein et al., Nature 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J. 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies also find use in the present method of the invention by providing multiple (either different or the same) detectable markers on each antibody for improved assay detection. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med. 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies can be prepared. Tutt et al., J. Immunol. 147:60 (1991).

6. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

7. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al., Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

8. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate) and/or a detectable label.

a. Chemotherapeutic Agents

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

B. LY6 Binding Oligopeptides

LY6 binding oligopeptides of the present invention are oligopeptides that bind, preferably specifically, to a LY6 polypeptide as described herein. LY6 binding oligopeptides may be chemically synthesized using known oligopeptide synthesis methodology or may be prepared and purified using recombinant technology. LY6 binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a LY6 polypeptide as described herein. LY6 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren et al., Gene, 215: 439 (1998); Zhu et al., Cancer Research, 58(15): 3209-3214 (1998); Jiang et al., Infection & Immunity, 65(11): 4770-4777 (1997); Ren et al., Gene, 195(2):303-311 (1997); Ren, Protein Sci., 5: 1833 (1996); Efimov et al., Virus Genes, 10: 173 (1995)) and T7 phage display systems (Smith and Scott, Methods in Enzymology, 217: 228-257 (1993); U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol. Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

In aspect, the present invention concerns ligands for the LYPD5 polypeptide. FIG. 32 demonstrates this showing untransfected COS cells (A) and COS cells transfected with GLG-1 and stained with LYPD5-Fc protein. In one embodiment, the ligand for LYPD5 is the golgi complex localized glycoprotein 1 (GLG-1) or E-selectin 1 (ESL-1) polypeptide as shown in SEQ ID NOS:18, 20, 22, or 24, encoded by the nucleic acid shown as SEQ ID NOS:17, 19, 21, or 23, respectively. In another embodiment, the polynucleotide encoding a GLG-1 polypeptide comprises at least 15, at least 25, at least, at least 50, at least 100, at least 250, at least 500, at least 750, at least 1000, at least 1250, at least 1500, at least 1750, at least 2000, at least 2040, at least 2090, at least 2150, at least 2200, at least 2300, at least 2400, at least 2500, at least 2600, at least 2700, at least 2800, at least 2900, at least 3000, at least 3100, at least 3200, at least 3300, at least 3400, at least 3500, at least 3600, at least 3700, or at least 3720 contiguous nucleotides of SEQ ID NOs 17, 19, 21, or 23, or the polynucleotide encoding a GLG-1 comprises SEQ ID NOs 17, 19, 21, or 23. In one embodiment, a polynucleotide that binds a polynucleotide encoding a GLG-1 (SEQ ID NOs:17, 19, 21, or 23), or fragment thereof, has at least 75%, at least 80%, at least 85%, at least 90%, at least 95%, at least 97%, at least 99% or 100% sequence identity with the GLG-1 polypeptide or fragment thereof. In one embodiment, the GLG-1 polypeptide comprises at least 10, at least 25, at least 50, at least 75, at least 100, at least 125, at least 150, at least 175, at least 200, at least 225, at least 250, at least 275, at least 300, at least 325, at least 350, at least 400, at least 450, at least 500, at least 550, at least 600, at least 650, at least 700, at least 750, at least 800, at least 850, at least 900, at least 950, at least 1000, at least 1050, at least 100, at least 1150, or at least 1200 contiguous amino acids of SEQ ID NOs: 18, 20, 22, or 24, or the GLG-1 polypeptide comprises SEQ ID NOs: 18, 20, 22, or 24. GLG-1 or ESL-1 is expressed on neutrophils, believe to be involved in extravasation of neutrophils into tissues, and thought to play an important role in inflammation (see Hidalgo et al. (2007) Immunity, 26(4): 477-489 incorporated herein by reference in its entirety). GLG-1 or ESL-1 has 14 cysteine rich GLG1 domains. The extracellular domain (ECD) is lengthy and as described below, variants or fragments of the GLG-1 ECD were found to have the ability to bind LYPD5.

In another embodiment, the LYPD5 ligand is a variant or fragment a GLG-1 or ESL-1 molecule described herein. As shown in FIG. 33A-B, GLG-1 or ESL-1 may be viewed as fragments 1, 2, 3, and 4 and as described in Example 1, any one of the 4 fragments are sufficient for LYPD5 binding.

Figure 34A:
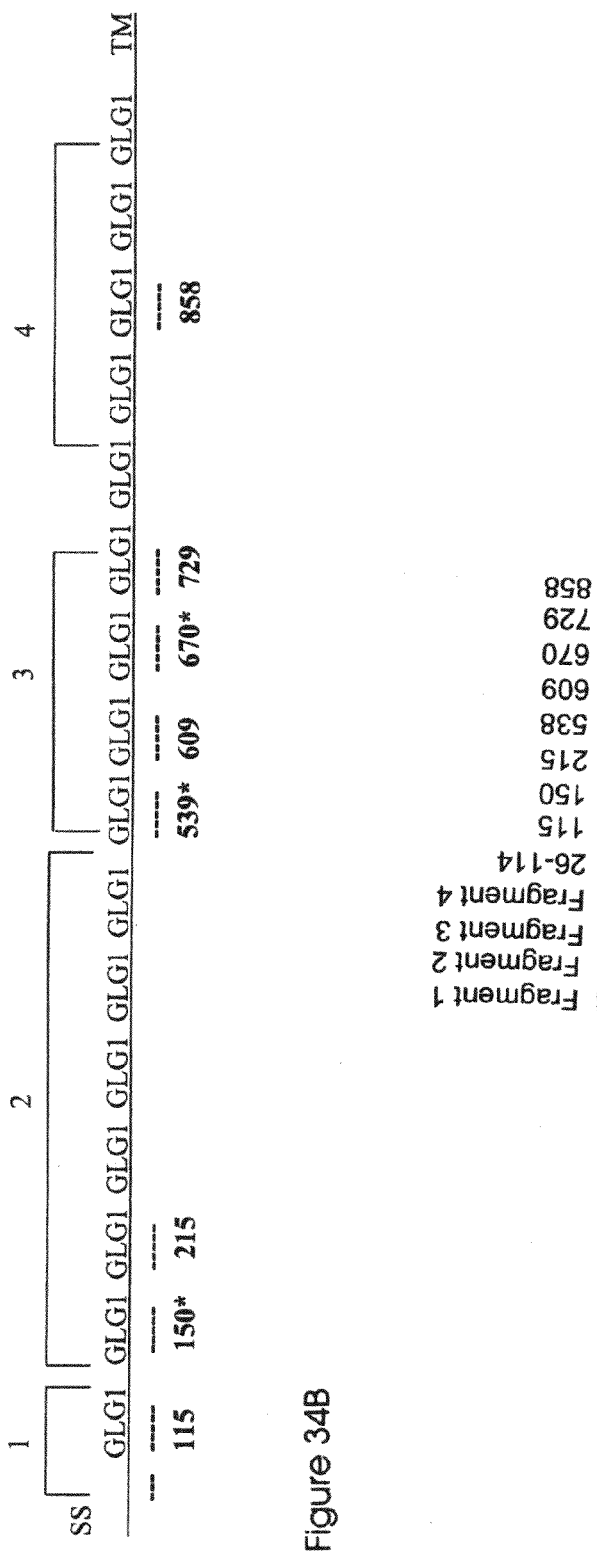
FIG. 34A depicts the structure of GLG-1 or ESL-1 and various fragments suitable for characterizing the binding of LYPD5 and FIG. 34B shows the results of a co-immunoprecipitation study characterizing the binding of LYPD5 and an LYPD5 ligand.
Figure 34B:
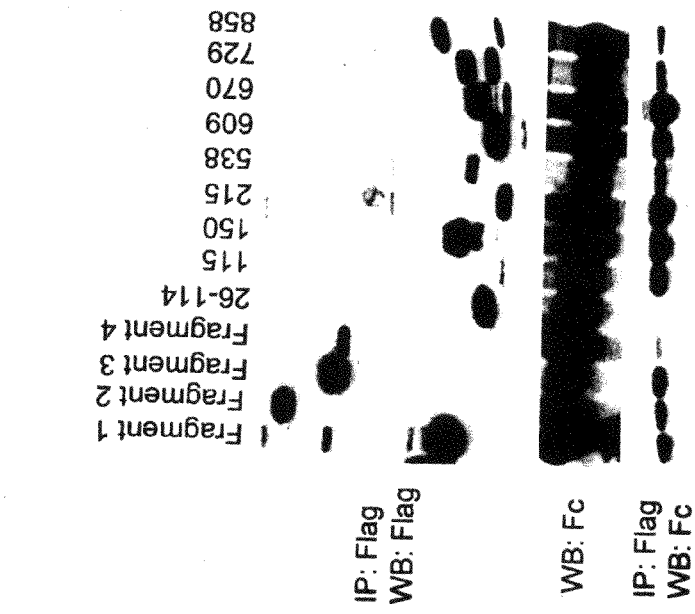

In another embodiment, the LYPD5 ligand is a variant or fragment of GLG-1 or ESL-1 that is a single GLG-1 domain. As shown in FIG. 34A-B, GLG-1 is made up of multiple GLG-1 domains and as described in Example 11, single GLG-1 domains are sufficient for LYPD5 binding.

Figures 35A, 35B:
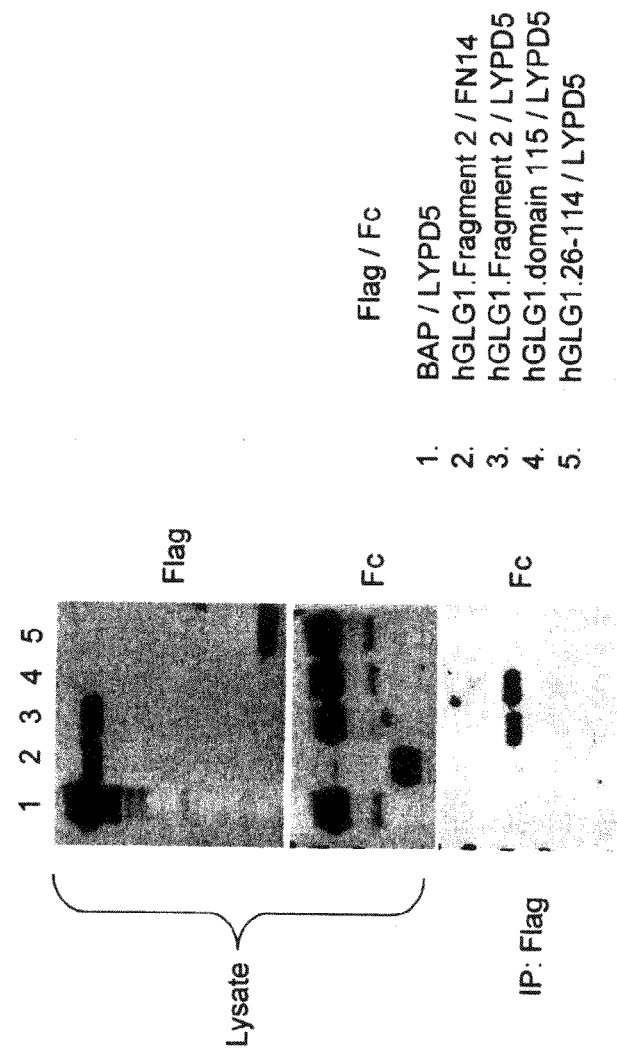
FIG. 35A depicts the structure of GLG-1 or ESL-1 and various fragments suitable for characterizing the binding of LYPD5 and FIG. 35B shows the results of a co-immunoprecipitation study characterizing the binding of LYPD5 and an LYPD5 ligand.

In another embodiment, the LYPD5 ligand is a variant or fragment of GLG-1 or ESL-1 that is specific for LYPD5. As shown in FIG. 35A-B, GLG-1 includes domains 26-114, domain 115, and domain 150 and as described in Example 11, domain 115 binds LYPD5 but domains 26-114 does not bind LYPD5.

The present invention contemplates variants of GLG-1 in the same manner it contemplates variants for LY6 family members.

C. Polypeptide Variants

In addition to the polypeptides, antibodies and LY6 binding polypeptides described herein, it is contemplated that variants of such molecules can be prepared for use with the invention herein. Such variants can be prepared by introducing appropriate nucleotide changes into the encoding DNA, and/or by synthesis of the desired antibody or polypeptide. Those skilled in the art will appreciate that amino acid changes may alter post-translational processes of these molecules, such as changing the number or position of glycosylation sites or altering the membrane anchoring characteristics.

Variations in amino acid sequence can be made, for example, using any of the techniques and guidelines for conservative and non-conservative mutations set forth, for instance, in U.S. Pat. No. 5,364,934. Variations may be a substitution, deletion or insertion of one or more codons encoding the amino acid sequence that results in a change in the amino acid sequence as compared with the native sequence. Optionally the variation is by substitution of at least one amino acid with any other amino acid in one or more of the domains of the amino acid sequence of interest. Guidance in determining which amino acid residue may be inserted, substituted or deleted without adversely affecting the desired activity may be found by comparing the sequence of the amino acid sequence of interest with homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Fragments of the various polypeptides are provided herein. Such fragments may be truncated at the N-terminus or C-terminus, or may lack internal residues, for example, when compared with a full length native antibody or protein. Such fragments which lack amino acid residues that are not essential for a desired biological activity are also useful with the disclosed methods.

The above polypeptide fragments may be prepared by any of a number of conventional techniques. Desired peptide fragments may be chemically synthesized. An alternative approach involves generating such fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding the desired fragment by polymerase chain reaction (PCR). Oligonucleotides that define the desired termini of the DNA fragment are employed at the 5' and 3' primers in the PCR. Preferably, such fragments share at least one biological and/or immunological activity with the corresponding full length molecule.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened in order to identify the desired variant.

TABLE 6

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser, Ala | Ser |
| Gln (Q) | Asn; Glu | Asn |
| Glu (E) | Asp, Gln | Asp |

TABLE 6-continued

| Original Residue | Exemplary Substitutions | Preferred Substitutions |
| --- | --- | --- |
| Gly (G) | Pro; Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Leu |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the LY6 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: Norleucine, Met, Ala, Val, Leu, Ile;
(2) neutral hydrophilic: Cys, Ser, Thr; Asn; Gln
(3) acidic: Asp, Glu;
(4) basic: H is, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., Nucl. Acids Res., 13:4331 (1986); Zoller et al., Nucl. Acids Res., 10:6487 (1987)), cassette mutagenesis (Wells et al., Gene, 34:315 (1985)), restriction selection mutagenesis (Wells et al., Philos. Trans. R. Soc. London SerA, 317:415 (1986)) or other known techniques can be performed on the cloned DNA to produce the anti-LY6 molecule.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244:1081-1085 (1989)). Alanine is also typically preferred because it is the most common amino acid. Further, it is frequently found in both buried and exposed positions (Creighton, The Proteins, (W.H. Freeman & Co., N.Y.); Chothia, J. Mol. Biol., 150:1 (1976)). If alanine substitution does not yield adequate amounts of variant, an isoteric amino acid can be used.

Any cysteine residue not involved in maintaining the proper conformation of the LY6 polypeptide also may be substituted, generally with serine, to improve the oxidative stability of the molecule and prevent aberrant crosslinking. Conversely, cysteine bond(s) may be added to such a molecule to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of LY6 polypeptides are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of a native sequence or an earlier prepared variant.

D. Modifications of Polypeptides

Polypeptides and/or antibodies that have been covalently modified may also be suitable for use within the scope of this invention. One type of covalent modification includes reacting targeted amino acid residues of such antibodies and polypeptides with an organic derivatizing agent that is capable of reacting with selected side chains or the N- or C-terminal residues of such antibodies and polypeptides. Derivatization with bifunctional agents is useful, for instance, for crosslinking the preceding molecules to a water-insoluble support matrix or surface for use in purification. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79-86 (1983)), acetylation of the N-terminal amine, and amidation of any C-terminal carboxyl group.

Another type of covalent modification of the polypeptides or antibodies comprises altering the native glycosylation pattern of the antibody or polypeptide. "Altering the native glycosylation pattern" is intended for purposes herein to mean deleting one or more carbohydrate moieties found in native sequence (either by removing the underlying glycosylation site or by deleting the glycosylation by chemical and/or enzymatic means), and/or adding one or more glycosylation sites that are not present in the respective native sequence. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites may be accomplished by altering the amino acid sequence such that it contains one or more of the above-described tripeptide sequences (for N-linked glycosylation sites). The alteration may also be made by the addition of, or substitution by, one or more serine or threonine residues to the sequence of the original such antibody or polypeptide (for O-linked glycosylation sites). Such antibody or polypeptide sequence may optionally be altered through changes at the DNA level, particularly by mutating the DNA encoding the preceding amino acid sequences at preselected bases such that codons are generated that will translate into the desired amino acids.

Another means of increasing the number of carbohydrate moieties is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification comprises linking to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. The LY6 polypeptide may also be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

Modifications forming chimeric molecules results from fusions of one polypeptide to another, heterologous polypeptide or amino acid sequence are contemplated for use with the present methods.

In one embodiment, such a chimeric molecule comprises a fusion of a polypeptide with a tag polypeptide which provides an epitope to which an anti-tag antibody can selectively bind. The epitope tag is generally placed at the amino- or carboxyl-terminus of such antibody or polypeptide. The presence of such epitope-tagged forms of such antibodies or polypeptides can be detected using an antibody against the tag polypeptide. Also, provision of the epitope tag enables such antibodies or polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-1210 (1988)); the KT3 epitope peptide (Martin et al., Science, 255:192-194 (1992)); an α-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

In an alternative embodiment, the chimeric molecule may comprise a fusion of a polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a preceding antibody or polypeptide in the place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

E. Preparation of Polypeptides

The description below relates primarily to production of polypeptides by culturing cells transformed or transfected with a vector containing nucleic acid such antibodies, polypeptides and oligopeptides. The term "polypeptides" may include antibodies, polypeptides and oligopeptides. It is, of course, contemplated that alternative methods, which are well known in the art, may be employed to prepare such antibodies, polypeptides and oligopeptides. For instance, the appropriate amino acid sequence, or portions thereof, may be produced by direct peptide synthesis using solid-phase techniques [see, e.g., Stewart et al., Solid-Phase Peptide Synthesis, W.H. Freeman Co., San Francisco, Calif. (1969); Merrifield, J. Am. Chem. Soc., 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of such antibodies, polypeptides or oligopeptides may be chemically synthesized separately and combined using chemical or enzymatic methods to produce the desired product.

1. Isolation of DNA Encoding a Polypeptide

DNA encoding a polypeptide may be obtained from a cDNA library prepared from tissue believed to possess such antibody, polypeptide or oligopeptide mRNA and to express it at a detectable level. Accordingly, DNA encoding such polypeptides can be conveniently obtained from a cDNA library prepared from human tissue, a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). Alternatively, PCR methodology may be used. [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for LY6 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: A Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally employed for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789, 199 (Joly et al.), and U.S. Pat. No. 5,840,523 (Simmons et al.)

which describes translation initiation region (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed in suitable cells (e.g., CHO cells).

In addition to prokaryotes, eukaryotic microbes such as filamentous fungi or yeast are suitable cloning or expression hosts for vectors encoding desired polypeptides. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., K lactis (MW98-8C, CBS683, CBS4574; Louvencourt et al., *J. Bacteriol.,* 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula.* A list of specific species that are exemplary of this class of yeasts may be found in C. Anthony, *The Biochemistry of Methylotrophs,* 269 (1982).

Suitable host cells for the expression of glycosylated polypeptide production are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for desired polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding the respective LY6 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The desired polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the DNA encoding the mature sequence that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up nucleic acid encoding the desire protein, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the nucleic acid sequence encoding the desired amino acid sequence, in order to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Delgarno (S.D.) sequence operably linked to the DNA encoding the desired protein sequence.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

DNA Transcription in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the desired polypeptide may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the coding sequence of the preceding amino acid sequences, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the respective antibody, polypeptide or oligopeptide described in this section.

Still other methods, vectors, and host cells suitable for adaptation to the synthesis of the respective antibody, polypeptide or oligopeptide in recombinant vertebrate cell culture are described in Gething et al., *Nature*, 293:620-625 (1981); Mantei et al., *Nature*, 281:40-46 (1979); EP 117,060; and EP 117,058.

4. Culturing the Host Cells

The host cells used to produce the LY6 polypeptide may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN₁ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies suitable for the present method may be prepared against a native sequence polypeptide or oligopeptide, or against exogenous sequence fused to DNA and encoding a specific antibody epitope of such a polypeptide or oligopeptide.

6. Protein Purification

Polypeptides may be recovered from culture medium or from host cell lysates. If membrane-bound, it can be released from the membrane using a suitable detergent solution (e.g. Triton-X 100) or by enzymatic cleavage. Cells employed in expression of the preceding can be disrupted by various physical or chemical means, such as freeze-thaw cycling, sonication, mechanical disruption, or cell lysing agents.

It may be desirable to purify the preceding from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the desired molecules. Various methods of protein purification may be employed and such methods are known in the art and described for example in Deutscher, *Methods in Enzymology*, 182 (1990); Scopes, *Protein Purification: Principles and Practice*, Springer-Verlag, New York (1982). The purification step(s) selected will depend, for example, on the nature of the production process used and the particular antibody, polypeptide or oligopeptide produced for the claimed methods.

When using recombinant techniques, the LY6 polypeptide can be produced intracellularly, in the periplasmic space, or directly secreted into the medium. If such molecules are produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

Purification can occur using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABXJresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSEJ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

H. Pharmaceutical Formulations

Therapeutic formulations ("therapeutic agent") used in accordance with the present invention may be prepared for storage by mixing the therapeutic agent(s) having the desired degree of purity with optional pharmaceutically acceptable carriers, excipients or stabilizers (*Remington: The Science of Practice of Pharmacy*, 20th edition, Gennaro, A. et al., Ed., Philadelphia College of Pharmacy and Science (2000)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN7, PLURONICS7 or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to the preceding therapeutic agent(s), it may be desirable to include in the formulation, an additional antibody, e.g., a second such therapeutic agent, or an antibody to some other target such as a growth factor that affects the growth of the glioma. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy*, supra.

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT7 (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

Methods for the Diagnosis and/or Treatment of Inflammatory Bowel Disease

To determine LY6 expression in gastrointestinal tissue or cells of a mammal, such as a mammal experiencing IBD, various diagnostic assays are available. In one embodiment, LY6 polypeptide overexpression may be analyzed by RT-PCR, in-situ hybridization, microarray analysis, and/or immunohistochemistry (IHC). Fresh, frozen and/or parafin embedded tissue sections from a gastrointestinal biopsy (such as from the colon or, more specifically, the sigmoid colon) from a mammal (such as without limitation a human) may be subjected to the RT-PCR, in situ hybridization, microarray analysis and/or IHC assay.

Alternatively, or additionally, FISH assays such as the INFORM7 (sold by Ventana, Arizona) or PATHVISION7 (Vysis, Illinois) may be carried out on formalin-fixed, paraffin-embedded tissue to determine the extent (if any) of LY6 expression and/or upregulation in a tissue sample or biopsy.

LY6 expression may be evaluated using an in vivo diagnostic assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

Currently, depending on the stage of the IBD, treatment involves one or a combination of the following therapies: surgery to remove affected bowel tissue, administration of therapeutic agents, including without limitation chemotherapy; dietary changes, and lifestyle management. Therapeutic agents or chemotherapeutic agents useful in the treatment of IBD are known in the art and representative therapeutic and chemotherapeutic agents are disclosed herein.

In particular, combination therapy with palictaxel and modified derivatives (see, e.g., EP0600517) is contemplated. The preceding antibody, polypeptide, oligopeptide or organic molecule will be administered with a therapeutically effective dose of the chemotherapeutic agent. In another embodiment, such antibody, polypeptide, oligopeptide or organic molecule is administered in conjunction with chemotherapy to enhance the activity and efficacy of the chemotherapeutic agent, e.g., paclitaxel. The Physicians=Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

Therapeutic agents or chemotherapeutic agents are administered to a human patient, in accord with known methods, such as intravenous administration, e.g., as a bolus or by continuous infusion over a period of time, by intracranial, intracerobrospinal, intra-articular, intrathecal, intravenous, intraarterial, subcutaneous, oral, topical, or inhalation routes.

The present invention provides methods that involve a diagnostic step and a therapeutic treatment step. In one embodiment, the present invention provides methods of detecting inflammatory bowel disease (IBD) in a mammalian subject that include the steps of (1) detecting the level of expression of a nucleic acid or a gene encoding a LY6 polypeptide (a) in a test sample of tissue or cells obtained from the subject, and (b) in a control sample where a higher level of expression of the LY6 nucleic acid or gene in the test sample, as compared to the control sample, indicates the presence of an IBD in the subject from which the test sample was obtained; and (2) administering to the subject an effective amount of an IBD therapeutic agent. In one embodiment, the IBD therapeutic agent is an antagonist of another IBD-associated molecule. The present invention contemplates various IBD-associated molecules that are differentially expressed in IBD. In one embodiment, the IBD-associated molecule is a molecule that is differentially expressed in an IBD. In another embodiment, the IBD-associated molecule is over-expressed in an IBD. In yet another embodiment, the over-expressed IBD-associate molecule is an integrin. In one other embodiment, the IBD-associated molecule is integrin, beta 7 (ITGB2) (see WO 2006/026759, which is incorporated herein by reference in its entirety) The term "IBD therapeutic agent" as used herein refers to an antagonist of an IBD-associated molecule. In one embodiment, the IBD therapeutic agent is an antagonist of an integrin. In another embodiment, the IBD therapeutic agent is an antagonist of ITGB7. In yet another embodiment, the IBD therapeutic agent is an antagonist of the polypeptide shown as SEQ ID NO: 69 encoded by the nucleic acid sequence shown as SEQ ID NO: 68.

J. Articles of Manufacture and Kits

For diagnostic applications, the article of manufacture comprises a container and a label or package insert on or associated with the container indicating a use for detecting and expression of LY6 (such as, without limitation LY6, LYPD1, LYPD3, and/or LYPD5) in a gastrointestinal tissue or cell of a mammal. In one embodiment, the mammal is a human. In one embodiment, the tissue or cell is gastrointestinal tissue or cell. In one embodiment, detecting includes quantitation relative to a control sample. In an embodiment, the container, label or package insert indicates that the gastrointestinal tissue or cells are from colon of a mammal. In an embodiment, the container, label or package insert indicates that increased LY6 expression relative to a control sample is indicative of IBD, including without limitation CD and/or UC, in the mammal. Suitable containers include, for example, bottles, vials, syringes, etc. The containers may be formed from a variety of materials such as glass or plastic. Additionally, the article of manufacture may further comprise a second container comprising a buffer or other reagent (such as detectable label) useful for carrying out the detection. It may further include other materials desirable from a commercial and user standpoint, including other buffers, diluents, filters, and dyes.

For isolation and purification of LY6 polypeptide, the kit can contain the LY6-binding reagent coupled to beads (e.g., sepharose beads). Kits can be provided which contain such molecules for detection and quantitation of LY6 polypeptide in vitro, e.g., in an ELISA or a Western blot. As with the article of manufacture, the kit comprises a container and a label or package insert on or associated with the container. The container holds a composition comprising at least one such LY6 binding antibody, oligopeptide or organic molecule useable with the invention. Additional containers may be included that contain, e.g., diluents and buffers, control antibodies. The label or package insert may provide a description of the composition as well as instructions for the intended in vitro or diagnostic use.

K. Sense and Anti-Sense LY6-Encoding Nucleic Acids

Molecules that would be expected to bind to nucleic acids encoding an LY6 gene include sense and antisense oligonucleotides, which comprise a single-stranded nucleic acid sequence (either RNA or DNA) capable of binding to target LY6 mRNA or DNA sequences. Antisense or sense oligonucleotides, according to the present invention, comprise a fragment of the coding region of the LY6 DNA or its complement. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

The sense and/or antisense oligonucleotides hybridizable to a LY6 gene are useful, for example, for detecting the presence of LY6 DNA or mRNA in a tissue or cell sample gastrointestinal tissue or cells of mammal according to the invention. The sense and/or antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Patents that teach the preparation of such uptake, distribution and/or absorption assisting formulations include, but are not limited to, U.S. Pat. Nos. 5,108, 921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Sense and antisense oligonucleotides include without limitation primers and probes useful in PCR, RT-PCR, hybridization methods, in-situ hybridization, and the like.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

EXAMPLES

The following nonlimiting examples are provided for illustrative purposes and are not intended to limit the scope of the invention. Commercially available reagents referred to in the examples were used according to manufacturer's instructions unless otherwise indicated. The source of those cell lines identified in the following examples, and/or throughout the specification, by ATCC accession numbers is the American Type Culture Collection, Manassas, Va.

Example 1

Materials and Methods

Reagents, cells and mice: IFNγ, TNFα, and IL1β were obtained from Peprotech™ (Rocky Hill, N.J.). IFNα was obtained from Hycult Biotechnology™ (The Netherlands). For crosslinking experiments, anti-KLH control antibody, anti-LY6A (clone E13-161.7 or D7) were obtained from Pharmingen™ (San Diego, Calif.). Anti-LY6C (clone HK1.4) was obtained from Southern Biotech™ (Birmingham, Ala.).

Chronic $CD45RB^{high}$ transfer colitis was induced as described previously in SCID mice on a Balb/c background (Powrie, F. et al., (1994) *Immunity* 1:553-562). IL10−/− mice (Kuhn, R. et al., (1993) *Cell* 75:263-274) on a 129 background, which develop spontaneous colitis, were sacrificed between 11 and 13 weeks of age. Colons were snap frozen in OCT until used in experiments as described. Proximal colon, middle colon, distal colon and rectum were scored using a scale of 0-5 (0=normal bowel, 5=severe disease). Scores were summed to achieve a total colitis severity score for each animal.

The young adult mouse colonocyte (YAMC) cell line (provided by Robert Whitehead, Vanderbilt University Medical Center, Nashville, Tenn.) was derived from the Immortomouse™ a transgenic animal containing a temperature-sensitive T-antigen (tsTag) under the control of an interferon-γ-dependent promoter, as previously described (Whitehead, R. H. et al, (1993) *Proc Natl Acad Sci USA* 90:587-591). YAMC cells proliferate under permissive conditions of 32° C. in the presence of 5 units/ml IFN-γ (Peprotech™, New Jersey), but no longer proliferate upon removal of IFN-γ at 37° C. (non-permissive conditions).

YAMC cells were cultured in RPMI containing 5% FBS, 2 mM L-glutamine, penicillin/streptomycin, 5 U/ml IFNγ and N-2 supplement (Invitrogen™, Carlsbad, Calif.). Cells were cultured under non-permissive conditions for 24 hours prior to experiments, and for the duration of experimentation.

CMT93 cells were obtained from ATCC (ATCC Number® CCL-223™, ATCC, Manassas, Va.) cultured in DMEM containing 10% FBS, 2 mM L-glutamine, and penicillin/streptomycin.

Laser capture microscopy and RNA purification: 10-12 µm sections were applied to LCM membrane slides (Molecular Machines™, Glattbrugg, Switzerland). Slides were subjected to an abbreviated H&E stain (total time of about five minutes) before crypt epithelial cells were histologically identified and dissected using an MMI Cellcut™ microscope (Molecular Machines, Glattbrugg, Switzerland). RNA was purified from the dissected cells using the Arcturus™ Picopure™ RNA purification kit and manufacturer's protocols (Arcturus™, Sunnyvale, Calif.) and quantified using the NanoDrop ND-1000™ Spectrophotometer (NanoDrop Technologies™, Wilmington, Del.).

Microarray hybridization and data analysis: The quantity and quality of input total RNA samples was determined using ND-1000 spectrophotometer (NanoDrop™ Technologies, Montchanin, Del.) and Bioanalyzer 2100™ (Agilent™ Technologies, Palo Alto, Calif.), respectively. The method for preparation of Cy-dye labeled cRNA and array hybridization was provided by Agilent™ Technologies (Palo Alto, Calif.). Briefly, total RNA sample was converted to double-stranded cDNA and then to labeled cRNA using a Low RNA Input Fluorescent Linear Amplification™ Kit (Agilent™, Product# 5184-3523). The labeled cRNA was purified using RNeasy™ mini kit (Qiagen™, San Diego, Calif.) and then quantified using ND-1000™ spectrophotometer (Nanodrop™ Technologies). Cy-dye incorporation was determined by running the labeled cRNA on a Novex™ TBE-Urea gel (Invitrogen™, Carlsbad, Calif.) followed by gel scanning on a Typhoon™ scanner (GE Healthcare™, Piscataway, N.J.). To determine the amount of Cy-dye fluorescent counts, the gel images were analyzed using ImageQuant™ software (GE Healthcare™). Approximately 500,000 counts of Cy-dye labeled cRNA was fragmented and hybridized to the Agilent's whole mouse genome array as described in Agilent's In situ Hybridization kit-plus (Agilent™, Product# 5184-3568). LCM samples were labeled with Cy5 dye and hybridized against Cy3 dye labeled universal mouse reference (Stratagene™, La Jolla, Calif.). Following hybridization, the arrays were washed, dried with acetonitrile and scanned on the Agilent™ DNA microarray scanner. The array image files were analyzed using Agilent™'s Feature Extraction™ software 7.5 and further data analysis was performed using Resolver™ (Merck™, Seattle, Wash.).

Data was analyzed using Rosetta Resolver™ software (Rosetta Biosoftware™, Seattle, Wash.). Briefly, healthy and colitic samples were grouped separately and probes that passed two-tailed anova (p<0.05) were selected. These probes were analyzed further for probes that demonstrated a two fold or greater change in colitic samples versus healthy samples.

Real time quantitative RT-PCR: RT-PCR was performed on extracted RNA using Taqman™ Gold™ RT-PCR kit and reagents (Applied Biosystems™, Foster City, Calif.). All samples were run with gene specific primers using 5'-FAM and 3'-TAMRA labeled internal probes. Analysis was performed compared to housekeeping gene, SPF31, specific primers by the $2^{-\Delta\Delta Ct}$ method as described (Livak, K. J., and T. D. Schmittgen (2001) *Methods* 25:402-408). Primers and probes were either designed using Primer3™ software (Rozen, S., and H. Skaletsky (2000) *Methods Mol Biol* 132:365-386) or obtained commercially (Applied Biosystems™). Primers and probes used for these assays were the following, shown in the 5'-3' direction:

```
LY6A:
                                         (SEQ ID NO:39)
Sense:       CTT ACC CAT CTG CCC TCC TA (SEQ ID NO:40)
Antisense:   CCT CCA TTG GGA ACT GCT AC (SEQ ID NO:41)
Probe:       TCC TGT TGC CAG GAA GAC CTC TGC LY6C:
                                         (SEQ ID NO:42)
Sense:       ACT TCC TGC CCA GCA GTT AC (SEQ ID NO:43)
Antisense:   GGC ACT GAC GGG TCT TTA GT (SEQ ID NO:44)
Probe:       CTG CCG CGC CTC TGA TGG AT
```

Immunofluorescent staining: Frozen tissues were cut into 5 µm sections and stained with biotinylated anti-LY6C (Southern Biotech™, Birmingham, Ala.) or anti-SCA-1 at 2.5 ng/ml (R&D Systems™, Minneapolis, Minn.). Slides were washed and labeled with Alexa Fluor™ 488 conjugated streptavidin, mounted using Prolong Gold™ with DAPI (Invitrogen™, Carlsbad, Calif.) and visualized by confocal microscopy.

Crosslinking LY6 molecules: The ability of crosslinked LY6 polypeptide to effect chemokine production was tested by incubating YAMC cells with plate-bound anti-LY6C or anti-KLH (control) antibodies and measuring the production of chemokines CXCL2, CXCL5, and CCL7. Because lipid raft formation in the cell membrane is required for crosslinking, chemokine production was tested under conditions of normal raft formation (non-cholesterol depletion) and under conditions of cholesterol depletion.

For crosslinking using plate-bound antibody, 100 µl of anti-LY6C or anti-KLH (control) antibody at 5 µg/1 mL concentration was added to a 96 well plate, or 2 mL were added to a 60 mm² dish and allowed to bind to the plate for 15 hours at 4° C. YAMC cells, grown in cholesterol depleting or non-depleting conditions (as provided in Example 5, herein) were incubated with the plate-bound antibodies for 15 hours at 32° C. under cholesterol non-depleting conditions RNA was collected and expression levels of CXCL2, CXCL5, and CCL7 were determined. The assay is further described and results are shown in Example 5, herein.

siRNA inhibition: Individual siRNA directed against murine LY6C were obtained from Dharmacon (Lafayette, Colo.). SiRNA was transfected into YAMC cells using lipofectamine 2000 (Invitrogen) and standard protocols. 72 hours after transfection, cells were collected to determine knockdown efficiency. One siRNA was chosen for crosslinking experiments based on superior knockdown efficiency (95% inhibition by quantitative RT-PCR).

CXCL5 secretion: Supernatants were collected at the indicated time point from stimulated cells and cytokine CXCL5 concentrations were determined by ELISA using a commercially available kit from R&D Systems™ and manufacturer's protocols. The level of detection was 15 pg/ml of CXCL5.

Cholesterol depletion: YAMC cells were cultured for 72 hours in serum free medium at 37° C. in the presence of 4 µM lovastatin and 250 µM mevalonate (Sigma). Cells were plated and maintained in lovastatin and mevalonate throughout the experiment.

Example 2

Gene Expression Patterns of IEC are Altered During Colitis

Studies have indicated that gene expression patterns of IEC are significantly altered in mouse models of colitis, as well as human IBD (Fahlgren, A., et al. (2004) *Clin Exp Immunol* 137:379-385; Brand, S. et al. (2006) *Am J Physiol Gastrointest Liver Physiol* 290:G827-838; Ruiz, P. A. et al. (2005) *J Immunol* 174:2990-2999). In this example, evaluated gene expression patterns in IEC of healthy and colitic mice were examined in order to illuminate novel genes and pathways altered in IBD.

The identification of genes involved in the immunopathology of IBD was sought by evaluating intestinal epithelial cells (IEC) from the CD45RB$^{Hi}$ T cell transfer colitis mouse model as well as the IL10$^{-/-}$ mouse model, both of which result from Th1 dysregulation and share many features of human Crohn's disease (Elson, C. O. et al. (2005) *Immunol Rev* 206:260-276; Bouma, G., and W. Strober (2003) *Nat Rev Immunol* 3:521-533). Laser capture microdissection (LCM) was used to isolate crypt IEC from the colons of healthy and colitic mice in the two models of murine IBD. RNA was extracted from these samples and analyzed by microarray technology as described herein in Example 1. The gene expression profile of IEC of colitic mice in the transfer colitis model identified 1770 probes with >2 fold expression changes compared to control mice, while the IL10 −/− model identified 1140 probes. Overlapping in both models, there were 540 probes with >2 fold changes in expression, corresponding to approximately 400 different genes (data not shown).

Example 3

Pathways and Genes Affected in IEC During Colitis

Of the approximately 400 genes affected in both models, genes involved in antigen presentation, TLR signaling and cell migration were overrepresented (Table 7). In Table 7, numbers represent the mean with standard deviation of the fold change compared to universal standard RNA of colitic mice over healthy mice in either the IL10$^{-/-}$ model of colitis or the CD45RB$^{Hi}$ model of colitis, as indicated. The results indicated that some IEC expressed genes show altered expression patterns in murine models of IBD. Many of these genes, including TLR2, CCL7, CXCL5 and ICAM-1 have been described previously as having increased epithelial expression during colitis (Breider, M. A. et al. (1997) *Vet Pathol* 34:598-604; Uguccioni, M. et al. (1999) *Am J Pathol* 155:331-336; Z'Graggen, K. et al. (1997) *Gastroenterology* 113:808-816; Singh, J. C. et al. (2005) *Am J Physiol Gastrointest Liver Physiol* 288:G514-524), suggesting that the gene expression pattern obtained in these microarrays are an accurate reflection of the biology of IEC in colitis.

TABLE 7

| | Fold change (p value): | |
|---|---|---|
| | IL10 -/- model | CD45RBhi model |
| Cell migration | | |
| CXCL1 | +3.89 (<0.0001) | +2.09 (0.00066) |
| CXCL5 | +21.82 (<0.0001) | +23.34 (<0.0001) |
| CXCL13 | +3.01 (<0.0001) | +2.85 (<0.0001) |

TABLE 7-continued

| | Fold change (p value): | |
|---|---|---|
| | IL10 -/- model | CD45RBhi model |
| CCL6 | −3.47 (<0.0001) | −2.5 (<0.0001) |
| CCL7 | +4.2 (<0.0001) | +5.54 (0.00026) |
| CCL11 | −3.43 (<0.0001) | −3.6 (0.00607) |
| TLR signaling | | |
| TLR2 | +2.15 (<0.0001) | +2.68 (<0.0001) |
| Fos | +3.64 (<0.0001) | +2.03 (<0.0001) |
| LBP | +2.34 (<0.0001) | +2.57 (<0.0001) |
| NFKBIA | +2.37 (<0.0001) | +2.15 (<0.0001) |
| Antigen presentation | | |
| H2-D1 | +2.77 (<0.0001) | +2.23 (<0.0001) |
| HLA-A | +2.83 (<0.0001) | +2.40 (<0.0001) |
| HLA-B | +2.71 (<0.0001) | +2.44 (<0.0001) |
| HLA-E | +2.31 (<0.0001) | +2.34 (<0.0001) |
| ICAM-1 | +2.51 (<0.0001) | +2.587 (<0.0001) |
| PSMB8 | +8.10 (<0.0001) | +3.09 (<0.0001) |
| PSMB9 | +6.61 (<0.0001) | +2.72 (<0.0001) |
| TAP1 | +4.05 (<0.0001) | +4.10 (<0.0001) |
| TAP2 | +2.08 (<0.0001) | +2.18 (<0.0001) |

IEC can function as non-professional APC (Snoeck, V. et al., (2005) *Microbes Infect* 7:997-1004; and Shao, L et al., (2005) *Immunol Rev* 206:160-176), and the gene expression pattern obtained in these microarrays indicate that these functions are enhanced during colitis by upregulation in genes associated with antigen processing, such as LMP7 and TAP1, as well as MHC class I and II genes which would serve to enhance presentation of antigens on the surface of the IEC.

The microarray data supports the concept that colitic IEC attract immune cells to the colon through altered chemokine expression, and may present antigen to infiltrating T cells by upregulating expression of genes associated with antigen presentation.

Example 4

Expression of LY6 Family Members is Strongly Upregulated on the Surface of Colitic IEC Members of the mouse LY6 family of molecules were overrepresented in number as well as degree of upregulation in both the transfer colitis mouse model and the IL10−/− mouse model (FIGS. 23A and 23B). These results were confirmed by real-time quantitative RT-PCR of pooled and amplified IEC RNA in the transfer colitis model (data not shown). Expression of the LY6 family members was unique to the disease state, so no healthy mice expressed appreciable levels of any of these LY6 family members.

While expression of murine LY6 molecules on the surface of cells of hematopoietic origin is known, expression on EC has not been previously described (Bamezai, A. (2004) *Arch Immunol Ther Exp (Warsz)* 52:255-266; and Rock, K. L. et al. (1989) *Immunol Rev* 111:195-224). Expression of murine LY6A and LY6C is detectable on many non-epithelial cells present within the colon, such as T cells and granulocytes. Immunofluorescent staining was performed for both murine LY6A and LY6C on healthy and colitic colons. Levels of murine LY6A and LY6C were minimal or absent on the surface of healthy EC (FIGS. 24A and 24C, respectively). Expression of both murine LY6A and LY6C was detectable on the surface of EC throughout the colons of colitic mice (FIGS. 24B and 24D, respectively). There was no evidence of Statistics: Student's t test was used for comparison between groups (* indicates p<0.05).

polarization of either LY6A or LY6C, and staining was present on both the apical and basolateral membranes, making LY6 molecules potentially accessible to ligands on either surface. These results indicate that the microarray analysis results showing upregulation of murine LY6A and LY6C in murine colitic models was not due to the influx of contaminating immune cells.

Example 4

Transcription of LY6 Genes is Stimulated by Inflammatory Cytokines

LY6 expression on T cells is induced and enhanced by both type I and type II IFNs (Khodadoust, M. M., K. D. Khan, and A. L. Bothwell. 1999. Complex regulation of Ly-6E gene transcription in T cells by IFNs. *J Immunol* 163:811-819). Furthermore, expression of a number of cytokines, is elevated in the colon during active colitis (Niessner, M., and B. A. Volk. 1995. Altered Th1/Th2 cytokine profiles in the intestinal mucosa of patients with inflammatory bowel disease as assessed by quantitative reversed transcribed polymerase chain reaction (RT-PCR). *Clin Exp Immunol* 101:428-435).

To determine if cytokines present during colitis affect transcription of LY6 family members in IEC, we treated YAMC cells, a conditionally immortalized murine IEC line, with IL-1β, IFNα, TNFα, IFNγ or the combination of TNFα and IFNγ and analyzed the transcription of all identified murine LY6 genes by real-time quantitative RT-PCR (Table 8). Briefly, mRNA levels of the indicated LY6 family member in EC was determined by real time quantitative RT-PCR after 15 hours of treatment with the indicated cytokine. Number represents the fold change (determined by $2^{-\Delta\Delta Ct}$ method) versus the untreated, media control. *, P<0.05 versus media control. †, p<0.05 versus IFNγ treated cells. The following LY6 family members were tested, but not detected in samples, regardless of treatment: LY6K, Lypd3, Lypd4, Lypd5, LY6g5b, Ly6g6d, Ly6g6e, Slurp1. The results indicate that EC upregulate LY6 family members in response to inflammatory cytokines.

TABLE 8

|  | Media | IL1β | TNFα | IFNα | IFNγ | IFNγ & TNFα |
|---|---|---|---|---|---|---|
| Ly6A | 1.0 | 1.8* | 2.2* | 2.8* | 33.1* | 65.4*† |
| Ly6C | 1.0 | 1.6* | 1.2* | 2.4* | 65.6* | 63.6* |
| Ly6D | 1.0 | 2.7* | 2.1* | 1.5* | 1.0 | 0.9 |
| Ly6E | 1.0 | 1.4* | 1.5* | 2.1* | 1.9* | 2.9*† |
| Ly6F | 1.0 | 2.5* | 0.6* | 7.1* | 108.2* | 169.7*† |
| Ly6H | 1.0 | 1.0 | 1.1 | 1.2 | 3.7* | 1.4† |
| Lypd1 | 1.0 | 1.5* | 2.1* | 1.3* | 1.3* | 2.9*† |
| Lypd2 | 1.0 | 0.1* | ND | 0.4* | 0.1* | ND |
| Ly6g5c | 1.1 | 1.3 | 0.8 | 0.9 | 1.3 | 1.1 |
| Ly6g6c | 1.0 | 0.7 | 0.7 | 0.6 | 0.6* | 0.3*† |
| Slurp2/Lynx1 | 1.1 | 0.7 | 0.4 | 0.7 | 1.5 | 0.4* |

While many of the LY6 family members were not detected in either the presence or absence of inflammatory cytokines, we detected a strong upregulation in the transcription of murine LY6A, LY6C and LY6F in response to the majority of the cytokines tested, as well as more moderate upregulation of murine LY6E, LY6H and LYPD1 in response to some cytokines tested. However, IFNγ was by far the most potent cytokine in inducing LY6 upregulation. Furthermore, TNFα enhanced the effects of IFNγ on the expression of LY6A, LY6F, LY6E and LYPD1. Similar upregulation of LY6 family members were seen in another murine IEC line, CMT93 (data not shown).

Figure 25:
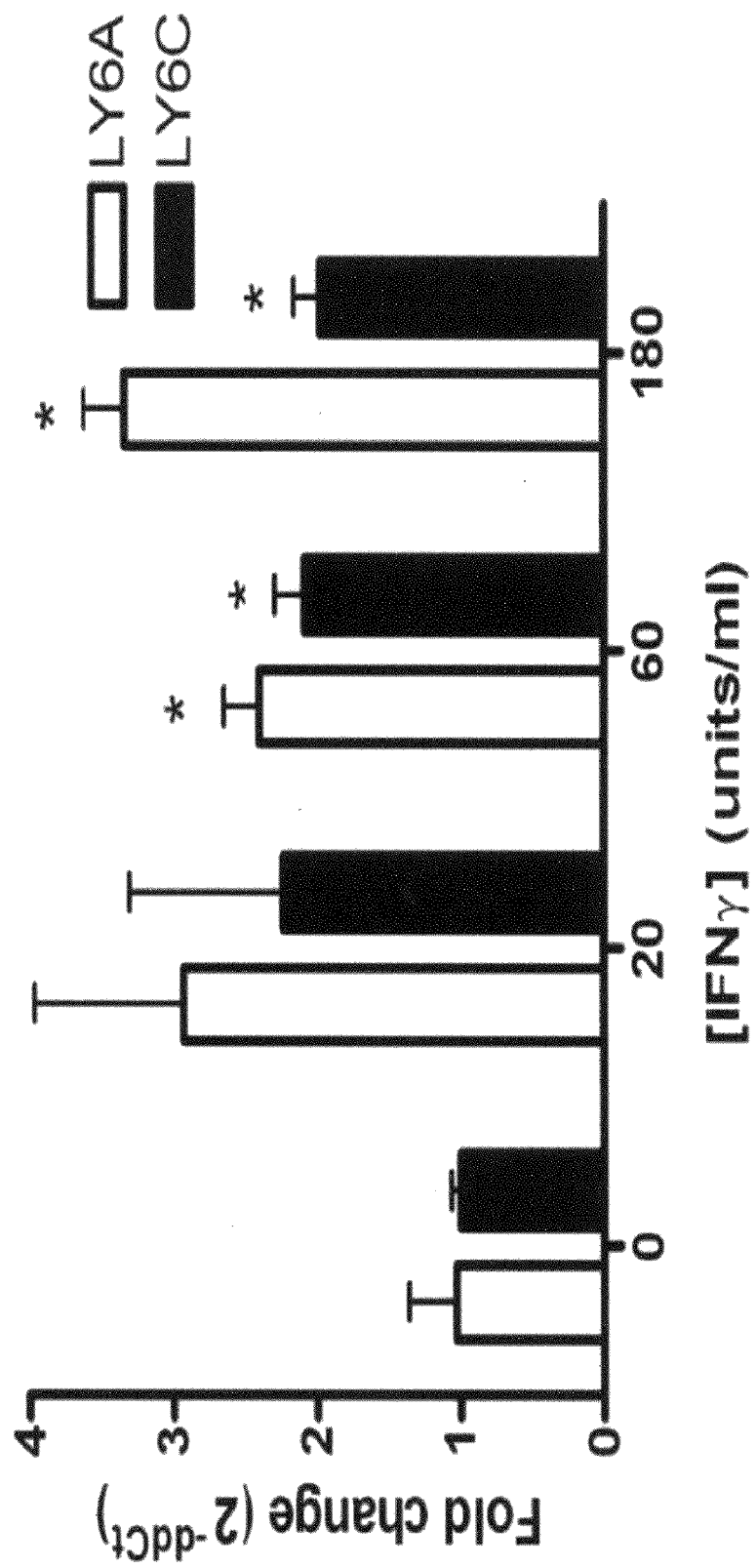
FIGS. 25A-25I show that surface expression of LY6A and LY6C are upregulated in response to inflammatory cytokines, particularly IFNγ. YAMC cells were treated with the indicated cytokine for 15 hours and stained for surface expression of LY6C (FIG. 25A) and LY6A (FIG. 25B). YAMC cells were cultured for 15 hours in the presence of increasing doses of IFNγ and analyzed by flow cytometry for expression of LY6C (FIG. 25C) and LY6A (FIG. 25D). IFNγ stimulated YAMC cells were collected at various time points, as indicated, and analyzed by flow cytometry for expression of LY6C (FIG. 25E) and LY6A (FIG. 25F). IL-22 upregulated expression of both LY6C (FIG. 25G) and LY6A (FIG. 25H). Levels of both LY6A and LY6C were upregulated in the murine IEC line, CMT93 in response to treatment with IFNγ (FIG. 25I).

To examine the surface expression of LY6 family members in response to cytokines, YAMC cells were exposed to the above cytokines and analyzed by flow cytometry for expression of murine LY6A and LY6C, for which commercial antibodies are available, as described herein in Example 1. High levels of murine LY6A was expressed on YAMC cells even in the absence of added cytokines (FIG. 25B, media). Expression of murine LY6C (FIG. 25A, media) was considerably lower than expression of LY6A.

IL-1β and TNFα induced slight increases in the surface expression of both murine LY6A and LY6C, in agreement with the RNA expression (FIGS. 25A and 25B). A more moderate increase in expression was noted when IFNα was added to the cells, while IFNγ induced dramatic increases in surface expression of both LY6A and LY6C (FIGS. 25A and 25B). Surface protein expression closely mirrored RNA expression. Th2 cytokines, such as IL4, IL10 or IL13 had no effect on surface expression of either LY6A or LY6C (data not shown).

Induction of both LY6A (FIG. 25D) and LY6C (FIG. 25C) by IFNγ was dose dependent. Doses as low as 6.25 units/ml of IFNγ resulted in detectable increases in both LY6 molecules by flow cytometry. Furthermore, the increase in both LY6A (FIG. 25F) and LY6C (FIG. 25E) surface expression became evident between 2 and 4 hours after IFNγ treatment, and steadily increased for at least 24 hours after IFNγ treatment. This data indicates that relatively low concentrations of IFNγ are sufficient to increase surface expression of LY6 molecules within hours.

There is evidence that IL-22, which is secreted primarily from activated T cells, functions through the IL-22R complex, present on IEC to promote cytokine production and an inflammatory phenotype (Brand, S. F. et al. Am J Physiol Gastrointest Liver Physiol 290:G827-838 (2006)). Furthermore, IL-22 is involved in the immunopathogenesis of Crohn's Disease. To examine whether IL-22 affects LY6 molecule expression on murine IEC, YAMC cells were cultured in the presence of IL-22 and analyzed for expression of LY6C (FIG. 25G) and LY6A ((FIG. 25H). Both LY6 molecules were substantially increased in the presence of IL-22 at comparable levels to the induction seen after treatment with IFNγ.

To ensure that the upregulation of LY6 molecules was not specific to the YAMC cell line, RNA levels of murine LY6A and LY6C in the murine colonic epithelial tumor cell line CMT93 was examined. Levels of both murine LY6A and murine LY6C were upregulated upon treatment with IFNγ (FIG. 25I). Though the levels of upregulation of LY6 molecules were more modest in CMT93 cells, flow cytometry analysis indicated that levels were quite high even in untreated cells (data not shown), which is likely a result of the tumor phenotype of CMT93 cells.

This data supports the data obtained by real time quantitative RT-PCR in confirming that EC upregulate LY6 family members in response to inflammatory cytokines.

Example 5

LY6 Stimulation of IEC is Associated with Lipid Raft Formation

As GPI-anchored proteins, LY6 family members do not possess a unique intracellular domain associated with traditional outside-in signaling. Rather, they are present within lipid raft microdomains (Bohuslav, J. et al. Eur J Immunol 23:825-831 (1993)). However, it has been suggested that cross-linking of LY6 family members on the surface of cells results in redistribution of other cell surface molecules as well as reorganization of lipid raft structures, suggesting a mechanism by which LY6 molecules can affect signal transduction and downstream cellular functions (Simons, K. et al., Nat Rev Mol Cell Biol 1:31-39 (2000)).

Few ligands for LY6 proteins have been identified to date, and no ligand for LY6A or LY6C is currently known (Paret, C. et al., (2005) Int J Cancer 115:724-733; Apostolopoulos, J. et al., (2000) Immunity 12:223-232; and Classon, B. J. (2001) Trends Immunol. 22:126-127). Cholesterol is required to maintain lipid raft integrity. (Simons, K., et al. J Clin Invest 110:597-603 (2002)), and depletion of cholesterol is often used to inhibit lipid raft biosynthesis in vitro (von Tresckow, B. et al. J Immunol 172:4324-4331 (2004)).

To analyze whether lipid raft reorganization occurs in EC in response to LY6 crosslinking, YAMC cells were grown in cholesterol-depleting conditions (conditions under which lipid rafts are depleted from cells) and cholesterol non-depleting conditions (conditions permissive for lipid raft formation). For cholesterol depleting conditions, YAMC cells were grown in the absence of serum and in the presence of 4 µM lovastatin and 0.25 mM mevalonate (Sigma Chemical Co., St. Louis, Mo.) for 72 hours at 37° C. The same growth conditions were use for YAMC cells under cholesterol non-depleting conditions, except that no lovastatin or mevalonate were added to the growth medium. Cells were then lifted and LY6C was crosslinked as described above in Example 1. RNA was collected and expression levels of CXCL2, CXCL5, and CCL7 were determined.

The results of these studies indicated that lipid raft depletion results in an inhibition of LY6C-mediated chemokine production. FIGS. 26A-26C show that cholesterol depleted (dark bars) YAMC cells produced less chemokine than cells that were not depleted of cholesterol (open bars). Cholesterol depletion affected chemokine production in control anti-KLH stimulated groups, irrespective of LY6C stimulation, however the response was minimal and not in a consistent direction. To examine whether cholesterol depletion globally affected cell viability, we measured cell death, by 7AAD exclusion, and determined that cholesterol depletion did not significantly affect the viability of the YAMC cells (92% viability versus 86% in the cholesterol depleted cells, data not shown). Surface expression of both LY6A (FIG. 26D) and LY6C (FIG. 26E) were both significantly lower in cholesterol depleted YAMC cells, suggesting that plasma membrane cholesterol levels and lipid raft integrity affect the levels of LY6 expression on the surface of cells. This data suggests that lipid raft integrity, influenced by cholesterol biosynthesis, allows for the expression of LY6 molecules on the surface, and is potentially involved in the LY6C mediated induction of chemokines. Thus, the enhancement of chemokine production mediated by interaction of LY6C polypeptides in the cell membrane requires the presence of lipid rafts on the cell surface.

Example 6

Crosslinking LY6C Results in Increased Surface Expression of LY6 Molecules

It has been reported that crosslinking LY6C on the surface of T cells results in shedding of LY6C (Jaakkola, I. et al. (2003) J Immunol 170:1283-1290). However, unlike T cells, when murine LY6C was crosslinked on the surface of IEC, no shedding of either LY6A or LY6C occurred (FIGS. 27A and 27B, respectively). To the contrary, in the absence of IFNγ, surface expression levels of both LY6A and LY6C were increased on EC with crosslinked LY6C, but not LY6A. When IEC were preincubated with IFNγ, much of this effect was abolished (FIG. 27C), however a slight upregulation of LY6A was still detected (FIG. 27D).

These data indicate a positive feedback loop whereby stimulation through LY6C on IEC results in increased surface expression of LY6 molecules.

Example 7

Stimulation of LY6A Results in Increased Secretion of Chemokines

Functions for LY6 molecules have not been fully elucidated. To examine the role of LY6 molecules in the immunopathology of colitis, stimulation of LY6 molecules was studied for affects on the transcription and secretion of chemokines from IEC.

To analyze production of chemokines from EC in response to crosslinking of murine LY6 molecules, YAMC cells, either pretreated with IFNγ or untreated, were cultured on plates coated with either anti-KLH control antibody, anti-LY6A or anti-LY6C. Twenty four hours later, mRNA from these cells was obtained and analyzed by quantitative RT-PCR for expression of CCL2, CCL4, CCL5, CCL7, CCL8, CCL25, CXCL1, CXCL2, CXCL5, CXCL10, CXCL12 and CX3CL1, which are chemokines that have been implicated in colitis (Table 9) (Papadakis, K. A. (2004) Curr Allergy Asthma Rep 4:83-89; Banks, C. et al., (2003) J Pathol 199: 28-35; and Papadakis, K. A., and S. R. Targan (2000) Inflamm Bowel Dis 6:303-313). The assay was performed under non-permissive growth conditions (37° C. in the absence of IFNγ) to rule out the possibility of increased proliferation of IEC in response to IFNγ stimulation.

TABLE 9

| | Pre-treatment | | | | | |
|---|---|---|---|---|---|---|
| | Media | | | IFN | | |
| | Crosslink | | | | | |
| | Anti-KLH | Anti-LY6A | Anti-LY6C | Anti-KLH | Anti-LY6A | Anti-LY6C |
| CCL2 | 1.01 | −1.38 | 8.81 | 3.53 | 2.83 | 16.12 |
| | (0.14) | (0.13) | (0.72) | (0.21) | (0.21) | (0.56) |
| CCL4 | 1.31 | 1.83 | 3.15 | 5.35 | 3.65 | 16.12 |
| | (1.14) | (0.49) | (1.17) | (0.48) | (0.69) | (0.56) |
| CCL5 | 1.00 | 1.09 | 3.31 | 2.73 | 2.76 | 10.13 |
| | (0.10) | (0.02) | (0.15) | (0.13) | (0.23) | (0.27) |
| CCL7 | 1.00 | 1.06 | 3.37 | 2.82 | 1.39 | 5.81 |
| | (0.11) | (0.08) | (0.15) | (0.44) | (0.33) | (0.51) |
| CCL8 | 1.03 | 2.05 | 12.78 | 74.22 | 74.44 | 110.44 |
| | (0.30) | (0.37) | (3.14) | (8.94) | (9.81) | (3.36) |
| CCL25 | 1.01 | 1.06 | 1.16 | 1.38 | 1.32 | 1.46 |
| | (0.16) | (0.11) | (0.00) | (0.36) | (0.15) | (0.19) |
| CXCL1 | 1.00 | −3.17 | 11.58 | −1.13 | −1.64 | 13.36 |
| | (0.07) | (0.11) | (0.12) | (0.10) | (0.17) | (0.35) |
| CXCL2 | 1.33 | ND | 21.81 | 14.30 | 10.95 | 113.20 |
| | (1.10) | | (3.13) | (3.30) | (3.05) | (16.23) |
| CXCL5 | 1.08 | ND | 118.45 | 1.70 | ND | 150.99 |
| | (0.53) | | (65.14) | (1.15) | | (55.50) |
| CXCL10 | 1.00 | 1.02 | 5.11 | 5.68 | 5.22 | 12.22 |
| | (0.05) | (0.06) | (0.19) | (0.31) | (0.22) | (0.51) |
| CXCL12 | 1.01 | 1.12 | −1.99 | −1.11 | −1.23 | −3.02 |
| | (0.14) | (0.05) | (0.14) | (0.05) | (0.21) | (0.06) |
| CX3CL1 | 1.00 | −1.18 | 1.92 | 2.21 | 1.87 | 3.22 |
| | (0.08) | (0.15) | (0.07) | (0.11) | (0.16) | (0.42) |

Cells pretreated with IFNγ showed upregulation of many of these chemokine genes (see Media, Anti-KLH group versus IFNγ, Anti-KLH group of Table 9). However, with the exception of an upregulation of CCL8 and a downregulation of CXCL1, anti-LY6A stimulated YAMC cells showed similar gene expression patterns as anti-KLH stimulated YAMC cells. However, YAMC cells stimulated with anti-LY6C showed increased expression of all chemokines analyzed except for CCL25, which remained essentially unchanged, and CXCL12, which was downregulated in response to LY6C stimulation. While the increased gene expression of chemokines induced by LY6C crosslinking was not dependent upon IFNγ, cells pretreated with IFNγ showed increased expression of chemokines versus cells that had not been pretreated with IFNγ.

To analyze the kinetics of chemokine induction induced by murine LY6C stimulation, 96 well plates were coated with anti-KLH antibody or either anti-LY6A or anti-LY6C monoclonal antibodies. YAMC cells, either pretreated or not with IFNγ, were added for 24, 48 or 72 hours. At the indicated time point RNA was collected for quantitative RT-PCR analysis and supernatants were collected for ELISA.

Figure 28A:
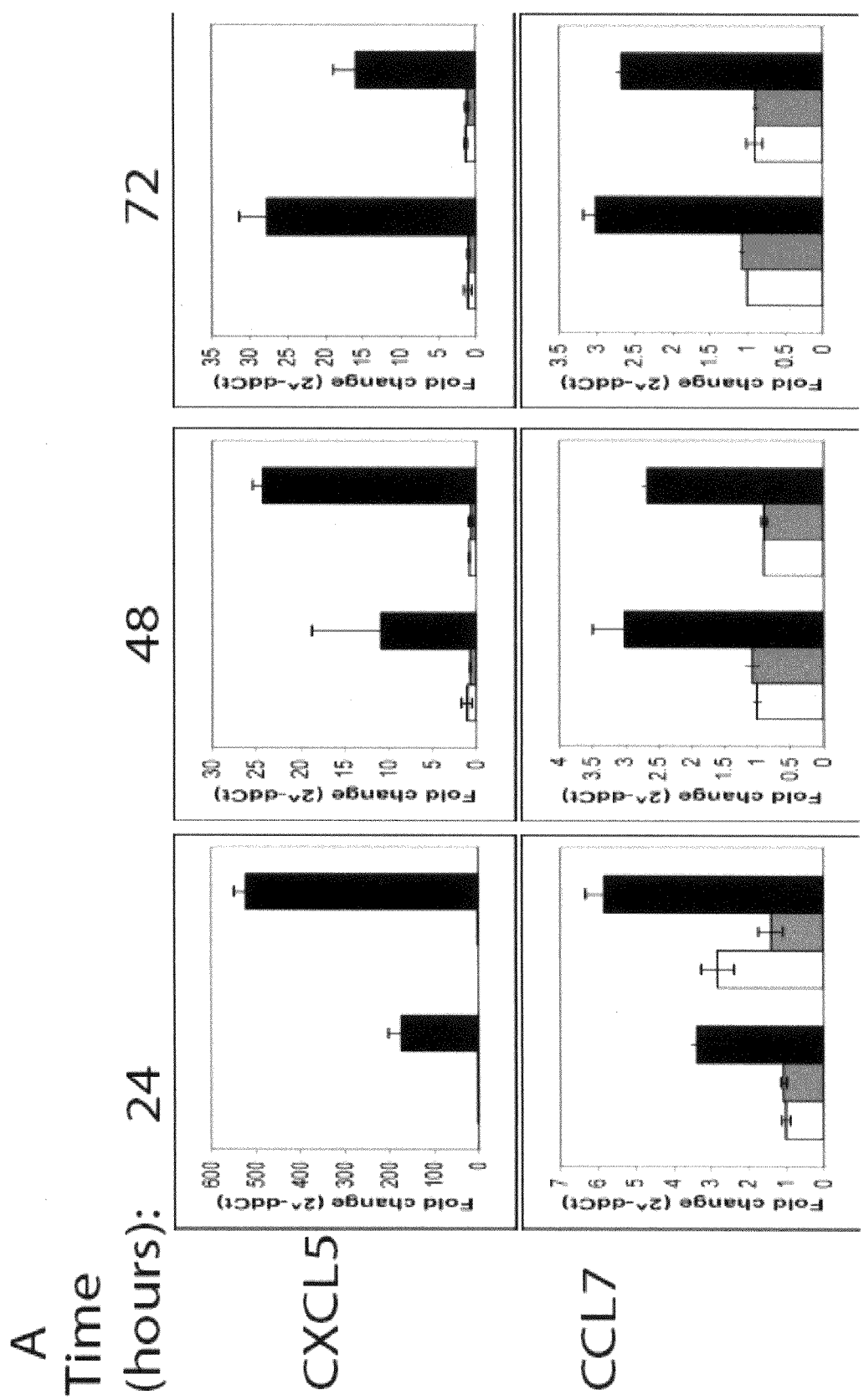
FIGS. 28A-28C show that crosslinking LY6C, but not LY6A, induces secretion of chemokines.

Within 24 hours, a spike in transcription of both CXCL5 and CCL7 was detected on cells with crosslinked LY6C, but not LY6A (FIG. 28A). Increased expression of CXCL5 and CCL7 diminished over time but was still detectable after 72 hours in culture. Though IFNγ was not required to enhance chemokine transcription, IFNγ acted synergistically with LY6C stimulation in inducing transcription of both CXCL5 and CCL7 at early time points.

Figure 28B:
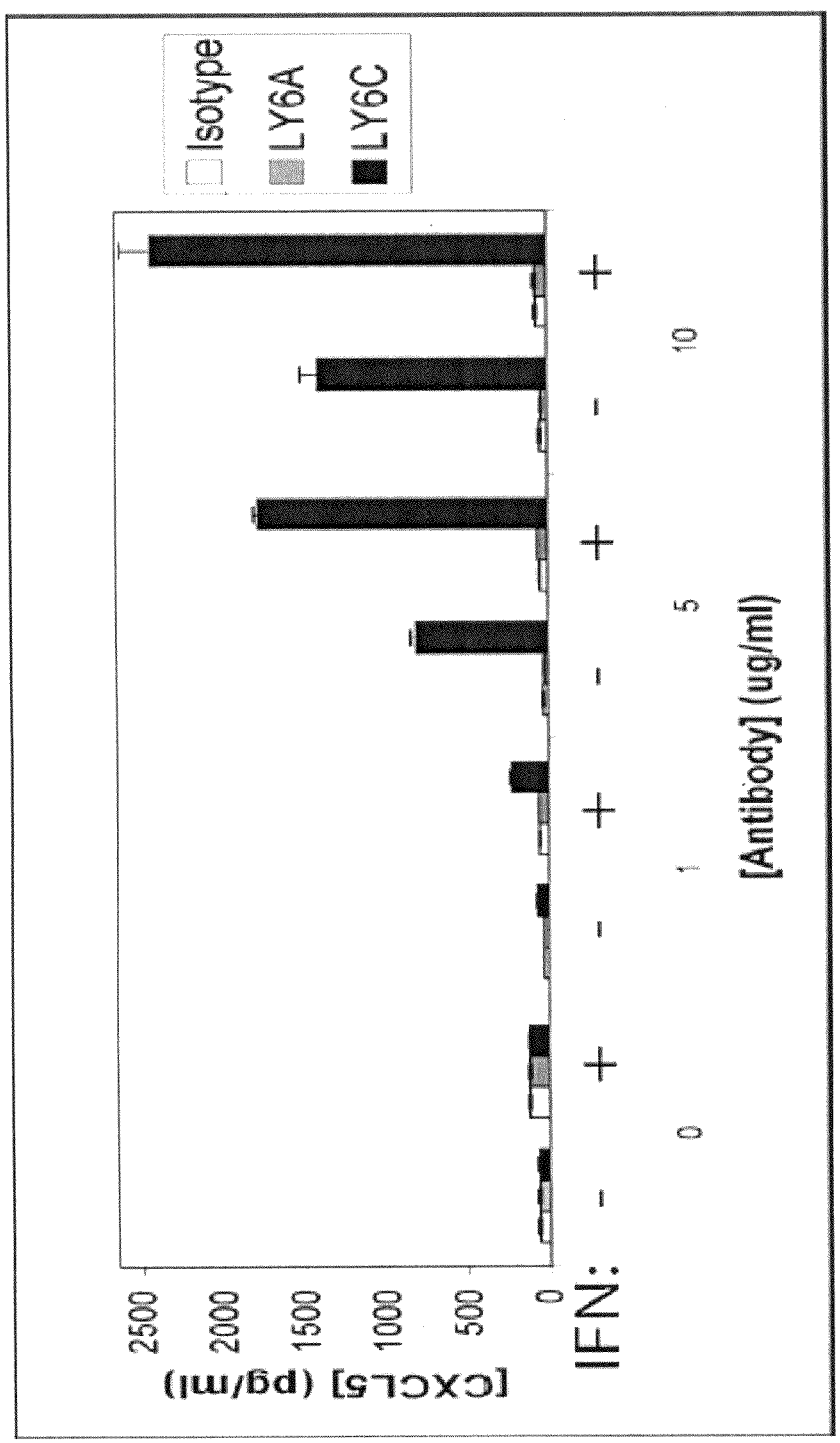

In parallel with the gene expression, supernatants of LY6C, but not LY6A, crosslinked cells contained significantly higher concentrations of CXCL5 at 48 hours (FIG. 28B). The effect was dose dependent, and detectable with as little as 1 µg/ml of coated anti-LY6C. Like transcription, secretion of CXCL5 was enhanced when cells were pretreated with IFNγ, but IFNγ was not required for the effect. Increased secretion of CXCL5 was noted at both the 24 and 72 hour time points as well.

Figure 28C:
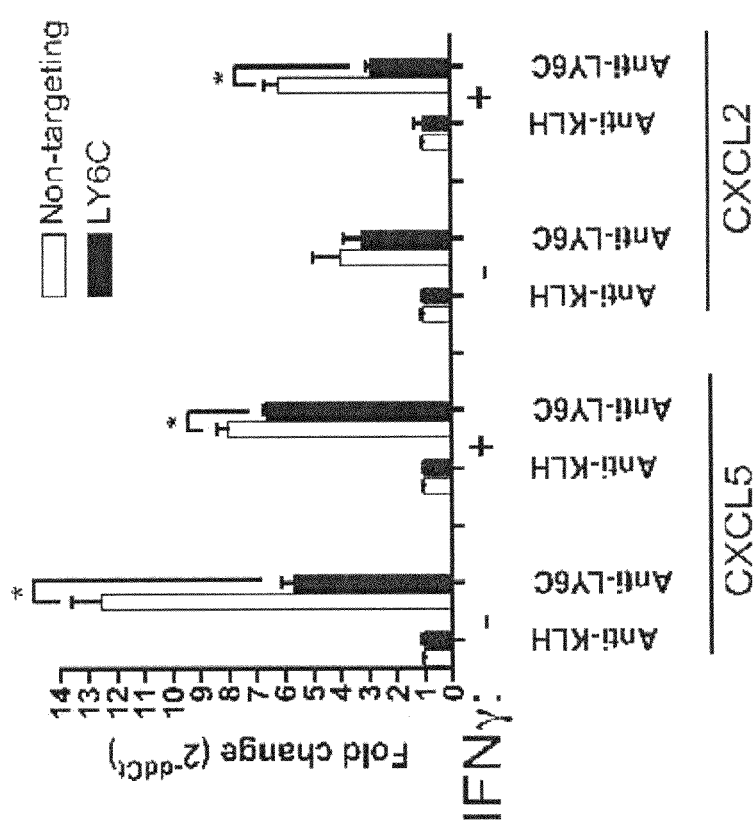

To ensure that LY6C was involved in the observed upregulation of chemokines, we used siRNA to knockdown LY6C. LY6C transcript was inhibited by 95% in the absence of IFNγ and about 90% in the presence of IFNγ by real time quantitative RT-PCR which corresponded to significantly lower levels of LY6C on the surface of the YAMC cells (data not shown). Cells with decreased levels of LY6C on the surface showed a diminished response to LY6C crosslinking with regard to transcription of chemokines (FIG. 28C). Secretion of CXCL5 was markedly inhibited by knocking down LY6C as well (data not shown).

These results indicate that crosslinking of LY6C, but not LY6A, on the surface of IEC results in increased secretion of chemokines.

Example 8

IEC In Vivo Show a Similar Chemokine Gene Expression to LY6C Stimulated Cells

The above data establishes a model whereby EC stimulated through murine LY6C significantly upregulate expression of chemokine genes.

Analyzing the microarray data from laser capture microdissected IEC in murine models of colitis, the expression of the same 12 chemokine genes in healthy and colitic mice in the two murine models of colitis was examined to determine if the chemokines stimulated by LY6C crosslinking in vitro correlate with the chemokines secreted by EC in vivo (FIGS. 29A and 29B). Though the expression pattern is not identical to the upregulation of chemokines resulting from LY6C stimulation, expression of CXCL5, which was the most highly upregulated chemokine gene in in vitro studies, was also the highest upregulated chemokine in murine models of colitis. We saw significant upregulation in expression of CXCL1, CXCL10, CCL5 and CCL7 in both models of colitis. In addition, we saw upregulation of CCL4 and CCL8 in the transfer colitis model or the IL10 −/− model, respectively.

Interestingly, the only chemokine that was down-regulated as a result of murine LY6C stimulation in vitro, CXCL12 was also the only one of these chemokines downregulated in vivo.

Example 9

Expression of Human LY6 Genes in Colon Cells

Expression of human LY6H, LYPD1, LYPD3, and LYPD5 in a human colon cell line, Colo 205 cells (a cell line derived from human colon carcinoma, ATCC™ accession number CCL-222™), was examined. Human Colo 205 cells were treated with the cytokines IFN-r, LPS, TNFα, IFN-r+TNFα, IFN-r+LPS, or LPS+TNFα (all at 100 ng/ml, except LPS at 1 ug/ml) for 18 hours (LYPD3) or 24 hours (LY6H or LYPD5). RNA was collect and purified and expression of the indicated LY6 family member was determined by quantitative RT-PCR using reagents from Applied Biosystems™ according to manufacturer's instructions. Primers and probes used for RT-PCR analysis were the following:

```
LYPD1:
                                         (SEQ ID NO:59)
Sense:        CAT GAT CCT CCG AAT CTG GT (SEQ ID NO:60)
Antisense:    AGC ACA GAA CAG AGG GGC TA (SEQ ID NO:61)
Probe:        ATA CGG CCA ATG TCA CAA CA LYPD3:
                                         (SEQ ID NO:62)
Sense:        ACT TCC TGT TCC CAC CAC TG (SEQ ID NO:63)
Antisense:    AGA GGA CAA GCG GAG AGA CA (SEQ ID NO:64)
Probe:        TTC TGG CAG GGG TGT TCT AG LY6H:
                                         (SEQ ID NO:65)
Sense:        AGC AGC AGC AGG AAG GAT (SEQ ID NO:66)
Antisense:    AAA AGT GCC GCT TAA CGA AG (SEQ ID NO:67)
Probe:        CAA GAT GTG TGC TTC CTC CTG CGA
```

LYPD5 primers and probes were purchased from Applied Biosysems™ (catalog number HS00289062-m1).

Figure 30A:
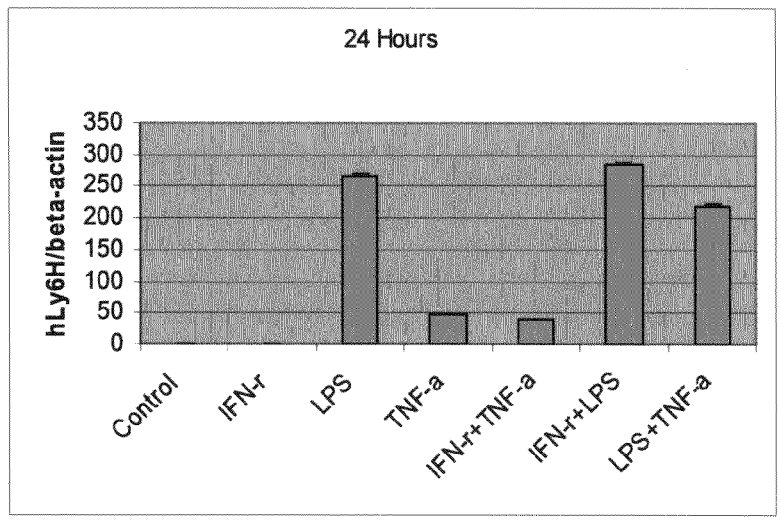
FIGS. 30A-30C show that expression of human LY6 family genes is upregulated in colon cells treated with cytokines. Human Colo-205 cells were treated with the indicated cytokines, or combinations of cytokines, for 18 or 24 hours. The fold increase in expression of human LY6H (FIG. 30A), human LYPD3 (FIG. 30B), and human LYPD5 (FIG. 30C) are shown relative to human β-actin control.
Figure 30B:
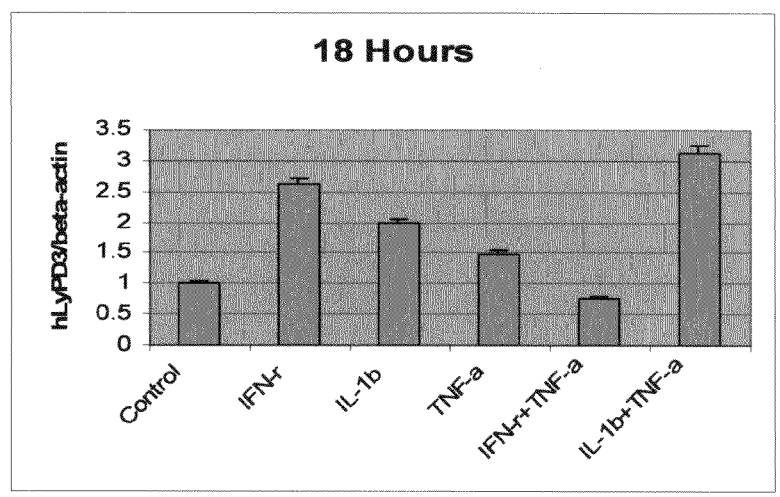
Figure 30C:
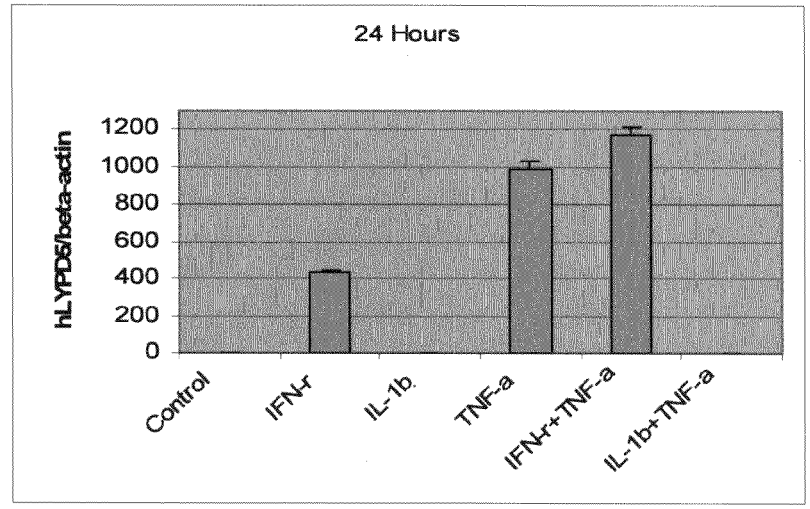

The results plotted in FIGS. 30A-30C indicate fold increases in expression of these human LY6 genes relative to human B-actin control. Significant increases in expression of human LY6H, LYPD3, and LYPD5 were observed following treatment with the indicated cytokines.

Example 10

Expression of Human LY6 Genes in Colon Biopsy Tissue

Figure 31A:
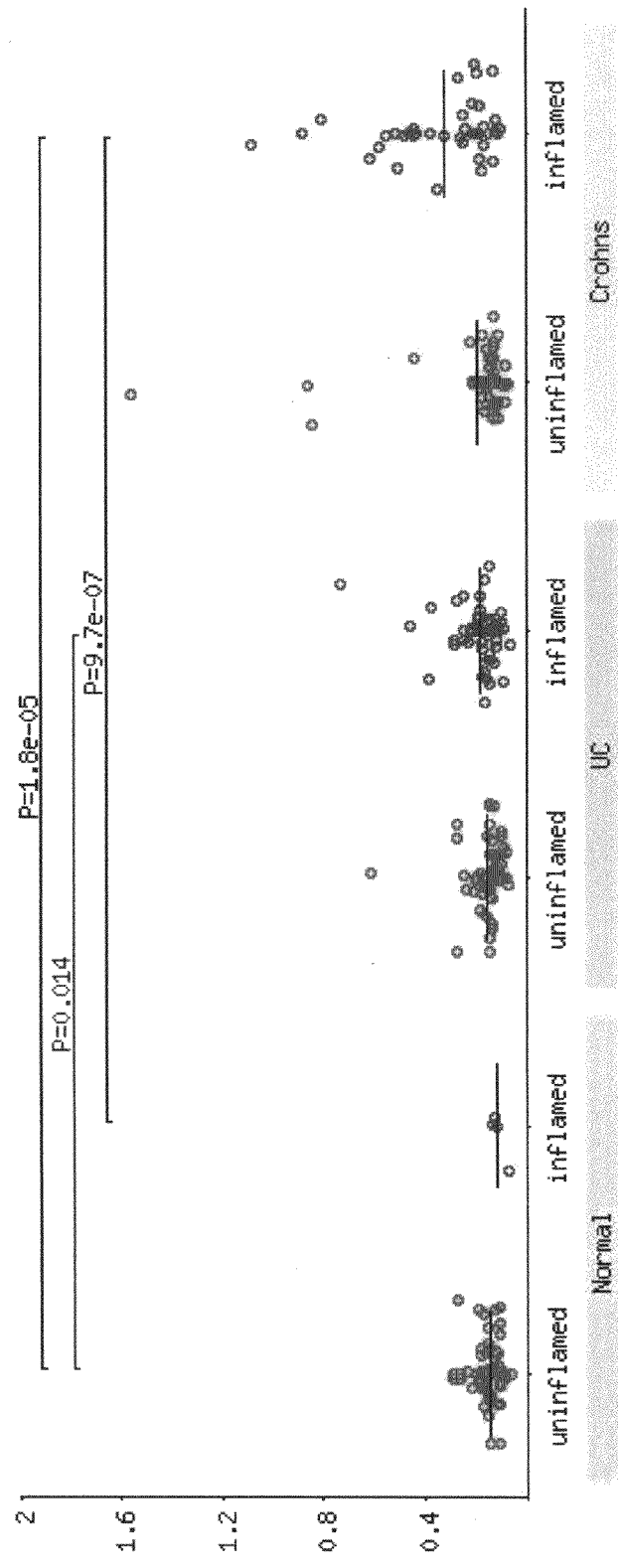
FIGS. 31A-31B show that patients with Crohn's Disease have elevated levels of LYPD1 (FIG. 31A) and LYPD5 (FIG. 31B) in the colon. Tissue samples from human IBD patients were obtained and LYPD1 and LYPD5 gene expression was determined. Statistically significant increases in expression of LYPD1 and LYPD5 were observed in inflamed tissue of CD patients. A statistically significant increase in expression of LYPD5 was also observed in inflamed tissue of UC patients. Y-axis values reflect gene expression relative to a universal RNA standard.
Figure 31B:
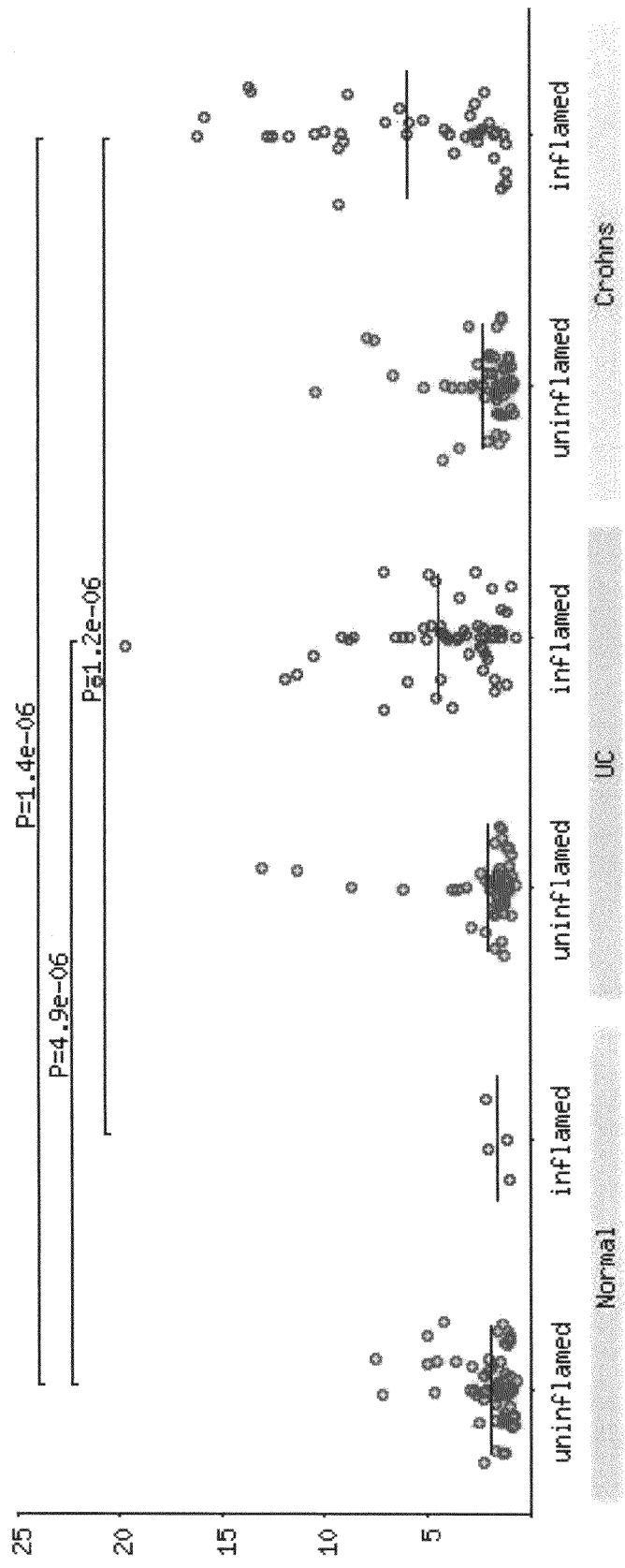

To further investigate the source of the increased LYPD1 and LYPD5 expression in the colon of patients with CD and UC, was undertaken in a cohort of biopsies of patients with UC, CD and controls. Microarray analysis for LYPD1 expression using RNA extracted from colon biopsies showed statistically increased expression in inflamed colon tissue of CD patients (FIG. 31A). In the UC and CD biopsies taken from the colon, statistically increased LYPD5 expression was observed in inflamed UC and CD patients (FIG. 31B). This was not observed in the non-inflamed control biopsies.

Expression of human LY6H in terminal ileum biopsies of inflamed IBD tissue was analyzed relative to control (non-IBD) terminal ileum biopsies using RT-PCR (Taqman™) analysis. Human LY6H expression was at least 1.5 fold greater in inflamed IBD biopsies relative to control.

Human LYPD3 expression in inflamed UC colon biopsies was upregulated and less than 2 fold greater in inflamed IBD biopsies relative to control.

The results of these examples demonstrated expression of LY6 molecules on the surface of EC, and further indicated that expression is unique to EC in the context of inflammation. Furthermore, surface expression levels of LY6A and LY6C were high on IEC of colitic mice, and nearly universal throughout the colon. As molecules both specific to the diseased state, and ubiquitously expressed during disease, detection of human LY6 gene or polypeptide expression, particularly human LY6H, LYPD1, LYPD3, and LYPD5, is a useful method for detecting IBD, including UC and/or CD in humans. Additionally, the method of detecting human LY6 expression is useful for diagnosing IBD, UC and/or CD in a human and monitoring response to IBD therapeutic agents.

In the Examples disclosed herein, the functional significance of LY6 expression in IEC was demonstrated. YAMC cells were strongly positive for LY6A, and expressed lower levels of LY6C. However, upon stimulation with a number of cytokines present within the colon during colitis, including IL-1β, TNFα, IFNα, and in particular IL-22 and IFNγ, expression levels of both LY6 molecules were greatly enhanced. YAMC cells pretreated with IFNγ to upregulate expression of LY6 molecules, were a useful in vitro model to analyze functional significance for LY6 expression.

The conditionally immortalized nature of the YAMC cells comes from MHC II promoter driven expression of the SV40 large T antigen; low levels (2.5-5 U/ml) of IFNγ are used to drive proliferation of these cells (Whitehead, R. H. et al. (1993) *Proc Natl Acad Sci USA* 90:587-591; Whitehead, R. H., and J. L. Joseph. (1994) *Epithelial Cell Biol* 3:119-125). YAMC cells are often used as an in vitro model for cytokine treatments of murine IEC (Mei, J. M. et al. (2000) *Faseb J* 14:1188-1201; Yan, F., and D. B. Polk (2002) *J Biol Chem* 277:50959-50965). The SV40 large T antigen that these cells contained is temperature sensitive, and non-functional at 37° C. All experiments performed herein involved IFNγ treatment under these non-permissive conditions. In addition, YAMC cells were serum starved (and IFNγ starved) at 37° C. for 24 hours prior to experiments. Under such conditions, effects indicating residual T antigen expression, such as proliferation of cells, were not observed. As a result, effects of IFNγ treatment were due to inherent effects of IFNγ rather than effects stemming from driving expression of the T antigen. Furthermore, the upregulation of LY6 family members was detected in a second murine cell line, CMT93, confirming that this is effect is broadly applicable to IEC.

Furthermore, IFNγ was not unique among cytokines for inducing LY6 molecules as modest upregulation of LY6 expression was noted after treatment with TNFα, IL-1β and, IL-22. The upregulation of LY6 molecules on IEC in response to IL-22 is interesting in light of recent data demonstrating a potential role for IL-22 in Crohn's Disease (Wolk, K., et al. *J Immunol* 178:5973-5981 (2007)). Though homology between mouse and human LY6 molecules are often complicated, there is evidence to suggest that the upregulation of LY6 molecules is not restricted to mice. Previous studies in rats have suggested upregulation of LY6 molecules in the small intestine in colitis models, and it has been suggested that such expression is involved in inflammation, cell/cell interactions as well as signaling within the rat IEC (Baksheev, L. et al. J Gastroenterol 41:1041-1052 (2006)).

The data described above indicates that there is a possibility that lipid raft integrity is involved in LY6C mediated signal transduction in EC. This implies that disruption of lipid rafts might serve to attenuate downstream affects of LY6C stimulation both by downregulating LY6C expression and disrupting the structural components of LY6C signaling. Recently, it has been determined that cholesterol depletion of EC with statins inhibits proinflammatory gene expression through NF-κB modulation (Lee, J. et al., Int Immunopharmacol 7:241-248 (2007)). Furthermore, statins have been effective therapeutics in murine models of colitis (Naito, Y., et al. *Int J Mol Med* 17:997-1004 (2006)). The mechanism linking lipid raft motility and NF-κB blockade remain undetermined, but our data suggests that activation through LY6C could be one hypothesis to explain the mechanism of action.

In this study, we identify LY6 molecules as a potential upstream switch in the expression of chemokine genes. Crosslinking of the LY6C receptor with monoclonal antibodies resulted in dramatic upregulation of nearly all chemokines analyzed, including CXCL5. We further confirmed that CXCL5 secretion is greatly enhanced in LY6C crosslinked IEC. It is interesting that even though both LY6A and LY6C are anchored to the cell surface by a GPI moiety, and despite higher levels of expression of LY6A than LY6C on the surface of EC, that the downstream effects on chemokine secretion are seen with LY6C crosslinking and not consistently with LY6A crosslinking.

Example 11

Identification of a Ligand for LYPD5

In this study, a search for ligands of LYPD5 was performed through techniques well known to those of ordinary skill in the art, namely by expression cloning of about 14,000 human genes under CMV promoter into COS cells. Pools of 100 genes were transfected into the COS cells grown in 140 wells on 12 well plates. Following transfection, the cells were stained with LYPD5-Fc protein (see FIG. 32). Wells with positive staining were identified and individual clones were transfected into COS cells. A single well expressing a single protein, GLG-1 (ESL-1) was identified as a ligand for LYPD5. GLG-1 is characterized by a lengthy extracellular domain (ECD), a transmembrane domain and a cytoplasmic domain. A series of co-immunoprecipitation studies were conducted using techniques known to those of ordinary skill in the art to assess the ability of various regions of the GLG-1 ECD to bind LYPD5. It was found that variants or fragments of the GLG-1 ECD (see FIGS. 33-35) were able to serve as a ligand for LYPD5. FIG. 33B shows the results of co-immunoprecipitation studies using Fragments 1, 2, 3, or 4 as depicted in FIG. 33A and demonstrates that any one of the fragments is sufficient for LYPD5 binding.

In addition, a GLG-1 ECD domain by itself was found to be sufficient for LYPD5 binding. As shown in FIG. 33, GLG-1 is made up of multiple GLG-1 domains and single GLG-1 domains can bind LYPD5. FIG. 34B shows the results of a co-immunoprecipitation demonstrating that Fragments 1, 2, 3, and 4, as well as single GLG-1 domains 115, 150, 215, 538, 609, 670, 729, and 858 (as shown in FIG. 34A) were able to bind LYPD5.

Through another co-immunoprecipitation study, binding was shown to be specific based on fragments of LYPD5 (see FIG. 35A) in which LYPD5 was found not to bind BAP negative control, an FN14 negative control was not found to bind GLG-1 fragment 2, the human GLG-1 domain 115 binds LYPD5, domain 115 is not always expressed at detectable levels but still pulls down LYPD5, and the fraction of human GLG-1 fragment 1 that lacks domain 115 (residues 26-114) does not bind LYPD5 (FIG. 35B).

The "*" in FIGS. 34A and 35A indicates a potential fucosylation site.

Although the foregoing invention has been described in some detail by way of illustration and example for purposes of clarity of understanding, the descriptions and examples should not be construed as limiting the scope of the invention. The disclosures of all patent and scientific literatures cited herein are expressly incorporated in their entirety by reference.

What is claimed is:

1. A method of detecting inflammatory bowel disease (IBD) in a mammal, comprising detecting the level of expression of a gene encoding a LY6 polypeptide (a) in a test sample of tissue or cells obtained from said mammal, and (b) in a control sample, wherein a higher level of expression of the LY6 nucleic acid or polypeptide in the test sample, as compared to the control sample, is indicative of the presence of IBD in the mammal from which the test sample was obtained.

2. The method of claim 1, wherein the tissue or cells of the test sample are from the gastrointestinal tract of the mammal.

3. The method of claim 2, wherein the tissue or cells of the test sample are from the colon of the mammal.

4. The method of claim 1, wherein the control sample is a sample of normal non-IBD tissue or cells of the same tissue origin or type, or multiple samples of non-IBD tissue or cells of the same tissue origin or type the expression levels of which are averaged, or a universal control representing gene expression in multiple samples of healthy, normal tissue of the same species.

5. The method of claim 1, wherein the tissue or cells of the test sample are inflamed.

6. The method of claim 1, wherein the tissue or cells of the test sample are not inflamed.

7. The method of claim 1, comprising:
(a) contacting the test sample with a detectable agent that specifically binds a polynucleotide that encodes LY6 polypeptide or fragment thereof; (b) contacting the control sample with the detectable agent; and (c) detecting the formation of a complex between the agent and the polynucleotide of the test sample and the control sample, wherein the formation of less complex in the test sample relative to the control sample is indicative of the presence of IBD in the mammal.

8. The method of claim 7, wherein the polynucleotide comprises the nucleic acid sequence of SEQ ID NO:8, 9, 1, 3, 4, 6, or a fragment thereof comprising at least 15 contiguous nucleotides of SEQ ID NO:8, 9, 1, 3, 4, or 6.

9. The method of claim 7, wherein the tissue or cells of the test sample are from the gastrointestinal tract of the mammal.

10. The method of claim 9, wherein the tissue or cells of the test sample are from the colon of the mammal.

11. The method of claim 10, wherein the control sample is a sample of normal non-IBD tissue or cells of the same tissue origin or type, or multiple samples of non-IBD tissue or cells of the same tissue origin or type the expression levels of which are averaged, or a universal control representing gene expression in multiple samples of healthy, normal tissue of the same species.

12. The method of claim 7, wherein the agent is a second polynucleotide that hybridizes to a polynucleotide having the sequence SEQ ID NO:8, 9, 1, 3, 4, 6 or its complement.

13. The method of claim 12, wherein the second polynucleotide comprises a detectable label or attached to a solid support.

14. The method of claim 13, wherein the detectable label is directly detectable.

15. The method of claim 14, wherein the detectable label is indirectly detectable.

16. The method of claim 12, wherein the detectable label is a fluorescent label.

17. The method of claim 7, wherein the method is in situ hybridization assay.

18. The method of claim 7, wherein the method is real time polymerase chain reaction (RT-PCR) assay.

19. The method of claim 1, comprising:
(a) contacting the test sample with a detectable agent that specifically binds a LY6 polypeptide or fragment thereof; (b) contacting the control sample with the detectable agent; and (c) detecting the formation of a complex between the agent and the polypeptide of the test sample and the control sample, wherein the formation of less complex in the test sample relative to the control sample is indicative of the presence of IBD in the mammal.

20. The method of claim 19, wherein the LY6 polypeptide comprises SEQ ID NO:10, 2, 5, 7 or a fragment thereof comprising at least 10 continguous amino acids of SEQ ID NO:10, 2, 5, or 7.

21. The method of claim 19, wherein the tissue or cells of the test sample are from the gastrointestinal tract of the mammal.

22. The method of claim 21, wherein the tissue or cells of the test sample are from the colon of the mammal.

23. The method of claim 19, wherein the agent is an antibody or binding fragment thereof 24. The method of claim 23, wherein the antibody or binding fragment thereof comprises a detectable label.

25. The method of claim 24, wherein the detectable label is directly detectable.

26. The method of claim 24, wherein the detectable label is indirectly detectable.

27. The method of claim 24, wherein the detectable label is a fluorescent label or a radiolabel.

28. The method of claim 7 or 19, wherein the tissue or cells of the test sample are inflamed.

29. The method of claim 7 or 19, wherein the tissue or cells of the test sample are not inflamed.

30. The method of claim 1, claim 7 or claim 19, wherein the test sample of tissue or cells is obtained from a mammal suspected of experiencing IBD.

31. The method of claim 1, claim 7, or claim 19, wherein the test sample of tissue or cells is obtained from a mammal suspected of experiencing ulcerative colitis (UC).

32. The method of claim 1, claim 7, or claim 19, wherein the tissues or cells of the mammal have been contacted with a therapeutic agent, and wherein the level of LY6 expression is indicative of the presence or absence of a response to the therapeutic agent in the tissue or cells of the mammal.

33. The method of claim 1, claim 7, or claim 19, wherein the tissues or cells of the mammal have been contacted with a therapeutic agent, wherein the detecting is a second or subsequent detecting, and wherein the level of LY6 expression is indicative of the presence or absence of a response to the therapeutic agent in the tissue or cells of the mammal.

34. The method of claim 1, claim 7, or claim 19, wherein the increase in LY6 expression in the test sample is at least 1.5 fold, at least 2 fold, at least 3 fold, at least 5 fold, at least 6 fold, at least 7 fold, at least 8 fold, at least 9 fold, or at least 10 fold greater than the control sample.

* * * * *

UNITED STATES PATENT AND TRADEMARK OFFICE
CERTIFICATE OF CORRECTION

PATENT NO. : 7,875,431 B2
APPLICATION NO. : 12/036183
DATED : January 25, 2011
INVENTOR(S) : Lauri Diehl et al.

It is certified that error appears in the above-identified patent and that said Letters Patent is hereby corrected as shown below:

Column 181, line 3, "continguous" should be changed to --contiguous--.

Signed and Sealed this
Nineteenth Day of April, 2011

David J. Kappos
*Director of the United States Patent and Trademark Office*